United States Patent
Artero Allepuz et al.

(10) Patent No.: US 11,202,794 B2
(45) Date of Patent: Dec. 21, 2021

(54) MODULATION OF MICRORNAS AGAINST MYOTONIC DYSTROPHY TYPE 1 AND ANTAGONISTS OF MICRORNAS THEREFOR

(71) Applicants: UNIVERSITAT DE VALENCIA, Valencia (ES); AUM LifeTech, Inc., Philadelphia, PA (US)

(72) Inventors: Rubén D. Artero Allepuz, Valencia (ES); María Beatriz LlamusíTroisi, Valencia (ES); Estefanía Cerro Herreros, Valencia (ES); Juan M. Fernández Costa, Valencia (ES); Veenu Aishwarya, Philadelphia, PA (US); Thorleif Møller, Årslev (DK)

(73) Assignees: UNIVERSITAT DE VALENCIA, Valencia (ES); AUM LIFETECH, INC., Philadelphia, PA (US)

( * ) Notice: Subject to any disclaimer, the term of this patent is extended or adjusted under 35 U.S.C. 154(b) by 22 days.

(21) Appl. No.: 16/334,725

(22) PCT Filed: Sep. 19, 2017

(86) PCT No.: PCT/EP2017/073685
§ 371 (c)(1),
(2) Date: Mar. 19, 2019

(87) PCT Pub. No.: WO2018/050930
PCT Pub. Date: Mar. 22, 2018

(65) Prior Publication Data
US 2019/0231809 A1    Aug. 1, 2019

(30) Foreign Application Priority Data
Sep. 19, 2016  (ES) .................. 201631216

(51) Int. Cl.
*A61K 31/7115* (2006.01)
*C12N 15/113* (2010.01)
*A61P 25/14* (2006.01)
*A61P 21/00* (2006.01)

(52) U.S. Cl.
CPC .......... *A61K 31/7115* (2013.01); *A61P 21/00* (2018.01); *A61P 25/14* (2018.01); *C12N 15/113* (2013.01); *C12N 2310/113* (2013.01); *C12N 2310/141* (2013.01)

(58) Field of Classification Search
CPC ............ C12N 15/113; C12N 2310/113; C12N 2310/141; A61K 31/7115; A61P 21/00; A61P 25/14
USPC ..................... 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 2011/0130442 A1 | 6/2011 | Kosaka et al. |
| 2013/0150428 A1 | 6/2013 | Rogler et al. |

FOREIGN PATENT DOCUMENTS

| | | |
|---|---|---|
| JP | 2012-528797 A | 11/2012 |
| WO | 2005/013901 A2 | 2/2005 |
| WO | 2005/079397 A2 | 9/2005 |
| WO | 2006/069584 A2 | 7/2006 |
| WO | 2008/036406 A2 | 3/2008 |
| WO | 2008/116267 A1 | 10/2008 |
| WO | 2009/148137 A1 | 12/2009 |
| WO | 2009/149182 A1 | 12/2009 |
| WO | 2010/115050 A2 | 10/2010 |
| WO | 2010/139026 A1 | 12/2010 |
| WO | 2012/012443 A2 | 1/2012 |
| WO | 2013/117713 A1 | 8/2013 |
| WO | 2013/159091 A2 | 10/2013 |

OTHER PUBLICATIONS

Alexander M. S. et al, "Skeletal muscle micro RNAs: Their diagnostic and therapeutic potential in human muscle diseases", Journal of Neuromuscular Diseases, 2015, vol. 2, pp. 1-11.
Goodwin, Marianne, et al, "MBNL sequestration by toxic RNAs and RNA mis-processing in the myotonic dystrophy brain", Cell Reports, 2015, vol. 12, No. 7, p. 1159-1168.
Japanese Office Action of corresponding Japanese Patent Application No. 2019-536689, dated Aug. 18, 2020, 10 pages.

(Continued)

*Primary Examiner* — Jane J Zara
(74) *Attorney, Agent, or Firm* — Seed IP Law Group LLP

(57) ABSTRACT

Modulation of microRNAs against myotonic dystrophy type 1 and antagonists of microRNAs therefor. The invention provides the use of inhibitors of microRNAs repressors of MBNL1 and/or MBNL2 genes for the manufacture of a medicinal product for the treatment of myotonic dystrophy 1. Inhibiting these microRNAs allows to increase the endogenous levels of the corresponding proteins MBNL1 and/or MBNL2, thereby alleviating symptoms of the disease, especially when inhibiting repressors that are expressed in the main affected organs: skeletal muscle, heart or organs of the central nervous system. The inhibition of the microRNAs miR-23b-3p and miR-218-5p is preferred. It also provides oligoribonucleotide or oligoribonucleotide analogue antagonists suitable therefor, preferably antagomiRs directed against the microRNAs mentioned with chemical modifications that enhance their interaction with the target, their stability in vivo and their ability to penetrate into the cells and distribute throughout tissues and organs.

18 Claims, 29 Drawing Sheets
Specification includes a Sequence Listing.

(56) References Cited

OTHER PUBLICATIONS

Teplyuk, et al., "Therapeutic potential of targeting microRNA-10b in established intracranial glioblastoma: first steps toward the clinic", EMBO Molecular Medicine, Feb. 9, 2016, p. 268-287.
Koutsoulidou et al., "Elevated Muscle-Specific miRNAs in Serum of Myotonic Dystrophy Patients Relate to Muscle Disease Progress," *PLoS ONE* 10(4): e0125341, 2015. (20 pages).
Konieczny et al., "MBNL proteins and their target RNAs, interaction and splicing regulation," *Nucleic Acids Research* 42(17): 10873-10887, 2014.
Zhang et al., "miR-30-5p Regulates Muscle Differentiation and Alternative Splicing of Muscle-Related Genes by Targeting MBNL," *Int. J. Mol. Sci.* 17:182, 2016, (16 pages).

SEQUENCE LISTING

```
<160> NUMBER OF SEQ ID NOS: 104

<210> SEQ ID NO 1
<211> LENGTH: 21
<212> TYPE: RNA
<213> ORGANISM: Artificial sequence
<220> FEATURE:
<223> OTHER INFORMATION: Complementary sequence to human miR-218-5p,
      base for the generation of inhibitors thereof

<400> SEQUENCE: 1
acaugguuag aucaagcaca a                                              21

<210> SEQ ID NO 2
<211> LENGTH: 21
<212> TYPE: RNA
<213> ORGANISM: Artificial sequence
<220> FEATURE:
<223> OTHER INFORMATION: Complementary sequence to miR-23b-3p, base for
      the generation of inhibitors thereof

<400> SEQUENCE: 2
gguaaucccu ggcaauguga u                                              21

<210> SEQ ID NO 3
<211> LENGTH: 21
<212> TYPE: RNA
<213> ORGANISM: Homo sapiens
```

```
<220> FEATURE:
<221> NAME/KEY: misc_RNA
<222> LOCATION: (1)..(21)
<223> OTHER INFORMATION: Mature human microRNA miR-218-5p
<220> FEATURE:
<221> NAME/KEY: misc_RNA
<222> LOCATION: (2)..(8)
<223> OTHER INFORMATION: Seed region

<400> SEQUENCE: 3
uugugcuuga ucuaaccaug u                                               21

<210> SEQ ID NO 4
<211> LENGTH: 21
<212> TYPE: RNA
<213> ORGANISM: Homo sapiens
<220> FEATURE:
<221> NAME/KEY: misc_RNA
<222> LOCATION: (1)..(21)
<223> OTHER INFORMATION: Mature human microRNA miR-23b-3p
<220> FEATURE:
<221> NAME/KEY: misc_RNA
<222> LOCATION: (2)..(8)
<223> OTHER INFORMATION: Seed region

<400> SEQUENCE: 4
aucacauugc cagggauuac c                                               21

<210> SEQ ID NO 5
<211> LENGTH: 699
<212> TYPE: DNA
<213> ORGANISM: Artificial sequence
<220> FEATURE:
<223> OTHER INFORMATION: Plasmid Insert (product No. SC400649) that
      encodes the RNA hsa-miR7 (MI0000265) with hairpin loop that
      originates hsa-miR-7-5p
<220> FEATURE:
<221> NAME/KEY: misc_feature
<222> LOCATION: (293)..(402)
<223> OTHER INFORMATION: Sequence corresponding to the RNA hsa-miR-7
      (MI0000265) with hairpin loop that originates hsa-miR-7-5p
<220> FEATURE:
<221> NAME/KEY: misc_feature
<222> LOCATION: (324)..(346)
<223> OTHER INFORMATION: Part corresponding to mature hsa-miR-7-5p
      (MIMAT0000252)

<400> SEQUENCE: 5
ctggagtgag ctgtgattgc accactgcac tacagcctgg gtgacagagc aagaccctgt     60
ctcaccaaaa caaaacaaaa caactgtgtc cattatagaa agtagaacac tccagaaaaa    120
agggaaaagt aagaaaaaat aatttctcca gggaattctg aggtgaggag aggtgttcaa    180
agatgaactt agtaatagga gcggagacaa cgcctcgcct gaaggagcat ccagaccgct    240
gacctggtgg cgaggggagg ggggtggtcc tcgaacgcct tgcagaactg gcctggatac    300
agagtggacc ggctggcccc atctggaaga ctagtgattt tgttgttgtc ttactgcgct    360
caacaacaaa tcccagtcta cctaatggtg ccagccatcg cagcggggtg caggaaatgg    420
gggcagcccc cctttttggc tatccttcca cgtgttcttt tttgtatctt tgtgtttcc     480 tagaaaacat ctcaggtcac caccctaaac acccatcggc agactcttcc agaaacatgg    540
acaaactatg tgtgagcag ggaagtgggg cagggtctct gttttcaggg agcagtggac     600
tgcttccata ccactacctg aagggcaggg ggagaaaaac cctccttaat tactaattcc    660
cccaacaatc actttggggc acctataatg gaggcacct                           699

<210> SEQ ID NO 6
```

<211> LENGTH: 650
<212> TYPE: DNA
<213> ORGANISM: Artificial sequence
<220> FEATURE:
<223> OTHER INFORMATION: Plasmid Insert (product No. SC400295) that encodes the RNA hsa-miR-23b (MI0000439) with hairpin loop that originates the mature hsa-miR-23b-3p
<220> FEATURE:
<221> NAME/KEY: misc_feature
<222> LOCATION: (281)..(377)
<223> OTHER INFORMATION: Part corresponding to RNA hsa-miR-23b (MI0000439) with hairpin loop that originates the mature hsa-miR-23b-3p
<220> FEATURE:
<221> NAME/KEY: misc_feature
<222> LOCATION: (299)..(320)
<223> OTHER INFORMATION: Part corresponding to mature hsa-miR-23b-3p (MIMAT0000418)

<400> SEQUENCE: 6

```
gaggcagtaa actaatagca aggacagctg cctttagcaa ttgtgtgtgt cgcatggccg      60
gtccctgcat ttttcttcag ttccaaagct gcactggcat ttttatggtc atctctggag     120
tccctttgat tcaagaaatt atacctctag gatgccaact aaacgaacaa caaacagaaa     180
ctccacctgt ttgctagcat aacaggcgtg aaggcggcag tgtcgccggc gtccttccgc     240
ggaagcccag tgtgtgcaga cagcacgggg tggcgctgct ctcaggtgct ctggctgctt     300
gggttcctgg catgctgatt tgtgacttaa gattaaaatc acattgccag ggattaccac     360
gcaaccacga ccttggctgc cctccagaa accgtggtcg cgctcactgc agattggaga      420
acaggtgcat ctcgtagctc ttctttggaa acaaaagaag ccaccagctg aggaagatgc     480
tcaccggtca ccgtccctt atttatgccc agcgatgacc tctctaacaa ggtgcagagc      540
ttagctgatt ggtgaacagt gattggtttc cgctttgttc acagtggcta agttctgcac     600
ctgaagagaa ggtgagatgg ggacagttaa gttggagccg ctggggcaga                650
```

<210> SEQ ID NO 7
<211> LENGTH: 665
<212> TYPE: DNA
<213> ORGANISM: Artificial sequence
<220> FEATURE:
<223> OTHER INFORMATION: Plasmid insert (product No. SC400179) that encodes the RNA hsa-miR-146b (MI0003129) with hairpin loop that originates the hsa-miR-146b
<220> FEATURE:
<221> NAME/KEY: misc_feature
<222> LOCATION: (294)..(366)
<223> OTHER INFORMATION: Part corresponding to mature RNA hsa-miR-146b (MI0003129) with hairpin loop that originates hsa-miR-146b
<220> FEATURE:
<221> NAME/KEY: misc_feature
<222> LOCATION: (302)..(323)
<223> OTHER INFORMATION: Part corresponding to mature hsa-miR-146b (MIMAT0002809)

<400> SEQUENCE: 7

```
aacacatctg ggcaggaagc gacagatgga tccctgccat ggccctgagc ccctcccct       60
cttaacctac tccaattcct gttggaattt atggaactcc tgtccatttc cttagctgtg     120
ggcccccatt ttcagctcca agctcagacc ctccctggaa taggagttct cttggtatca     180
caagttcctt atgtgaccca tcctgggcct caacttactc atcctgggaa cgggagacga     240
ttcacagaag aaagcatgca agagcagcgt ccaggctgaa agaactttgg ccacctggca     300
ctgagaactg aattccatag gctgtgagct ctagcaatgc cctgtggact cagttctggt     360
gcccggcagt gctacaacat caatgccaag gccgtggggc agctgatggt ttgggctccc     420
```

-continued

```
aacttcccag ccaggtgctt ctgcaggccc acatcttgcc cactggccaa acctttaaat      480
aactttgact cgggctactc ttatgctcaa agacgtcagg ggctctccca aatctcttta      540
ccctgccaga aagtcttcta tagtacggcc tccacttagc tttcacgcct gatcttccat      600
cgcatcctgc tcataacctg ccactagtga acccctgctg ctccggctcc acacttctca      660
tgctg                                                                  665
```

<210> SEQ ID NO 8
<211> LENGTH: 702
<212> TYPE: DNA
<213> ORGANISM: Artificial sequence
<220> FEATURE:
<223> OTHER INFORMATION: Plasmid insert (product No. SC400283) that
      encodes the RNA hsa-miR-218 (MI0000295) with hairpin loop that
      originates the hsa-miR-218-5p
<220> FEATURE:
<221> NAME/KEY: misc_feature
<222> LOCATION: (299)..(408)
<223> OTHER INFORMATION: Part corresponding to mature RNA hsa-miR-218
      (MI0000295) with hairpin loop that originates the hsa-miR-218-5p
<220> FEATURE:
<221> NAME/KEY: misc_feature
<222> LOCATION: (324)..(343)
<223> OTHER INFORMATION: Part corresponding to mature hsa-miR-218-5p
      (MIMAT0000275)

<400> SEQUENCE: 8

```
gtgataggat cacagatgtc tgagtgttct ttctttcctt gggaaggaac catgctgtcc      60
tgaagctccc gagtatgggc atccagtgat ttccctcccg ttcttctccc ttcctactgt     120
gtctccctgg ggtggggcac aagggcagca gggctgcaat cttcggaagt gttccagtgg     180
aaccccactc ctgatactaa tcacgctcag tgggggcctg ctccggcttc gcttctcca     240 cgctgcttcc tctgagcgct cctgtcctct ctctgacgct gcttcctgac cttgactctg     300
accagtcgct gcggggcttt cctttgtgct tgatctaacc atgtggtgga acgatggaaa     360
cggaacatgt ttctgtcaag caccgcggaa agcaccgtgc tctcctgcag catggcccgc     420
caccgccgcc accaccgctg gacacctctc ctctgctctg gagcaccgca gcccaccacc     480
tgccagaccc acctctccca gtctcaactc accaaaggca ggagggtagg agtctcaaag     540
gatgcagata cagagggaaa tgggtctgga gaagcaccct ggggaaagag atctgtatcc     600
acatctcttt cccaaaatgg agtcaccctc ccccaaatct agtctggatg tcagacaagg     660
agtaataact aggttcaagc tcagaaacta ctgtgtctct tc                        702
```

<210> SEQ ID NO 9
<211> LENGTH: 625
<212> TYPE: DNA
<213> ORGANISM: Artificial sequence
<220> FEATURE:
<223> OTHER INFORMATION: Plasmid insert (product No. SC400368) that
      encodes the RNA hsa-miR-372 (MI0000780) with hairpin loop that
      originates the hsa-miR-372
<220> FEATURE:
<221> NAME/KEY: misc_feature
<222> LOCATION: (278)..(344)
<223> OTHER INFORMATION: Part corresponding to mature RNA hsa-miR-372
      (MI0000780) with hairpin loop that originates the hsa-miR-372-3p
<220> FEATURE:
<221> NAME/KEY: misc_feature
<222> LOCATION: (319)..(341)
<223> OTHER INFORMATION: Part corresponding to mature hsa-miR-372-3p
      (MIMAT0000724)

<400> SEQUENCE: 9

```
gcctcttctg atgggtaagt gcttccactt gcgatcgccg ccttgccgca tcccctcagc      60
```

```
ctgtggcact caaactgtgg gggcactttc tgctctctgg tgaaagtgcc gccatctttt    120
gagtgttacc gcttgagaag actcaacctg cggagaagat accattttga ttgggtgagg    180
gggcgggtag caggatggcc ctagaccctg cctatggccg tttcctcgtg atataaattt    240
cttggccggg gctcttgcag atggagctgc tcaccctgtg ggcctcaaat gtggagcact    300
attctgatgt ccaagtggaa agtgctgcga catttgagcg tcaccggtga cgcccatatc    360
aacggatgcc gtggagctcg gtcttctgca ggaactaaag agcctgtggt ttcgattccc    420
agccggaaac tgtcttgggt acaggtccct tacagcgtct ggctgtaatg ctccggaaa     480 acctggggaa gggaagggg  cctcctgggc tctcacctga cacaactaag ggaatctggg    540
ttagatggtg aaaggaagag aaggttcaga gggcggctgt gcgcctgcgc cgggcgcggc    600
ggctcacacc tgtaatccca gcacg                                          625
```

<210> SEQ ID NO 10
<211> LENGTH: 21
<212> TYPE: RNA
<213> ORGANISM: Artificial sequence
<220> FEATURE:
<223> OTHER INFORMATION: Base sequence of the antagomiR-218-5p, which
      includes modified nucleotides
<220> FEATURE:
<221> NAME/KEY: modified_base
<222> LOCATION: (1)..(21)
<223> OTHER INFORMATION: Nucleotide with 2'-O-methyl (2'-methoxy)
      modification
<220> FEATURE:
<221> NAME/KEY: modified_base
<222> LOCATION: (1)..(2)
<223> OTHER INFORMATION: Nucleotide bound to the next by
      phosphorothioate group
<220> FEATURE:
<221> NAME/KEY: modified_base
<222> LOCATION: (18)..(20)
<223> OTHER INFORMATION: Nucleotide bound to the next by a
      phosphorothioate bond
<220> FEATURE:
<221> NAME/KEY: modified_base
<222> LOCATION: (21)..(21)
<223> OTHER INFORMATION: Nucleotide bound to 4 cholesterol groups; the
      nucleotide bond to the first cholesterol group is through a
      phosphorothioate group

<400> SEQUENCE: 10
acaugguuag aucaagcaca a                                              21

<210> SEQ ID NO 11
<211> LENGTH: 21
<212> TYPE: RNA
<213> ORGANISM: Artificial sequence
<220> FEATURE:
<223> OTHER INFORMATION: Secuencia del antagomir23b-5p
<220> FEATURE:
<221> NAME/KEY: modified_base
<222> LOCATION: (1)..(21)
<223> OTHER INFORMATION: Nucletido con modificacin 2'-O-metil
      (2'-metoxi)
<220> FEATURE:
<221> NAME/KEY: modified_base
<222> LOCATION: (1)..(2)
<223> OTHER INFORMATION: Nucleotide bound to the next by
      phosphorothioate group
<220> FEATURE:
<221> NAME/KEY: modified_base
<222> LOCATION: (18)..(20)
<223> OTHER INFORMATION: Nucleotide bound to the next by a
      phosphorothioate bond
<220> FEATURE:
<221> NAME/KEY: modified_base

```
<222> LOCATION: (21)..(21)
<223> OTHER INFORMATION: Nucleotide bound to 4 cholesterol groups; the
      nucleotide bond to the first cholesterol group is through a
      phosphorothioate group

<400> SEQUENCE: 11
gguaaucccu ggcaauguga u                                            21

<210> SEQ ID NO 12
<211> LENGTH: 21
<212> TYPE: RNA
<213> ORGANISM: Homo sapiens
<220> FEATURE:
<221> NAME/KEY: misc_RNA
<222> LOCATION: (1)..(21)
<223> OTHER INFORMATION: microRNA-23b: mature hsa-miR-23b-3p
      (MIMAT0000418)

<400> SEQUENCE: 12
aucacauugc cagggauuac c                                            21

<210> SEQ ID NO 13
<211> LENGTH: 21
<212> TYPE: RNA
<213> ORGANISM: Homo sapiens
<220> FEATURE:
<221> NAME/KEY: misc_RNA
<222> LOCATION: (1)..(21)
<223> OTHER INFORMATION: microRNA-218: mature hsa-miR-218-5p
      (MIMAT0000275)

<400> SEQUENCE: 13
uugugcuuga ucuaaccaug u                                            21

<210> SEQ ID NO 14
<211> LENGTH: 20
<212> TYPE: DNA
<213> ORGANISM: Artificial sequence
<220> FEATURE:
<223> OTHER INFORMATION: Direct primer of gene PCR transcript
      amplification GAPDH

<400> SEQUENCE: 14
catcttccag gagcgagatc                                              20

<210> SEQ ID NO 15
<211> LENGTH: 21
<212> TYPE: DNA
<213> ORGANISM: Artificial sequence
<220> FEATURE:
<223> OTHER INFORMATION: Inverse primer of gene PCR transcript
      amplification GAPDH

<400> SEQUENCE: 15
gttcacaccc atgacgaaca t                                            21

<210> SEQ ID NO 16
<211> LENGTH: 24
<212> TYPE: DNA
<213> ORGANISM: Artificial sequence
<220> FEATURE:
<223> OTHER INFORMATION: Direct primer of gene PCR transcript
      amplification cTNT

<400> SEQUENCE: 16
atagaagagg tggtggaaga gtac                                         24
```

<210> SEQ ID NO 17
<211> LENGTH: 24
<212> TYPE: DNA
<213> ORGANISM: Artificial sequence
<220> FEATURE:
<223> OTHER INFORMATION: Inverse primer of gene PCR transcript
      amplification cTNT

<400> SEQUENCE: 17
gtctcagcct ctgcttcagc atcc                                          24

<210> SEQ ID NO 18
<211> LENGTH: 20
<212> TYPE: DNA
<213> ORGANISM: Artificial sequence
<220> FEATURE:
<223> OTHER INFORMATION: Direct primer of gene PCR transcript
      amplification IR

<400> SEQUENCE: 18
tgctgctcct gtccaaagac                                               20

<210> SEQ ID NO 19
<211> LENGTH: 19
<212> TYPE: DNA
<213> ORGANISM: Artificial sequence
<220> FEATURE:
<223> OTHER INFORMATION: Inverse primer of gene PCR transcript
      amplification IR

<400> SEQUENCE: 19
gaagtgttgg ggaaagctg                                                19

<210> SEQ ID NO 20
<211> LENGTH: 24
<212> TYPE: DNA
<213> ORGANISM: Artificial sequence
<220> FEATURE:
<223> OTHER INFORMATION: Direct primer of gene PCR transcript
      amplification BIN1

<400> SEQUENCE: 20
ctcaaccaga acctcaatga tgtg                                          24

<210> SEQ ID NO 21
<211> LENGTH: 21
<212> TYPE: DNA
<213> ORGANISM: Artificial sequence
<220> FEATURE:
<223> OTHER INFORMATION: Inverse primer of gene PCR transcript
      amplification BIN1

<400> SEQUENCE: 21
ctgagatggg gacttgggga g                                             21

<210> SEQ ID NO 22
<211> LENGTH: 22
<212> TYPE: DNA
<213> ORGANISM: Artificial sequence
<220> FEATURE:
<223> OTHER INFORMATION: Direct primer of gene PCR transcript
      amplification DMD

<400> SEQUENCE: 22
gtgaggaaga tcttctcagt cc                                            22

<210> SEQ ID NO 23

```
<211> LENGTH: 21
<212> TYPE: DNA
<213> ORGANISM: Artificial sequence
<220> FEATURE:
<223> OTHER INFORMATION: Inverse primer of gene PCR transcript
      amplification DMD

<400> SEQUENCE: 23
ctccatcgct ctgcccaaat c                                          21

<210> SEQ ID NO 24
<211> LENGTH: 21
<212> TYPE: DNA
<213> ORGANISM: Artificial sequence
<220> FEATURE:
<223> OTHER INFORMATION: Direct primer of gene PCR transcript
      amplification SERCA1

<400> SEQUENCE: 24
gatgatcttc aagctccggg c                                          21

<210> SEQ ID NO 25
<211> LENGTH: 20
<212> TYPE: DNA
<213> ORGANISM: Artificial sequence
<220> FEATURE:
<223> OTHER INFORMATION: Inverse primer of gene PCR transcript
      amplification SERCA1

<400> SEQUENCE: 25
cagctctgcc tgaagatgtg                                            20

<210> SEQ ID NO 26
<211> LENGTH: 22
<212> TYPE: RNA
<213> ORGANISM: Drosophila melanogaster
<220> FEATURE:
<221> NAME/KEY: misc_RNA
<222> LOCATION: (1)..(22)
<223> OTHER INFORMATION: Mature microRNA dme-mR-92a-3p (MIMAT0000334)

<400> SEQUENCE: 26
cauugcacuu gucccggccu au                                         22

<210> SEQ ID NO 27
<211> LENGTH: 22
<212> TYPE: RNA
<213> ORGANISM: Drosophila melanogaster
<220> FEATURE:
<221> NAME/KEY: misc_RNA
<222> LOCATION: (1)..(22)
<223> OTHER INFORMATION: Mature microRNA dme-miR-100-5p (MIMAT0000357)

<400> SEQUENCE: 27
aacccguaaa uccgaacuug ug                                         22

<210> SEQ ID NO 28
<211> LENGTH: 23
<212> TYPE: RNA
<213> ORGANISM: Drosophila melanogaster
<220> FEATURE:
<221> NAME/KEY: misc_RNA
<222> LOCATION: (1)..(23)
<223> OTHER INFORMATION: Mature microRNA dme-miR-124-3p (MIMAT0000351)

<400> SEQUENCE: 28
uaaggcacgc ggugaaugcc aag                                        23
```

```
<210> SEQ ID NO 29
<211> LENGTH: 23
<212> TYPE: RNA
<213> ORGANISM: Drosophila melanogaster
<220> FEATURE:
<221> NAME/KEY: misc_RNA
<222> LOCATION: (1)..(23)
<223> OTHER INFORMATION: Mature microRNA dme-miR-277-3p (MIMAT0000338)

<400> SEQUENCE: 29
uaaaugcacu aucugguacg aca                                            23

<210> SEQ ID NO 30
<211> LENGTH: 23
<212> TYPE: RNA
<213> ORGANISM: Drosophila melanogaster
<220> FEATURE:
<221> NAME/KEY: misc_RNA
<222> LOCATION: (1)..(23)
<223> OTHER INFORMATION: Mature microRNA dme-miR-304-5p (MIMAT0000390)

<400> SEQUENCE: 30
uaaucucaau uuguaaaugu gag                                            23

<210> SEQ ID NO 31
<211> LENGTH: 25
<212> TYPE: DNA
<213> ORGANISM: Artificial sequence
<220> FEATURE:
<223> OTHER INFORMATION: Direct primer of qRT-PCR of mbl

<400> SEQUENCE: 31
ttgaatcaaa attatagccc aagct                                          25

<210> SEQ ID NO 32
<211> LENGTH: 21
<212> TYPE: DNA
<213> ORGANISM: Artificial sequence
<220> FEATURE:
<223> OTHER INFORMATION: Inverse primer of qRT-PCR of mbl

<400> SEQUENCE: 32
cgattttgct cgttagcgtt t                                              21

<210> SEQ ID NO 33
<211> LENGTH: 27
<212> TYPE: DNA
<213> ORGANISM: Artificial sequence
<220> FEATURE:
<223> OTHER INFORMATION: Direct primer of qRT-PCR of mblA

<400> SEQUENCE: 33
cagacaccga aatactctct acaaaca                                        27

<210> SEQ ID NO 34
<211> LENGTH: 30
<212> TYPE: DNA
<213> ORGANISM: Artificial sequence
<220> FEATURE:
<223> OTHER INFORMATION: Inverse primer of qRT-PCR of mblA

<400> SEQUENCE: 34
aaaatcagga gtaaacaaat acacgtagac                                     30

<210> SEQ ID NO 35
<211> LENGTH: 26
```

```
<212> TYPE: DNA
<213> ORGANISM: Artificial sequence
<220> FEATURE:
<223> OTHER INFORMATION: Direct primer of qRT-PCR of mblB

<400> SEQUENCE: 35
cacacatcca gatatgctac ttacca                                          26

<210> SEQ ID NO 36
<211> LENGTH: 22
<212> TYPE: DNA
<213> ORGANISM: Artificial sequence
<220> FEATURE:
<223> OTHER INFORMATION: Inverse primer of qRT-PCR of mblB

<400> SEQUENCE: 36
tgagcgattt cgattgattt tg                                              22

<210> SEQ ID NO 37
<211> LENGTH: 23
<212> TYPE: DNA
<213> ORGANISM: Artificial sequence
<220> FEATURE:
<223> OTHER INFORMATION: Direct primer of qRT-PCR of mblC

<400> SEQUENCE: 37
cagcaaacac acatcaccta cca                                             23

<210> SEQ ID NO 38
<211> LENGTH: 23
<212> TYPE: DNA
<213> ORGANISM: Artificial sequence
<220> FEATURE:
<223> OTHER INFORMATION: Inverse primer of qRT-PCR of mblC

<400> SEQUENCE: 38
ctatcgagca ggaggatgaa gag                                             23

<210> SEQ ID NO 39
<211> LENGTH: 20
<212> TYPE: DNA
<213> ORGANISM: Artificial sequence
<220> FEATURE:
<223> OTHER INFORMATION: Direct primer of qRT-PCR of mblD

<400> SEQUENCE: 39
gcctctggaa aatgctgcaa                                                 20

<210> SEQ ID NO 40
<211> LENGTH: 20
<212> TYPE: DNA
<213> ORGANISM: Artificial sequence
<220> FEATURE:
<223> OTHER INFORMATION: Inverse primer of qRT-PCR of mblD

<400> SEQUENCE: 40
cagcaaccgc aaaagagctt                                                 20

<210> SEQ ID NO 41
<211> LENGTH: 19
<212> TYPE: DNA
<213> ORGANISM: Artificial sequence
<220> FEATURE:
<223> OTHER INFORMATION: Direct primer of qRT-PCR of Serca

<400> SEQUENCE: 41
```

```
gcagatgttc ctgatgtcg                                               19

<210> SEQ ID NO 42
<211> LENGTH: 19
<212> TYPE: DNA
<213> ORGANISM: Artificial sequence
<220> FEATURE:
<223> OTHER INFORMATION: Inverse primer of qRT-PCR of Serca

<400> SEQUENCE: 42
cgtcctcctt cacattcac                                               19

<210> SEQ ID NO 43
<211> LENGTH: 20
<212> TYPE: DNA
<213> ORGANISM: Artificial sequence
<220> FEATURE:
<223> OTHER INFORMATION: Direct primer of qRT-PCR of Cyp6w1

<400> SEQUENCE: 43
ttgcgcacaa aaatctctcc                                              20

<210> SEQ ID NO 44
<211> LENGTH: 20
<212> TYPE: DNA
<213> ORGANISM: Artificial sequence
<220> FEATURE:
<223> OTHER INFORMATION: Inverse primer of qRT-PCR of Cyp6w1

<400> SEQUENCE: 44
gtcctgcaag ttctttccaa                                              20

<210> SEQ ID NO 45
<211> LENGTH: 26
<212> TYPE: DNA
<213> ORGANISM: Artificial sequence
<220> FEATURE:
<223> OTHER INFORMATION: Direct primer of qRT-PCR of Rp49

<400> SEQUENCE: 45
ggatcgatat gctaagctgt cgcaca                                       26

<210> SEQ ID NO 46
<211> LENGTH: 24
<212> TYPE: DNA
<213> ORGANISM: Artificial sequence
<220> FEATURE:
<223> OTHER INFORMATION: Inverse primer of qRT-PCR of Rp49

<400> SEQUENCE: 46
ggtgcgcttg ttcgatccgt aacc                                         24

<210> SEQ ID NO 47
<211> LENGTH: 20
<212> TYPE: DNA
<213> ORGANISM: Artificial sequence
<220> FEATURE:
<223> OTHER INFORMATION: Direct primer of qRT-PCR of Fhos

<400> SEQUENCE: 47
gtcatggagt cgagcagtga                                              20

<210> SEQ ID NO 48
<211> LENGTH: 20
<212> TYPE: DNA
<213> ORGANISM: Artificial sequence
```

```
<220> FEATURE:
<223> OTHER INFORMATION: Inverse primer of qRT-PCR of Fhos

<400> SEQUENCE: 48
tgtgatgcgg gtatctacga                                              20

<210> SEQ ID NO 49
<211> LENGTH: 18
<212> TYPE: DNA
<213> ORGANISM: Artificial sequence
<220> FEATURE:
<223> OTHER INFORMATION: Direct primer of qRT-PCR of Tnt

<400> SEQUENCE: 49
cgacgatgaa gagtacac                                                18

<210> SEQ ID NO 50
<211> LENGTH: 22
<212> TYPE: DNA
<213> ORGANISM: Artificial sequence
<220> FEATURE:
<223> OTHER INFORMATION: Inverse primer of qRT-PCR of Tnt

<400> SEQUENCE: 50
actcggtgat gtattctttc ag                                           22

<210> SEQ ID NO 51
<211> LENGTH: 3438
<212> TYPE: DNA
<213> ORGANISM: Homo sapiens
<220> FEATURE:
<221> NAME/KEY: 3'UTR
<222> LOCATION: (1)..(3438)
<223> OTHER INFORMATION: 3'UTR region of the transcript of the MBNL1
      gene (NM_207297.1) inserted in the plasmid pEZX-MT05
<220> FEATURE:
<221> NAME/KEY: misc_binding
<222> LOCATION: (3130)..(3150)
<223> OTHER INFORMATION: miR-23b binding region

<400> SEQUENCE: 51
ccacaagtat gttacccaga tgtagaattt tcatcactaa acaatcatgc taaagaggaa    60
aggacagtgt gcttggttag agtaaaggac gaggtcatta gccatattgt atatatcgtc   120
aagcaacaca cacaaaagtt cctcagccac aagacatcca catattgcat gttaaccaga   180
agaaaagaca acattttccg gaaatccact gcacactgtt gcctatacac tttgtacatt   240
taattgatat ttgtgctgag gtgatattcc tgtctaaaag aacaacattg tctttctttt   300
ctagcacaga gttatgcatt caaagatgca tacctagtta gtttcctata tattcatgcc   360
atcttgaaaa gacagactat ggtgtaacca tgattctatt atgtattggt acgtctgtag   420
accaagatat aatttttta aaataagttt atttctttca aggtttacaa ataacaaagg   480
tgcaccttgt atttaaaatt gccattatag atgagagcgt gcatgcacag tcatttttgt   540
ttaagagtaa tattttttaat gtaatagatt gtaagacgtg gtgagggagg gatctgacag   600
agatgaatgt gccaagcaaa accacaactg tgtatatttt aaagcacatc atggctttaa   660
gtaccatgtt gttaaggatt ctcatgaagt gccatagact gtacatcaaa ttagagtatt   720
atttcttcag tgttattgtt ttcagagcca catttgttg catatttgct agtactaatc   780
agtcaaaggg caccattctt ttttttttt tttgaaacca agctgtctc agaaatggcc    840 aatttaactt tacagtaaca atagacagca caacacaaac tctctcaata cagataaact   900
cacacatact ggagatatat ataatagaa tatatataaa attattttaa tgcattgtag   960
```

```
tgtaatattt atgcatacta tactgtataa catgttattc aaaagggatt gccatttctg    1020
agacacagta acaaaaaaat gaggaaatta ttttgcttct atttatagcc tctgtcaaaa    1080
gtcaaaagac tataaatgct ttgcaaaaat ggtttcacgt ttgcttaaat gcttcatcac    1140
agtcacattc aaaatagtga ctctaaacaa agaagaaagc agcactgtca tcagatgcat    1200
gataaaccaa aatatgaaaa tgggaaatgt ttaattaacc tagtaattgg gtgggttaag    1260
tacatgggtg aattttatat gtgatttttg ttttgttttg ttttgttcag attaactgct    1320
tatagcctta gaaagccttt tacaaaatta aaaaaaaaat agatgtgcat tcagttttta    1380
agaatggaat catccaaagg aattccttttt tttgaggttt ggatgttgca gctagtaaag    1440
gatatttttg ctctgttcag cagttctaaa aattgctgaa gtaggggcca ggtcactggt    1500
agttatagta tggaatggga gaagtgaaag ttcagttata gaactttcca tacttccaag    1560
tttactgcaa gttttttatgc ttgagagaga tgctttctaa tataagactg atgtgttgat    1620
tttactgatt gtactgtaca tctattaaag cctttagatta ttacattacg ggttggaacc    1680
cataccaatg taatttcaat cgtgttaaga aagtaatggt gacttcacat gttattgtag    1740
ttagttacat tatagaatat tacttatttt tcttgttaaa atgtagtttt tcatttccta    1800
catttattag attttcattt tctattaaca attgaatacc atttcagttt atagacttgt    1860
tttattagat tttaccaatg aattttttcaa aatacaaaaa aaagtagttt ttccttcata    1920
acatactcag ttttgaatta catgtagtgt cacatgaata ttcgtattgt taactaaatg    1980
atttatattt tactgattta atattacagt gtaagaatgt cagtcattgt tagttccttgt    2040 ctagttttca ttaaaagaac aaagatcttt tatatggata tcttataaat atataatcat    2100
tgctaagtaa gaagttaagt tgttgctatc gcaacaatcc tggcagacaa ttgagtaata    2160
ttttgatgat ttatttttgtt tgtaattagt tattataaga agatctagat cctagatatt    2220
agaataaaat ttatttttcta ctgtatccat ttcaaatgtt aaaatattgt ttaatatttt    2280
tgaaatccct gagtatcagg ccttgttata ataagctgc ataatcaata aatagaacaa    2340 gggactttttt gttgataatc caaatactca aagtttacgt aatgaaaatt atagcgtgtg    2400
tgcaaactct tgagggttga ttatgctgca atttagcatg ttggaacgtc tagggagaag    2460
gttgactttt tgcacttctg tatatagtca aaagagagaa acctgtataa tagtaagatc    2520
ttattttgaa taaaaacgtc tataattaca aggagttttg ttaaggctaa tacaatgaca    2580
gactgagcaa aattgcttgc aaaagtggca cagagttagc actccatacc ccttcaaaca    2640
tgttgctttg ctttcttgtg gacagcttgt agtttgccag gatttttttca gctggaaaga    2700 tacgccatcc tttcaaaccc tcatgactga caaaaactcc atgggccaa atctgcctga    2760 agatcattac caaaaatagc aggtacttct accattaagg tgaaatcatg gatcagatat    2820
tccttacatt tttcaaaact actgcatgtt taaaacttca acaaaaaaag agagaaagaa    2880
ctatactaag aacatatatt attcagatca gtttctgcca atttcagtgg tttattgttc    2940
acaaaaaaat cttcaaaaca agtattgact ttcacaaaat ttaaatcata aacaggcaaa    3000
ccaaacagca cactgtagct atagttgtta tgtgattgtt ttttaattgc tgtaggatcc    3060
tgttctttca gcaggtgaaa aataaaacgc agttcaaatt tcatggtttt aattttcaac    3120
tcagaagcac tcaaaaatgc aaaatgtgat aatgggcact tgtttaaaag aattagtgta    3180
tccagccttc actccagctg gttaaaaatg ttgcacttat cagcaaccct accactttca    3240
tctgctgaaa ggacaaatgt gcttggtttt actattatgt aatcacaact tactttctgc    3300
```

```
ttgtagttgc ttaaaattat gtattttgtc ttgggctgca atttgtttta tgcttatttt      3360
attattactg cagtagttga ctttgctgta tggaaaaata aagtgaaatt gccctaataa      3420
aacttctctt tcttaagt                                                    3438

<210> SEQ ID NO 52
<211> LENGTH: 3430
<212> TYPE: DNA
<213> ORGANISM: Artificial sequence
<220> FEATURE:
<223> OTHER INFORMATION: 3'UTR region of MBNL1 with Seed region of
      miR-23b deleted (3UTR MUT-23b)
<220> FEATURE:
<221> NAME/KEY: misc_feature
<222> LOCATION: (3142)..(3143)
<223> OTHER INFORMATION: Nucleotides flanking the fragment of the
      deleted seed region

<400> SEQUENCE: 52
ccacaagtat gttacccaga tgtagaattt tcatcactaa acaatcatgc taaagaggaa        60
aggacagtgt gcttggttag agtaaaggac gaggtcatta gccatattgt atatatcgtc       120
aagcaacaca cacaaaagtt cctcagccac aagacatcca catattgcat gttaaccaga       180
agaaaagaca acattttccg gaaatccact gcacactgtt gcctatacac tttgtacatt       240
taattgatat ttgtgctgag gtgatattcc tgtctaaaag aacaacattg tctttctttt       300
ctagcacaga gttatgcatt caaagatgca tacctagtta gtttcctata tattcatgcc       360
atcttgaaaa gacagactat ggtgtaacca tgattctatt atgtattggt acgtctgtag       420
accaagatat aatttttttaa aaataagttt atttctttca aggtttacaa ataacaaagg       480
tgcaccttgt atttaaaatt gccattatag atgagagcgt gcatgcacag tcattttttgt       540 ttaagagtaa tattttttaat gtaatagatt gtaagacgtg gtgagggagg gatctgacag       600
agatgaatgt gccaagcaaa accacaactg tgtatatttt aaagcacatc atggctttaa       660
gtaccatgtt gttaaggatt ctcatgaagt gccatagact gtacatcaaa ttagagtatt       720
atttcttcag tgttattgtt ttcagagcca catttttgttg catatttgct agtactaatc       780
agtcaaaggg caccattctt tttttttttt tttgaaacca aagctgtctc agaaatggcc       840
aatttaactt tacagtaaca atagacagca caacacaaac tctctcaata cagataaact       900
cacacatact ggagatatat atataataga tatatataaa attattttaa tgcattgtag       960 tgtaatatt atgcatacta tactgtataa catgttattc aaaagggatt gccatttctg      1020
agacacagta acaaaaaaat gaggaaatta ttttgcttct atttatagcc tctgtcaaaa      1080
gtcaaaagac tataaatgct ttgcaaaaat ggtttcacgt ttgcttaaat gcttcatcac      1140
agtcacattc aaaatagtga ctctaaacaa agaagaaagc agcactgtca tcagatgcat      1200
gataaaccaa aatatgaaaa tgggaaatgt ttaattaacc tagtaattgg gtgggttaag      1260
tacatgggtg aatttatat gtgattttttg ttttgttttg ttttgttcag attaactgct      1320
tatagcctta gaaagccttt tacaaaatta aaaaaaaaat agatgtgcat tcagttttta      1380
agaatggaat catccaaagg aattcctttt tttgaggttt ggatgttgca gctagtaaag      1440 gatattttg ctctgttcag cagttctaaa aattgctgaa gtaggggcca ggtcactggt       1500
agttatagta tggaatggga gaagtgaaag ttcagttata gaactttcca tacttccaag      1560
tttactgcaa gttttttatgc ttgagagaga tgctttctaa tataagactg atgtgttgat      1620
tttactgatt gtactgtaca tctattaaag ccttagatta ttcattacg ggttggaacc       1680 cataccaatg taatttcaat cgtgttaaga aagtaatggt gacttcacat gttattgtag      1740
```

```
ttagttacat tatagaatat tacttatttt tcttgttaaa atgtagtttt tcatttccta    1800
catttattag attttcattt tctattaaca attgaatacc atttcagttt atagacttgt    1860
tttattagat tttaccaatg aattttttcaa aatacaaaaa aaagtagttt ttccttcata   1920
acatactcag ttttgaatta catgtagtgt cacatgaata ttcgtattgt taactaaatg    1980
atttatattt tactgattta atattacagt gtaagaatgt cagtcattgt tagttcttgt   2040
ctagttttca ttaaaagaac aaagatcttt tatatgata  tcttataaat atataatcat   2100
tgctaagtaa gaagttaagt tgttgctatc gcaacaatcc tggcagacaa ttgagtaata   2160
ttttgatgat ttattttgtt tgtaattagt tattataaga agatctagat cctagatatt  2220
agaataaaat ttattttcta ctgtatccat ttcaaatgtt aaaatattgt ttaatatttt   2280
tgaaatccct gagtatcagg ccttgttata aataagctgc ataatcaata aatagaacaa   2340 gggactttt  gttgataatc caaatactca aagtttacgt aatgaaaatt atagcgtgtg   2400
tgcaaactct tgagggttga ttatgctgca atttagcatg ttggaacgtc tagggagaag   2460
gttgactttt tgcacttctg tatatagtca aaagagagaa acctgtataa tagtaagatc   2520 ttatttttgaa taaaaacgtc tataattaca aggagttttg ttaaggctaa tacaatgaca   2580
gactgagcaa aattgcttgc aaaagtggca cagagttagc actccatacc ccttcaaaca   2640
tgttgctttg ctttcttgtg gacagcttgt agtttgccag gatttttca  gctgaaaga   2700 tacgccatcc tttcaaaccc tcatgactga caaaaactcc atggggccaa atctgcctga   2760
agatcattac caaaaatagc aggtacttct accattaagg tgaaatcatg gatcagatat   2820
tccttacatt tttcaaaact actgcatgtt taaaacttca acaaaaaaag agagaaagaa   2880
ctatactaag aacatatatt attcagatca gtttctgcca atttcagtgg tttattgttc   2940
acaaaaaaat cttcaaaaca agtattgact ttcacaaaat ttaaatcata aacaggcaaa   3000
ccaaacagca cactgtagct atagttgtta tgtgattgtt ttttaattgc tgtaggatcc   3060
tgttctttca gcaggtgaaa aataaaacgc agttcaaatt tcatggtttt aattttcaac   3120
tcagaagcac tcaaaaatgc aaaatgggca cttgtttaaa agaattagtg tatccagcct   3180
tcactccagc tggttaaaaa tgttgcactt atcagcaacc ctaccacttt catctgctga   3240
aaggacaaat gtgcttggtt ttactattat gtaatcacaa cttactttct gcttgtagtt   3300
gcttaaaatt atgtatttg tcttgggctg caatttgttt tatgcttatt ttattattac    3360
tgcagtagtt gactttgctg tatggaaaaa taaagtgaaa ttgccctaat aaaacttctc   3420
tttcttaagt                                                          3430
```

<210> SEQ ID NO 53
<211> LENGTH: 3438
<212> TYPE: DNA
<213> ORGANISM: Artificial sequence
<220> FEATURE:
<223> OTHER INFORMATION: Insert of plasmid pEZX-MT05 with the 3'UTR of
      MBNL1 modified (3UTR PM-23b)
<220> FEATURE:
<221> NAME/KEY: misc_binding
<222> LOCATION: (3130)..(3150)
<223> OTHER INFORMATION: Region modified for perfect complementarity
      with miR-23b

<400> SEQUENCE: 53

```
ccacaagtat gttacccaga tgtagaattt tcatcactaa acaatcatgc taaagaggaa      60
aggacagtgt gcttggttag agtaaaggac gaggtcatta gccatattgt atatatcgtc    120
```

```
aagcaacaca cacaaaagtt cctcagccac aagacatcca catattgcat gttaaccaga    180
agaaaagaca acattttccg gaaatccact gcacactgtt gcctatacac tttgtacatt    240
taattgatat ttgtgctgag gtgatattcc tgtctaaaag aacaacattg tctttctttt    300
ctagcacaga gttatgcatt caaagatgca tacctagtta gtttcctata tattcatgcc    360
atcttgaaaa gacagactat ggtgtaacca tgattctatt atgtattggt acgtctgtag    420
accaagatat aatttttaa aaataagttt atttctttca aggtttacaa ataacaaagg     480
tgcaccttgt atttaaaatt gccattatag atgagagcgt gcatgcacag tcattttgt     540
ttaagagtaa tatttttaat gtaatagatt gtaagacgtg gtgagggagg gatctgacag    600
agatgaatgt gccaagcaaa accacaactg tgtatatttt aaagcacatc atggctttaa    660
gtaccatgtt gttaaggatt ctcatgaagt gccatagact gtacatcaaa ttagagtatt    720
atttcttcag tgttattgtt ttcagagcca cattttgttg catatttgct agtactaatc    780
agtcaaaggg caccattctt tttttttttt tttgaaacca aagctgtctc agaaatggcc    840
aatttaactt tacagtaaca atagacagca caacacaaac tctctcaata cagataaact    900
cacacatact ggagatatat atataataga tatatataaa attatttta tgcattgtag     960
tgtaatattt atgcatacta tactgtataa catgttattc aaaagggatt gccatttctg   1020
agacacagta acaaaaaat gaggaaatta ttttgcttct atttatagcc tctgtcaaaa    1080
gtcaaaagac tataaatgct ttgcaaaaat ggtttcacgt ttgcttaaat gcttcatcac   1140
agtcacattc aaaatagtga ctctaaacaa agaagaaagc agcactgtca tcagatgcat   1200
gataaaccaa aatatgaaaa tgggaaatgt ttaattaacc tagtaattgg gtgggttaag   1260
tacatgggtg aattttatat gtgattttg ttttgttttg ttttgttcag attaactgct    1320
tatagcctta gaaagccttt tacaaaatta aaaaaaaaat agatgtgcat tcagttttta   1380
agaatggaat catccaaagg aattcctttt tttgaggttt ggatgttgca gctagtaaag   1440
gatatttttg ctctgttcag cagttctaaa aattgctgaa gtaggggcca ggtcactggt   1500
agttatagta tggaatggga gaagtgaaag ttcagttata gaacttttcca tacttccaag  1560
tttactgcaa gttttatgc ttgagagaga tgctttctaa tataagactg atgtgttgat    1620
tttactgatt gtactgtaca tctattaaag ccttagatta ttacattacg ggttggaacc   1680
cataccaatg taatttcaat cgtgttaaga aagtaatggt gacttcacat gttattgtag   1740
ttagttacat tatagaatat tacttatttt tcttgttaaa atgtagtttt tcatttccta   1800
catttattag atttcattt tctattaaca attgaatacc atttcagttt atagacttgt    1860
tttattagat tttaccaatg aatttttcaa aatacaaaaa aaagtagttt ttccttcata   1920
acatactcag ttttgaatta catgtagtgt cacatgaata ttcgtattgt taactaaatg   1980
atttatattt tactgattta atattacagt gtaagaatgt cagtcattgt tagttcttgt   2040
ctagttttca ttaaaagaac aaagatcttt tatatggata tcttataaat atataatcat   2100
tgctaagtaa gaagttaagt tgttgctatc gcaacaatcc tggcagacaa ttgagtaata   2160
ttttgatgat ttattttgtt tgtaattagt tattataaga agatctagat cctagatatt   2220
agaataaaat ttattttcta ctgtatccat ttcaaatgtt aaaatattgt ttaatatttt   2280
tgaaatccct gagtatcagg ccttgttata aataagctgc ataatcaata aatagaacaa   2340
gggactttt gttgataatc caaatactca aagtttacgt aatgaaaatt atagcgtgtg   2400
tgcaaactct tgagggttga ttatgctgca atttagcatg ttggaacgtc tagggagaag   2460
gttgactttt tgcacttctg tatatagtca aaagagagaa acctgtataa tagtaagatc   2520
```

```
ttattttgaa taaaaacgtc tataattaca aggagttttg ttaaggctaa tacaatgaca    2580
gactgagcaa aattgcttgc aaaagtggca cagagttagc actccatacc ccttcaaaca    2640
tgttgctttg ctttcttgtg gacagcttgt agtttgccag gattttttca gctggaaaga    2700
tacgccatcc tttcaaaccc tcatgactga caaaaactcc atggggccaa atctgcctga    2760
agatcattac caaaaatagc aggtacttct accattaagg tgaaatcatg gatcagatat    2820
tccttacatt tttcaaaact actgcatgtt taaaacttca acaaaaaaag agagaaagaa    2880
ctatactaag aacatatatt attcagatca gtttctgcca atttcagtgg tttattgttc    2940
acaaaaaaat cttcaaaaca agtattgact ttcacaaaat ttaaatcata aacaggcaaa    3000
ccaaacagca cactgtagct atagttgtta tgtgattgtt ttttaattgc tgtaggatcc    3060
tgttctttca gcaggtgaaa aataaaacgc agttcaaatt tcatggtttt aattttcaac    3120
tcagaagcag gtaatccctg gcaatgtgat aatgggcact tgtttaaaag aattagtgta    3180
tccagccttc actccagctg gttaaaaatg ttgcacttat cagcaaccct accactttca    3240
tctgctgaaa ggacaaatgt gcttggtttt actattatgt aatcacaact tactttctgc    3300
ttgtagttgc ttaaaattat gtattttgtc ttgggctgca atttgttta tgcttatttt    3360 attattactg cagtagttga ctttgctgta tggaaaaata aagtgaaatt gccctaataa    3420
aacttctctt tcttaagt                                                 3438

<210> SEQ ID NO 54
<211> LENGTH: 2783
<212> TYPE: DNA
<213> ORGANISM: Homo sapiens
<220> FEATURE:
<221> NAME/KEY: 3'UTR
<222> LOCATION: (1)..(2783)
<223> OTHER INFORMATION: 3'UTR region of the gene MBNL2 (NM_144778.2 )
      inserted in the plasmid pEZX-MT05
<220> FEATURE:
<221> NAME/KEY: misc_binding
<222> LOCATION: (582)..(601)
<223> OTHER INFORMATION: miR-218 binding region 1
<220> FEATURE:
<221> NAME/KEY: misc_binding
<222> LOCATION: (646)..(665)
<223> OTHER INFORMATION: miR-23b binding region
<220> FEATURE:
<221> NAME/KEY: misc_binding
<222> LOCATION: (1368)..(1388)
<223> OTHER INFORMATION: miR-218 binding region 2
<220> FEATURE:
<221> NAME/KEY: misc_binding
<222> LOCATION: (2085)..(2105)
<223> OTHER INFORMATION: miR-218 binding region 1

<400> SEQUENCE: 54
tcagcagaaa cggaatggaa tgccaagaat ctgcattgag aataactaaa cattgttact     60
gtacatacta tcctgtttcc tcctcaatag aattgccaca aactgcatgc taaataaaga    120
tgtagttctt ctggacagac cacaactcta agaagctagt gctgctatct catatatgag    180
tattaaatat ggtatgctta gtatattcca acctaagata gttaactacc tgagaccagc    240
tgtgatgttt aaagacataa aggataaagt ttacttttaa agggtttcta aacatagttt    300
ctgtcctagg aatattgtct tatctccata actatagctg atgcagaaag tccagccagt    360
ttactcattt cgattcagaa tatttcaaat ttagcaataa acaattagca ttagttaaaa    420
aagaaacata ttccaagggc aggttcgatt ctagctctaa ttactgtcat gtcatttacc    480
cactggatca aagggtatgt tcacttctt gacaatataa atgctgcagc aaagatgaga    540
```

```
ggtgaagtaa aaccgatacc tgtcctgcag gtctaaaatt tgaatggaaa ttcaagcaca      600
agtactgggg acacatcaaa gtgtggtgtt tggtttgcct ggagatgcca cgttgaatca      660
tgtgattcta gattaacatt aaatagattg aaaagaaac tttgcacggt atgagcttca       720
taccccacca aacaaagtct tgaaggtatt attttacaag tatattttta aagttgtttt      780
ataagagaga ctttgtagaa gtgcctagat tttgccagac ttcatccagc ttgacaagat      840
tgagaggccc atgccaacag tctaatctaa gagattagtc tttcaaactc accatccagt      900
tgcctgttac agaataactc ttcttaacta aaaacctagt caaacaagga agctgtaggt      960
gaggagatct gtataatatt ctaatttaag taagtttgag tttagtcact gcaaatttga     1020
ctgtgacttt aatctaaatt actatgtaaa caaaagtag atagtttcac ttttttaaaaa     1080
atccattact gttttgcatt tcaaaagttg gattaaaggg ttgtaactga ctacagcatg     1140
gaaaaaaata gttcttttaa ttctttcacc ttaaagcata ttttatgtct caaaagtata     1200
aaaaacttta atacaagtac atacatatta tatatacaca tacatatata tactatatat     1260
ggatgaaaca tattttaatg ttgtttactt ttttaaatac ttggttgatc ttcaaggtaa     1320
tagcgataca attaaatttt gttcagaaag tttgtttta agtttattttt aagcactatc     1380
gtaccaaata tttcatattt cacattttat atgttgcaca tagcctatac agtacctaca     1440
tagtttttaa attattgttt aaaaaacaaa acagctgtta taaatgaata ttatgtgtaa     1500
ttgtttcaaa catccatttt ctttgtgaac atattagtga ttgaagtatt ttgacttttg     1560
agattgaatg taaatatttt taaatttggg atcatcgcct gttctgaaaa ctagatgcac     1620
caaccgtatc attatttgtt tgaggaaaaa agaaatctg cattttaatt catgttggtc       1680
aaagtcgaat tactatctat ttatcttata tcgtagatct gataaccta tctaaaagaa       1740
agtcacacgc taaatgtatt cttacatagt gcttgtatcg ttgcatttgt tttaatttgt     1800
ggaaaagtat tgtatctaac ttgtattact ttggtagttt catctttatg tattattgat     1860
atttgtaatt ttctcaacta taacaatgta gttacgctac aacttgccta aaacattcaa     1920
acttgttttc tttttttctgt ttttttcttt gttaattcat ttaaactcat tgaaaacata    1980
gtatacatta ctaaaaggta aattatggga atcactgaaa tattttgtta gattaattgt     2040
tgtaacattg tctttctttt ttttcttttg tttcatgatt ttgattttta aaattattag     2100
cacacaacta ttttcagccc tttaataatg gagcatcaaa aacatcacct gtaacccaa      2160
gcaaatatag aagactgtat tttttactat gatatccatt ttccagaatt gtgattacaa     2220
tatgcaaaga gtcataaata tgccatttac aataaggagg aggcaaggca aatgcataga    2280
tgtacaaata tatgtacaac agattttgct ttttatttat ttataatgta atttataga     2340
ataattctgg gatttgagag gatctaaaac tattttttctg tataaatatt attttgccaaa   2400
agtttgttta tattcagaag tctgactatg atgaataaat cttaaatgct ttgtttaatt    2460
aaaaaacaaa aatcaccaat atccaagaca tgaagatatc agttcaacaa atactgtagt    2520
taagagacta actctccact tgtatgggaa ctacattcca ctcttggttt tcaggatata    2580
acagcacttc accgaaatat tctttcagcc ataccactgg taacatttct actaaatctt    2640
tctgtaacac ttaagaatt ccctcattca ttaccttaca gtgtaaacag gagtctaatt     2700
tgtatcaata ctatgttttg gttgtaatat tcagttcact cacccaatgt acaaccaatg    2760
aaataaaaga agcatttaaa agg                                             2783
```

<210> SEQ ID NO 55

<211> LENGTH: 2777
<212> TYPE: DNA
<213> ORGANISM: Artificial sequence
<220> FEATURE:
<223> OTHER INFORMATION: 3'UTR of MBNL2 with Seed region of miR-23b deleted (3UTR MUT-23b)
<220> FEATURE:
<221> NAME/KEY: misc_feature
<222> LOCATION: (659)..(660)
<223> OTHER INFORMATION: Nucleotides flanking the fragment of the deleted seed region of miR-23b

<400> SEQUENCE: 55

```
tcagcagaaa cggaatggaa tgccaagaat ctgcattgag aataactaaa cattgttact      60
gtacatacta tcctgtttcc tcctcaatag aattgccaca aactgcatgc taaataaaga     120
tgtagttctt ctggacagac cacaactcta agaagctagt gctgctatct catatatgag     180
tattaaatat ggtatgctta gtatattcca acctaagata gttaactacc tgagaccagc     240
tgtgatgttt aaagacataa aggataaagt ttacttttaa agggtttcta aacatagttt     300
ctgtcctagg aatattgtct tatctccata actatagctg atgcagaaag tccagccagt     360
ttactcattt cgattcagaa tatttcaaat ttagcaataa acaattagca ttagttaaaa     420
aagaaacata ttccaagggc aggttcgatt ctagctctaa ttactgtcat gtcatttacc     480
cactggatca aagggtatgt ttcacttctt gacaatataa atgctgcagc aaagatgaga     540
ggtgaagtaa aaccgatacc tgtcctgcag gtctaaaatt tgaatggaaa ttcaagcaca     600
agtactgggg acacatcaaa gtgtggtgtt tggtttgcct ggagatgcca cgttgaatct     660
tctagattaa cattaaatag attgaaaaag aaacttgca cggtatgagc ttcatacccc      720
accaaacaaa gtcttgaagg tattatttta caagtatatt tttaaagttg ttttataaga     780
gagactttgt agaagtgcct agattttgcc agacttcatc cagcttgaca agattgagag     840
gcccatgcca acagtctaat ctaagagatt agtctttcaa actcaccatc cagttgcctg     900
ttacagaata actcttctta actaaaaacc tagtcaaaca aggaagctgt aggtgaggag     960
atctgtataa tattctaatt taagtaagtt tgagtttagt cactgcaaat ttgactgtga    1020
ctttaatcta aattactatg taaacaaaaa gtagatagtt tcacttttta aaaaatccat    1080
tactgttttg catttcaaaa gttggattaa agggttgtaa ctgactacag catggaaaaa    1140
aatagttctt ttaattcttt caccttaaag catattttat gtctcaaaag tataaaaaac    1200
tttaatacaa gtacatacat attatatata cacatacata tatatactat atatggatga    1260
aacatatttt aatgttgttt acttttttaa atacttggtt gatcttcaag gtaatagcga    1320
tacaattaaa ttttgttcag aaagtttgtt ttaaagttta ttttaagcac tatcgtacca    1380
aatatttcat atttcacatt ttatatgttg cacatagcct atacagtacc tacatagttt    1440
ttaaattatt gttaaaaaa caaacagct gttataaatg aatattatgt gtaattgttt    1500
caaacatcca ttttctttgt gaacatatta gtgattgaag tattttgact tttgagattg    1560
aatgtaaaat atttaaatt tgggatcatc gcctgttctg aaaactagat gcaccaaccg    1620
tatcattatt tgtttgagga aaaaagaaa tctgcatttt aattcatgtt ggtcaaagtc    1680
gaattactat ctatttatct tatatcgtag atctgataac cctatctaaa agaaagtcac    1740
acgctaaatg tattcttaca tagtgcttgt atcgttgcat ttgttttaat ttgtggaaaa    1800
gtattgtatc taacttgtat tactttggta gttcatcttt tatgtattat tgatatttgt    1860
aattttctca actataacaa tgtagttacg ctacaacttg cctaaaacat tcaaacttgt    1920
tttcttttttt ctgttttttt ctttgttaat tcatttaaac tcattgaaaa catagtatac    1980
```

```
attactaaaa ggtaaattat gggaatcact gaaatatttt tgtagattaa ttgttgtaac    2040
attgtctttc ttttttttct tttgtttcat gattttgatt tttaaaatta ttagcacaca    2100
actattttca gcccttaat aatggagcat caaaaacatc acctgtaacc ccaagcaaat     2160
```

```
actattttca gcccttaat aatggagcat caaaaacatc acctgtaacc ccaagcaaat    2160
atagaagact gtattttta ctatgatatc catttccag aattgtgatt acaatatgca    2220
aagagtcata aatatgccat ttacaataag gaggaggcaa ggcaaatgca tagatgtaca    2280
aatatatgta caacagattt tgctttttat ttatttataa tgtaattta tagaataatt    2340 ctgggatttg agaggatcta aaactatttt tctgtataaa tattatttgc caaagtttg    2400 tttatattca gaagtctgac tatgatgaat aaatcttaaa tgctttgttt aattaaaaaa    2460
caaaaatcac caatatccaa gacatgaaga tatcagttca acaaatactg tagttaagag    2520
actaactctc cacttgtatg ggaactacat ttcactcttg gttttcagga taacagca    2580 cttcaccgaa atattctttc agccatacca ctggtaacat ttctactaaa tctttctgta    2640
acacttaaag aattccctca ttcattacct tacagtgtaa acaggagtct aatttgtatc    2700
aatactatgt tttggttgta atattcagtt cactcaccca atgtacaacc aatgaaataa    2760
aagaagcatt taaaagg                                                   2777
```

<210> SEQ ID NO 56
<211> LENGTH: 2783
<212> TYPE: DNA
<213> ORGANISM: Artificial sequence
<220> FEATURE:
<223> OTHER INFORMATION: Insert of plasmid pEZX-MT05 with the 3'UTR of MBNL2 modified to have perfect complementarity with miR-23b (3UTR PM-23b)
<220> FEATURE:
<221> NAME/KEY: misc_binding
<222> LOCATION: (646)..(666)
<223> OTHER INFORMATION: Region modified for perfect complementarity with miR23b

<400> SEQUENCE: 56

```
tcagcagaaa cggaatggaa tgccaagaat ctgcattgag ataactaaa cattgttact     60 gtacatacta tcctgtttcc tcctcaatag aattgccaca aactgcatgc taaataaaga    120
tgtagttctt ctggacagac cacaactcta agaagctagt gctgctatct catatatgag    180 tattaaaatat ggtatgctta gtatattcca acctaagata gttaactacc tgagaccagc    240
tgtgatgttt aaagacataa aggataaagt ttacttttaa agggtttcta aacatagttt    300
ctgtcctagg aatattgtct tatctccata actatagctg atgcagaaag tccagccagt    360
ttactcattt cgattcagaa tatttcaaat ttagcaataa acaattagca ttagttaaaa    420
aagaaacata ttccaagggc aggttcgatt ctagctctaa ttactgtcat gtcatttacc    480
cactggatca aagggtatgt ttcacttctt gacaatataa atgctgcagc aaagatgaga    540
ggtgaagtaa aaccgatacc tgtcctgcag gtctaaaatt tgaatggaaa ttcaagcaca    600
agtactgggg acacatcaaa gtgtggtgtt tggtttgcct ggagaggtaa tccctggcaa    660
tgtgattcta gattaacatt aaatagattg aaaagaaac tttgcacggt atgagcttca    720 tacccccacca aacaaagtct tgaaggtatt attttacaag tatattttta aagttgtttt    780
ataagagaga ctttgtagaa gtgcctagat tttgccagac ttcatccagc ttgacaagat    840
tgagaggccc atgccaacag tctaatctaa gagattagtc tttcaaactc accatccagt    900
tgcctgttac agaataactc ttcttaacta aaaacctagt caaacaagga agctgtaggt    960
gaggagatct gtataatatt ctaatttaag taagtttgag tttagtcact gcaaatttga    1020
```

```
ctgtgacttt aatctaaatt actatgtaaa caaaaagtag atagtttcac ttttaaaaa      1080 atccattact gttttgcatt tcaaaagttg gattaaaggg ttgtaactga ctacagcatg      1140 gaaaaaata gttctttaa ttctttcacc ttaaagcata ttttatgtct caaaagtata      1200
aaaaacttta atacaagtac atacatatta tatatacaca tacatatata tactatatat      1260
ggatgaaaca tattttaatg ttgtttactt ttttaaatac ttggttgatc ttcaaggtaa      1320
tagcgataca attaaatttt gttcagaaag tttgttttaa agtttatttt aagcactatc      1380
gtaccaaata tttcatattt cacattttat atgttgcaca tagcctatac agtacctaca      1440 tagttttaa attattgttt aaaaaacaaa acagctgtta taaatgaata ttatgtgtaa      1500
ttgtttcaaa catccatttt ctttgtgaac atattagtga ttgaagtatt ttgacttttg      1560
agattgaatg taaaatattt taaatttggg atcatcgcct gttctgaaaa ctagatgcac      1620
caaccgtatc attatttgtt tgaggaaaaa aagaaatctg cattttaatt catgttggtc      1680
aaagtcgaat tactatctat ttatcttata tcgtagatct gataaccta tctaaaagaa      1740 agtcacacgc taaatgtatt cttacatagt gcttgtatcg ttgcatttgt tttaatttgt      1800
ggaaaagtat tgtatctaac ttgtattact ttggtagttt catctttatg tattattgat      1860
atttgtaatt ttctcaacta taacaatgta gttacgctac aacttgccta aaacattcaa      1920
acttgttttc ttttttctgt ttttttcttt gttaattcat ttaaactcat tgaaaacata      1980
gtatacatta ctaaaaggta aattatggga atcactgaaa tattttgta gattaattgt      2040 tgtaacattg tcttctttt tttctttg tttcatgatt ttgattttta aaattattag      2100
cacacaacta ttttcagccc tttaataatg gagcatcaaa aacatcacct gtaacccaa      2160 gcaaatatag aagactgtat ttttactat gatatccatt ttccagaatt gtgattacaa      2220
tatgcaaaga gtcataaata tgccatttac aataaggagg aggcaaggca aatgcataga      2280
tgtacaaata tatgtacaac agattttgct ttttattat ttataatgta attttataga      2340
ataattctgg gatttgagag gatctaaaac tatttttctg tataaatatt atttgccaaa      2400
agtttgttta tattcagaag tctgactatg atgaataaat cttaaatgct ttgtttaatt      2460
aaaaaacaaa aatcaccaat atccaagaca tgaagatatc agttcaacaa atactgtagt      2520
taagagacta actctccact tgtatgggaa ctacatttca ctcttggttt tcaggatata      2580
acagcacttc accgaaatat tctttcagcc ataccactgg taacatttct actaaatctt      2640
tctgtaacac ttaaagaatt ccctcattca ttaccttaca gtgtaaacag gagtctaatt      2700
tgtatcaata ctatgttttg gttgtaatat tcagttcact cacccaatgt acaaccaatg      2760
aaataaaaga agcatttaaa agg                                             2783
```

<210> SEQ ID NO 57
<211> LENGTH: 2776
<212> TYPE: DNA
<213> ORGANISM: Artificial sequence
<220> FEATURE:
<223> OTHER INFORMATION: Insert area of plasmid pEZX-MT05 with the 3'UTR of MBNL2 Swith eed region of miR-218 deleted (3UTR MUT1-218)
<220> FEATURE:
<221> NAME/KEY: misc_feature
<222> LOCATION: (593)..(594)
<223> OTHER INFORMATION: Flanking nucleotides of the deletion in the seed region of miR-218

<400> SEQUENCE: 57

```
tcagcagaaa cggaatggaa tgccaagaat ctgcattgag aataactaaa cattgttact      60
```

| | | | | |
|---|---|---|---|---|
| gtacatacta | tcctgtttcc | tcctcaatag | aattgccaca | aactgcatgc | taaataaaga | 120 |
| tgtagttctt | ctggacagac | cacaactcta | agaagctagt | gctgctatct | catatatgag | 180 |
| tattaaatat | ggtatgctta | gtatattcca | acctaagata | gttaactacc | tgagaccagc | 240 |
| tgtgatgttt | aaagacataa | aggataaagt | ttacttttaa | agggtttcta | aacatagttt | 300 |
| ctgtcctagg | aatattgtct | tatctccata | actatagctg | atgcagaaag | tccagccagt | 360 |
| ttactcattt | cgattcagaa | tatttcaaat | ttagcaataa | acaattagca | ttagttaaaa | 420 |
| aagaaacata | ttccaagggc | aggttcgatt | ctagctctaa | ttactgtcat | gtcatttacc | 480 |
| cactggatca | aagggtatgt | ttcacttctt | gacaatataa | atgctgcagc | aaagatgaga | 540 |
| ggtgaagtaa | aaccgatacc | tgtcctgcag | gtctaaaatt | tgaatggaaa | ttcagtactg | 600 |
| gggacacatc | aaagtgtggt | gtttggtttg | cctggagatg | ccacgttgaa | tcatgtgatt | 660 |
| ctagattaac | attaaataga | ttgaaaaaga | aactttgcac | ggtatgagct | tcataccca | 720 |
| ccaaacaaag | tcttgaaggt | attattttac | aagtatattt | ttaaagttgt | tttataagag | 780 |
| agactttgta | gaagtgccta | gattttgcca | gacttcatcc | agcttgacaa | gattgagagg | 840 |
| cccatgccaa | cagtctaatc | taagagatta | gtctttcaaa | ctcaccatcc | agttgcctgt | 900 |
| tacagaataa | ctcttcttaa | ctaaaaacct | agtcaaacaa | ggaagctgta | ggtgaggaga | 960 |
| tctgtataat | attctaattt | aagtaagttt | gagtttagtc | actgcaaatt | tgactgtgac | 1020 |
| tttaatctaa | attactatgt | aaacaaaaag | tagatagttt | cacttttttaa | aaaatccatt | 1080 |
| actgttttgc | atttcaaaag | ttggattaaa | gggttgtaac | tgactacagc | atggaaaaaa | 1140 |
| atagttcttt | taattctttc | acctaaagc | atattttatg | tctcaaaagt | ataaaaaact | 1200 |
| ttaatacaag | tacatacata | ttatatatac | acatacatat | atatactata | tatggatgaa | 1260 |
| acatatttta | atgttgttta | ctttttttaaa | tacttggttg | atcttcaagg | taatagcgat | 1320 |
| acaattaaat | tttgttcaga | aagtttgttt | taaagtttat | tttaagcact | atcgtaccaa | 1380 |
| atatttcata | tttcacattt | tatatgttgc | acatagccta | tacagtacct | acatagtttt | 1440 |
| taaattattg | tttaaaaaac | aaaacagctg | ttataaatga | atattatgtg | taattgtttc | 1500 |
| aaacatccat | tttctttgtg | aacatattag | tgattgaagt | attttgactt | ttgagattga | 1560 |
| atgtaaaata | ttttaaattt | gggatcatcg | cctgttctga | aaactagatg | caccaaccgt | 1620 |
| atcattattt | gtttgaggaa | aaaagaaat | ctgcattttta | attcatgttg | gtcaaagtcg | 1680 |
| aattactatc | tatttatctt | atatcgtaga | tctgataacc | ctatctaaaa | gaaagtcaca | 1740 |
| cgctaaatgt | attcttacat | agtgcttgta | tcgttgcatt | tgttttaatt | tgtggaaaag | 1800 |
| tattgtatct | aacttgtatt | actttggtag | tttcatcttt | atgtattatt | gatatttgta | 1860 |
| attttctcaa | ctataacaat | gtagttacgc | tacaacttgc | ctaaaacatt | caaacttgtt | 1920 |
| ttctttttc | tgttttttc | tttgttaatt | catttaaact | cattgaaaac | atagtataca | 1980 |
| ttactaaaag | gtaaattatg | ggaatcactg | aaatattttt | gtagattaat | tgttgtaaca | 2040 |
| ttgtctttct | ttttttcttt | ttgtttcatg | attttgattt | ttaaaattat | tagcacacaa | 2100 |
| ctattttcag | cccttttaata | atggagcatc | aaaaacatca | cctgtaaccc | caagcaaata | 2160 |
| tagaagactg | tatttttttac | tatgatatcc | attttccaga | attgtgatta | caatatgcaa | 2220 |
| agagtcataa | atatgccatt | tacaataagg | aggaggcaag | gcaaatgcat | agatgtacaa | 2280 |
| atatatgtac | aacagatttt | gcttttttatt | tatttataat | gtaatttttat | agaataattc | 2340 |
| tgggatttga | gaggatctaa | aactatttttt | ctgtataaat | attatttgcc | aaaagtttgt | 2400 |
| ttatattcag | aagtctgact | atgatgaata | aatcttaaat | gctttgttta | attaaaaaac | 2460 |

```
aaaaatcacc aatatccaag acatgaagat atcagttcaa caaatactgt agttaagaga    2520
ctaactctcc acttgtatgg gaactacatt tcactcttgg ttttcaggat ataacagcac    2580
ttcaccgaaa tattctttca gccataccac tggtaacatt tctactaaat ctttctgtaa    2640
cacttaaaga attccctcat tcattacctt acagtgtaaa caggagtcta atttgtatca    2700
atactatgtt ttggttgtaa tattcagttc actcacccaa tgtacaacca atgaaataaa    2760
agaagcattt aaaagg                                                   2776
```

<210> SEQ ID NO 58
<211> LENGTH: 2776
<212> TYPE: DNA
<213> ORGANISM: Artificial sequence
<220> FEATURE:
<223> OTHER INFORMATION: Insert area of plasmid pEZX-MT05 with the 3'UTR
      of MBNL2 with Seed region of miR-218 deleted (3UTR MUT2-218)
<220> FEATURE:
<221> NAME/KEY: misc_feature
<222> LOCATION: (1370)..(1371)
<223> OTHER INFORMATION: Flanking nucleotides of the miR-218 binding
      seed region deleted

<400> SEQUENCE: 58

```
tcagcagaaa cggaatggaa tgccaagaat ctgcattgag aataactaaa cattgttact     60
gtacatacta tcctgtttcc tcctcaatag aattgccaca aactgcatgc taaataaaga    120
tgtagttctt ctggacagac cacaactcta agaagctagt gctgctatct catatatgag    180 tattaaaatat ggtatgctta gtatattcca acctaagata gttaactacc tgagaccagc    240
tgtgatgttt aaagacataa aggataaagt ttactttttaa agggtttcta aacatagttt    300
ctgtcctagg aatattgtct tatctccata actatagctg atgcagaaag tccagccagt    360
ttactcattt cgattcagaa tatttcaaat ttagcaataa acaattagca ttagttaaaa    420
aagaaacata ttccaagggc aggttcgatt ctagctctaa ttactgtcat gtcatttacc    480
cactggatca aagggtatgt ttcacttctt gacaatataa atgctgcagc aaagatgaga    540
ggtgaagtaa aaccgatacc tgtcctgcag gtctaaaatt tgaatggaaa ttcaagcaca    600
agtactgggg acacatcaaa gtgtggtgtt tggtttgcct ggagatgcca cgttgaatca    660
tgtgattcta gattaacatt aaatagattg aaaagaaac tttgcacggt atgagcttca    720
taccccacca aacaaagtct tgaaggtatt attttacaag tatatttta aagttgtttt    780 ataagagaga ctttgtagaa gtgcctagat tttgccagac ttcatccagc ttgacaagat    840
tgagaggccc atgccaacag tctaatctaa gagattagtc tttcaaactc accatccagt    900
tgcctgttac agaataactc ttcttaacta aaaacctagt caaacaagga agctgtaggt    960
gaggagatct gtataatatt ctaatttaag taagtttgag tttagtcact gcaaatttga   1020
ctgtgacttt aatctaaatt actatgtaaa caaaaagtag atagtttcac tttttaaaaa   1080
atccattact gttttgcatt tcaaaagttg gattaaaggg ttgtaactga ctacagcatg   1140
gaaaaaaata gttctttaa ttctttcacc ttaaagcata ttttatgtct caaaagtata   1200 aaaaactta atacaagtac atacatatta tatatacaca tacatatata tactatatat   1260
ggatgaaaca tattttaatg ttgtttactt ttttaaatac ttggttgatc ttcaaggtaa   1320
tagcgataca attaaatttt gttcagaaag tttgttttaa agtttatttt atcgtaccaa   1380
atatttcata tttcacattt tatatgttgc acatagccta tacagtacct acatagtttt   1440
taaattattg tttaaaaaac aaaacagctg ttataaatga atattatgtg taattgtttc   1500
```

```
aaacatccat tttctttgtg aacatattag tgattgaagt attttgactt ttgagattga    1560
atgtaaaata ttttaaattt gggatcatcg cctgttctga aaactagatg caccaaccgt    1620
atcattattt gtttgaggaa aaaagaaat ctgcatttta attcatgttg gtcaaagtcg     1680
aattactatc tatttatctt atatcgtaga tctgataacc ctatctaaaa gaaagtcaca    1740
cgctaaatgt attcttacat agtgcttgta tcgttgcatt tgttttaatt tgtggaaaag    1800
tattgtatct aacttgtatt actttggtag tttcatcttt atgtattatt gatatttgta    1860
attttctcaa ctataacaat gtagttacgc tacaacttgc ctaaaacatt caaacttgtt    1920 ttctttttc  tgttttttc  tttgttaatt catttaaact cattgaaaac atagtataca    1980
ttactaaaag gtaaattatg ggaatcactg aaatattttt gtagattaat tgttgtaaca    2040
ttgtctttct tttttttctt ttgtttcatg attttgattt ttaaaattat tagcacacaa    2100
ctattttcag ccctttaata atggagcatc aaaaacatca cctgtaaccc caagcaaata    2160
tagaagactg tattttttac tatgatatcc attttccaga attgtgatta caatatgcaa    2220
agagtcataa atatgccatt tacaataagg aggaggcaag gcaaatgcat agatgtacaa    2280
atatatgtac aacagatttt gcttttatt tatttataat gtaattttat agaataattc     2340
tgggatttga gaggatctaa aactattttt ctgtataaat attatttgcc aaaagtttgt    2400
ttatattcag aagtctgact atgatgaata atcttaaat  gctttgttta attaaaaaac    2460
aaaaatcacc aatatccaag acatgaagat atcagttcaa caaatactgt agttaagaga    2520
ctaactctcc acttgtatgg gaactacatt tcactcttgg ttttcaggat ataacagcac    2580
ttcaccgaaa tattctttca gccataccac tggtaacatt tctactaaat ctttctgtaa    2640
cacttaaaga attccctcat tcattacctt acagtgtaaa caggagtcta atttgtatca    2700
atactatgtt ttggttgtaa tattcagttc actcacccaa tgtacaacca atgaaataaa    2760
agaagcattt aaaagg                                                   2776
```

<210> SEQ ID NO 59
<211> LENGTH: 2777
<212> TYPE: DNA
<213> ORGANISM: Artificial sequence
<220> FEATURE:
<223> OTHER INFORMATION: Insert area of plasmid pEZX-MT05 with the 3'UTR
    of MBNL2 with Seed region of miR-218 deleted (3UTR MUT3-218)
<220> FEATURE:
<221> NAME/KEY: misc_feature
<222> LOCATION: (2088)..(2089)
<223> OTHER INFORMATION: Flanking nucleotides of the miR-218 binding
    seed region deleted

<400> SEQUENCE: 59

```
tcagcagaaa cggaatggaa tgccaagaat ctgcattgag aataactaaa cattgttact     60
gtacatacta tcctgtttcc tcctcaatag aattgccaca aactgcatgc taaataaaga    120
tgtagttctt ctggacagac cacaactcta agaagctagt gctgctatct catatatgag    180
tattaaatat ggtatgctta gtatattcca acctaagata gttaactacc tgagaccagc    240
tgtgatgttt aaagacataa aggataaagt ttactttaa  agggtttcta acatagtttt    300
ctgtcctagg aatattgtct tatctccata actatagctg atgcagaaag tccagccagt    360
ttactcattt cgattcagaa tatttcaaat ttagcaataa acaattagca ttagttaaaa    420
aagaaacata ttccaagggc aggttcgatt ctagctctaa ttactgtcat gtcatttacc    480
cactggatca aagggtatgt ttcacttctt gacaatataa atgctgcagc aaagatgaga    540
ggtgaagtaa aaccgatacc tgtcctgcag gtctaaaatt tgaatggaaa ttcaagcaca    600
```

```
agtactgggg acacatcaaa gtgtggtgtt tggtttgcct ggagatgcca cgttgaatca    660
tgtgattcta gattaacatt aaatagattg aaaagaaac tttgcacggt atgagcttca     720
taccccacca aacaaagtct tgaaggtatt atttacaag tatatttta aagttgtttt     780 ataagagaga ctttgtagaa gtgcctagat tttgccagac ttcatccagc ttgacaagat    840
tgagaggccc atgccaacag tctaatctaa gagattagtc tttcaaactc accatccagt    900
tgcctgttac agaataactc ttcttaacta aaaacctagt caaacaagga agctgtaggt    960
gaggagatct gtataatatt ctaatttaag taagtttgag tttagtcact gcaaatttga   1020
ctgtgacttt aatctaaatt actatgtaaa caaaaagtag atagtttcac ttttttaaaaa  1080 atccattact gttttgcatt tcaaagttg gattaaaggg ttgtaactga ctacagcatg    1140
gaaaaaaata gttcttttaa ttctttcacc ttaaagcata tttatgtct caaaagtata    1200 aaaaactta atacaagtac atacatatta tatatacaca tacatatata tactatatat    1260
ggatgaaaca tattttaatg ttgtttactt ttttaaatac ttggttgatc ttcaaggtaa   1320
tagcgataca attaaatttt gttcagaaag tttgttttaa agtttatttt aagcactatc   1380
gtaccaaata tttcatattt cacattttat atgttgcaca tagcctatac agtacctaca   1440 tagttttaa attattgttt aaaaaacaaa acagctgtta taaatgaata ttatgtgtaa    1500
ttgtttcaaa catccatttt ctttgtgaac atattagtga ttgaagtatt ttgacttttg   1560
agattgaatg taaatatttt taaatttggg atcatcgcct gttctgaaaa ctagatgcac   1620
caaccgtatc attatttgtt tgaggaaaaa aagaaatctg cattttaatt catgttggtc   1680
aaagtcgaat tactatctat ttatcttata tcgtagatct gataaccta tctaaaagaa    1740 agtcacacgc taaatgtatt cttacatagt gcttgtatcg ttgcatttgt tttaatttgt   1800
ggaaaagtat tgtatctaac ttgtattact ttggtagttt catctttatg tattattgat   1860
atttgtaatt ttctcaacta taacaatgta gttacgctac aacttgccta aaacattcaa   1920
acttgttttc ttttttctgt tttttttctt gttaattcat ttaaactcat tgaaaacata   1980
gtatacatta ctaaaaggta aattatggga atcactgaaa tatttttgta gattaattgt   2040
tgtaacattg tctttctttt ttttctttg tttcatgatt ttgatttta aaattattca    2100 actatttca gcccttttaat aatggagcat caaaaacatc acctgtaacc ccaagcaaat   2160
atagaagact gtattttta ctatgatatc cattttccag aattgtgatt acaatatgca    2220
aagagtcata aatatgccat ttacaataag gaggaggcaa ggcaaatgca tagatgtaca   2280
aatatatgta caacagattt tgcttttat ttatttataa tgtaattta tagaataatt    2340 ctgggatttg agaggatcta aaactatttt tctgtataaa tattatttgc caaaagtttg   2400
tttatattca gaagtctgac tatgatgaat aaatcttaaa tgctttgttt aattaaaaaa   2460
caaaaatcac caatatccaa gacatgaaga tatcagttca acaaatactg tagttaagag   2520
actaactctc cacttgtatg ggaactacat ttcactcttg gttttcagga tataacagca   2580
cttcaccgaa atattctttc agccatacca ctggtaacat ttctactaaa tctttctgta   2640
acacttaaag aattccctca ttcattacct tacagtgtaa acaggagtct aatttgtatc   2700
aatactatgt tttggttgta atattcagtt cactcaccca atgtacaacc aatgaaataa   2760
aagaagcatt taaaagg                                                 2777

<210> SEQ ID NO 60
<211> LENGTH: 2784
<212> TYPE: DNA
```

<213> ORGANISM: Artificial sequence
<220> FEATURE:
<223> OTHER INFORMATION: Insert of plasmid pEZX-MT05 with the 3'UTR of
      MBNL2 modified to have perfect complementarity with miR-23b (3UTR
      PM-2218)
<220> FEATURE:
<221> NAME/KEY: misc_binding
<222> LOCATION: (582)..(602)
<223> OTHER INFORMATION: Region modified for perfect complementarity
      with miR-218
<220> FEATURE:
<221> NAME/KEY: misc_binding
<222> LOCATION: (1359)..(1379)
<223> OTHER INFORMATION: RRegion modified for perfect complementarity
      with miR-218
<220> FEATURE:
<221> NAME/KEY: misc_binding
<222> LOCATION: (2086)..(2106)
<223> OTHER INFORMATION: Region modified for perfect complementarity
      with miR-218

<400> SEQUENCE: 60

| | | | | | |
|---|---|---|---|---|---|
| tcagcagaaa | cggaatggaa | tgccaagaat | ctgcattgag | aataactaaa | cattgttact | 60 |
| gtacatacta | tcctgtttcc | tcctcaatag | aattgccaca | aactgcatgc | taaataaaga | 120 |
| tgtagttctt | ctggacagac | cacaactcta | agaagctagt | gctgctatct | catatatgag | 180 |
| tattaaatat | ggtatgctta | gtatattcca | acctaagata | gttaactacc | tgagaccagc | 240 |
| tgtgatgttt | aaagacataa | aggataaagt | ttacttttaa | agggtttcta | aacatagttt | 300 |
| ctgtcctagg | aatattgtct | tatctccata | actatagctg | atgcagaaag | tccagccagt | 360 |
| ttactcattt | cgattcagaa | tatttcaaat | ttagcaataa | acaattagca | ttagttaaaa | 420 |
| aagaaacata | ttccaagggc | aggttcgatt | ctagctctaa | ttactgtcat | gtcatttacc | 480 |
| cactggatca | aagggtatgt | ttcacttctt | gacaatataa | atgctgcagc | aaagatgaga | 540 |
| ggtgaagtaa | aaccgatacc | tgtcctgcag | gtctaaaatt | tacatggtta | gatcaagcac | 600 |
| aagtactggg | gacacatcaa | agtgtggtgt | ttggtttgcc | tggagatgcc | acgttgaatc | 660 |
| atgtgattct | agattaacat | taaatagatt | gaaaagaaa | ctttgcacgg | tatgagcttc | 720 |
| atacccacc | aaacaaagtc | ttgaaggtat | tattttacaa | gtatattttt | aaagttgttt | 780 |
| tataagagag | actttgtaga | agtgcctaga | ttttgccaga | cttcatccag | cttgacaaga | 840 |
| ttgagaggcc | catgccaaca | gtctaatcta | agagattagt | ctttcaaact | caccatccag | 900 |
| ttgcctgtta | cagaataact | cttcttaact | aaaaacctag | tcaaacaagg | aagctgtagg | 960 |
| tgaggagatc | tgtataatat | tctaatttaa | gtaagtttga | gtttagtcac | tgcaaatttg | 1020 |
| actgtgactt | taatctaaat | tactatgtaa | acaaaaagta | gatagtttca | cttttttaaaa | 1080 |
| aatccattac | tgttttgcat | ttcaaaagtt | ggattaaagg | gttgtaactg | actacagcat | 1140 |
| ggaaaaaaat | agttctttta | attctttcac | cttaaagcat | attttatgtc | tcaaaagtat | 1200 |
| aaaaaacttt | aatacaagta | catacatatt | atatatacac | atacatatat | atactatata | 1260 |
| tggatgaaac | atatttttaat | gttgtttact | tttttaaata | cttggttgat | cttcaaggta | 1320 |
| atagcgatac | aattaaattt | tgttcagaaa | gtttgtttac | atggttagat | caagcacaat | 1380 |
| cgtaccaaat | atttcatatt | tcacatttta | tatgttgcac | atagcctata | cagtacctac | 1440 |
| atagtttta | aattattgtt | taaaaaacaa | aacagctgtt | ataatgaat | attatgtgta | 1500 |
| attgtttcaa | acatccattt | tctttgtgaa | catattagtg | attgaagtat | tttgactttt | 1560 |
| gagattgaat | gtaaaatatt | ttaaatttgg | gatcatcgcc | tgttctgaaa | actagatgca | 1620 |
| ccaaccgtat | cattatttgt | ttgaggaaaa | aaagaaatct | gcatttaat | tcatgttggt | 1680 |

-continued

```
caaagtcgaa ttactatcta tttatcttat atcgtagatc tgataaccct atctaaaaga    1740
aagtcacacg ctaaatgtat tcttacatag tgcttgtatc gttgcatttg ttttaatttg    1800
tggaaaagta ttgtatctaa cttgtattac tttggtagtt tcatctttat gtattattga    1860
tatttgtaat tttctcaact ataacaatgt agttacgcta caacttgcct aaaacattca    1920
aacttgtttt cttttttctg tttttttctt tgttaattca tttaaactca ttgaaaacat    1980
agtatacatt actaaaaggt aaattatggg aatcactgaa atattttgt agattaattg     2040 ttgtaacatt gtctttcttt tttttctttt gtttcatgat tttgaacatg gttagatcaa    2100
gcacaaaact attttcagcc ctttaataat ggagcatcaa aaacatcacc tgtaacccca    2160
agcaaatata gaagactgta ttttttacta tgatatccat tttccagaat tgtgattaca    2220
atatgcaaag agtcataaat atgccattta caataaggag gaggcaaggc aaatgcatag    2280
atgtacaaat atatgtacaa cagatttttgc tttttattta tttataatgt aattttatag   2340
aataattctg ggatttgaga ggatctaaaa ctattttttct gtataaatat tatttgccaa   2400
aagtttgttt atattcagaa gtctgactat gatgaataaa tcttaaatgc tttgtttaat    2460
taaaaaacaa aaatcaccaa tatccaagac atgaagatat cagttcaaca aatactgtag    2520
ttaagagact aactctccac ttgtatggga actacatttc actcttggtt ttcaggatat    2580
aacagcactt caccgaaata ttctttcagc cataccactg gtaacatttc tactaaatct    2640
ttctgtaaca cttaaagaat tccctcattc attccttac agtgtaaaca ggagtctaat     2700
ttgtatcaat actatgtttt ggttgtaata ttcagttcac tcacccaatg tacaaccaat    2760
gaaataaaag aagcatttaa aagg                                           2784
```

<210> SEQ ID NO 61
<211> LENGTH: 20
<212> TYPE: DNA
<213> ORGANISM: Artificial sequence
<220> FEATURE:
<223> OTHER INFORMATION: Probe for the detection of foci in thorax of
      flies (CAG probe)
<220> FEATURE:
<221> NAME/KEY: misc_feature
<222> LOCATION: (1)..(1)
<223> OTHER INFORMATION: Fluorforo Cy3 unido en 5'
<220> FEATURE:
<221> NAME/KEY: misc_feature
<222> LOCATION: (20)..(20)
<223> OTHER INFORMATION: Fluorophore Cy3 bound at 3'

<400> SEQUENCE: 61

```
cagcagcagc agcagcagca                                                  20
```

<210> SEQ ID NO 62
<211> LENGTH: 496
<212> TYPE: DNA
<213> ORGANISM: Artificial sequence
<220> FEATURE:
<223> OTHER INFORMATION: Sequence of the fragment of sponge construct
      with 20 repeat targets for dme-miR-92a
<220> FEATURE:
<221> NAME/KEY: misc_feature
<222> LOCATION: (1)..(21)
<223> OTHER INFORMATION: Target of microRNA dme-miR-92a
<220> FEATURE:
<221> NAME/KEY: misc_feature
<222> LOCATION: (22)..(25)
<223> OTHER INFORMATION: Spacer fragment
<220> FEATURE:
<221> NAME/KEY: misc_feature
<222> LOCATION: (26)..(46)
<223> OTHER INFORMATION: Target of microRNA dme-miR-92a

```
<220> FEATURE:
<221> NAME/KEY: misc_feature
<222> LOCATION: (47)..(50)
<223> OTHER INFORMATION: Spacer fragment
<220> FEATURE:
<221> NAME/KEY: misc_feature
<222> LOCATION: (51)..(71)
<223> OTHER INFORMATION: Target of microRNA dme-miR-92a
<220> FEATURE:
<221> NAME/KEY: misc_feature
<222> LOCATION: (72)..(75)
<223> OTHER INFORMATION: Spacer fragment
<220> FEATURE:
<221> NAME/KEY: misc_feature
<222> LOCATION: (76)..(96)
<223> OTHER INFORMATION: Target of microRNA dme-miR-92a
<220> FEATURE:
<221> NAME/KEY: misc_feature
<222> LOCATION: (97)..(100)
<223> OTHER INFORMATION: Spacer fragment
<220> FEATURE:
<221> NAME/KEY: misc_feature
<222> LOCATION: (101)..(121)
<223> OTHER INFORMATION: Target of microRNA dme-miR-92a
<220> FEATURE:
<221> NAME/KEY: misc_feature
<222> LOCATION: (122)..(125)
<223> OTHER INFORMATION: Spacer fragment
<220> FEATURE:
<221> NAME/KEY: misc_feature
<222> LOCATION: (126)..(146)
<223> OTHER INFORMATION: Target of microRNA dme-miR-92a
<220> FEATURE:
<221> NAME/KEY: misc_feature
<222> LOCATION: (147)..(150)
<223> OTHER INFORMATION: Spacer fragment
<220> FEATURE:
<221> NAME/KEY: misc_feature
<222> LOCATION: (151)..(171)
<223> OTHER INFORMATION: Target of microRNA dme-miR-92a
<220> FEATURE:
<221> NAME/KEY: misc_feature
<222> LOCATION: (172)..(175)
<223> OTHER INFORMATION: Spacer fragment
<220> FEATURE:
<221> NAME/KEY: misc_feature
<222> LOCATION: (176)..(196)
<223> OTHER INFORMATION: Target of microRNA dme-miR-92a
<220> FEATURE:
<221> NAME/KEY: misc_feature
<222> LOCATION: (197)..(200)
<223> OTHER INFORMATION: Spacer fragment
<220> FEATURE:
<221> NAME/KEY: misc_feature
<222> LOCATION: (201)..(221)
<223> OTHER INFORMATION: Target of microRNA dme-miR-92a
<220> FEATURE:
<221> NAME/KEY: misc_feature
<222> LOCATION: (222)..(225)
<223> OTHER INFORMATION: Spacer fragment
<220> FEATURE:
<221> NAME/KEY: misc_feature
<222> LOCATION: (226)..(246)
<223> OTHER INFORMATION: Target of microRNA dme-miR-92a
<220> FEATURE:
<221> NAME/KEY: misc_feature
<222> LOCATION: (247)..(250)
<223> OTHER INFORMATION: Spacer fragment
<220> FEATURE:
<221> NAME/KEY: misc_feature
<222> LOCATION: (251)..(271)
<223> OTHER INFORMATION: Target of microRNA dme-miR-92a
<220> FEATURE:
<221> NAME/KEY: misc_feature
<222> LOCATION: (272)..(275)
<223> OTHER INFORMATION: Spacer fragment
<220> FEATURE:
<221> NAME/KEY: misc_feature
<222> LOCATION: (276)..(296)
```

```
<223> OTHER INFORMATION: Target of microRNA dme-miR-92a
<220> FEATURE:
<221> NAME/KEY: misc_feature
<222> LOCATION: (297)..(300)
<223> OTHER INFORMATION: Spacer fragment
<220> FEATURE:
<221> NAME/KEY: misc_feature
<222> LOCATION: (301)..(321)
<223> OTHER INFORMATION: Target of microRNA dme-miR-92a
<220> FEATURE:
<221> NAME/KEY: misc_feature
<222> LOCATION: (322)..(325)
<223> OTHER INFORMATION: Spacer fragment
<220> FEATURE:
<221> NAME/KEY: misc_feature
<222> LOCATION: (326)..(346)
<223> OTHER INFORMATION: Target of microRNA dme-miR-92a
<220> FEATURE:
<221> NAME/KEY: misc_feature
<222> LOCATION: (347)..(350)
<223> OTHER INFORMATION: Spacer fragment
<220> FEATURE:
<221> NAME/KEY: misc_feature
<222> LOCATION: (351)..(371)
<223> OTHER INFORMATION: Target of microRNA dme-miR-92a
<220> FEATURE:
<221> NAME/KEY: misc_feature
<222> LOCATION: (372)..(375)
<223> OTHER INFORMATION: Spacer fragment
<220> FEATURE:
<221> NAME/KEY: misc_feature
<222> LOCATION: (376)..(396)
<223> OTHER INFORMATION: Target of microRNA dme-miR-92a
<220> FEATURE:
<221> NAME/KEY: misc_feature
<222> LOCATION: (397)..(400)
<223> OTHER INFORMATION: Spacer fragment
<220> FEATURE:
<221> NAME/KEY: misc_feature
<222> LOCATION: (401)..(421)
<223> OTHER INFORMATION: Target of microRNA dme-miR-92a
<220> FEATURE:
<221> NAME/KEY: misc_feature
<222> LOCATION: (422)..(425)
<223> OTHER INFORMATION: Spacer fragment
<220> FEATURE:
<221> NAME/KEY: misc_feature
<222> LOCATION: (426)..(446)
<223> OTHER INFORMATION: Target of microRNA dme-miR-92a
<220> FEATURE:
<221> NAME/KEY: misc_feature
<222> LOCATION: (447)..(450)
<223> OTHER INFORMATION: Spacer fragment
<220> FEATURE:
<221> NAME/KEY: misc_feature
<222> LOCATION: (451)..(471)
<223> OTHER INFORMATION: Target of microRNA dme-miR-92a
<220> FEATURE:
<221> NAME/KEY: misc_feature
<222> LOCATION: (472)..(475)
<223> OTHER INFORMATION: Spacer fragment
<220> FEATURE:
<221> NAME/KEY: misc_feature
<222> LOCATION: (476)..(496)
<223> OTHER INFORMATION: Target of microRNA dme-miR-92a

<400> SEQUENCE: 62
ataggccggg gttgtgcaat ggcgcatagg ccggggttgt gcaatgggcc ataggccggg      60
gttgtgcaat gggctatagg ccggggttgt gcaatggggg ataggccggg gttgtgcaat     120
gggatatagg ccggggttgt gcaatgggtc ataggccggg gttgtgcaat gggtgatagg     180
ccggggttgt gcaatgggtt ataggccggg gttgtgcaat ggaccatagg ccggggttgt     240
gcaatgggtg ataggccggg gttgtgcaat ggcgcatagg ccggggttgt gcaatgggcc     300
ataggccggg gttgtgcaat gggctatagg ccggggttgt gcaatggggg ataggccggg     360
```
gttgtgcaat gggatatagg ccggggttgt gcaatgggtc ataggccggg gttgtgcaat    420
gggtgatagg ccggggttgt gcaatgggtt ataggccggg gttgtgcaat ggaccatagg    480
ccggggttgt gcaatg    496

<210> SEQ ID NO 63
<211> LENGTH: 496
<212> TYPE: DNA
<213> ORGANISM: Artificial sequence
<220> FEATURE:
<223> OTHER INFORMATION: Sequence of the fragment of sponge construct
      with 20 repeat targets for dme-miR-100
<220> FEATURE:
<221> NAME/KEY: misc_feature
<222> LOCATION: (1)..(21)
<223> OTHER INFORMATION: Target of microRNA dme-miR-100
<220> FEATURE:
<221> NAME/KEY: misc_feature
<222> LOCATION: (22)..(25)
<223> OTHER INFORMATION: Spacer fragment
<220> FEATURE:
<221> NAME/KEY: misc_feature
<222> LOCATION: (26)..(46)
<223> OTHER INFORMATION: Target of microRNA dme-miR-100
<220> FEATURE:
<221> NAME/KEY: misc_feature
<222> LOCATION: (47)..(50)
<223> OTHER INFORMATION: Spacer fragment
<220> FEATURE:
<221> NAME/KEY: misc_feature
<222> LOCATION: (51)..(71)
<223> OTHER INFORMATION: Target of microRNA dme-miR-100
<220> FEATURE:
<221> NAME/KEY: misc_feature
<222> LOCATION: (72)..(75)
<223> OTHER INFORMATION: Spacer fragment
<220> FEATURE:
<221> NAME/KEY: misc_feature
<222> LOCATION: (76)..(96)
<223> OTHER INFORMATION: Target of microRNA dme-miR-100
<220> FEATURE:
<221> NAME/KEY: misc_feature
<222> LOCATION: (97)..(100)
<223> OTHER INFORMATION: Spacer fragment
<220> FEATURE:
<221> NAME/KEY: misc_feature
<222> LOCATION: (101)..(121)
<223> OTHER INFORMATION: Target of microRNA dme-miR-100
<220> FEATURE:
<221> NAME/KEY: misc_feature
<222> LOCATION: (122)..(125)
<223> OTHER INFORMATION: Spacer fragment
<220> FEATURE:
<221> NAME/KEY: misc_feature
<222> LOCATION: (126)..(146)
<223> OTHER INFORMATION: Target of microRNA dme-miR-100
<220> FEATURE:
<221> NAME/KEY: misc_feature
<222> LOCATION: (147)..(150)
<223> OTHER INFORMATION: Spacer fragment
<220> FEATURE:
<221> NAME/KEY: misc_feature
<222> LOCATION: (151)..(171)
<223> OTHER INFORMATION: Target of microRNA dme-miR-100
<220> FEATURE:
<221> NAME/KEY: misc_feature
<222> LOCATION: (172)..(175)
<223> OTHER INFORMATION: Spacer fragment
<220> FEATURE:
<221> NAME/KEY: misc_feature
<222> LOCATION: (176)..(196)
<223> OTHER INFORMATION: Target of microRNA dme-miR-100
<220> FEATURE:
<221> NAME/KEY: misc_feature
<222> LOCATION: (197)..(200)
<223> OTHER INFORMATION: Spacer fragment -continued

```
<220> FEATURE:
<221> NAME/KEY: misc_feature
<222> LOCATION: (201)..(221)
<223> OTHER INFORMATION: Target of microRNA dme-miR-100
<220> FEATURE:
<221> NAME/KEY: misc_feature
<222> LOCATION: (222)..(225)
<223> OTHER INFORMATION: Spacer fragment
<220> FEATURE:
<221> NAME/KEY: misc_feature
<222> LOCATION: (226)..(246)
<223> OTHER INFORMATION: Target of microRNA dme-miR-100
<220> FEATURE:
<221> NAME/KEY: misc_feature
<222> LOCATION: (247)..(250)
<223> OTHER INFORMATION: Spacer fragment
<220> FEATURE:
<221> NAME/KEY: misc_feature
<222> LOCATION: (251)..(271)
<223> OTHER INFORMATION: Target of microRNA dme-miR-100
<220> FEATURE:
<221> NAME/KEY: misc_feature
<222> LOCATION: (272)..(275)
<223> OTHER INFORMATION: Spacer fragment
<220> FEATURE:
<221> NAME/KEY: misc_feature
<222> LOCATION: (276)..(296)
<223> OTHER INFORMATION: Target of microRNA dme-miR-100
<220> FEATURE:
<221> NAME/KEY: misc_feature
<222> LOCATION: (297)..(300)
<223> OTHER INFORMATION: Spacer fragment
<220> FEATURE:
<221> NAME/KEY: misc_feature
<222> LOCATION: (301)..(321)
<223> OTHER INFORMATION: Target of microRNA dme-miR-100
<220> FEATURE:
<221> NAME/KEY: misc_feature
<222> LOCATION: (322)..(325)
<223> OTHER INFORMATION: Spacer fragment
<220> FEATURE:
<221> NAME/KEY: misc_feature
<222> LOCATION: (326)..(346)
<223> OTHER INFORMATION: Target of microRNA dme-miR-100
<220> FEATURE:
<221> NAME/KEY: misc_feature
<222> LOCATION: (347)..(350)
<223> OTHER INFORMATION: Spacer fragment
<220> FEATURE:
<221> NAME/KEY: misc_feature
<222> LOCATION: (351)..(371)
<223> OTHER INFORMATION: Target of microRNA dme-miR-100
<220> FEATURE:
<221> NAME/KEY: misc_feature
<222> LOCATION: (372)..(375)
<223> OTHER INFORMATION: Spacer fragment
<220> FEATURE:
<221> NAME/KEY: misc_feature
<222> LOCATION: (376)..(396)
<223> OTHER INFORMATION: Target of microRNA dme-miR-100
<220> FEATURE:
<221> NAME/KEY: misc_feature
<222> LOCATION: (397)..(400)
<223> OTHER INFORMATION: Spacer fragment
<220> FEATURE:
<221> NAME/KEY: misc_feature
<222> LOCATION: (401)..(421)
<223> OTHER INFORMATION: Target of microRNA dme-miR-100
<220> FEATURE:
<221> NAME/KEY: misc_feature
<222> LOCATION: (422)..(425)
<223> OTHER INFORMATION: Spacer fragment
<220> FEATURE:
<221> NAME/KEY: misc_feature
<222> LOCATION: (426)..(446)
<223> OTHER INFORMATION: Target of microRNA dme-miR-100
<220> FEATURE:
<221> NAME/KEY: misc_feature
<222> LOCATION: (447)..(450)
```

<223> OTHER INFORMATION: Spacer fragment
<220> FEATURE:
<221> NAME/KEY: misc_feature
<222> LOCATION: (451)..(471)
<223> OTHER INFORMATION: Target of microRNA dme-miR-100
<220> FEATURE:
<221> NAME/KEY: misc_feature
<222> LOCATION: (472)..(475)
<223> OTHER INFORMATION: Spacer fragment
<220> FEATURE:
<221> NAME/KEY: misc_feature
<222> LOCATION: (476)..(496)
<223> OTHER INFORMATION: Target of microRNA dme-miR-100

<400> SEQUENCE: 63

```
cacaagttcg taatacgggt tccgccacaa gttcgtaata cgggttccgg cacaagttcg      60
taatacgggt tcctccacaa gttcgtaata cgggttcctg cacaagttcg taatacgggt     120
tcggacacaa gttcgtaata cgggttcgac cacaagttcg taatacgggt tcgtacacaa     180
gttcgtaata cgggttctgc cacaagttcg taatacgggt tctggcacaa gttcgtaata     240
cgggttcgac cacaagttcg taatacgggt tccgccacaa gttcgtaata cgggttccgg     300
cacaagttcg taatacgggt tcctccacaa gttcgtaata cgggttcctg cacaagttcg     360
taatacgggt tcggacacaa gttcgtaata cgggttcgac cacaagttcg taatacgggt     420
tcgtacacaa gttcgtaata cgggttctgc cacaagttcg taatacgggt tctggcacaa     480
gttcgtaata cgggtt                                                     496
```

<210> SEQ ID NO 64
<211> LENGTH: 516
<212> TYPE: DNA
<213> ORGANISM: Artificial sequence
<220> FEATURE:
<223> OTHER INFORMATION: Sequence of the fragment of sponge construct
      with 20 repeat targets for dme-miR-124
<220> FEATURE:
<221> NAME/KEY: misc_feature
<222> LOCATION: (1)..(22)
<223> OTHER INFORMATION: Sequence of target of microRNA dme-miR-124
<220> FEATURE:
<221> NAME/KEY: misc_feature
<222> LOCATION: (23)..(26)
<223> OTHER INFORMATION: Spacer fragment
<220> FEATURE:
<221> NAME/KEY: misc_feature
<222> LOCATION: (27)..(48)
<223> OTHER INFORMATION: Sequence of target of microRNA dme-miR-124
<220> FEATURE:
<221> NAME/KEY: misc_feature
<222> LOCATION: (49)..(52)
<223> OTHER INFORMATION: Spacer fragment
<220> FEATURE:
<221> NAME/KEY: misc_feature
<222> LOCATION: (53)..(74)
<223> OTHER INFORMATION: Sequence of target of microRNA dme-miR-124
<220> FEATURE:
<221> NAME/KEY: misc_feature
<222> LOCATION: (75)..(78)
<223> OTHER INFORMATION: Spacer fragment
<220> FEATURE:
<221> NAME/KEY: misc_feature
<222> LOCATION: (79)..(100)
<223> OTHER INFORMATION: Sequence of target of microRNA dme-miR-124
<220> FEATURE:
<221> NAME/KEY: misc_feature
<222> LOCATION: (101)..(104)
<223> OTHER INFORMATION: Spacer fragment
<220> FEATURE:
<221> NAME/KEY: misc_feature
<222> LOCATION: (105)..(126)
<223> OTHER INFORMATION: Sequence of target of microRNA dme-miR-124
<220> FEATURE:

```
<221> NAME/KEY: misc_feature
<222> LOCATION: (127)..(130)
<223> OTHER INFORMATION: Spacer fragment
<220> FEATURE:
<221> NAME/KEY: misc_feature
<222> LOCATION: (131)..(152)
<223> OTHER INFORMATION: Sequence of target of microRNA dme-miR-124
<220> FEATURE:
<221> NAME/KEY: misc_feature
<222> LOCATION: (153)..(156)
<223> OTHER INFORMATION: Spacer fragment
<220> FEATURE:
<221> NAME/KEY: misc_feature
<222> LOCATION: (157)..(178)
<223> OTHER INFORMATION: Sequence of target of microRNA dme-miR-124
<220> FEATURE:
<221> NAME/KEY: misc_feature
<222> LOCATION: (179)..(182)
<223> OTHER INFORMATION: Spacer fragment
<220> FEATURE:
<221> NAME/KEY: misc_feature
<222> LOCATION: (183)..(204)
<223> OTHER INFORMATION: Sequence of target of microRNA dme-miR-124
<220> FEATURE:
<221> NAME/KEY: misc_feature
<222> LOCATION: (205)..(208)
<223> OTHER INFORMATION: Spacer fragment
<220> FEATURE:
<221> NAME/KEY: misc_feature
<222> LOCATION: (209)..(230)
<223> OTHER INFORMATION: Sequence of target of microRNA dme-miR-124
<220> FEATURE:
<221> NAME/KEY: misc_feature
<222> LOCATION: (231)..(234)
<223> OTHER INFORMATION: Spacer fragment
<220> FEATURE:
<221> NAME/KEY: misc_feature
<222> LOCATION: (235)..(256)
<223> OTHER INFORMATION: Sequence of target of microRNA dme-miR-124
<220> FEATURE:
<221> NAME/KEY: misc_feature
<222> LOCATION: (257)..(260)
<223> OTHER INFORMATION: Spacer fragment
<220> FEATURE:
<221> NAME/KEY: misc_feature
<222> LOCATION: (261)..(282)
<223> OTHER INFORMATION: Sequence of target of microRNA dme-miR-124
<220> FEATURE:
<221> NAME/KEY: misc_feature
<222> LOCATION: (283)..(286)
<223> OTHER INFORMATION: Spacer fragment
<220> FEATURE:
<221> NAME/KEY: misc_feature
<222> LOCATION: (287)..(308)
<223> OTHER INFORMATION: Sequence of target of microRNA dme-miR-124
<220> FEATURE:
<221> NAME/KEY: misc_feature
<222> LOCATION: (309)..(312)
<223> OTHER INFORMATION: Spacer fragment
<220> FEATURE:
<221> NAME/KEY: misc_feature
<222> LOCATION: (313)..(334)
<223> OTHER INFORMATION: Sequence of target of microRNA dme-miR-124
<220> FEATURE:
<221> NAME/KEY: misc_feature
<222> LOCATION: (335)..(338)
<223> OTHER INFORMATION: Spacer fragment
<220> FEATURE:
<221> NAME/KEY: misc_feature
<222> LOCATION: (339)..(360)
<223> OTHER INFORMATION: Sequence of target of microRNA dme-miR-124
<220> FEATURE:
<221> NAME/KEY: misc_feature
<222> LOCATION: (361)..(364)
<223> OTHER INFORMATION: Spacer fragment
<220> FEATURE:
<221> NAME/KEY: misc_feature
<222> LOCATION: (365)..(386)
<223> OTHER INFORMATION: Sequence of target of microRNA dme-miR-124
```

<220> FEATURE:
<221> NAME/KEY: misc_feature
<222> LOCATION: (387)..(390)
<223> OTHER INFORMATION: Spacer fragment
<220> FEATURE:
<221> NAME/KEY: misc_feature
<222> LOCATION: (391)..(412)
<223> OTHER INFORMATION: Sequence of target of microRNA dme-miR-124
<220> FEATURE:
<221> NAME/KEY: misc_feature
<222> LOCATION: (413)..(416)
<223> OTHER INFORMATION: Spacer fragment
<220> FEATURE:
<221> NAME/KEY: misc_feature
<222> LOCATION: (417)..(438)
<223> OTHER INFORMATION: Sequence of target of microRNA dme-miR-124
<220> FEATURE:
<221> NAME/KEY: misc_feature
<222> LOCATION: (439)..(442)
<223> OTHER INFORMATION: Spacer fragment
<220> FEATURE:
<221> NAME/KEY: misc_feature
<222> LOCATION: (443)..(464)
<223> OTHER INFORMATION: Sequence of target of microRNA dme-miR-124
<220> FEATURE:
<221> NAME/KEY: misc_feature
<222> LOCATION: (465)..(468)
<223> OTHER INFORMATION: Spacer fragment
<220> FEATURE:
<221> NAME/KEY: misc_feature
<222> LOCATION: (469)..(490)
<223> OTHER INFORMATION: Sequence of target of microRNA dme-miR-124
<220> FEATURE:
<221> NAME/KEY: misc_feature
<222> LOCATION: (491)..(494)
<223> OTHER INFORMATION: Spacer fragment
<220> FEATURE:
<221> NAME/KEY: misc_feature
<222> LOCATION: (495)..(516)
<223> OTHER INFORMATION: Sequence of target of microRNA dme-miR-124

<400> SEQUENCE: 64
cttggcattc agcggtgcct taccctcttg gcattcagcg gtgccttacc gccttggcat    60
tcagcggtgc cttaccggct tggcattcag cggtgcctta ccgacttggc attcagcggt   120
gccttaccgt cttggcattc agcggtgcct tacgcgcttg gcattcagcg gtgccttacg   180
ctcttggcat tcagcggtgc cttacggact tggcattcag cggtgcctta cggtcttggc   240
attcagcggt gccttaccga cttggcattc agcggtgcct taccctcttg gcattcagcg   300
gtgccttacc gccttggcat tcagcggtgc cttaccggct tggcattcag cggtgcctta   360
ccgacttggc attcagcggt gccttaccgt cttggcattc agcggtgcct tacgcgcttg   420
gcattcagcg gtgccttacg ctcttggcat tcagcggtgc cttacggact tggcattcag   480
cggtgcctta cggtcttggc attcagcggt gcctta                              516

<210> SEQ ID NO 65
<211> LENGTH: 516
<212> TYPE: DNA
<213> ORGANISM: Artificial sequence
<220> FEATURE:
<223> OTHER INFORMATION: Sequence of the fragment of sponge construct
      with 20 repeat targets for dme-miR-277
<220> FEATURE:
<221> NAME/KEY: misc_feature
<222> LOCATION: (1)..(22)
<223> OTHER INFORMATION: Sequence of target of microRNA dme-miR-277
<220> FEATURE:
<221> NAME/KEY: misc_feature
<222> LOCATION: (23)..(26)
<223> OTHER INFORMATION: Spacer fragment
<220> FEATURE:
<221> NAME/KEY: misc_feature

```
<222> LOCATION: (27)..(48)
<223> OTHER INFORMATION: Sequence of target of microRNA dme-miR-277
<220> FEATURE:
<221> NAME/KEY: misc_feature
<222> LOCATION: (49)..(52)
<223> OTHER INFORMATION: Spacer fragment
<220> FEATURE:
<221> NAME/KEY: misc_feature
<222> LOCATION: (53)..(74)
<223> OTHER INFORMATION: Sequence of target of microRNA dme-miR-277
<220> FEATURE:
<221> NAME/KEY: misc_feature
<222> LOCATION: (75)..(78)
<223> OTHER INFORMATION: Spacer fragment
<220> FEATURE:
<221> NAME/KEY: misc_feature
<222> LOCATION: (79)..(100)
<223> OTHER INFORMATION: Sequence of target of microRNA dme-miR-277
<220> FEATURE:
<221> NAME/KEY: misc_feature
<222> LOCATION: (101)..(104)
<223> OTHER INFORMATION: Spacer fragment
<220> FEATURE:
<221> NAME/KEY: misc_feature
<222> LOCATION: (105)..(126)
<223> OTHER INFORMATION: Sequence of target of microRNA dme-miR-277
<220> FEATURE:
<221> NAME/KEY: misc_feature
<222> LOCATION: (127)..(130)
<223> OTHER INFORMATION: Spacer fragment
<220> FEATURE:
<221> NAME/KEY: misc_feature
<222> LOCATION: (131)..(152)
<223> OTHER INFORMATION: Sequence of target of microRNA dme-miR-277
<220> FEATURE:
<221> NAME/KEY: misc_feature
<222> LOCATION: (153)..(156)
<223> OTHER INFORMATION: Spacer fragment
<220> FEATURE:
<221> NAME/KEY: misc_feature
<222> LOCATION: (157)..(178)
<223> OTHER INFORMATION: Sequence of target of microRNA dme-miR-277
<220> FEATURE:
<221> NAME/KEY: misc_feature
<222> LOCATION: (179)..(182)
<223> OTHER INFORMATION: Spacer fragment
<220> FEATURE:
<221> NAME/KEY: misc_feature
<222> LOCATION: (183)..(204)
<223> OTHER INFORMATION: Sequence of target of microRNA dme-miR-277
<220> FEATURE:
<221> NAME/KEY: misc_feature
<222> LOCATION: (205)..(208)
<223> OTHER INFORMATION: Spacer fragment
<220> FEATURE:
<221> NAME/KEY: misc_feature
<222> LOCATION: (209)..(230)
<223> OTHER INFORMATION: Sequence of target of microRNA dme-miR-277
<220> FEATURE:
<221> NAME/KEY: misc_feature
<222> LOCATION: (231)..(234)
<223> OTHER INFORMATION: Spacer fragment
<220> FEATURE:
<221> NAME/KEY: misc_feature
<222> LOCATION: (235)..(256)
<223> OTHER INFORMATION: Sequence of target of microRNA dme-miR-277
<220> FEATURE:
<221> NAME/KEY: misc_feature
<222> LOCATION: (257)..(260)
<223> OTHER INFORMATION: Spacer fragment
<220> FEATURE:
<221> NAME/KEY: misc_feature
<222> LOCATION: (261)..(282)
<223> OTHER INFORMATION: Sequence of target of microRNA dme-miR-277
<220> FEATURE:
<221> NAME/KEY: misc_feature
<222> LOCATION: (283)..(286)
<223> OTHER INFORMATION: Spacer fragment
<220> FEATURE:
```

<221> NAME/KEY: misc_feature
<222> LOCATION: (287)..(308)
<223> OTHER INFORMATION: Sequence of target of microRNA dme-miR-277
<220> FEATURE:
<221> NAME/KEY: misc_feature
<222> LOCATION: (309)..(312)
<223> OTHER INFORMATION: Spacer fragment
<220> FEATURE:
<221> NAME/KEY: misc_feature
<222> LOCATION: (313)..(334)
<223> OTHER INFORMATION: Sequence of target of microRNA dme-miR-277
<220> FEATURE:
<221> NAME/KEY: misc_feature
<222> LOCATION: (335)..(338)
<223> OTHER INFORMATION: Spacer fragment
<220> FEATURE:
<221> NAME/KEY: misc_feature
<222> LOCATION: (339)..(360)
<223> OTHER INFORMATION: Sequence of target of microRNA dme-miR-277
<220> FEATURE:
<221> NAME/KEY: misc_feature
<222> LOCATION: (361)..(364)
<223> OTHER INFORMATION: Spacer fragment
<220> FEATURE:
<221> NAME/KEY: misc_feature
<222> LOCATION: (365)..(386)
<223> OTHER INFORMATION: Sequence of target of microRNA dme-miR-277
<220> FEATURE:
<221> NAME/KEY: misc_feature
<222> LOCATION: (387)..(390)
<223> OTHER INFORMATION: Spacer fragment
<220> FEATURE:
<221> NAME/KEY: misc_feature
<222> LOCATION: (391)..(412)
<223> OTHER INFORMATION: Sequence of target of microRNA dme-miR-277
<220> FEATURE:
<221> NAME/KEY: misc_feature
<222> LOCATION: (413)..(416)
<223> OTHER INFORMATION: Spacer fragment
<220> FEATURE:
<221> NAME/KEY: misc_feature
<222> LOCATION: (417)..(438)
<223> OTHER INFORMATION: Sequence of target of microRNA dme-miR-277
<220> FEATURE:
<221> NAME/KEY: misc_feature
<222> LOCATION: (439)..(442)
<223> OTHER INFORMATION: Spacer fragment
<220> FEATURE:
<221> NAME/KEY: misc_feature
<222> LOCATION: (443)..(464)
<223> OTHER INFORMATION: Sequence of target of microRNA dme-miR-277
<220> FEATURE:
<221> NAME/KEY: misc_feature
<222> LOCATION: (465)..(468)
<223> OTHER INFORMATION: Spacer fragment
<220> FEATURE:
<221> NAME/KEY: misc_feature
<222> LOCATION: (469)..(490)
<223> OTHER INFORMATION: Sequence of target of microRNA dme-miR-277
<220> FEATURE:
<221> NAME/KEY: misc_feature
<222> LOCATION: (491)..(494)
<223> OTHER INFORMATION: Spacer fragment
<220> FEATURE:
<221> NAME/KEY: misc_feature
<222> LOCATION: (495)..(516)
<223> OTHER INFORMATION: Sequence of target of microRNA dme-miR-277

<400> SEQUENCE: 65

```
tgtcgtacca gatctgcatt tagccctgtc gtaccagatc tgcatttagc ggtgtcgtac      60
cagatctgca tttagcaatg tcgtaccaga tctgcattta gacctgtcgt accagatctg     120
catttagacg tgtcgtacca gatctgcatt tagatctgtc gtaccagatc tgcatttaga    180
tgtgtcgtac cagatctgca tttagtcgtg tcgtaccaga tctgcattta gtaatgtcgt    240
accagatctg catttagatg tgtcgtacca gatctgcatt tagccctgtc gtaccagatc    300
```

```
tgcatttagc ggtgtcgtac cagatctgca tttagcaatg tcgtaccaga tctgcattta    360
gacctgtcgt accagatctg catttagacg tgtcgtacca gatctgcatt tagatctgtc    420
gtaccagatc tgcatttaga tgtgtcgtac cagatctgca tttagtcgtg tcgtaccaga    480
tctgcattta gtaatgtcgt accagatctg cattta                              516
```

<210> SEQ ID NO 66
<211> LENGTH: 516
<212> TYPE: DNA
<213> ORGANISM: Artificial sequence
<220> FEATURE:
<223> OTHER INFORMATION: Sequence of the fragment of sponge construct
      with 20 repeat targets for dme-miR-304
<220> FEATURE:
<221> NAME/KEY: misc_feature
<222> LOCATION: (1)..(22)
<223> OTHER INFORMATION: Sequence of target of microRNA dme-miR-304
<220> FEATURE:
<221> NAME/KEY: misc_feature
<222> LOCATION: (23)..(26)
<223> OTHER INFORMATION: Spacer fragment
<220> FEATURE:
<221> NAME/KEY: misc_feature
<222> LOCATION: (27)..(48)
<223> OTHER INFORMATION: Sequence of target of microRNA dme-miR-304
<220> FEATURE:
<221> NAME/KEY: misc_feature
<222> LOCATION: (49)..(52)
<223> OTHER INFORMATION: Spacer fragment
<220> FEATURE:
<221> NAME/KEY: misc_feature
<222> LOCATION: (53)..(74)
<223> OTHER INFORMATION: Sequence of target of microRNA dme-miR-304
<220> FEATURE:
<221> NAME/KEY: misc_feature
<222> LOCATION: (75)..(78)
<223> OTHER INFORMATION: Spacer fragment
<220> FEATURE:
<221> NAME/KEY: misc_feature
<222> LOCATION: (79)..(100)
<223> OTHER INFORMATION: Sequence of target of microRNA dme-miR-304
<220> FEATURE:
<221> NAME/KEY: misc_feature
<222> LOCATION: (101)..(104)
<223> OTHER INFORMATION: Spacer fragment
<220> FEATURE:
<221> NAME/KEY: misc_feature
<222> LOCATION: (105)..(126)
<223> OTHER INFORMATION: Sequence of target of microRNA dme-miR-304
<220> FEATURE:
<221> NAME/KEY: misc_feature
<222> LOCATION: (127)..(130)
<223> OTHER INFORMATION: Spacer fragment
<220> FEATURE:
<221> NAME/KEY: misc_feature
<222> LOCATION: (131)..(152)
<223> OTHER INFORMATION: Sequence of target of microRNA dme-miR-304
<220> FEATURE:
<221> NAME/KEY: misc_feature
<222> LOCATION: (153)..(156)
<223> OTHER INFORMATION: Spacer fragment
<220> FEATURE:
<221> NAME/KEY: misc_feature
<222> LOCATION: (157)..(178)
<223> OTHER INFORMATION: Sequence of target of microRNA dme-miR-304
<220> FEATURE:
<221> NAME/KEY: misc_feature
<222> LOCATION: (179)..(182)
<223> OTHER INFORMATION: Spacer fragment
<220> FEATURE:
<221> NAME/KEY: misc_feature
<222> LOCATION: (183)..(204)
<223> OTHER INFORMATION: Sequence of target of microRNA dme-miR-304
<220> FEATURE:
<221> NAME/KEY: misc_feature

```
<222> LOCATION: (205)..(208)
<223> OTHER INFORMATION: Spacer fragment
<220> FEATURE:
<221> NAME/KEY: misc_feature
<222> LOCATION: (209)..(230)
<223> OTHER INFORMATION: Sequence of target of microRNA dme-miR-304
<220> FEATURE:
<221> NAME/KEY: misc_feature
<222> LOCATION: (231)..(234)
<223> OTHER INFORMATION: Spacer fragment
<220> FEATURE:
<221> NAME/KEY: misc_feature
<222> LOCATION: (235)..(256)
<223> OTHER INFORMATION: Sequence of target of microRNA dme-miR-304
<220> FEATURE:
<221> NAME/KEY: misc_feature
<222> LOCATION: (257)..(260)
<223> OTHER INFORMATION: Spacer fragment
<220> FEATURE:
<221> NAME/KEY: misc_feature
<222> LOCATION: (261)..(282)
<223> OTHER INFORMATION: Sequence of target of microRNA dme-miR-304
<220> FEATURE:
<221> NAME/KEY: misc_feature
<222> LOCATION: (283)..(286)
<223> OTHER INFORMATION: Spacer fragment
<220> FEATURE:
<221> NAME/KEY: misc_feature
<222> LOCATION: (287)..(308)
<223> OTHER INFORMATION: Sequence of target of microRNA dme-miR-304
<220> FEATURE:
<221> NAME/KEY: misc_feature
<222> LOCATION: (309)..(312)
<223> OTHER INFORMATION: Spacer fragment
<220> FEATURE:
<221> NAME/KEY: misc_feature
<222> LOCATION: (313)..(334)
<223> OTHER INFORMATION: Sequence of target of microRNA dme-miR-304
<220> FEATURE:
<221> NAME/KEY: misc_feature
<222> LOCATION: (335)..(338)
<223> OTHER INFORMATION: Spacer fragment
<220> FEATURE:
<221> NAME/KEY: misc_feature
<222> LOCATION: (339)..(360)
<223> OTHER INFORMATION: Sequence of target of microRNA dme-miR-304
<220> FEATURE:
<221> NAME/KEY: misc_feature
<222> LOCATION: (361)..(364)
<223> OTHER INFORMATION: Spacer fragment
<220> FEATURE:
<221> NAME/KEY: misc_feature
<222> LOCATION: (365)..(386)
<223> OTHER INFORMATION: Sequence of target of microRNA dme-miR-304
<220> FEATURE:
<221> NAME/KEY: misc_feature
<222> LOCATION: (387)..(390)
<223> OTHER INFORMATION: Spacer fragment
<220> FEATURE:
<221> NAME/KEY: misc_feature
<222> LOCATION: (391)..(412)
<223> OTHER INFORMATION: Sequence of target of microRNA dme-miR-304
<220> FEATURE:
<221> NAME/KEY: misc_feature
<222> LOCATION: (413)..(416)
<223> OTHER INFORMATION: Spacer fragment
<220> FEATURE:
<221> NAME/KEY: misc_feature
<222> LOCATION: (417)..(438)
<223> OTHER INFORMATION: Sequence of target of microRNA dme-miR-304
<220> FEATURE:
<221> NAME/KEY: misc_feature
<222> LOCATION: (439)..(442)
<223> OTHER INFORMATION: Spacer fragment
<220> FEATURE:
<221> NAME/KEY: misc_feature
<222> LOCATION: (443)..(464)
<223> OTHER INFORMATION: Sequence of target of microRNA dme-miR-304
<220> FEATURE:
```

```
<221> NAME/KEY: misc_feature
<222> LOCATION: (465)..(468)
<223> OTHER INFORMATION: Spacer fragment
<220> FEATURE:
<221> NAME/KEY: misc_feature
<222> LOCATION: (469)..(490)
<223> OTHER INFORMATION: Sequence of target of microRNA dme-miR-304
<220> FEATURE:
<221> NAME/KEY: misc_feature
<222> LOCATION: (491)..(494)
<223> OTHER INFORMATION: Spacer fragment
<220> FEATURE:
<221> NAME/KEY: misc_feature
<222> LOCATION: (495)..(516)
<223> OTHER INFORMATION: Sequence of target of microRNA dme-miR-304

<400> SEQUENCE: 66
ctcacattta cttatgagat tagcgactca catttactta tgagattagc agctcacatt      60
tacttatgag attagctact cacatttact tatgagatta ggcgctcaca tttacttatg     120
agattaggca ctcacattta cttatgagat tagggctca catttactta tgagattagg     180
agctcacatt tacttatgag attaaccgct cacatttact tatgagatta acggctcaca     240
tttacttatg agattaggag ctcacattta cttatgagat tagcgactca catttactta     300
tgagattagc agctcacatt tacttatgag attagctact cacatttact tatgagatta     360
ggcgctcaca tttacttatg agattaggca ctcacattta cttatgagat tagggctca     420 catttactta tgagattagg agctcacatt tacttatgag attaaccgct cacatttact     480
tatgagatta acggctcaca tttacttatg agatta                               516

<210> SEQ ID NO 67
<211> LENGTH: 21
<212> TYPE: DNA
<213> ORGANISM: Artificial sequence
<220> FEATURE:
<223> OTHER INFORMATION: Forward primer of gene PCR transcript
      amplification DLG1

<400> SEQUENCE: 67
agcccgatta aaaaacagtg a                                                21

<210> SEQ ID NO 68
<211> LENGTH: 22
<212> TYPE: DNA
<213> ORGANISM: Artificial sequence
<220> FEATURE:
<223> OTHER INFORMATION: Reverse primer of gene PCR transcript
      amplification DLG1

<400> SEQUENCE: 68
cgtattcttc ttcgaccacg gt                                               22

<210> SEQ ID NO 69
<211> LENGTH: 23
<212> TYPE: DNA
<213> ORGANISM: Artificial sequence
<220> FEATURE:
<223> OTHER INFORMATION: Forward primer of gene PCR transcript
      amplification CAPZB

<400> SEQUENCE: 69
ggagaaggat gaaactgtga gtg                                              23

<210> SEQ ID NO 70
<211> LENGTH: 21
<212> TYPE: DNA
```

<210> SEQ ID NO 71
<211> LENGTH: 23
<212> TYPE: DNA
<213> ORGANISM: Artificial sequence
<220> FEATURE:
<223> OTHER INFORMATION: Reverse primer of gene PCR transcript amplification CAPZB

<400> SEQUENCE: 70
cagaggttta gcattgctgc t                                              21

<210> SEQ ID NO 71
<211> LENGTH: 23
<212> TYPE: DNA
<213> ORGANISM: Artificial sequence
<220> FEATURE:
<223> OTHER INFORMATION: Forward primer of gene PCR transcript amplification Atp2a1

<400> SEQUENCE: 71
gctcatggtc ctcaagatct cac                                            23

<210> SEQ ID NO 72
<211> LENGTH: 20
<212> TYPE: DNA
<213> ORGANISM: Artificial sequence
<220> FEATURE:
<223> OTHER INFORMATION: Reverse primer of gene PCR transcript amplification Atp2a1

<400> SEQUENCE: 72
gggtcagtgc ctcagctttg                                                20

<210> SEQ ID NO 73
<211> LENGTH: 21
<212> TYPE: DNA
<213> ORGANISM: Artificial sequence
<220> FEATURE:
<223> OTHER INFORMATION: Forward primer of gene PCR transcript amplification Clcn1

<400> SEQUENCE: 73
gtcctcagca agtttatgtc c                                              21

<210> SEQ ID NO 74
<211> LENGTH: 20
<212> TYPE: DNA
<213> ORGANISM: Artificial sequence
<220> FEATURE:
<223> OTHER INFORMATION: Reverse primer of gene PCR transcript amplification Clcn1

<400> SEQUENCE: 74
gaatcctcgc cagtaattcc                                                20

<210> SEQ ID NO 75
<211> LENGTH: 20
<212> TYPE: DNA
<213> ORGANISM: Artificial sequence
<220> FEATURE:
<223> OTHER INFORMATION: Forward primer of gene PCR transcript amplification Nfix

<400> SEQUENCE: 75
tcgacgacag tgagatggag                                                20

<210> SEQ ID NO 76
<211> LENGTH: 20
<212> TYPE: DNA
<213> ORGANISM: Artificial sequence

```
<220> FEATURE:
<223> OTHER INFORMATION: Reverse primer of gene PCR transcript
      amplification Nfix

<400> SEQUENCE: 76
caaactcctt cagcgagtcc                                                   20

<210> SEQ ID NO 77
<211> LENGTH: 24
<212> TYPE: DNA
<213> ORGANISM: Artificial sequence
<220> FEATURE:
<223> OTHER INFORMATION: Forward primer of gene PCR transcript
      amplification Capzb

<400> SEQUENCE: 77
gcacgctgaa tgagatctac tttg                                              24

<210> SEQ ID NO 78
<211> LENGTH: 20
<212> TYPE: DNA
<213> ORGANISM: Artificial sequence
<220> FEATURE:
<223> OTHER INFORMATION: Reverse primer of gene PCR transcript
      amplification Capzb

<400> SEQUENCE: 78
ccggttagcg tgaagcagag                                                   20

<210> SEQ ID NO 79
<211> LENGTH: 20
<212> TYPE: DNA
<213> ORGANISM: Artificial sequence
<220> FEATURE:
<223> OTHER INFORMATION: Forward primer of gene PCR transcript
      amplification of mouse Gapdh

<400> SEQUENCE: 79
atcaacggga agcccatcac                                                   20

<210> SEQ ID NO 80
<211> LENGTH: 21
<212> TYPE: DNA
<213> ORGANISM: Artificial sequence
<220> FEATURE:
<223> OTHER INFORMATION: Reverse primer of gene PCR transcript
      amplification of mouse Gapdh

<400> SEQUENCE: 80
cttccacaat gccaaagttg t                                                 21

<210> SEQ ID NO 81
<211> LENGTH: 97
<212> TYPE: RNA
<213> ORGANISM: Homo sapiens
<220> FEATURE:
<221> NAME/KEY: misc_RNA
<222> LOCATION: (1)..(97)
<223> OTHER INFORMATION: pre-miRNA of hsa-mir-23b-3p

<400> SEQUENCE: 81
cucaggugcu cuggcugcuu ggguuccugg caugcugauu ugugacuuaa gauuaaaauc        60
acauugccag ggauuaccac gcaaccacga ccuuggc                                 97

<210> SEQ ID NO 82
<211> LENGTH: 110
```

```
<212> TYPE: RNA
<213> ORGANISM: Homo sapiens
<220> FEATURE:
<221> NAME/KEY: misc_RNA
<222> LOCATION: (1)..(110)
<223> OTHER INFORMATION: pre-miRNA-1 of hsa-mir-218

<400> SEQUENCE: 82
gugauaaugu agcgagauuu ucuguugugc uugaucuaac caugugguug cgagguauga    60
guaaaacaug guuccgucaa gcaccaugga acgucacgca gcuuucuaca              110

<210> SEQ ID NO 83
<211> LENGTH: 110
<212> TYPE: RNA
<213> ORGANISM: Homo sapiens
<220> FEATURE:
<221> NAME/KEY: misc_RNA
<222> LOCATION: (1)..(110)
<223> OTHER INFORMATION: pre-miRNA-2 of hsa-mir-218

<400> SEQUENCE: 83
gaccagucgc ugcggggcuu uccuuugugc uugaucuaac caugugguggaacgauggaa    60 acggaacaug guucugucaa gcaccgcgga aagcaccgug cucuccugca              110

<210> SEQ ID NO 84
<211> LENGTH: 16
<212> TYPE: DNA
<213> ORGANISM: Artificial sequence
<220> FEATURE:
<223> OTHER INFORMATION: Antagonist MbloCKnoMIR
<220> FEATURE:
<221> NAME/KEY: modified_base
<222> LOCATION: (1)..(2)
<223> OTHER INFORMATION: LNA nucleotide
<220> FEATURE:
<221> NAME/KEY: modified_base
<222> LOCATION: (1)..(15)
<223> OTHER INFORMATION: Phosphorothioate bond
<220> FEATURE:
<221> NAME/KEY: modified_base
<222> LOCATION: (3)..(10)
<223> OTHER INFORMATION: 2'-O-methyl-nucleotide
<220> FEATURE:
<221> NAME/KEY: modified_base
<222> LOCATION: (3)..(10)
<223> OTHER INFORMATION: 2'-O-methyl-nucleotide
<220> FEATURE:
<221> NAME/KEY: modified_base
<222> LOCATION: (11)..(16)
<223> OTHER INFORMATION: LNA nucleotide

<400> SEQUENCE: 84
tgcaccuuug ttattt                                                    16

<210> SEQ ID NO 85
<211> LENGTH: 16
<212> TYPE: DNA
<213> ORGANISM: Artificial sequence
<220> FEATURE:
<223> OTHER INFORMATION: Antagonist M1bloCK23-1
<220> FEATURE:
<221> NAME/KEY: modified_base
<222> LOCATION: (1)..(15)
<223> OTHER INFORMATION: Phosphorothioate bond
<220> FEATURE:
<221> NAME/KEY: modified_base
<222> LOCATION: (1)..(6)
<223> OTHER INFORMATION: LNA nucleotide
<220> FEATURE:
<221> NAME/KEY: modified_base
<222> LOCATION: (7)..(14)
```

```
<223> OTHER INFORMATION: 2'-O-methyl-nucleotide
<220> FEATURE:
<221> NAME/KEY: modified_base
<222> LOCATION: (15)..(16)
<223> OTHER INFORMATION: LNA nucleotide

<400> SEQUENCE: 85
ccattaucac auuutg                                               16

<210> SEQ ID NO 86
<211> LENGTH: 16
<212> TYPE: DNA
<213> ORGANISM: Artificial sequence
<220> FEATURE:
<223> OTHER INFORMATION: Antagonist M2bloCK23-1
<220> FEATURE:
<221> NAME/KEY: modified_base
<222> LOCATION: (1)..(14)
<223> OTHER INFORMATION: Phosphorothioate bond
<220> FEATURE:
<221> NAME/KEY: modified_base
<222> LOCATION: (1)..(1)
<223> OTHER INFORMATION: LNA nucleotide
<220> FEATURE:
<221> NAME/KEY: modified_base
<222> LOCATION: (2)..(8)
<223> OTHER INFORMATION: 2'-O-methyl-nucleotide
<220> FEATURE:
<221> NAME/KEY: modified_base
<222> LOCATION: (9)..(15)
<223> OTHER INFORMATION: LNA nucleotide

<400> SEQUENCE: 86
aucacaugat tcaacg                                               16

<210> SEQ ID NO 87
<211> LENGTH: 16
<212> TYPE: DNA
<213> ORGANISM: Artificial sequence
<220> FEATURE:
<223> OTHER INFORMATION: Antagonist M1bloCK218-1
<220> FEATURE:
<221> NAME/KEY: modified_base
<222> LOCATION: (1)..(15)
<223> OTHER INFORMATION: Phosphorothioate bond
<220> FEATURE:
<221> NAME/KEY: modified_base
<222> LOCATION: (1)..(2)
<223> OTHER INFORMATION: LNA nucleotide
<220> FEATURE:
<221> NAME/KEY: modified_base
<222> LOCATION: (3)..(10)
<223> OTHER INFORMATION: 2'-O-methyl-nucleotide
<220> FEATURE:
<221> NAME/KEY: modified_base
<222> LOCATION: (11)..(16)
<223> OTHER INFORMATION: LNA nucleotide

<400> SEQUENCE: 87
gaugugcuuu aaatat                                               16

<210> SEQ ID NO 88
<211> LENGTH: 16
<212> TYPE: DNA
<213> ORGANISM: Artificial sequence
<220> FEATURE:
<223> OTHER INFORMATION: Antagonist M1bloCK218-2
<220> FEATURE:
<221> NAME/KEY: modified_base
<222> LOCATION: (1)..(15)
<223> OTHER INFORMATION: Phosphorothioate bond
<220> FEATURE:
<221> NAME/KEY: modified_base
```

```
<222> LOCATION: (1)..(1)
<223> OTHER INFORMATION: LNA nucleotide
<220> FEATURE:
<221> NAME/KEY: modified_base
<222> LOCATION: (2)..(9)
<223> OTHER INFORMATION: 2'-O-methyl-nucleotide
<220> FEATURE:
<221> NAME/KEY: modified_base
<222> LOCATION: (10)..(16)
<223> OTHER INFORMATION: LNA nucleotide

<400> SEQUENCE: 88
guugugcugt ctattg                                               16

<210> SEQ ID NO 89
<211> LENGTH: 16
<212> TYPE: DNA
<213> ORGANISM: Artificial sequence
<220> FEATURE:
<223> OTHER INFORMATION: Antagonist M2bloCK218-1
<220> FEATURE:
<221> NAME/KEY: modified_base
<222> LOCATION: (1)..(15)
<223> OTHER INFORMATION: Phosphorothioate bond
<220> FEATURE:
<221> NAME/KEY: modified_base
<222> LOCATION: (1)..(3)
<223> OTHER INFORMATION: LNA nucleotide
<220> FEATURE:
<221> NAME/KEY: modified_base
<222> LOCATION: (4)..(10)
<223> OTHER INFORMATION: 2'-O-methyl-nucleotide
<220> FEATURE:
<221> NAME/KEY: modified_base
<222> LOCATION: (11)..(16)
<223> OTHER INFORMATION: LNA nucleotide
<220> FEATURE:
<221> NAME/KEY: modified_base
<222> LOCATION: (14)..(14)
<223> OTHER INFORMATION: 2'-O-methyl-nucleotide

<400> SEQUENCE: 89
actugugcuu gaautt                                               16

<210> SEQ ID NO 90
<211> LENGTH: 16
<212> TYPE: DNA
<213> ORGANISM: Artificial sequence
<220> FEATURE:
<223> OTHER INFORMATION: Antagonist M2bloCK218-2
<220> FEATURE:
<221> NAME/KEY: modified_base
<222> LOCATION: (1)..(15)
<223> OTHER INFORMATION: Phosphorothioate bond
<220> FEATURE:
<221> NAME/KEY: modified_base
<222> LOCATION: (1)..(4)
<223> OTHER INFORMATION: LNA nucleotide
<220> FEATURE:
<221> NAME/KEY: modified_base
<222> LOCATION: (5)..(11)
<223> OTHER INFORMATION: 2'-O-methyl-nucleotide
<220> FEATURE:
<221> NAME/KEY: modified_base
<222> LOCATION: (12)..(16)
<223> OTHER INFORMATION: LNA nucleotide

<400> SEQUENCE: 90
gttgugugcu aataat                                               16

<210> SEQ ID NO 91
<211> LENGTH: 15
<212> TYPE: DNA
```

```
<213> ORGANISM: Artificial sequence
<220> FEATURE:
<223> OTHER INFORMATION: Antagonist M2bloCK218-3
<220> FEATURE:
<221> NAME/KEY: modified_base
<222> LOCATION: (1)..(14)
<223> OTHER INFORMATION: Phosphorothioate bond
<220> FEATURE:
<221> NAME/KEY: modified_base
<222> LOCATION: (1)..(5)
<223> OTHER INFORMATION: LNA nucleotide
<220> FEATURE:
<221> NAME/KEY: modified_base
<222> LOCATION: (6)..(11)
<223> OTHER INFORMATION: 2'-O-methyl-nucleotide
<220> FEATURE:
<221> NAME/KEY: modified_base
<222> LOCATION: (12)..(15)
<223> OTHER INFORMATION: LNA nucleotide

<400> SEQUENCE: 91
cgatagugcu uaaaa                                                    15

<210> SEQ ID NO 92
<211> LENGTH: 15
<212> TYPE: DNA
<213> ORGANISM: Artificial sequence
<220> FEATURE:
<223> OTHER INFORMATION: Antagonist AntimiR-23b
<220> FEATURE:
<221> NAME/KEY: modified_base
<222> LOCATION: (1)..(14)
<223> OTHER INFORMATION: Phosphorothioate bond
<220> FEATURE:
<221> NAME/KEY: modified_base
<222> LOCATION: (1)..(1)
<223> OTHER INFORMATION: LNA nucleotide
<220> FEATURE:
<221> NAME/KEY: modified_base
<222> LOCATION: (2)..(6)
<223> OTHER INFORMATION: 2'-O-methyl-nucleotide
<220> FEATURE:
<221> NAME/KEY: modified_base
<222> LOCATION: (7)..(7)
<223> OTHER INFORMATION: LNA nucleotide
<220> FEATURE:
<221> NAME/KEY: modified_base
<222> LOCATION: (8)..(8)
<223> OTHER INFORMATION: 2'-O-methyl-nucleotide
<220> FEATURE:
<221> NAME/KEY: modified_base
<222> LOCATION: (9)..(9)
<223> OTHER INFORMATION: LNA nucleotide
<220> FEATURE:
<221> NAME/KEY: modified_base
<222> LOCATION: (10)..(12)
<223> OTHER INFORMATION: 2'-O-methyl-nucleotide
<220> FEATURE:
<221> NAME/KEY: modified_base
<222> LOCATION: (13)..(13)
<223> OTHER INFORMATION: LNA nucleotide
<220> FEATURE:
<221> NAME/KEY: modified_base
<222> LOCATION: (14)..(14)
<223> OTHER INFORMATION: 2'-O-methyl-nucleotide
<220> FEATURE:
<221> NAME/KEY: modified_base
<222> LOCATION: (15)..(15)
<223> OTHER INFORMATION: LNA nucleotide

<400> SEQUENCE: 92
cgatagugcu uaaaa                                                    15

<210> SEQ ID NO 93
<211> LENGTH: 15
```

```
<212> TYPE: DNA
<213> ORGANISM: Artificial sequence
<220> FEATURE:
<223> OTHER INFORMATION: Antagonist AntimiR-218
<220> FEATURE:
<221> NAME/KEY: modified_base
<222> LOCATION: (1)..(14)
<223> OTHER INFORMATION: Phosphorothioate bond
<220> FEATURE:
<221> NAME/KEY: modified_base
<222> LOCATION: (1)..(1)
<223> OTHER INFORMATION: LNA nucleotide
<220> FEATURE:
<221> NAME/KEY: modified_base
<222> LOCATION: (2)..(3)
<223> OTHER INFORMATION: 2'-O-methyl-nucleotide
<220> FEATURE:
<221> NAME/KEY: modified_base
<222> LOCATION: (4)..(4)
<223> OTHER INFORMATION: LNA nucleotide
<220> FEATURE:
<221> NAME/KEY: modified_base
<222> LOCATION: (5)..(7)
<223> OTHER INFORMATION: 2'-O-methyl-nucleotide
<220> FEATURE:
<221> NAME/KEY: modified_base
<222> LOCATION: (8)..(8)
<223> OTHER INFORMATION: LNA nucleotide
<220> FEATURE:
<221> NAME/KEY: modified_base
<222> LOCATION: (9)..(10)
<223> OTHER INFORMATION: 2'-O-methyl-nucleotide
<220> FEATURE:
<221> NAME/KEY: modified_base
<222> LOCATION: (11)..(11)
<223> OTHER INFORMATION: LNA nucleotide
<220> FEATURE:
<221> NAME/KEY: modified_base
<222> LOCATION: (12)..(12)
<223> OTHER INFORMATION: 2'-O-methyl-nucleotide
<220> FEATURE:
<221> NAME/KEY: modified_base
<222> LOCATION: (13)..(13)
<223> OTHER INFORMATION: LNA nucleotide
<220> FEATURE:
<221> NAME/KEY: modified_base
<222> LOCATION: (14)..(14)
<223> OTHER INFORMATION: 2'-O-methyl-nucleotide
<220> FEATURE:
<221> NAME/KEY: modified_base
<222> LOCATION: (15)..(15)
<223> OTHER INFORMATION: LNA nucleotide

<400> SEQUENCE: 93
tuagaucaag gacaa                                                    15

<210> SEQ ID NO 94
<211> LENGTH: 16
<212> TYPE: DNA
<213> ORGANISM: Artificial sequence
<220> FEATURE:
<223> OTHER INFORMATION: Antagonist AntimiR-SC
<220> FEATURE:
<221> NAME/KEY: modified_base
<222> LOCATION: (1)..(15)
<223> OTHER INFORMATION: Phosphorothioate bond
<220> FEATURE:
<221> NAME/KEY: modified_base
<222> LOCATION: (1)..(6)
<223> OTHER INFORMATION: LNA nucleotide
<220> FEATURE:
<221> NAME/KEY: modified_base
<222> LOCATION: (7)..(14)
<223> OTHER INFORMATION: 2'-O-methyl-nucleotide
<220> FEATURE:
<221> NAME/KEY: modified_base
<222> LOCATION: (15)..(16)
```

```
<223> OTHER INFORMATION: LNA nucleotide

<400> SEQUENCE: 94
gcataaugac uuuatg                                                    16

<210> SEQ ID NO 95
<211> LENGTH: 21
<212> TYPE: DNA
<213> ORGANISM: Artificial sequence
<220> FEATURE:
<223> OTHER INFORMATION: FANA oligonucleotide AUM-miR-23b-1
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 95
gguaauccct ggcaauguga u                                              21

<210> SEQ ID NO 96
<211> LENGTH: 21
<212> TYPE: DNA
<213> ORGANISM: Artificial sequence
<220> FEATURE:
<223> OTHER INFORMATION: FANA oligonucleotide AUM-miR-23b-2
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 96
gguaatccct ggcaatgtga u                                              21

<210> SEQ ID NO 97
<211> LENGTH: 21
<212> TYPE: DNA
<213> ORGANISM: Artificial sequence
<220> FEATURE:
<223> OTHER INFORMATION: FANA oligonucleotide AUM-miR-23b-3
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 97
gguaaucccu ggcaauguga u                                              21
```

```
<210> SEQ ID NO 98
<211> LENGTH: 21
<212> TYPE: DNA
<213> ORGANISM: Artificial sequence
<220> FEATURE:
<223> OTHER INFORMATION: FANA oligonucleotide AUM-miR-23b-4
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 98
gguaatccct ggcaatgtga u                                         21

<210> SEQ ID NO 99
<211> LENGTH: 21
<212> TYPE: DNA
<213> ORGANISM: Artificial sequence
<220> FEATURE:
<223> OTHER INFORMATION: FANA oligonucleotide AUM-miR-218-1
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 99
acauggutag atcaagcaca a                                         21

<210> SEQ ID NO 100
<211> LENGTH: 21
<212> TYPE: DNA
<213> ORGANISM: Artificial sequence
<220> FEATURE:
<223> OTHER INFORMATION: FANA oligonucleotide AUM-miR-218-2
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 100
acatgguuag atcaagcaca a                                         21

<210> SEQ ID NO 101
<211> LENGTH: 21
<212> TYPE: DNA
<213> ORGANISM: Artificial sequence
<220> FEATURE:
<223> OTHER INFORMATION: FANA oligonucleotide AUM-miR-218-3
<220> FEATURE:
```

```
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 101
acaugguuag aucaagcaca a                                              21

<210> SEQ ID NO 102
<211> LENGTH: 21
<212> TYPE: DNA
<213> ORGANISM: Artificial sequence
<220> FEATURE:
<223> OTHER INFORMATION: FANA oligonucleotide AUM-miR-218-4
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 102
acatggutag atcaagcaca a                                              21

<210> SEQ ID NO 103
<211> LENGTH: 21
<212> TYPE: DNA
<213> ORGANISM: Artificial sequence
<220> FEATURE:
<223> OTHER INFORMATION: FANA oligonucleotide AUM-SC-1
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
<220> FEATURE:
<221> NAME/KEY: modified_base
<222> LOCATION: (21)..(21)
<223> OTHER INFORMATION: 2'-fluoroarabinonucleotide

<400> SEQUENCE: 103
auauccutgt cgtaucccag u                                              21

<210> SEQ ID NO 104
<211> LENGTH: 21
<212> TYPE: DNA
<213> ORGANISM: Artificial sequence
<220> FEATURE:
<223> OTHER INFORMATION: FANA oligonucleotide AUM-SC-2
<220> FEATURE:
<221> NAME/KEY: modified_base
<222> LOCATION: (1)..(1)
<223> OTHER INFORMATION: 2'-fluoroarabinonucleotide
<220> FEATURE:
<221> NAME/KEY: modified_base
<222> LOCATION: (1)..(20)
<223> OTHER INFORMATION: Phosphorothioate bond
```

```
<220> FEATURE:
<221> NAME/KEY: modified_base
<222> LOCATION: (21)..(21)
<223> OTHER INFORMATION: 2'-fluoroarabinonucleotide

<400> SEQUENCE: 104
auauccutgt cgtaucccag u                                              21
```

MODULATION OF MICRORNAS AGAINST MYOTONIC DYSTROPHY TYPE 1 AND ANTAGONISTS OF MICRORNAS THEREFOR

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920182_401USPC_SEQUENCE_LISTING.txt. The text file is 96.7 KB, was created on Mar. 18, 2019, and is being submitted electronically via EFS-Web.

TECHNICAL FIELD

The invention relates to the use of small molecules that comprise units of ribonucleotides or analogues thereof for their therapeutic application against diseases. More specifically, the invention relates to the use of microRNA antagonists, such as antagomiRs, for the treatment of myotonic dystrophy type 1.

BACKGROUND OF THE INVENTION

Myotonic dystrophy type 1 (DM1) is an incurable neuromuscular disorder that constitutes a serious clinical concern because in addition to being the most common adult-onset muscular dystrophy, it is highly disabling. Clinically, DM1 is considered a multisystemic disorder that mainly affects skeletal and smooth muscle, the nervous system, and the heart, and is characterized by a reduction in muscle mass (muscular dystrophy), which can lead to respiratory failure and death, iridescent posterior subcapsular cataracts, cardiac impulse conduction defects, endocrine changes, myotonia (difficulty relaxing the muscle after a voluntary contraction), and dysfunctions of the central nervous system that include attention deficits, characteristic personality patterns, sleep disorders, and dysexecutive syndrome. This clinical picture includes a highly variable onset age, ranging from congenital forms (from birth) to infantile DM1, onset during adulthood and old age. The most common form of the disease, that being the onset in adolescence or the teens, reduces the patients' life expectancy to 48-55 years (Harper, 2001 Gagnon et al., 2007). DM1 is classified as a rare disease as its prevalence in the population is estimated to be less than 1 in 2000.

Genetically, DM1 is known to be an autosomal dominant hereditary disease and is caused by the presence of expanded CTG*CAG repeats in the 3' untranslated region (3' UTR) of the protein kinase gene of myotonic dystrophy (DMPK: dystrophia myotonica-protein kinase) (for a recent review, see for example Thornton, 2014). The normal human DMPK gene (HCNG: 2933, Entrez Gene: 1760, Ensembl: ENSG00000104936, OMIM: 605377, UniProtKB: O09013) has 5-37 copies of the trinucleotide motif, but a dynamic mutation can increase this number to more than 5000 copies of the repeat. The severity of the disease correlates roughly with the number of repeats, i.e. the size of the expansion.

There is also the so-called myotonic dystrophy type 2 (DM2), less frequent, which is due to mutations in a different gene, the CNBP gene, present in the human chromosome 23. In DM2 there is also muscular dysfunction, but mainly involving the muscles at the root of the extremities (shoulders, buttocks, thighs . . . ), while DM1 primarily involves muscles of the distal portion of the extremities. Unlike DM1, DM2 does not seem to affect life expectancy and often presents with more moderate symptoms.

The expression of expanded DM1 alleles results in mutant DMPK mRNA nuclear retention and reduced levels of DMPK protein (Davis et al., 1997). Mutant transcripts sequester the splicing factors which are similar to the Drosophila Muscleblind protein (MBNL, abbreviation of Muscleblind-like), which gives rise to the abnormal alternative splicing of many other transcripts and the expression of foetal forms of the corresponding proteins in adults suffering DM1 (Lin et al., 2006; Du et al., 2010). In fact, both the Drosophila Muscleblind protein (UniProtKB 016011, CG33197) and its equivalent MBNL1-3 of vertebrates are known to be splicing regulators Transcripts of MBNL1 and MBNL2 genes, for their part, are themselves subjected to alternative splicing, generating numerous protein isoforms (Pascual et al, 2006). MBNL1 is strongly expressed in skeletal and cardiac muscle tissue and during myoblast differentiation. Its expression is lower in other tissues such as brain, placenta, lungs, liver, kidney, and pancreas. MBNL2 has a largely overlapping expression and is detected in the heart, brain, placenta, lungs, liver, skeletal muscle, kidneys, and pancreas. MBNL3, on the other hand, is expressed in the placenta and satellite cells. For more detailed information, please see the Fernandez-Costa et al. review. (Fernandez-Costa et al., 2011).

Therefore, spliceopathy is believed to be the main factor underlying DM1 pathogenesis. However, different alternative mechanisms such as additional changes in gene expression, antisense transcripts, translation effectiveness, deregulation of alternative polyadenylation and miRNA deregulation may contribute to DM1 pathogenesis (Batra et al., 2014; Yadava et al., 2016; Kalsotra et al., 2014).

Several therapeutic approaches have been tested in DM1 animal models. Among them, the most interesting results derive from blocking the interaction between MBNLs and the toxic RNA using small molecules, peptides, Morpholinos or antisense oligonucleotides, and gapmers to degrade the mutant DMPK transcripts (revised by Klein et al., 2015).

A less explored alternative in DM1 is the therapeutic modulation of the MBNL1 and MBNL2 gene expression (HONG: 6923, Entrez Gene: 4154, Ensembl: ENSG00000152601, OMIM: 606516, UniProtKB: Q9NR56, which was previously identified in HONG with the symbol MBNL). Although the expression of CUG expansions triggers different molecular alterations, current evidence points to the sequestration of MBNL proteins as the main cause of the symptoms of the disease. The mouse model with inactivated Mbnl1 gene (knockout mouse, abbreviated KO, for Mbnl1) shows myotonia, incorrect splicing of muscle transcripts and cataracts, which are all characteristic symptoms of DM1 disease (Kanadia et al., 2003). More recently, in two-month-old Mbnl1 mutant mice, the most relevant features of cardiac dysfunction have been described (hypertrophy, interstitial fibrosis and splicing alterations), suggesting a role of Mbnl1 reduction in DM1 cardiac problems (Dixon et al., 2015). In addition, genetic polymorphisms in the human MBNL1 gene promoter have been associated with the severity of the disease (Huin et al., 2013).

However, KO mice for Mbnl1 do not show the whole set of symptoms of DM1. Thus, it has been hypothesized that Mbnl2 could compensate for the loss of function of Mbnl1 in these mice. In fact, the KO mice for Mbnl1 with reduced expression of Mbnl2 (Mbnl1$^{-/-}$; Mbnl2$^{+/-}$), are viable, but they develop most of the cardinal defects of the disease, including reduced life expectancy, cardiac blockage, severe myotonia, atrophic fibres and progressive weakness of skeletal muscles. In support of the compensation hypothesis it is noted that the Mbnl2 levels are increased in KO mice for Mbn/1$^{-/-}$ and Mbnl2 can regulate exons that normally are regulated by Mbnl1 (Lee et al., 2013).

Several observations suggest that overexpression of MBNL1 may have potential for the treatment of DM1 pathology. First, MBNL1 overexpression is well tolerated in the skeletal muscle of transgenic mice, causing only relatively minor changes in splicing, but without affecting longevity (Chamberlain et al., 2012). Secondly, administration of recombinant Mbnl1 protein to a HSA$^{LR}$ mouse model of DM1, rescues myotonia and splicing alterations characteristics of DM1 (Kanadia et al., 2006).

Given the severity of the symptoms of DM1, which can lead to premature death of the patient, and the absence at present of effective treatments for it, it is of interest to explore alternative therapeutic strategies.

Thus, it would be interesting to see if the overexpression of MBNL1, alone or in combination with the modulation of MBNL2, could also have a therapeutic application in humans with DM1. However, since the design and authorization of the application of safe expression vectors for their administration in humans is complex, it would be interesting to find a way to increase the levels of the MBNL1 or MBNL2 protein in humans, in the same tissues where they are normally transcribed, by some alternative method to the expression of this protein from an artificial vector. Moreover, preferably this increase in level would occur, at least, in one or more of the relevant tissues and organs in which specifically significant symptoms of the disease appear: skeletal and smooth muscle, heart, and nervous system.

The present invention provides a solution to that problem.

SUMMARY OF THE INVENTION

This invention is based on compensating for insufficient amounts of MBNL (Muscleblind-like) proteins that are available to interact with their natural targets in patients with myotonic dystrophy 1 (DM1), because this protein, among other mechanisms that can affect its expression, subcellular distribution and activity in vivo, is sequestered in ribonuclear foci together with mutant transcripts of the DMPK gene. By compensating the quantities of MBNL proteins, an improvement in the symptoms of the disease is attempted. In order to do so, the present inventors propose to achieve an up-regulation of these protein levels, caused by an increase in the expression thereof, by blocking the action of microRNAs (miRNAs) that intervene negatively in the regulation of their translation and stability, preferably by means of oligoribonucleotides, analogues thereof or, in general, oligoribonucleotide molecules, able to specifically block the action of certain miRNAs repressors of MBNL1 and/or MBNL2 genes.

Thus, a first aspect of the present invention relates to an oligoribonucleotide and/or oligoribonucleotide analogue molecule which is an antagonist of a microRNA that downregulates the expression of the human gene MBNL1 and/or MBNL2, or a mixture of two or more of said molecules. Said molecule shall be considered an oligoribonucleotide or oligoribonucleotide analogue molecule of the invention. Preferably, the molecule is an antagonist of a microRNA expressed at least in one or more organs selected from the group of the brain, cerebellum, hippocampus, skeletal muscle and heart, or in one or more cells from a primary culture of one of said organs or of an established cell line derived from one of said organs (including induced pluripotent stem cells, known as iPSCs) or stem cells of one of said organs. It is preferred that the molecule is complementary and comprises a fragment of ribonucleotide or ribonucleotide analogue unit sequence, wherein the sequence of the nitrogenous bases of the ribonucleotide or ribonucleotide analogue units is at least 50% (or at least 55%, 60%, 70%, 80%, 85%, 90%, 91%, 92%, 93%, 94%, 95%, 96%, 97%, 98%, 99% or 99.5%, or 100%) complementary to the sequence of the nitrogenous bases of the endogenous molecule (the microRNA or the messenger RNA) to which it should bind. Preferably, the molecule is an antagonist of the human microRNA-218-5p or of the human microRNA-23b-3p. Compatibly with any of the above preferences, it is preferred that the antagonist is an antagomiR, a blockmiR, an antimiR or a microRNA sponge, and especially preferred that the molecule is an antagomiR and, among these, an antagomiR in which the sequence of the nitrogenous bases of the ribonucleotide or ribonucleotide analogue units is at least 80% complementary/identical to the sequence of the nitrogenous bases of the microRNA to which it should bind. Especially in the case that the molecule is an antagomiR, an antimiR or a microRNA sponge, preferably the molecule is complementary to the sequence of human microRNA-218-5p or microRNA-23b-3p or comprises a sequence of ribonucleotide or ribonucleotide analogue units, wherein the sequence of the nitrogenous bases of the ribonucleotide or ribonucleotide analogue units is at least 80% (or at least 85%, 90%, 91%, 92%, 93%, 94%, 95%, 96%, 97%, 98%, 99% or 99.5%, or 100%) identical to the sequence of the nitrogen bases of the oligoribonucleotide of SEQ ID NO: 1 or of SEQ ID NO: 2. Especially when the molecule is an antagomiR, preferably this molecule is complementary to the sequence of the human microRNA-218-5p or that of the human microRNA-23b-3p or it comprises a sequence of ribonucleotide or ribonucleotide analogue units, wherein the sequence of the nitrogenous bases of the ribonucleotide or ribonucleotide analogue units is at least 50% (or at least 55%, 60%, 70%, 80%, 85%, 90%, 91%, 92%, 93%, 94%, 95%, 96%, 97%, 98%, 99% or 99.5%, or 100%) complementary to that of the human microRNA-218-5p or of the human microRNA-23b-3p, being especially preferred that it is at least 80% complementary. Very preferably, the molecule is an antagomiR-type oligoribonucleotide analogue in which at least one of the units is a ribonucleotide analogue that presents one or more chemical modifications in the ribose moiety, in the phosphate bond or in both, the sequence of the nitrogenous bases of the ribonucleotide or ribonucleotide analogue units is identical to the sequence of nitrogenous bases of the ribonucleotide units of the oligoribonucleotide of SEQ ID NO:1 or of the oligoribonucleotide of SEQ ID NO:2 and which, optionally, presents at the 5'-end and/or at the 3'-end one or more additional moieties that are not adenoribonucleotide or ribonucleotide moieties. Most preferably of all, the molecule is the antagomiR-218 (SEQ ID NO:10) or the antagomiR-23b (SEQ ID NO:11). In another possible embodiment, especially interesting in the case of antimiRs, the oligoribonucleotide and/or the oligoribonucleotide analogue comprises a fragment that is 100% complementary to the seed region of the microRNA with respect to which it is an antagonist. Another possible embodiment, especially interesting in the case of blockmiRs, is a oligoribonucleotide and/or oligoribonucleotide analogue molecule comprising a fragment composed of a succession of ribonucleotide or ribonucleotide analogue units in which the sequence of the nitrogenous bases of the ribonucleotide or ribonucleotide analogue units is at least 80% complementary to the sequence of the nitrogenous bases of the region recognized by the microRNA with respect to which it is an antagonist in a target mRNA (i.e., down-regulated by that microRNA).

In a second aspect, this invention relates to a composition comprising at least one of the oligoribonucleotide and/or oligoribonucleotide analogue molecules of the present invention, a mixture thereof, or an expression vector that comprises the coding sequence of at least one of said oligoribonucleotide molecules. In one possible embodiment, the composition additionally comprises a carrier and/or one or more pharmaceutically acceptable excipients. In another possible preferred embodiment, compatible with the preceding one, the composition comprises the antagomiR-type oligoribonucleotide analogue represented by SEQ ID NO:10 (antagomiR-218-5p) or the antagomiR-type oligoribonucleotide analogue represented by SEQ ID NO:11 (antagomiR-23b-3p) or a mixture thereof. In another possible embodiment, compatible with all the preceding ones and especially preferred when antagomiR-23b-3p and/or antagomiR-218-5p are present in the composition, the oligoribonucleotide or oligoribonucleotide analogue molecule is at a concentration of 50 nM to 200 nM, both included.

In one more aspect, the invention relates to the use of one of the oligoribonucleotide or oligoribonucleotide analogue molecules of the invention, a mixture of two or more thereof, or a composition comprising at least one of said molecules, for the manufacture of a medicinal product for the treatment of myotonic dystrophy type 1. Therefore, comprised within the scope of the invention and considered one aspect thereof, is one of the oligoribonucleotide or oligoribonucleotide analogue molecules of the invention, a mixture of two or more thereof, or a composition for use in the treatment of myotonic dystrophy type 1. Preferably, in this aspect of the invention referred to the use for the manufacture of a medicinal product and, therefore, related to the use in the treatment of myotonic dystrophy type 1, a possible embodiment is that wherein the molecule is, or the composition comprises, an antagonist of the human microRNA-218-5p, an inhibitor of the human microRNA-23b-5p, a mixture thereof or a composition that comprises them. In one possible embodiment, treatment is a palliative treatment of one or more symptoms of myotonic dystrophy type 1. Within the foregoing, a possible preference is that treatment is a palliative treatment of one or more of the muscular disorders that are part of the symptoms of myotonic dystrophy type 1.

DETAILED DESCRIPTION OF THE INVENTION

Figure 1:
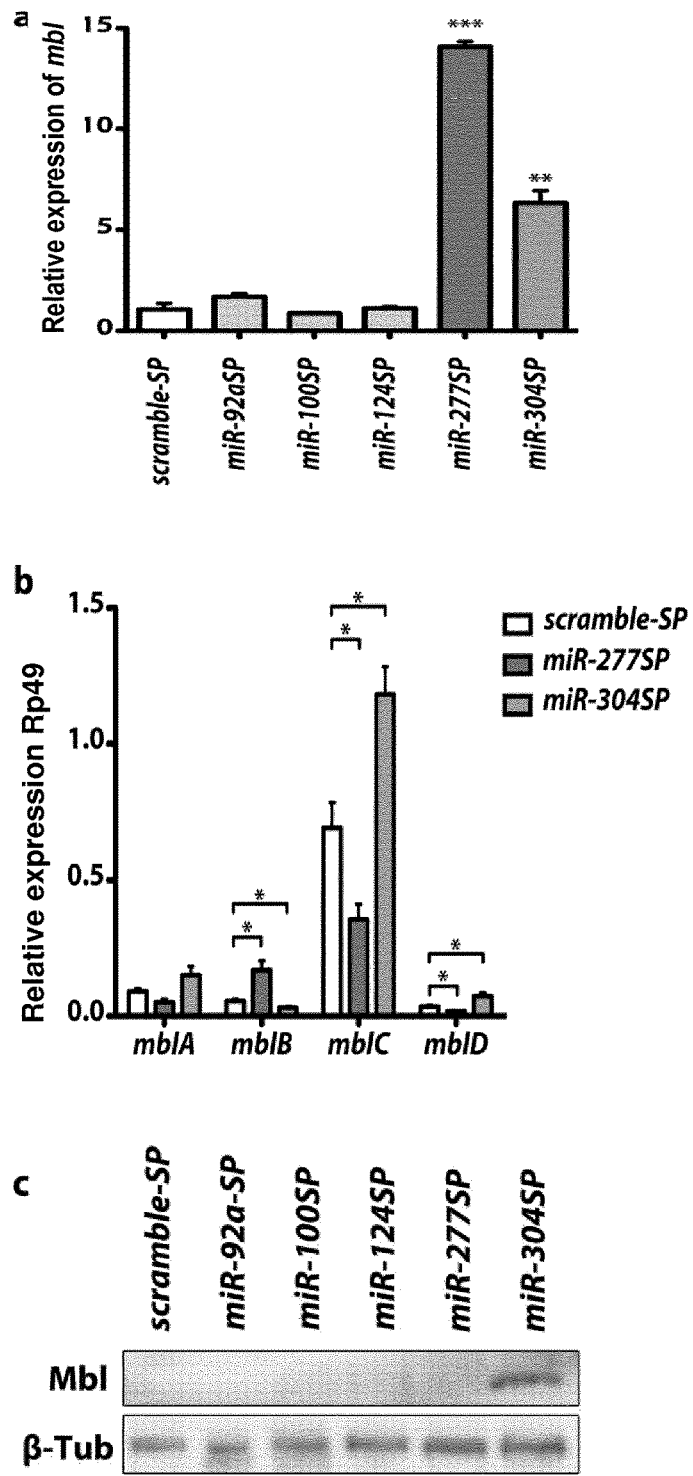
FIG. 1. Specific dme-miR-277 and dme-miR-304 tissue silencing causes overexpression of muscleblind at the RNA and proteins levels in the Drosophila muscle. (A): Levels of expression of muscleblind relative to an endogenous control obtained by amplification by qRT-PCR from flies expressing the miRNA sponge constructs for dme-miR-92a, dme-miR-100, dme-miR-124, dme-miR-277 and dme-miR-304 in the muscle: the levels of expression of muscleblind were strongly up-regulated in flies that expressed the microRNA sponges mir-277SP and mir-304SP with respect to flies expressing a UAS-ScrambledSP construct (B): Analysis of the levels of isoforms of muscleblind by qRT-PCR, where it is observed that the silencing of dme-miR-277 in the muscle caused an up-regulation of the isoform mblB, while the levels of expression of the isoforms mblC and mblD were reduced in flies that expressed miR-277SP; conversely, the levels of mblC and mblD increased and those of the isoform mblB were reduced in flies that expressed miR-304SP. (c) Detection of the muscleblind protein by Western Blot, where overexpression of the Muscleblind protein was detected in the flies expressing miR-304SP. All the transgenes specified were directed to the muscle using Mhc-Gal4. *$p<0.05$, $p<0.01$, *$p<0.001$ (Student's t test).

As commented above, this invention is based on knowledge suggesting that in patients with DM1, the activity of MBNL-family proteins is limiting; this originates, at least in part, because the transcript mRNAs of mutant alleles of the DMPK gene, which present hundreds of additional CUG repeats in the UTR region of 3', accumulate in foci in which muscleblind-like (MBNL) proteins are sequestered, leading them away from their functional targets. Therefore, the present inventors propose that the up-regulation of the levels of endogenous MBNL proteins represents a therapeutic approach to DM1, which would help to alleviate its symptoms.

The basis of this invention is the identification of miRNAs that act negatively on the expression of MBNL proteins and the blocking or inhibition thereof, to decrease or prevent their negative effect on the levels of MBNL proteins, resulting in an increase in these levels.

The fundamental role of the miRNA in regulating gene expression has been well established. The microRNAs (commonly abbreviated as miRNAs) are endogenous non-coding RNAs, with an approximate length of 22 nucleotides, that act post-transcriptionally and exert their regulatory effects mainly by binding the region 3'UTR of the target mRNA, which results in the deadenylation of mRNA and thus cause the decrease or suppression of translation or, rarely, mRNA excision. This last effect, mRNA excision, can occur when there is a full complementarity between an mRNA and a miRNA that binds to it, which allows a member of the protein family called Argonauts to act, specifically Ago2, which is capable of mRNA excision leading to direct degradation thereof. For a microRNA to bind to the corresponding messenger RNA, such mRNA essentially needs to have the so-called "seed region", which is a fragment of about 6-8 nucleotides (usually 7), which is part of the mRNA area to which the microRNA binds and has a perfect complementarity with a part of the microRNA, usually nucleotides 2 to 8 or 9 thereof, which is often called the seed region. Although the complementarity between the microRNA and its corresponding mRNA is not perfect throughout the pairing zone, it is in the seed region; thus, the microRNA may be functional in regulating the expression of the gene that corresponds to the mRNA that contains it.

As reviewed, for instance, by Zhonghan Li and Tariq M. Rana (Li and Rana, 2014) or in Wikipedia (https://en.wikipedia.org/wiki/MicroRNA) animal microRNAs are usually transcribed from RNA polymerase II promoters as part of one arm of an RNA stem-loop that, in turn, forms part of one several hundred nucleotide-long miRNA precursor termed a primary miRNA (pri-miRNAs), which may contain from one to six miRNA precursors which form the hairpin loops with complementary sequences also present in the pri-miRNA. The pri-miRNA transcript is capped with a specially modified nucleotide at the 5' end, polyadenylated with a polyA tail and spliced. Each hairpin loop structure is composed of about 70-80 nucleotides each and is flanked by the sequences necessary for efficient processing. During canonical miRNA biogenesis, the double-stranded RNA structures of the hairpins are recognized by the enzyme Pasha, which form a complex with the enzyme Drosha, which cleaves the hairpin bases and liberates the hairpins. The products are called precursors-miRNA (pre-miRNA). Pre-miRNAs can be also generated by mRNA splicing machinery, circumventing Drosha-mediated digestion. Regardless of the generation process, pre-miRNA hairpins are exported from the nucleus by the shutter Exportin-5. Once in the cytoplasm, the pre-miRNA hairpin is cleaved by the enzyme Dicer, which cuts away the loop joining the 3' and 5' arms, yielding an imperfect miRNA:miRNA duplex about 22 nucleotides in length. Although either strand of the duplex may potentially act as a functional mature miRNA, only one strand is usually incorporated into the RNA-induced silencing complex (RISC) where the miRNA and its mRNA target interact.

Thus, the present inventors propose a therapeutic approach for the improvement of DM1 which consists in the modulation of the endogenous MBNL proteins causing the sequestration of one or more of the miRNAs that act negatively on expression, thus giving rise to an up-regulation and, as a consequence, an increase in the levels of endogenous MBNL proteins. Therefore, the aim is to cause the modulation of the endogenous protein by silencing or diminishing the repressive activity of specific miRNAs involved in the regulation of its expression. In particular, in the present case, miRNAs expressed in muscle are preferred, as this is one of the main organs affected by the disease.

According to the foregoing, and as used herein, miRNA inhibitors, silencers or blockers are compounds that are capable of producing a decrease in the endogenous activity of said miRNA. As is common in the literature related to similar strategies speaking of "antagonism" (see, e.g., the article by Landford et al., 2010, on silencing of the miR-122), these three terms have been included under the denomination of "antagonist" of a miRNA.

Commonly and traditionally, strategies for efficiently inhibiting the function of miRNAs have been designed in order to target direct mature miRNAs. However, alternative strategies in which miRNAs are targeted at their precursor stage may also become a valid approach for addressing this issue. For instance, Kloosterman et al. (Kloostermann et al., 2007) reported that the miRNA biogenesis and maturation process could be efficiently inhibited by morpholinos in a miRNA-specific manner. Kloosterman et al. reported that morpholinos could block processing of the primary miRNA (pri-miRNA) or the pre-miRNA, and they can inhibit the activity of the mature miRNA. In particular, it was shown that inhibition of miR-375 would lead to defective morphology of pancreatic islet cells, and this phenotype could be observed with multiple precursor-targeting morpholinos. WO 2016/091747A1, in turn, refers to inhibitors of the miR-17-92 cluster an their use as medicament, providing specifically an LNA/DNA gapmer which binds to a region of the primary miRNA (pri-miRNA) of the miR-17-92 cluster and that can be used for the treatment of tumors related to the overexpression of any of the miRNAs of the miR-17-92 cluster. Thus, it can be said that miRNA function can be inhibited or decreased by targeting the mature miRNA, the precursor miRNA or the primary miRNA. And, as Li and Rana comment in their review (Li and Rana, 2014), miRNA expression and function can be targeted by disrupting the generation of pri-miRNAs or pre-miRNAs. In the particular case of prim-miRNAs, as they usually contain sequences not found in mature miRNAs, and those sequences are not convserved among different miRNAs (even from the same family), chemically modified short oligonucleotides can be designed to bind specifically to these sequences and, as these oligonucleotides might have high binding affinity, it is quite feasible that they can disrupt the hairpin structure of a targeted miRNA and cause defects in its further processing by the Drosha-Pasha complex, thus reducing the level of downstream mature miRNA and its overall capacity of performing its function.

Since this invention focuses on reducing the activity of miRNAs repressors of the expression of certain genes, it is this repressive capacity that will be diminished by the presence of its inhibitors, silencers or blockers: their antagonists. While, strictly speaking, the term "silencing" could be interpreted as the absolute annulment of such activity, since the difference between such annulment or a non-absolute decrease in repressive activity may depend on the concentration of the compound used, the four terms (inhibitors, silencers, blockers or antagonists) are used as synonyms in this specification, being sufficient for a compound to result in a decrease in the repressive activity of a miRNA to be considered an inhibitor, silencer, blocker or, in short, an antagonist thereof. And, taking into account the knowledge about the possibility of inhibiting miRNA function by targeting the mature miRNA, the precursor miRNA or the primary miRNA, as it is used in the present application, a compound could be considered an miRNA inhibitor, silencer, blocker or antagonist according to the present invention if it targets the mature miRNA, but also if it targets the precursor miRNA or the primary miRNA, provided that it is capable of producing a decrease in the endogenous activity of said miRNA.

Analogously to the definition of a miRNA antagonist, the effect produced by an inhibitor, silencer or blocker is called inhibition, silencing or blocking of the miRNA in different parts of the specification, while it is understood that any of these three terms imply and mean an antagonism of the action thereof. In some specific points, particularly when related to trials in which miRNA sponges have been used, the term "depletion" is also used to refer to the effect that occurs when such sponges are present, since it can be considered that the number of binding sites in these sponges leads to the binding thereto of most or practically all of the miRNA molecules with complementary sequences, resulting in the depletion of available miRNA molecules for interaction with other molecules or compounds in the cell where the sponges are present.

This invention preferably relates to specific antagonists of these miRNAs, which are also, in turn, oligoribonucleotides or molecules derived therefrom that include, among others, some of the usual chemical modifications that modify the oligoribonucleotide molecules to make them more resistant to degradation or bioavailable, such as modification of part or all nucleotides with 2'-methoxy (2'-O-methyl: 2'-OMe), 2'-O-methoxyethyl (2'-MOE) groups, and/or phosphorothioates. As used in this specification, oligoribonucleotides are the molecules that result from the binding of a maximum of 50 units of the monomers that give rise to the molecule abbreviated as RNA, monomers that are composed of a phosphate group, the nitrogenous bases adenine (A), cytosine (C), guanine (G) or uracil (U), and pentose known as ribose. Based on their widespread use, molecules whose units include nucleotide inosine are also considered within that definition.

As used in this invention, the term "oligoribonucleotide molecules" includes both oligoribonucleotides as such, as defined above, as well as the "oligoribonucleotide analogues". "Oligoribonucleotide analogues" are the molecules derived therefrom that incorporate some chemical modification in at least one of the ribonucleotide units that form them, either in the phosphate group, the pentose or one of the nitrogenous bases; the modifications consisting in the addition of non-nucleotide groups at the 5' and/or 3' ends are also included. By extension, for the purposes of this invention and as used herein, the terms "oligoribonucleotide molecule" and "oligoribonucleotide analogue" or "oligonucleotide analogue molecule" also include sponges of miRNAs or miRNA sponges, as it can be considered that the main constituent of the same are tandem repeats of oligonucleotides, characterized in that each of these oligonucleotides are in themselves or contain a binding site of a microRNA of interest.

With regard to the possible chemical modifications included in the oligoribonucleotide analogues, the term will be applied especially in the case of one or more of the usual modifications known to those skilled in the art of molecular biology, in terms of basic research and, in particular, in the search for therapeutic applications of these molecules. Information on such modifications can be found in reviews such as that by Kole et al. (Kole et al., 2012). In particular, for the purposes of the invention, of special interest (and considered to be included within the modifications that give rise to molecules within the scope of the invention) are those modifications, valid for oligoribonucleotides or ribonucleic acids of greater length, which give rise to RNA analogues with increased resistance to hydrolysis, and which are usually modifications in ribose, such as those resulting in: 2'-O-methyl-substituted RNAs (2'-methoxy modifications); 2'-O-metoxietil-substituted RNAs; LNAs ("Locked Nucleic Acids": locked nucleic acid, in which the ribose moiety is modified with an extra bridge connecting the 2' oxygen and the 4' carbon and locks the ribose in the 3'-endo conformation); BNAs ("Bridged nucleic acid"); PMOs (nucleic acids where ribose has been substituted by a carbonylchloride group), or PNAs ("Peptide Nucleic Acid": peptide nucleic acid in which the ribose-phosphate group is replaced by an amino acid moiety, so that the skeleton of the nucleotide analogue is a structure of repeat units of N-(2-aminoethyl)-glycine linked by peptide bonds). Also known are 2'fluoro modifications (2'F: introduction of a fluorine atome at the ribose 2' position), which differ from the 2'-MOE and 2'-OMe modifications in that it locks the sugar ring into a high 3'-endo conformation, which is often found in A-form duplexes (RNA structure) and results in exceptional affinity for target RNAs.

Thus, modifications that could be useful for the purposes of the present invention and that give rise to molecules comprised within the scope of the invention are those of the FANA oligos (Souleimanian et al., 2012), which are antisense 2'-deoxy-2'-fluoroarabinonucleic acids (2'F-ANA) that are usually used as antisense oligonucleotides and that, additionally to an efficient knock down or regulation of the target RNA in a high sequence specific manner, show an efficient delivery without an external source such as a transfection agent, formulation, conjugate or viral vector, what is called a gymnotic delivery (see, for instance, AUM Biotech web page for more detailed information: https://www.aumlifetech.com/technology-platform/). It is meaningful (as it is explained in AUM Biotech web page: www.aumbiotech.com) that FANA single-stranded antisense oligonucleotides elicit RNase H-mediated cleavage of target mRNA: this mode of mRNA knockdown is simpler than siRNA mediated knockdown and eliminates RISC-associated offtarget effects often observed with siRNA. Besides, and unlike siRNAs that are processed in the cytoplasm, FANA oligos can go into the nucleus and can be used to target RNA present within the nucleus.

Recently, also nucleotides with an additional type of chemistry are being used: the CRN ("Conformationally Restricted Nucleotides"), in which the ribose moiety is locked in a rigid conformation by means of a chemical moiety that acts as a connector, modification that is mainly used to obtain antagomiRs with new properties (see, for example, the information provided on the website: http://www.marinabio.com/pipeline/nucleic-acid-drugs/).

Also common, and considered included within the possible modifications that give rise to oligoribonucleotide analogues of the invention, are the modifications that give rise to phosphorothioate bonds, which are modifications that affect phosphate groups that are part of the "skeleton" of the nucleotide chain, giving rise to the introduction of a sulphur atom in substitution of an oxygen atom of the phosphate group that is not acting as a bridge between nucleotides; these modifications cause the bonds between nucleotides to be resistant to degradation by nucleases, so they are commonly inserted between the last 3-5 nucleotides at the 5' or 3' ends of oligonucleotides to inhibit degradation by exonucleases, increasing their stability. Phosphorothioate ribonucleotide analogues are usually represented by placing an r before the abbreviation of the base and by placing an asterisk after it (e.g., (rA*), whereas the 2'-O-methylated bases bonded to phosphorothioate can be represented with a letter m in front of its abbreviation and followed by an asterisk (e.g., mA*).

Because of its frequent use within the group of antimiRs, also included among the chemical modifications that give rise to the oligoribonucleotide analogues of the invention, is the 5' methylation of the nitrogenous base cytosine (C), which seems to increase the stability of the duplexes formed with the target.

Other chemical modifications are possible and known, which are also comprised within the possible modifications that give rise to oligoribonucleotide analogues. As can be deduced from the definition of "oligoribonucleotide molecules" and that of "oligoribonucleotide analogues", also included within the definition of oligoribonucleotide analogues are hybrid molecules, in which some units present modifications and others do not, as well as hybrids between analogues of nucleic acids and peptides or, even, hybrid molecules in which some of the nucleotide units are ribonucleotides (or analogues thereof) and others are deoxyribonucleotides (nucleotides in which the sugar is deoxyribose), as well as analogues of the latter, i.e. RNA-DNA hybrids and analogues thereof.

For purposes of this invention, included within the oligoribonucleotide molecules or oligoribonucleotide analogues are miRNA inhibitors, blockers or antagonists of the types known as antagomiRs, blockmiRs, antimiRs and miRNA sponges, and those known as FANA oligonucleotides, whose mechanism of action can be found to be described as analogous to that of blockmiRs in that their sequence is complementary to that of the mRNA, but that can be designed as antagomiRs, antimiRs or blockmiRs, provided that the appropriate chemical modifications of FANA oligonucleotides are present in the molecule. Also comprised within the concept of oligoribonucleotide molecules or oligoribonucleotide analogues useful for the purpose of the present invention and comprised within its scope are those miRNA inhibitors, blockers or antagonists that act on pri-miRNAs or pre-miRNAs, usually altering miRNAs biogenesis and having a negative effect on miRNAs activity, mainly due to a decrease of the active available miRNA.

Thus, for instance, Example 1 of this specification uses molecules that correspond to this group of compounds and that are formed by several units of ribonucleotides, or miRNA sponges, which are transcripts expressed from strong promoters that contain multiple binding sites to a microRNA of interest, placed in tandem. The miRNA sponges are usually designed so that they inhibit miRNAs with a complementary heptameric or octameric fragment (seed region), such that a single sponge construct can be used to block a whole family of miRNAs sharing the same motif, although they may also contain the entire target sequence for a specific miRNA. The term "sponge construct" is sometimes used interchangeably to refer to the vectors from which the miRNA sponges are expressed and to the RNA molecules expressed therefrom. For the sake of clarity, the present specification has attempted to reserve the term "sponge construct" for the vector from which the miRNA sponge is expressed as such or for the specific fragment of the vector that encodes the expressed miRNA sponge, but reference is made to the effect of these constructs when referring to the effects found when the expression of the corresponding miRNA sponges has occurred in the cells or tissues in the test.

Since miRNA sponges are not entirely specific, but can block, silence or inhibit several miRNAs that share the same motif, to avoid as much as possible unwanted effects and affecting genes that have no involvement in the DM1, in this invention specific inhibitors of groups of the so-called blockmiRs, antimiRs or antagomiRs, especially the latter, are preferred. All three cases relate to oligonucleotides with chemical modifications that prevent a series of molecules from binding to a specific place of a mRNA molecule, although there are some differences between them.

As used herein, blockmiRs are small RNAs with a special chemistry designed against the sequence that a particular miRNA detects in a particular messenger RNA (mRNA), so that, in principle, each one of them should only derepress the effect of that miRNA on that transcript, a very specific effect being expected. Therefore, they are designed so that they have a sequence that is complementary to that of a fragment of the mRNA sequence that serves as a binding site for a miRNA, in such a way that they usually bond at the 3' end of the untranslated region (UTR) of a mRNA, in other words, in the area where the endogenous miRNAs usually bond.

The antagomiRs, on the other hand, are generally used to silence endogenous miRNAs. Therefore, antagomiRs refer to small synthetic RNAs, chemically modified with respect to the corresponding RNA oligomer composed only of ribonucleotide units, and that are complementary to a target miRNA. Therefore, they can be considered oligonucleotide analogues that bind specifically to particular miRNAs and therefore act as miRNA inhibitors/blockers. As a miRNA can have many target transcripts, the use of antagomiRs can sometimes result in undesirable side effects, by affecting mRNAs that were not to be modulated. Typically, antagomiRs include chemical modifications in their units, compared to ribonucleotides, such as 2-O-methyl groups, phosphorothioates, and conjugated cholesterol moieties; they also commonly include at least one modification that either gives rise to some type of impediment to the performance of the Ago2 protein or to an imperfect pairing between the antagomiR and the target miRNA, thus avoiding the Ago2-mediated cleavage. As described by Wang et al. in their review of the implications of microRNAs in liver disease (Wang et al., 2012), it has been reported that antagomiRs inhibit their target miRNA, in a dose-dependent manner, in different tissues of mice when administered intravenously as naked molecules. Among other effects, it is known that an antagomiR of miR-221 was able to block the growth of xenografts of HCC tumours in mice and prolong their survival. The cutaneous pathway is also a common route of administration of antagomiRs.

For their part, antimiRs are usually complementary to only a part of the mature miRNA that is their target, the so-called seed region, but they bind to it with great affinity, because they present modifications that greatly increase the bond with their target, such as those of the LNAs described above, or, sometimes also, as has been mentioned, 5' methylation of the nitrogenous base cytosine (C), which also seems to increase the stability of the duplexes that are formed with the target. Rottiers et al. observed not only the effective inhibition of miRNA families using antimiRs directed to the seed region of these miRNAs, with only 8 units of nucleotide analogues with LNA-type modifications, but also the efficacy and safety of these treatments in the long-term in non-human primates. As also described by Wang et al., in the aforementioned reference (Wang et al., 2012), these small molecules present a potent activity in a whole range of tissues in mouse, rat, ape and chimpanzee after their systemic administration as naked molecules, at considerably lower doses than those of other inhibitors. AntimiR SPC3649, for example (Landford et al., 2010) has been used in Phase 2a clinical trials for patients with chronic hepatitis C virus infection (ClinicalTrials.gov No. NCT01200420).

As can be deduced from the above definitions, the design of microRNA inhibitors/antagonists is usually based on a short basic sequence of ribonucleotides, which may be the sequence complementary to the microRNA to be inhibited (this is usual in antagomiRs and antimiRs, as well as in microRNA sponges) or the sequence of the microRNA itself or a sequence complementary to a mRNA area to which the microRNA binds (case of blockmiRs). As used in this specification, it is understood that two chains of nucleotide molecules are 100% complementary (or, as is expressed in a more abbreviated way herein, that their sequences are complementary) when the nucleotide or nucleotide analogue sequence of one of them, read in the 5'-3' sense, is the sequence of nucleotides or nucleotide analogues that present the nitrogenous bases which pair with the nitrogenous bases of nucleotides or nucleotide analogues of the other sequence, read in the 3'-5' sense. That is to say, the sequence 5'-UAGC-3' would be complementary to the sequences 3'-AUCG-5' (in the case of being the ribonucleotide or ribonucleotide analogue units) and 3'-ATCG-5' (in the case of being the deoxyribonucleotide or deoxyribonucleotide analogue units), which would be, respectively, sequences 5'-GCUA-3' and 5'-GCTA-3' read in the 5'-3' sense. In some cases, particularly in the design of antimiRs, importantly the antagonist molecule should comprise a fragment that is identical to the complementary sequence to that of the seed region of the microRNA to be antagonized, at least with regard to the complementarity of the nitrogenous bases. And often, especially in the case of antagomiRs and antimiRs, modifications are incorporated to the corresponding ribonucleotide units, which mainly affect the ribose moiety and/or phosphate, modifications that are difficult to depict in the usual representations of nucleotide sequences, in which the nucleotide present in a given position is identified by the abbreviation of the nitrogenous base that is part of it. Therefore, in the present invention, there are compared molecules of microRNA antagonists that refer to the percentage of identity between the sequences of the nitrogen bases of the ribonucleotide or ribonucleotide analogue units present in these units, as this is what indicates whether two molecules or sequence fragments are designed from the same original basic ribonucleotide sequence, although different chemical modifications may have been included in the ribonucleotides in each case.

To design the antagonist molecules, it is important to note that there is sufficient complementarity with the endogenous molecules to which they must bind so that the desired effect of inhibition/antagonism/silencing is actually produced. In this sense, examples can be taken into account where the "typical" complementarity between a miRNA and its target may be 50% (see, for example, the reference http://mirtarbase.mbc.nctu.edu.tw/php/detail.php?mirtid=MIRT000125#target), therefore it is advisable that the oligoribonucleotide molecule of the invention comprises a fragment of ribonucleotide or of ribonucleotide analogue unit sequence, in which the sequence of the nitrogenous bases of the ribonucleotide or ribonucleotide analogue units is at least 50% (or at least 55%, 60%, 70%, 80%, 85%, 90%, 91%, 92%, 93%, 94%, 95%, 96%, 97%, 98%, 99% or 99.5%, or 100%) identical to the sequence complementary to that of the fragment of the endogenous molecule with which it should pair, that is to say, to the sequence of endogenous microRNA with which it should bind (in the case of antagomiRs and the repeat sequence of sponge miRNAs) or the sequence of the messenger mRNA fragment (in the case of blockmiRs). In the case of antagomiRs, whose length is roughly equal to that of the miRNAs whose action is to be antagonized, it is especially preferred that the sequence of the nitrogen bases of the ribonucleotide or ribonucleotide analogue units is at least 80% (or at least 85%, 90%, 91%, 92%, 93%, 94%, 95%, 96%, 97%, 98%, 99% or 99.5%, or 100%) identical to the sequence complementary to that of the endogenous microRNA to be antagonized; this is the criterion that has been followed for the design of antagomiRs against human microRNAs miR-218-5p and miR-23b-3p. In the case of antimiRs, the most important thing is that they comprise a fragment in which the sequence of nitrogenous bases of nucleotides or nucleotide analogues is complementary (preferably, 100% complementary) to the sequence of nitrogen bases of the nucleotides of the seed region of the mature miRNA which is their target, so the complementarity in the rest of nucleotides or nucleotide analogues that are present in the antimiR, if any, is less important.

Sequence alignment for comparison can be carried out with Smith and Waterman's algorithms, Adv. Appl. Math. 2:482 (1981); o Needleman y Wunsch, J. Mol. Biol. 48:443 (1970); using the Pearson and Lipman similarity search method, Proc. Natl. Acad. Sci. 85:2444 (1988); or through computer applications based on these algorithms and methodologies, including but not limited to: CLUSTAL, in the PC/Gene program by Intelligenetics (Mountain View, Calif., USA); GAP, BESTFIT, BLAST, FASTA, and TFASTA in the software package from Wisconsin Genetics (Genetics Computer Group (GCG), Wisconsin USA). In particular, the BLAST family programs, which are based on the algorithm by Altschul et al. (.) (Altschul et al., 1990), are of public access (for example, through the webpage of the U.S. National Center for Biotechnological Information: http://blast.ncbi.nlm.nih.gov/Blast.cgi) and can be used to carry out searches and calculations of identity, especially for the purposes of the invention, BLASTN, dedicated to nucleotides.

As can be seen in the assays described and reported in the examples of this specification, the present inventors have started from proof of concept in a Drosophila melanogaster DM1 model, in which CUG trinucleotide repeats overexpressed in the muscle. This model was used to explore the therapeutic potential of specific microRNA (miRNAs) silencing by promoting the expression of muscleblind. The tests carried out with this model, described in Example 1, show that it is possible to up-regulate endogenous Drosophila muscleblind proteins by sequestration of miRNAs that negatively modulate their expression, specifically by the use of "sponge" constructs. To do this, the basis was a set of miRNA identified as potential Muscleblind regulators finding that only the specific silencing of two of the miRNAs of the initial set, dme-miR-277 or dme-miR-304, gave rise to the desired direct effect: an increase in levels of both the Muscleblind protein and the corresponding mRNA. This up-regulation resulted in the reversal of several erroneous splicing events and, thus, the rescue of several phenotypes similar to DM1 symptoms, such as the reduction of muscular atrophy. The flies tested showed an improvement in the muscular function in flight and surface ascent tests and an increase in life expectancy.

Analogously, the present specification describes the identification, in HeLa cells, of potential miRNAs that could negatively regulate MBNL in humans (MBNL1 and/or MBNL2), the selection of those that actually appeared to have regulatory effects, the verification in animal models, specifically mouse, of their expression in tissues of interest generally affected in cases of DM1, the design of inhibitors (specifically antagomiRs) for some specific miRNAs, verification of the effectiveness of the same to increase the expression of MBNL1 and/or MBNL2 in human myoblasts and verification of correspondence with the rescue of several events of alternative splicing typically altered in myoblasts in patients suffering from DM1. Such assays have been complemented by verifying the activity of inhibitors (particularly antagomiRs) in a mouse DM1 model, where it has been observed that the assayed antagomiRs reach skeletal muscle, increase Mbln protein expression, rescue missplicing of muscle transcripts, improve muscle histopathology and reduce myotonia grade. Also provided in the present application are assays carried out with antimiRs and blockmiRs, where it has been found that antimiRs and blockmiRs show a relatively low toxicity, and that blockmiRs, particularly those targeting miR-23b activity, give rise to significant increase of MBNL1 expression. These tests, together with the proof of concept carried out in Drosophila, demonstrate the effectiveness of the strategy designed.

The proof of concept carried out in Drosophila, described in Example 1, is also significant because it showed some notable facts to take into account for the design of miRNA-specific inhibitors, blockers or silencers, particularly for their application in the treatment of DM1 in mammals, especially in humans. In particular, the following are noteworthy:

As commented, although the basis was a set of miRNAs identified as potential muscleblind regulators based on previous data of the present inventors and on bioinformatic analyses, only the silencing of two them, dme-miR-277 (SEQ ID NO: 29) and dme-miR-304 (SEQ ID NO: 30), resulted in the up-regulation of the expression of the Drosophila muscleblind gene, both in terms of mRNA and of the proteins themselves. Therefore, the mere identification of structural motifs that may indicate that a miRNA may have an effect on the MBNL1 and/or MBNL2 expression regulation, it does not guarantee that it is a miRNA with a negative effect on its expression or that the design of a specific inhibitor thereof may result in the desired effects on the increase of levels of one protein and/or the other, especially when the aim is that this increase in the protein levels should occur in the appropriate tissues and should be accompanied by an improvement in DM1 symptoms.

It is also interesting to note that the quantitative analysis confirmed that each sponge construct gave rise to the increase of the levels of different Muscleblind isoforms. Interestingly, both sponge construct, miR-277SP and miR-304SP (the sponge constructs specifically designed to silence dme-miR-277 and dme-miR-304), were able to negatively regulate the expression of mblB and mblC isoforms, respectively, instead of increasing the expression, suggesting some type of inter-isoform regulation, as previously demonstrated for MBNL proteins (Kino et al., 2015; Terenzi et al., 2010). This fact induced the present inventors to consider the identification in human cells of miRNAs that were either inhibitors of MBNL1 or of MBNL2 or of both, to control possible regulatory or compensatory effects between the two proteins or between the miRNAs that regulate their expression.

Immunodetection tests of the protein in the muscular tissue of flies expressing one of the sponge constructs, miR-304SP and miR-277SP, showed the overexpression of muscleblind in both cases, although in different subcellular locations: miR-277SP caused an increase preferably in sarcomeric bands and miR-304SP in the nuclei. It is noteworthy that neither of these cases detected the retention of muscleblind in ribonuclear foci which are not detected in IFM sections of the fly thorax using a probe designed to detect the expansions ("CAG" probe). Finally, consistent with previous knowledge that indicates that the isoform MblC is located in the nucleus and with preferential regulation of the expression of MblC by miR-304SP, it was confirmed that the expression of miR-304SP allowed to rescue a number of erroneous splicing events dependent on Muscleblind. Taking them as a whole, these data confirm that the up-regulation of muscleblind achieved by silencing specific regulator miRNAs is sufficient to rescue the critical molecular characteristics altered in DM1 models in flies.

Example 1 also describes the positive effect of the expression of the sponge constructs miR-277SP and miR-304SP on the recovery of muscular atrophy, which is a characteristic phenotype of DM1.

Expressing the sponge constructs with the driver Mhc-Gal4, the effects of muscleblind overexpression in the long term were also tested. In the control flies, it was observed that the expression of miR-304SP, caused a 6-fold increase in the relative expression of muscleblind and had no effect on the muscle area, the survival or the function of the locomotive apparatus. However, the expression of miR-277SP, which produced a 15-fold up-regulation of muscleblind, caused a significant reduction in the muscle area, which correlates with a decreased landing height. In a background expressing CTG, however, the expression of any of the sponge constructs caused beneficial effects, suggesting that the limited overexpression of transcripts of additional natural targets of the blocked miRNAs is negligible compared to the positive effects of stimulating muscleblind expression. This is important, because deleterious effects of miR-277SP could occur by overexpression of several of its targets, as well as Muscleblind, since dme-miR-277 is one of the miRNAs with the highest expression in the muscle. Previous studies have confirmed that the long term overexpression of MBNL1 in mouse models is well tolerated when limited to the skeletal muscle. MBNL1 overexpression, increased in the range from 10 to 17 times, caused no detectable histopathology or functional anomalies (Chamberlain & Raum, 2012). These results were believed to support the strategy of attempting to inhibit/silence/decrease/ antagonize the activity of specific miRNAs involved in the negative regulation of MBNL1 and/or MBNL2 proteins in mammals, particularly humans, as a means to alleviate the symptoms of DM1, without producing undesirable side effects on other functions of the individual who is in need of treatment.

Thus, these results indicated that the blocking of miRNAs repressors of MBNL in humans or other mammals could also reduce the symptoms of DM1, providing a proof of concept of the therapeutic potential of the up-regulation of muscleblind through specific miRNA blockers in patients with DM1. Thus, the study with the Drosophila model of DM1 reported in the present specification lays the bases for the evaluation of blockers of miRNAs which repress the expression of muscleblind (or, rather, of homologous proteins in mammals such as humans) as a valid and effective therapeutic target for the treatment of DM1.

Based on this, the present inventors undertook a study of the identification of possible miRNAs repressors of human MBNL1 and/or MBNL2 proteins, to later verify if a similar strategy could be used to inhibit/block one or more of these miRNAs to increase the levels of the MBNL1 and/or MBNL2 proteins, and thus, rescue characteristic phenotypes of DM1, as evidence that the inhibition of these miRNAs could serve to treat typical symptoms of this disease.

As described in Example 2, an initial screening was performed to identify potential repressors of one of these genes or both, which identified a total of 23 candidate microRNAs, among which a pre-selection was made from bioinformatic programs, selecting those for which binding targets had been predicted in the 3' UTR regions of one or both genes. However, the validation tests carried out indicated that only some of the pre-selected microRNAs, effectively resulted in a decrease in the levels of the corresponding protein (MBNL1 or MBNL2) product of the genes that in principle were regulated by the miRNA, even though the presence of binding targets for the corresponding microRNA in the untranslated 3' region (3' UTR) was confirmed by complementary bioinformatic applications. The decrease of the levels of protein produced, in the cases in which it actually existed, was not the same for all the microRNAs, being more pronounced in some cases, highlighting those of the microRNAs miR-23b-3p (referred to abbreviated in the specification as miR-23b) and miR-218-5p (abbreviated as miR-218). (It must be noted that the abbreviations miR-23b and miR-218 have been used in certain points of the present application not only to denote the mature forms miR-23b-3p and miR-218-5p, but also to refer to the pri-miRNAs and pre-miRNAs that give rise to such mature forms). This shows, as already noted in the previous tests carried out in the Drosophila model, that the identification of hypothetical binding targets in the 3'UTR of the messenger RNA of a gene or of other motifs that may indicate a supposed interaction, does not guarantee or make expectable that a microRNA actually is a gene modulator, preferably direct, nor that blocking or inhibiting such microRNA actually results in the desired modulation that, in this case, was an increase in the levels of the MBNL1 and/or MBNL2 protein.

In addition, it was verified whether the pre-selected miRNAs were expressed in the organs most affected by the characteristic symptoms of the disease, such as the central nervous system organs, such as the brain, the cerebellum or the hippocampus, as well as the skeletal muscle and the heart. The tests performed with different mouse tissues showed that the expression of the endogenous microRNAs of this animal miR-23b and miR-218 in different tissues related to the listed organs (forebrain, cerebellum, hippocampus, heart, quadriceps and Gastrocnemius) were far higher than those of the remaining pre-selected microRNAs, especially in the case of miR-23b, which was far higher in all tissues. These data indicate that the inhibition of the same microRNAs could serve to treat cases of myotonic dystrophy 1 in other mammals.

Gene expression determinations were also conducted from muscle biopsies in humans, observing that the miR-218 and miR-23b levels were clearly increased in DM1 patients with respect to controls not afflicted by the disease. An increase of the miR-218 in fibroblasts obtained from patients with DM1 with respect to controls was also noted. These data are interesting as, taken in conjunction with the efficacy tests carried out with antagomiRs in Example 3, they indicate that the cultures of established lines or the primary cultures of cells obtained from tissues of interest of patients, such as skeletal muscle myocytes, can be useful to perform tests and to check the efficacy of possible blockers or inhibitors of different miRNAs and to observe if certain molecular abnormalities characteristic of the disease show an improvement or are alleviated by the inhibitors tested, as an indication of a palliative effect on symptoms of the disease. And that is important to facilitate the studies, since the existing mouse models do not reproduce all the symptoms of the human disease, but mainly the symptoms related to muscular dysfunction. And, indeed, at the end of Example 3, there are described assays where it can be seen that miR-23b and miR-218 upregulate MBNL proteins and restore their normal subcellular distribution in DM1 myoblasts. Finally, the verification of antagomiR effectivity in a mouse DM1 model described in Example 4 showed that the assayed antagomiRs reach skeletal muscle, increase Mbln protein expression, rescue missplicing of muscle transcripts, improve muscle histopathology and reduce myotonia grade, also finding that the specific antagomiRs used are effective at doses lower than those previously reported in muscle (Krutzfeldt et al., 2005; Dey et al., 2012). By inhibiting miR-23b and miR-218 with antimiRs in mouse muscle it was possible to upregulate MBNL1 and MBNL2 protein levels by approximately over 2- and 4-fold respectively. Importantly, MBNL protein upregulation through mir-23b or miR-218 silencing was well tolerated in mice, which had no detrimental phenotype during the four days of treatment. Furthermore, as antagomiRs act on mature MBNL transcripts, they are not expected to directly influence the set of MBNL proteins isoforms.

These tests, together with the tests to check the direct interaction of the microRNAs miR-218 and miR-23b with corresponding messenger mRNAs (qv Gaussia luciferase test), resulted in the choice of these microRNAs as the microRNAs of preference to be inhibited/antagonized, for which to develop inhibitors/antagonists.

This conclusion has been confirmed by the assays shown in Examples 5 and 6, where assays with blockmiRs, antimiRs and FANA oligonucleotides directed against miR-218 and miR-23b are described. In Example 5, it can be seen that blockmiRs and antimiRs showed a low toxicity in DM1 fibroblasts, making possible to increase their concentration for their use. However, antagomiRs showed to work better than antimRs. When miR-23b target was blocked, a significant increase of MBNL1 and MBNL2 was observed; the same did happen when miR-218 target was blocked, but their low toxicity makes possible to increase the administered concentration, which will probably result in the observation of an effect. As shown in Example 6, FANA RNA silencing and regulation technology showed that FANA oligonucleotides at 250 nanoM or 1 microM range are not very toxic to DM1 myoblasts and, although the antagomiRs of previous Examples seem to be more potent for MBNL1, at least the FANA oligonucleotide related to miR-23b increased MBNL1 and MBNL2 levels, confirming again the feasibility of the general approach of the present invention: the use of miR-23b and/or miR-218 antagonists for use in the treatment of myotonic dystrophy type 1.

It must be understood, as above indicated, that targeting the pri-miRNA and/or the pre-miRNA of miR-23b or miR-218 and altering their biogenesis so that the levels of said microRNAs is decreased should also result in a decrease of their activity. Therefore, for the purpose of the present invention, an antagonist of miR-23b or an antagonist of miR-218 must be understood to comprise not only those molecules capable of acting the mature forms, but also those molecules capable of acting on the pre-miRNA or the pre-RNA and decreasing the levels of the mature forms of miR-23b or miR-218. In order to design them, it must be taken into account that:

The primary microRNA (pri-miRNA) of hsa-mir-23b-3p is an intergenic microRNA which is inside the transcript of gene C9orf3 (ENSG00000148120), which gene (chr9:97488983-97849441) could be considered the pri-miR of miR-23b. Additionally to the mature sequence of miR-23b, there are other microRNAs that can be considered part of the same cluster, because they are close together within the same genomic region encoding for miR-23b mature microRNA (hsa-mir-27b: chr9:97847727-97847823 [+], hsa-mir-3074: chr9:97848296-97848376 [−] and hsa-mir-24-1: chr9: 97848303-97848370 [+]. Preferably, in order to avoid undesired secondary effects, if it is desired to have an antagonist targeting this pri-miRNA, it would be preferable to select it so that the other three miRNAs of the same cluster are not affected. For that same reason, it is preferred that an antagonist of miR-23b is designed so that it is an antagonist of the mature miRNA and/or of the pre-miRNA.

The microRNA precursor (pre-miRNA) of hsa-mir-23b-3p corresponds to genomic positions hg19 chr9: 97847490-97847586 [+] and to the sequence: CUCAG-GUGCUCUGGCUGCUUGGGUUCCUGGCAUGC-UGAUUUGUGACUUA AGAUUAAAAUCA-CAUUGCCAGGGAUUACCACGCAACCACGAC-CUUGGC (SEQ ID NO: 81). As this is a longer sequence than that of hsa-mir-23b, it is possible to design antagonist specific to the pre-miRNA.

hsa-mir-218-5p has two genomic position encoding for it and two precursor pre-miRNAs, Pre-miR-218-1 (chr4: 20529898-20530007): GUGAUAAUGUAGCGA-GAUUUUCUGUUGUGCUUGAUCUAACCAU-GUGGUU GCGAGGUAUGAGUAAAACAUG-GUUCCGUCAAGCACCAUGGAACGUCACGC AGCUUUCUACA (SEQ ID NO:82), and Pre-miR-218-2 (chr5:168195151-168195260): GACCAGU-CGCUGCGGGGCUUUCCUUUGUGCUUGAUC-UAACCAUGUGGUG GAACGAUGGAAACGGA-ACAUGGUUCUGUCAAGCACCGCGGAAAGC-ACCGU GCUCUCCUGCA (SEQ ID NO:83). Both precursors could be used for the design of antagonists The primary microRNA (pri-miRNA) of hsa-mir-218 is an intergenic microRNA which is inside the transcript of gene SLIT2 (ENSG00000145147: chr4:20254883-20622184) for miR-218-1 and inside the gene SLIT3 (ENSG00000184347, chr5:168088745-168728133 for miR-218-2). No other mature miRNAs are part of the same cluster. Then, in the case of has-miR-218, both the pre-miRNAs or the pri-mRNAs could be envisaged as possible targets of antagonists aimed to increased MBNL protein levels.

The microRNAs miR-218-5p and miR-23b-3p, unlike other microRNAs initially tested, have in common that they fulfil the characteristics that were intended to be met by the candidate microRNAs for the development of inhibitors against them, in order to palliate characteristic symptoms of DM1, such as:

Both appear to be microRNAs repressors of at least one of the genes to be acted on, the human genes equivalent to the Drosophila muscleblind gene, MBNL1 or MBNL2, repressors that, according to the tests in Example 2, have a direct action on the corresponding messenger RNAs, which decreases the risk of their potential inhibitors affecting other pathways or their effect being diminished by the endogenous regulation of necessary intermediate steps until their action on the target genes.

Both show expression in tissues of organs related to characteristic symptoms of the disease, such as muscle alterations, both related to mobility and cardiac disorders, or neurological disorders. In particular, both show a clear increase in their levels in samples of muscle biopsies from patients with DM1, therefore, the blocking or inhibition tests of these microRNAs in cells and the observation of their effects on molecular alterations related to the disease, such as alternative splicing alterations, may be indicative of the effectiveness of their blocking or inhibition to palliate symptoms of the disease.

In spite of these coincidences, which show that the preferential choice of these microRNAs to proceed to their blocking or inhibition responds to a single inventive concept, the significant difference between them should be noted, whereby miR-218 is only a repressor of MBNL2, while miR-23b is a repressor of both MBNL1 and MBNL2. In addition, miR-218 is significantly increased in patient muscle biopsies (miR-23b shows an upward trend, although not significant in the experimental data available) so that its blocking not only anticipates the derepression of MBNL2, which is already known to be a therapeutic target, but will mitigate the downstream effects that the overexpression of miR-218 could be causing on other muscle transcripts, thus constituting a therapeutic target in itself.

Furthermore, although the trials presented in this specification confirm the expression of both microRNAs in tissues of interest related to symptoms of the disease, the search of the expression tissues in the database miRGator, version 3.0 (v3.0) (http://mirgator.kobic.re.kr) reveals some differences between the two microRNAs, whereby miR-23b presents a wider range of tissues. Specifically, according to miRGator v3.0, miR-218 is expressed in: adipose tissue, brain, central nervous system, kidney, heart, liver and biliary system, lung, pharynx, nasopharynx, nose, placenta, spleen, stem cells, testicle, uterus; miR-23b, on the other hand, is expressed in: the central nervous system, gastrointestinal tract, adipose tissue, breast, bladder, heart, keratinocytes, kidney, liver and biliary system, lung, lymphoid cells, nose, pharynx, placenta, prostate, skin, spleen, stem cells, testicle, thyroid gland and uterus. Thus, a possible embodiment of the invention considered is an oligoribonucleotide and/or oligoribonucleotide analogue molecule which is an antagonist of a microRNA that down-regulates the expression of the human gene MBNL1 and/or MBNL2, or a mixture of two or more of said molecules and that is expressed at least in one or more organs selected from the group of the brain, cerebellum, hippocampus or other organ of the central nervous system, skeletal muscle, heart, adipose tissue, kidney, liver and biliary system, lung, pharynx, nasopharynx, nose, placenta, spleen, testicle, uterus, gastrointestinal tract, breast, bladder, prostate, skin, keratinocytes and lymphoid cells or in one or more cells of a primary culture from one of those organs or of an established cell line derived from one of those organs (including induced pluripotent stem cells, known by the acronym IPSCs) or stem cells from one of these organs. The choice of the specific microRNA to be antagonized, in particular, the choice specifically between the human microRNA-218-5p or the human microRNA-23b-3p, will also determine the range of tissues where the antagonistic effect can be exerted. On the other hand, the administration of the antagonist through a possible expression vector thereof allows to direct the expression to a tissue or group of specific tissues according to the tropism of the base vector itself and/or by choosing control elements that give rise to the expression of the coding sequence linked to them only in specific tissues. In addition, some specific dosage forms may favour greater access to one or other organs. Thus, also a possible embodiment, combinable with any other, of the aspect of the present invention more directly referring to the therapeutic application thereof, could be defined as: use of one of the oligoribonucleotide and/or oligoribonucleotide analogue molecules of the invention, a mixture of two or more of them, or a composition comprising at least one of said molecules, for the manufacture of a medicinal product for the treatment of myotonic dystrophy type 1 by inhibition or antagonism of the action of a microRNA that down-regulates the expression of the human gene MBNL1 and/or MBNL2 in at least one or more organs selected from the group of the brain, cerebellum, hippocampus, or other central nervous system organs, skeletal muscle, heart, adipose tissue, kidney, liver and biliary system, lung, pharynx, nasopharynx, nose, placenta, spleen, testicle, uterus, gastrointestinal tract, breast, bladder, prostate, skin, keratinocytes and lymphoid cells or stem cells from one or more of these organs. Since there is special preference for the inhibition or antagonistic action on human microRNA-218-5p, it is also preferred because the organ or organs are selected from the group of the brain, cerebellum, hippocampus or another organ of the central nervous system, skeletal muscle, heart, adipose tissue, kidney, liver and biliary system, lung, pharynx, nasopharynx, nose, placenta, spleen, testicle and uterus or stem cells from one of these organs, while the choice of miR-23b-3p allows the possibilities of choice to be extended, according to current knowledge, at least to the gastrointestinal tract, breast, bladder, prostate, skin, keratinocytes and lymphoid cells or stem cells from one or more of these organs, or combinations thereof, as desired or appropriate.

Human microRNAs miR-218-5p (miR-218) and miR-23b-3p (miR-23b) also differ in the sequence of ribonucleotides that form them, as well as in their seed region, which must be taken into account for the design of specific inhibitors/silencers/antagonists for each one of them. The sequences of their mature versions are shown below, wherein the seed region of each of them appears in bold, and their access code (Mimat) in the miRbase database (www.mirbse.org):

```
miR-128-5p (MIMAT000275):
                                        (SEQ ID NO: 3)
5'- UUGUGCUUGAUCUAACCAUGU-3' miR-23b-3p (MIMAT0000418):
                                        (SEQ ID NO: 4)
5'-AUCACAUUGCCAGGGAUUACC-3'
```

Although the tests carried out in the Drosophila model demonstrated the feasibility of inhibiting the action of repressor microRNAs by means of microRNA sponges, and the tests on the binding of the microRNAs miR-218 and miR-23b to 3' UTR indicated that the development of blockmiRs is also a possible strategy for the blocking/inhibition of the action of the microRNAs miR-218 or miR23b, the present inventors preferred to opt for antagomiRs, because, as explained above, the chemical modifications usually made on them give rise to an increase in the stability, which is interesting for their possible direct administration in human beings, as well as because of the addition of lipophilic or lipidic moieties that are often added to their ends, which usually facilitates their entry into the cells. That is why antagomiRs have been the inhibitors of preference with which the tests were developed, among the possible options for the development or identification of an oligoribonucleotide and/or oligoribonucleotide analogue molecule that is an inhibitor of a microRNA that down-regulates the expression of the human gene MBNL1 and/or MBNL2, for use in the treatment of myotonic dystrophy 1, and especially the inhibitors of the human microRNA-218-5p or of the human microRNA-23b-3p. But Examples 5 and 6 of the present application show that blockmiRs and antimiRs could be also designed for use with the same purpose and that they could be a useful alternative in some cases, since their toxicity is lower, what allows to think of increasing the administered concentration. Similar comments about their feasibility of use could be done regarding FANA oligonucleotides although, in that particular case, the fact that they need no transfection reagent might made of them of option of choice in certain cases.

As noted in Example 3, the specific antagomiRs developed, called antagomiR-218 and antagomiR-23b, present certain chemical modifications typical in this type of oligoribonucleotide analogues, such as the 2'-O-methyl (2'-methoxy) modifications in all ribose moieties, the substitution of some phosphate bonds between the analogous monomeric units of nucleotides by phosphorothioate or the incorporation of cholesterol moieties at one end of the molecule, specifically at the 3' end, although, as detailed above, other modifications are possible, which would also produce molecules compatible with this invention. Also the specific blockmiRs and antimiRs used in Example 5 present certain chemical modifications, such as the substitution of some phosphate bonds between the analogous monomeric units of nucleotides by phosphorothioate, 2'-O-methyl (2'-methoxy) modifications in many ribose moieties and, additionally, the presence of some LNA nucleotides, which make them stable molecules suitable for in vivo administration.

The antagomiRs-23b and 218 proved to be able to penetrate the cells in the transfection experiments carried out. Toxicity tests showed that concentrations giving an appreciable signal of detection of these antagomiRs in cells were lower than the inhibitory concentration that kills 10% of the cells (IC10) which supports their safety and their chances of becoming candidate molecules for use in the treatment of myotonic dystrophy 1, as well as allowing test continuation.

The antimiRs assayed in Example 5 seemed to be even less toxic than antagomiRs in DM1 fibroblasts, but they seem to work not so well as antagomiRs for the modification of MBNL protein expression.

The dose response trials performed in myoblasts of DM1 patients with one or other antagomiR, at different doses, showed that these antagomiRs are able to reverse the aberrant splicing of some genes characteristically having that process altered in DM1 patients, which supports their use for the preparation of a medicinal product for the treatment of myotonic dystrophy 1, particularly to alleviate symptoms of the disease, especially symptoms related to muscular dysfunction. There was no absolute coincidence between the events reversed by one or the other antagomiR, nor on the preferential concentrations, so the combination of both could be interesting in some cases, although in others there may be preference for antagomiR-218.

Given the stability of the antagomiRs, the antimiRs and the blockmiRs and, among them, FANA oligonucleotides, direct administration to human beings can be considered, for example via subcutaneous or systemic routes, preferably intravenously, for example dissolved or suspended in a pharmaceutically acceptable carrier, such as water or an aqueous solution such as saline or phosphate buffer. The composition in which they are administered may contain pharmaceutically acceptable excipients. In the particular case of FANA oligonucleotides, for in vivo delivery, resuspension of FANA oligonucleotides in sterile water or saline buffer is recommended (see, for instance, the information provided in: https://www.aumbiotech.com/InVivo), and a dose between 3-30 mg/kg might be appropriate, although other concentrations could be more suitable for organ or intratumoral delivery. As other oligonucleotides, FANA oligos can be administered via different routes: intravenous (IV), intraperitoneal (IP), intradermal (ID), intratumoral (IT), intranasal (IN), intratracheal, hydrodynamic tail injection, inhalation, or local organ delivery.

Also included within the scope of this invention are compositions that comprise: one of these antagomiRs or their mixtures, one as well as any other antagomiR directed against the human microRNA-218-5p or the human microRNA-23b-3p or mixtures thereof, or in general any oligoribonucleotide and/or oligoribonucleotide analogue molecule that is an inhibitor of one of these microRNAs or of another microRNA that down-regulates the expression of the human gene MBNL1 and/or MBNL2, including any one or a mixture of any of the blockmiRs, antimiRs or specific FANA oligonucleotides used in the Examples of the present application, and also including compositions which also comprise a pharmaceutically acceptable carrier and/or excipient. In addition, given the direct relationship between the expression vectors that express miRNAs sponges or, even, precursors of mature microRNAs that finally have a repressive effect, also comprised within the scope of this invention is a composition that comprises an expression vector of one of said oligoribonucleotide molecules, in particular the vectors comprising the coding sequence of a microRNA sponge comprising multiple tandem sites complementary to the human microRNA-218-5p or the human microRNA-23b-3p or a mixture of multiple tandem binding sites complementary to each one of them.

For its clinical application, the compositions of this invention, which will then be considered pharmaceutical compositions of this invention, can be prepared in an appropriate form for the desired application. As collected in publications also related to the clinical application of inhibitors/antagonists of microRNAs, such as the international application WO2012148373A1, this will generally imply the preparation of compositions that are essentially pyrogen-free, as well as free of other impurities that could be detrimental to humans or animals. The object of said international application WO2012148373A1 are compounds analogous to those of the present invention and therapeutic applications thereof, therefore, information on forms of preparation and presentation of pharmaceutical compositions, possible appropriate carriers for administration, or forms and routes of administration may be considered applicable to this invention and may be taken as a reference for the compositions of this invention. Some of said information is reproduced below.

In one possible embodiment, the pharmaceutical composition comprises an effective dose of an inhibitor or antagonist of the human microRNA-218-5p or of the human microRNA-23b-3p or a mixture thereof. For example, the pharmaceutical composition may include an inhibitor/antagonist of the human microRNA-218-5p or of the human microRNA-23b-3p, or mixtures thereof. Preferably, the inhibitor/antagonist of the human microRNA-218-5p present is the antagomiR type inhibitor used in the examples of this invention (represented by SEQ ID NO:10) and the inhibitor/antagonist of the human microRNA-23b-3p present is the antagomiR type inhibitor represented by SEQ ID NO:11. It is also a preferred that the inhibitor/antagonist of the human microRNA-218-5p present and/or the inhibitor/antagonist of the human microRNA-23b-3p present is any of the blockmiRs or antimiRs type inhibitor used in Examples 5 or 6 of the present application. More preferably, the inhibitor(s)/antagonist(s) present will be present at a concentration that allows the administration of a therapeutically effective dose.

An "effective dose" or "therapeutically effective dose" is a sufficient amount to achieve a beneficial or desired clinical outcome. An effective dose of an inhibitor/antagonist of a microRNA, according to previous results obtained with molecules directed against other microRNAs, can be from approximately 1 mg/kg to approximately 100 mg/kg, from approximately 2.5 mg/kg to approximately 50 mg/kg, or from approximately 5 mg/kg to approximately 25 mg/kg. The precise determination of what would be considered an effective dose can be based on individual factors for each patient, including size, age, and the nature of the inhibitor or antagonist (for example, if it is an expression construct, an antagomiR or antimiR type oligoribonucleotide analogue . . . ). Therefore, the dosages can be easily determined by ordinary experts skilled in the art based on this description and the knowledge in the art. It may be necessary or convenient to administer multiple doses to the subject during a particular treatment period, administering doses daily, weekly, monthly, every two months, every three months or every six months. In certain embodiments, the subject receives an initial dose at the beginning which is larger than one or more subsequent doses or maintenance doses.

Colloidal dispersion systems, such as macromolecule complexes, nanocapsules, micro-spheres, pearls and lipid-based systems that include oil-in-water emulsions, micelles, mixed micelles, and liposomes, can be used as administration vehicles of the inhibitors/antagonists of this invention, with which the pharmaceutical composition of the invention is formed. Commercially available fatty emulsions that are suitable for delivery of oligoribonucleotide molecules to a subject include Intralipid®, Liposyn®, Liposyn® II, Liposyn® III, Nutrilipid, and other similar lipid emulsions. A preferred colloidal system for use as an in vivo administration vehicle is a liposome (i.e. an artificial membrane vesicle). The preparation and use of such systems are well known in the art. Exemplary formulations are also described in U.S. Pat. Nos. 5,981,505; 6,217,900; 6,383,512; 5,783,565; 7,202,227; 6,379,965; 6,127,170; 5,837,533; 6,747,014; and WO03/093449, which are included here by reference in their entirety.

Another possibility, as previously mentioned, is to prepare the pharmaceutical compositions of the invention using appropriate salts and buffers to make the administration vehicles stable and to assist in the capture by the target cells. The compositions of this invention can be aqueous compositions that comprise an effective amount of the administration vehicle and which comprise either the oligoribonucleotide molecules of the invention, independently or forming liposomes or other complexes, or expression vectors thereof, dissolved or dispersed in a pharmaceutically acceptable carrier or aqueous medium. The expressions "pharmaceutically acceptable" or "pharmacologically acceptable" refer to molecular entities and compositions that do not produce any adverse, allergic or other reactions when administered to an animal or human being. As used herein, "pharmaceutically acceptable vehicle" includes solvents, buffers, solutions, dispersion media, coatings, antibacterial and antifungal agents, isotonic and absorption retarding agents and similar acceptable for use in formulation pharmaceuticals, such as pharmaceutical products suitable for administration to human beings. The use of such media and agents for pharmaceutical-active substances is well known in the art. Except where any conventional medium or agent is incompatible with the active ingredients of this invention, their use in the pharmaceutical compositions of the invention is contemplated. Additional active ingredients may also be incorporated into the compositions, provided that they do not inactivate the molecules of this invention or their expression vectors.

The active compositions of this invention can be administered by any of the common routes, provided that the target tissue is available through that route. This includes oral, nasal, or buccal routes and, preferably, administration may be via an intradermal, subcutaneous, intramuscular, intraperitoneal, or intravenous route. As previously commented, it is common for compositions comprising antagomiRs or antimiRs to be formulated for intravenous or subcutaneous administration. By way of illustration, the solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary storage and use conditions, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. These preparations are generally sterile and fluid insofar as easily injectable. Preparations must be stable in the manufacturing and storage conditions and must be conserved against the contaminating action of microorganisms, such as bacteria and fungi. Appropriate solvents or dispersion media may contain, for example, water, ethanol, polyol (e.g. glycerol, propylene glycol, and polyethylene glycol, and the like), suitable mixtures thereof, and vegetable oils. Appropriate fluidity can be maintained, for example, by the use of a coating, such as lecithin, by maintaining the required particle size in the case of dispersion and by the use of surfactants. The prevention of the action of microorganisms can be obtained by several antibacterial and antifungal agents, for example, parabens, chlorobutanol, phenol, sorbic acid, thimerosal, and the like. In many cases, it will be preferable to include isotonic agents, for example, sugars or sodium chloride. The prolonged absorption of the injectable compositions can be caused by the use in the compositions of agents that delay the absorption, for example, aluminium monostearate and gelatine.

Sterile injectable solutions may be prepared by incorporating the active compounds in an appropriate amount into a solvent along with any other ingredients (e.g. as specified above) as desired, followed by filtration sterilization. Dispersions are generally prepared by incorporating the various sterilized active ingredients in a sterile vehicle containing the basic dispersion medium and the other desired ingredients, for example, as specified above. In the case of sterile powders for the preparation of sterile injectable solutions, preferred methods of preparation include vacuum drying and lyophilisation techniques that produce a powder of the active ingredient(s) plus any additional ingredient desired from a previously sterilized filtration solution.

The compositions of this invention can usually be formulated in a neutral or salt form. Pharmaceutically acceptable salts include, for example, acid addition salts (formed with free amino groups of the protein) derived from inorganic acids (e.g., hydrochloric or phosphoric acids), or organic acids (e.g. acetic, oxalic, tartaric, mandelic acids), and the like. Salts formed with free carboxyl groups of the protein can also be derived from inorganic bases (for example, sodium, potassium, ammonium, calcium, or ferric hydroxides) or organic bases (e.g. isopropylamine, trimethylamine, histidine, procaine, and the like).

In any case, it is recommended that the preparation of the compositions of this invention follow practices that guarantee a minimum quality for use in humans, such as those contained in the Q7 Working Group Good Manufacturing Practice Guide for Active Pharmaceutical Ingredients of the International Conference on the Harmonization of Technical Requirements for the Registration of Pharmaceutical Agents for human use (ICH Q7 Guideline. Good Manufacturing Practice Guide for Active Pharmaceutical Ingredients", available on Internet at: http://www.ich.org/fileadmin/Public_Web_Site/ICH_Products/Guidelines/Quality/7/Step4/Q7_Guideline.pdf, together with its supplement of Questions and Answers, of 10th June 2015, available on Internet at: http://www.ich.org/fileadmin/Public_Web_Site/ICH_Products/Guidelines/Quality/Q7/ICH_Q7-IWG_QA_v5_0_14Apr2015_FINAL_for_publication_17June2015.pdf). Preferably, other quality guidelines of the same provenance will also be taken into account, which can be accessed at http://www.ich.org/products/guidelines/quality/article/quality-guidelines.html page, such as the Q8, concerning Pharmaceutical Development, or Q10, on the Pharmaceutical quality system.

After formulation, the solutions are preferably administered in a form that is compatible with the dosage formulation and in such a quantity that it is therapeutically effective. Formulations can be easily administered in a variety of dosage forms such as injectable solutions, drug release capsules, and the like. For parenteral administration in an aqueous solution, for example, the solution is usually buffered adequately and the liquid diluent must first be isotonic for example, with sufficient saline or glucose. Such aqueous solutions can be used, for example, for intravenous, intramuscular, subcutaneous, and intraperitoneal administration. Preferably, sterile aqueous media is used, as is known by those skilled in the art, selected in particular in light of this description. By way of illustration, a single dose can be dissolved in 1 ml of isotonic NaCl solution and added to 1000 ml of hypodermoclysis fluid or injected into the proposed infusion site, (see for example, "Remington Pharmaceutical Sciences" 15th edition, pages 1035-1038 and 1570 to 1580). Some variations in dosage will necessarily occur depending on the condition of the subject being treated. The person responsible for the administration, in any case, shall determine the appropriate dosage for the individual subject. On the other hand, for human administration, preparations must meet the biological standards of sterility, pyrogenicity, general safety and purity as required, for example, by the ICH quality guidelines cited above or FDA regulations.

The invention will now be illustrated in more detail with the help of the examples and figures shown below.

EXAMPLES

The tests described in the examples presented below were carried out with the following materials and methodologies:

Stocks of Drosophila

The line of flies MHC-Gal4 of the species Drosophila melanogaster expresses the transcription factor Gal4 of yeasts with the Drosophila myosin heavy chain gene expression pattern; it is therefore expressed in the entire musculature of the insect, including somatic or skeletal musculature, visceral or smooth musculature, the muscles of the pharynx and the dorsal vessel or heart, among others. They can be purchased from centralized repositories (http://flystocks.bio.indiana.edu/) by paying a fee to contribute to their maintenance. The lines with miRNA sponges (UAS-miR-SP) for the miRNAs of Drosophila dme-miR-92a, dme-miR-100, dme-miR-124, dme-miR-277, dme-miR-304 and against a random sequence as negative control (known as scrambled-SP, control) were obtained from Dr. T. Fulga (Fulga et al., 2015). Briefly, the constructs of miR-SP were designed with a silencing cassette of 20 repeat sequences complementary to the miRNAs separated by variable binding sequences of four nucleotides (miR-92SP: Seq ID NO:62; miR-100SP: Seq ID NO:63; miR-124SP: Seq ID NO:64; miR-277SP: Seq ID NO:65; miR-304SP: Seq ID NO:66). The recombinant line MHC-Gal4 UAS-i (CTG)480 was generated as described by Llamusi et al. (Llamusi et al., 2013). The construction and characteristics of the fly lines UAS-mblC and UAS-IR-mbl has been described previously (Garcia-Casado et al., 2002 and Llamusi et al., 2013, respectively): UAS-mblC is a transgene that expresses the isoform mblC (described in the access number NM_176210) of muscleblind under the control of the system GaL4/UAS, while UAS-IR-mbl is a transgene that expresses an interferential construct to silence all the transcripts generated by alternative splicing from the muscleblind gene and that in previous tests has been shown to reduce the expression of mbl to, at least, 50% of its normal values. All crosses were made at 25° C. with standard fly feeding.

Extraction of RNA, RT-PCR and qRT-PCR

For each biological replication, the total RNA of 10 adult males was extracted using Trizol (Sigma). A microgram of RNA was digested with DNase I (Invitrogen) and was retrotranscribed using SuperScript II (Invitrogen) using random hexanucleotides according to the manufacturer's recommendations. 20 ng of cDNA was used in a standard PCR reaction with Go Taq polymerase (Promega) and specific primers to analyse the splicing of exon 16' of the Fhos gene and exons 3-5 of the Tnt gene as an endogenous control Rp49 was used with 0.2 ng cDNA. The qRT-PCR was carried out from 2 ng cDNA mould with SYBR Green PCR Master Mix (Applied Biosystems) and specific primers (SEQ ID NO:31 to SEQ ID NO:50: See table 1). For the reference gene, Rp49, the qRT-PCR was carried out from 0.2 ng cDNA. The thermal cycle was carried out in the Step One Plus Real Time PCR system (Applied Biosystems) according to standard conditions. In each experiment three biological replicates and three technical replicates were carried out. The data of the relative expression regarding the endogenous gene and the control group were obtained by the method of $2^{-\Delta Ct}$. Sample pairs were compared using the two-tailed T-Test ($\alpha$=0.05), applying Welch correction when necessary.

TABLE 1

RT-qPCR of expression in *Drosophila melanogaster*

| Primer | Sequence (5' → 3') | SEQ ID NO: |
|---|---|---|
| mbl fwd | TTGAATCAAAATTATAGCCCAAGCT | 31 |
| mbl rev | CGATTTTGCTCGTTAGCGTTT | 32 |
| mblA fwd | CAGACACCGAAATACTCTCTACAAACA | 33 |
| mblA rev | AAAATCAGGAGTAAACAAATACACGTAGAC | 34 |
| mblB fwd | CACACATCCAGATATGCTACTTACCA | 35 |
| mblB rev | TGAGCGATTTCGATTGATTTTG | 36 |
| mblC fwd | CAGCAAACACACATCACCTACCA | 37 |
| mblC rev | CTATCGAGCAGGAGGATGAAGAG | 38 |
| mblD fwd | GCCTCTGGAAAATGCTGCAA | 39 |
| mblD rev | CAGCAACCGCAAAAGAGCTT | 40 |
| Serca fwd | GCAGATGTTCCTGATGTCG | 41 |
| Serca rev | CGTCCTCCTTCACATTCAC | 42 |
| Cyp6w1 fwd | TTGCGCACAAAAATCTCTCC | 43 |
| Cyp6w1 rev | GTCCTGCAAGTTCTTTCCAA | 44 |
| Rp49 fwd | GGATCGATATGCTAAGCTGTCGCACA | 45 |
| Rp49 rev | GGTGCGCTTGTTCGATCCGTAACC | 46 |
| Fhos fwd | GTCATGGAGTCGAGCAGTGA | 47 |
| Fhos rev | TGTGATGCGGGTATCTACGA | 48 |
| Tnt fwd | CGACGATGAAGAGTACAC | 49 |
| Tnt rev | ACTCGGTGATGTATTCTTTCAG | 50 |

Western Blot

For the extraction of total protein of Drosophila melanogaster, 20 female thoraces were homogenized in RIPA buffer (NaCl 150 mM, 1.0% IGEPAL, 0.5% sodium deoxycholate, 0.1% SDS, Tris-HCl 50 mM ph 8.0) plus protease and phosphatase inhibitor cocktails (Roche Applied Science). Total proteins were quantified with the BCA Protein Assay Kit (Pierce) using bovine serum albumin as standard. 20 μg of the samples were denatured for 5 min at 100° C., resolved in 12% SDS-PAGE gels and transferred to polyvinylidene difluoride (PVDF) membranes. The membranes were blocked with 5% skimmed-powder milk in PBS-T ($Na_2HPO_4$ 8 mM, NaCl 150 mM, $KH_2PO_4$ 2 mM, KCl 3 mM, 0.05% Tween 20, ph 7.4) and immunodetection was performed on the same following standard procedures. For the detection of the Mbl protein of Drosophila, anti-Mbl antibody (Houseley et al, 2005) was preabsorbed against early stage wild-type embryos (0-6 h after laying) to eliminate non-specific antibody binding. The membranes were incubated with the preabsorbed primary antibody (all night, 1:1000) followed by the secondary anti-sheep IgG antibody conjugated with horseradish peroxidase (HRP) (1 h, 1:5000, Sigma-Aldrich). Load control was performed with an anti-tubulin antibody (all night incubation, 1:5000, Sigma-Aldrich) followed by incubation with a HRP-conjugated secondary anti-mouse IgG antibody (1 h, 1:3000, Sigma-Aldrich). Bands were detected using the substrate for Western Blotting ECL (Pierce). The images were taken with ImageQuant LAS 4000 (GE Healthcare).

For total protein extraction from cells, HeLa and human myoblast cells were sonicated while mouse muscles (gastrocnemius and quadriceps) were homogenized in RIPA buffer (150 mM NaCl, 1.0% IGEPAL, 0.5% sodium deoxycholate, 0.1% SDS, 50 mM Tris-HCl pH 8.0) supplemented with protease and phosphatase inhibitor cocktails (Roche Applied Science). Total proteins were quantified with a BCA protein assay kit (Pierce) using bovine serum albumin as a standard concentration range. For the immunodetection assay, 20 µg of samples were denatured for 5 min at 100° C., electrophoresed on 12% SDS-PAGE gels, transferred onto 0.45 µm nitrocellulose membranes (GE Healthcare), and blocked with 5% non-fat dried milk in PBS-T (8 mM $Na_2HPO_4$, 150 mM NaCl, 2 mM $KH_2PO_4$, 3 mM KCl, 0.05% Tween 20, pH 7.4). For HeLa cells, human myoblast, and murine samples, membranes were incubated overnight at 4° C. either with primary mouse anti-MBNL1 (1:1000, ab77017, Abcam) or mouse 13 anti-CUG-BP1 (1:200, clone 3B1, Santa Cruz) antibodies. To detect MBNL2, mouse anti-MBNL2 (1:100, clone MB2a, Developmental Studies Hybridoma Bank) was used for human myoblast and mouse samples while rabbit anti-MBNL2 (1:1000, ab105331, Abcam) antibody was used for HeLa cells. All primary antibodies were detected using horseradish peroxidase (HRP)-conjugated anti-mouse-IgG secondary antibody (1 h, 1:5000, Sigma-Aldrich), except for the MBNL2 antibody in HeLa cell samples which required a HRP-conjugated anti-rabbit-IgG secondary antibody (1 h, 1:5000, Sigma-Aldrich). Loading controls were the anti-β-Actin antibody (1 h, 1:5000, clone AC-15, Sigma-Aldrich) for cell samples and anti-Gapdh (1 h, 1:5000, clone G-9, Santa Cruz) for mouse samples, followed by HRP-conjugated anti-mouse-IgG secondary antibody (1 h, 1:5000, Sigma-Aldrich). Immunoreactive bands were detected using an enhanced chemiluminescence Western Blotting Substrate (Pierce) and images were acquired with an ImageQuant LAS 4000 (GE Healthcare). Quantification was performed using ImageJ software (NIH), and statistical differences were estimated using Student t-tests ($p<0.05$) on normalized data.

Histological Analysis

Immunofluorescence detection of Muscleblind in fly muscle of the flies and the analysis of the muscular area in the thorax of Drosophila were performed as described previously (Llamusi et al., 2013). For the immunodetection of Mbl, cryosections of fly thorax were used, which were incubated 30 min with blocking solution and all night at 4° C. with anti-Mbl antibody at a dilution 1:500. The next day the excess antibody was washed with PBS-T and incubated 45 min with secondary antibody anti-sheep IG conjugated with biotin at a dilution 1:200. After washing the secondary antibody, it was incubated with ABC solution (VEC-TASTAIN ABC Kit) 30 min, excess reagent was washed and it was incubated 45 min with Streptavidin conjugated with the final fluorophore at 1:1000. The preparations were mounted in mounting medium with DAPI.

The muscular area was determined from thorax sections embedded in the epoxy resin. Briefly, we placed the thoraces in a tube with 200 µl of solution 1 (¼ paraformaldehyde 4%, ¼ glutaraldehyde 8%, ¼ $Na_2HPO_4$ 0.2 M and ¼ $NaH_2PO_4$ 0.2 M) in ice. Then, 200 µl of solution 2 (mixture 1:1 solution 1 and osmium tetroxide) were added and incubated 30 min in ice. The mixture was then replaced by 200 µl of solution 2 and incubated in ice for 1-2 h. After fixation, samples were dehydrated by 5-min passes through ethanol at 30%, 50% and 70% in ice, and at 90% and 100% (2x) at room temperature. Two 10-minute passes were then carried out in propylene oxide. Finally, the samples were left overnight in a 1:1 mixture of propylene oxide and epoxy resin. The next day, the liquid was replaced by pure epoxy resin, and it was allowed to penetrate into the samples for at least 4 h. After this time, the flies were placed and oriented in moulds with resin and they were allowed to polymerize all the night in a Pasteur furnace at 70° C. The samples were cut with a diamond blade in cross-sectional sections of 1.5 µm in an ultramicrotome. The sections were placed on slides gelled with a drop of DPX mounting medium and coverslipped for further observation under an optical microscope.

Detection of Foci

The thoraces of the flies to be analysed were fixed during one night in 4% paraformaldehyde in PBS at 4° C., then they were kept in a 30% sucrose solution in PBS for 2 days. After 2 days, the thorax was soaked in OCT and frozen in liquid nitrogen and kept at −80° C. until processed, at which point 15 µm transversal sections were obtained with the cryomicrotome Leica CM 1510S. Slides with thorax cuts were washed three times with PBS 1x (5 min) and the acetylation buffer was added. After 10 min, they were washed three times (5 min) with PBS 1x and were prehybridized for 30 min with hybridization solution (10 ml deionized formamide, 12 µl of 5 M NaCl, 400 µl of 1 M Tris-HCl pH=8, 20 µl 0.5 M EDTA pH=8, 2 g dextran sulphate, 400 µl Denhart's Solution 50x, 1 ml herring sperm (10 mg/m), $H_2O$ up to a final volume of 20 ml. The marked probe (Cy3-5' CAGCAGCAGCAGCAGCAGCA3'-Cy3: SEQ ID NO:61, Sigma) after heating it at 65° C. for 5 min was added to the slides dissolved in the hybridization buffer (1/100) and hybridized at 37° C. during the night in a humid and dark chamber. The next day it was washed with SSC 2x keeping preparations at 32° C. (2x15 min) and 3x5 min washed with PBS. Finally, the slides were mounted with Vectastain and photographs were taken using a confocal microscope FLUOVIEW FV1000 with the 40x lens.

Analysis of the Survival Rate in Drosophila

A total of 120 newborn flies with the appropriate genotypes were collected and kept at 29° C. The flies were transferred to fresh new nutritious media every two days and the number of deaths was counted daily. The survival curves were obtained using the Kaplan-Meier method and the statistical analysis was performed with a logarithmic range test (log-rank test, Mantel-Cox) ($\alpha=0.05$) using the GraphPad Prism5 software.

Functional Tests

The flight tests were carried out on day 5 according to the procedure described by Babcok et al. (Babcock et al., 2014) using 100 male flies per group. The test consists of launching a group of flies, through a funnel, to a cylinder approximately one metre high and 15 cm in diameter. This cylinder is covered by a plastic sheet impregnated with a glue so that the flies either fly and stay in the air in the upper part of the cylinder, getting stuck there, or they fall to the bottom of it and get stuck if they fly deficiently. The landing height was compared between the groups using the two-tailed t test ($\alpha$=0.05). To assess the ascent rate, groups of ten males 5 days of age were transferred to disposable pipettes (1.5 cm in diameter and 25 cm high) after a period of 24 h without anaesthesia. The height reached by each fly from the bottom of the vial in a 10 s period was recorded with a camera. Two groups of 30 flies were tested for each genotype. Sample pairs were compared using the two-tailed T-Test ($\alpha$=0.05), applying Welch correction when necessary.

Screening Based on Libraries of MicroRNA Mimetics (SureFIND Transcriptome PCR Array, Qiagen)

This study used the kit "Cancer miRNA SureFind Transcriptome PCR Array" (Qiagen) to identify possible MBNL1 and 2-regulating miRNAs. The qPCR multiplex trial was carried out using commercial TaqMan probes (QuantiFast probe PCR kits, Qiagen) to quantify the expression of MBNL1 and 2 (genes of interest, marked with the fluorescent marker FAM: fluorescein, by ThermoFisher) and GAPDH (as an endogenous gene, marked with the fluorophore known as Max or Fluoro-Max, also from ThermoFisher). qRT-PCR was performed using a StepOnPlus real-time thermal cycler and the changes in the expression of MBNL1 and 2 as a result of the treatment with each specific microRNA mimetic were analysed using Excel-based data-analysis software provided with the SureFIND miRNA Transcriptome PCR Array, were calculated with respect to the mimetic negative control (a non-existent microRNA in nature) and were standardized with respect to GAPDH. The observed changes were represented in the form of log 2 and submitted to statistical analysis $\Delta\Delta$Ct (MAD) for the selection of the positive miRNA candidates.

Validation Test

HeLa cells were cultured at 37° C. in DMEM culture medium with 1000 mg/L glucose (Sigma-Aldrich), supplemented with 10% bovine foetal serum and 1% penicillin/streptomycin (Sigma-Aldrich). The cells were seeded at a density of $4\times10^5$ cells/well in a volume of 2 ml medium in a 6-well plate. After 16 hours and with the cells at 80% of confluence, these were transfected with the vector using X-tremeGENE HP reagent (Roche) according to the manufacturer's instructions for use in HeLa cells.

HeLa cells were transfected with 2 μg of each of the versions of the vector for expression of microRNAs: a vector derived from the commercial plasmid pCMV-MIR (OriGene) containing, in each case, either the coding sequence of the individual precursor of one of the 5 microRNAs (hsa-miR-7, insert sequence: SEQ ID NO:5, hsa-miR-23b SEQ ID NO:6, hsa-miR-146b: SEQ ID NO:7; hsa-miR-218: SEQ ID NO:8 and hsa-miR-372: SEQ ID NO:9) operationally linked to and, therefore, under the control of the CMV promoter of the original vector, or the empty version, without the precursor sequence of microRNA.

The RNA from these cells was extracted at 48 hours after transfection with the plasmids, using Trizol (Sigma). A microgram of RNA was digested with DNase I (Invitrogen) and retrotranscribed with SuperScript II (Invitrogen) using random hexamers. The concentration of each RNA sample was determined with the Nanodrop-1000 spectrophotometer (Thermo Scientific, Waltham, Mass.). The quantification of the expression of MBNL1 and 2 at transcript level by qPCR was carried out from 10 ng of cDNA with commercial TaqMan probes (QuantiFast probe PCR kits, Qiagen), following the manufacturer's instructions as in the preceding section.

The total protein used in Western Blot trials was extracted at 72 hours post-transfection using RIPA buffer (150 mM NaCl, 1.0% IGEPAL, 0.5% sodium deoxycholate, 0.1% SDS, 50 mM Tris-HCl pH 8.0), plus protease and phosphatase inhibitors (Roche Applied Science). Samples were quantified using the BCA Protein Assay Kit (Pierce). 20 ng of samples were denatured for 5 min at 100° C. and used to load SDS-Page gels (12% acrylamide), where proteins were separated, using the Mini-protean Electrophoresis system (Bio-Rad). The immobilization of proteins in nitrocellulose membrane (GE Healthcare) was performed by electrotransference in the Trans-blot SD semi-dry transfer cell system (Bio-RAD). The transfer was carried out at constant voltage (15 V) for one hour. After electrophoresis, the membranes were balanced in PBST and blocked for 1 h in blocking solution (5% skimmed milk in PBST). These membranes were subsequently incubated with the primary antibody anti-MBNL1 and anti-MBNL2 (all night, 1:1000, Abcam), after washing 3 times with PBST, the secondary antibody, anti-mouse-HRP and anti-Rabbit-HRP respectively, was added (1 h, 1:5000, Sigma-Aldrich). As load control, anti-$\beta$-actin was used (all night, 1:5000, Sigma-Aldrich), followed by the appropriate washing and the secondary antibody, which in this case was anti-mouse-HRP (1 H, 1:5000, Sigma-Aldrich). Chemiluminescent detection was performed using the ECL Western Blotting Substrate (Pierce). The images were obtained using the documentation system ImageQuant LAS 4000 (GE Healthcare Australia Pty Ltd, Rydalmere, NSW, Australia).

Validation Test of the Activity of Candidate miRNAs on the 3' UTR Region (Dual Luciferase Kit)

HeLa cells were cultured at 37° C. in DMEM culture medium with 1000 mg/L glucose (Sigma-Aldrich), supplemented with 10% bovine foetal serum and 1% penicillin/streptomycin (P/S; Sigma-Aldrich). The cells were seeded at a density of $4\times10^5$ cells/well in a volume of 0.5 ml medium in a 24-well plate. After 16 hours and with the cells at 80% of confluence, these were co-transfected with the aforementioned microRNAs expressed from the corresponding derivative of the pCMV-MIR vector (OriGene), along with the pEZX-MT05 vector which carried the 3' UTR region of both genes MBNL1 and 2 (GeneCopoeia) using X-tremeGENE HP reagent (Roche) according to the manufacturer's instructions for use in HeLa cells. The sequences of the part corresponding to the 3' UTR, of the corresponding fragments inserted in each case in the pEZX-MT05 vector are indicated in SEQ ID NO:51 (3' UTR region of the MBNL1 gene: Product number HmiT011084-MT05) and SEQ ID NO:54 (3' UTR region of the MBNL2 gene: Product number HmiT000192-MT05).

For all the miRNAs that were positive for the first activity study, three types of constructs were tested: the wild type constructs (WT) that carry the 3' UTR of MBNL1 and 2 previously tested, and two new constructs: the mutated constructs (MUT) that were designed with a deletion (that of the sequence complementary to the seed region: 6, 7 or 8 nucleotides normally) in the predicted target of the microRNA, in order to prevent the binding of microRNA to 3' UTR and the constructs with a perfect complementary target (PM). All these constructs were synthesized by the company GeneCopoeia, following the orders given by the present inventors. The parts corresponding to the modified 3' UTR, are indicated in SEQ ID NO:52 (construct with deletion in the binding area to hsa-miR-23b with the 3'UTR of MBNL1: MUT-miR-23b), SEQ ID NO:53 (construct with perfect complementarity in the binding area of MiR-23b to the 3' UTR of MBNL1: PM-miR-23b), SEQ ID NO:55

(construct with deletion in the binding area of hsa-miR-23b to the 3' UTR of MBNL2: MUT-miR-23b), SEQ ID NO:56 (construct with perfect complementarity in the binding area of miR-23b to the 3' UTR of MBNL2: PM-miR-23b), SEQ ID NO:57, SEQ ID NO:58, Seq ID NO:59 (construct with deletion in the first, second or third binding area, respectively, of hsa-miR-218 to the 3' UTR of MBNL2: MUT1-miR-218, MUT2-miR-218, MUT3-miR-218) and SEQ ID NO:60 (construct with perfect complementarity in the 3 binding areas of hsa-miR-218 to the 3' UTR of MBNL2: PM-miR-218).

In all these constructs that carry the 3' UTR (WT, MUT, PM) for both genes, this is located downstream of a reporter gene that expresses Gaussia luciferase (Gluc) which is secreted to the medium. Both sequences, corresponding to the luciferase and corresponding to the 3' UTR region, are transcribed jointly under the promoter SV40 of expression in mammalian cells, giving rise to a chimeric mRNA. In addition, this vector (pEZX-MT05) has another reporter which is also secreted to the medium with constitutive expression, alkaline phosphatase (SEAP), which is expressed under the control of the CMV promoter and which serves as internal control for the normalization of the readings obtained for Gaussia luciferase.

The reading of these experiments was performed using Secrete-Pair™ Gaussia Luciferase Dual Luminescence Assay Kits (GeneCopoeia), following the manufacturer's instructions, in white 96-well plate format placed in the plate reader (Infinite 200 PRO Microplate Reader, Tecan). For each one of the constructs studied, three technical replicates were made in each of the three independent experiments.

Expression of Candidate miRNAs in the Relevant Tissues

The extraction of total RNA enriched with small RNAs, derived from mouse tissues (forebrain, cerebellum, hippocampus, heart, gastrocnemius and quadriceps), human muscle biopsies and cultures of human fibroblasts, was performed using the MiRNeasy kit from Qiagen. From 10 ng total RNA the fraction of miRNAs was retrotranscribed with the Universal cDNA Synthesis II kit from Exiqon. For the qRT-PCR 1/80 dilutions of the cDNA were carried out, of which 4 µl was used per technical replication. The qRT-PCR amplification of the miRNAs was performed with specific commercial primers for each miRNA (EXIQON) and the SyBR Green Mastermix Universal RT. Differences of expression were calculated using the $2^{-\Delta\Delta C t}$ method.

Test on Transfection with AntagomiRs

Healthy control fibroblasts were cultured making them grow in Dulbecco's Modified Eagle medium-high glucose (DMEM 4500 mg/l, Gibco) supplemented with 1% P/S and 10% inactivated bovine foetal serum in cell culture bottles.

The cells for this assay were seeded at a density of $10^5$ cells/ml in 96-well plates (10000 cells per well). About 16 hours after seeding the cells and with these to 80% of confluence, the transfection of these cells was carried out with the antagomiRs whose synthesis was commissioned to Creative Biogene (nucleotide base sequence of antagomiR-23b-3p: GGUAAUCCCUGGCAAUGUGAU (SEQ ID NO:2), and of antagomiR-218-5p: ACAUGGUUAGAU-CAAGCACAA (SEQ ID NO:1) using X-TremeGENE HP reagent (Roche) according to manufacturer's instructions for use in fibroblasts, instructions to which small modifications were made, since a smaller volume of transfection reagent (0.5 µl and 1 µl) than that recommended by the manufacturer was used, as antagomiRs carry a special chemistry incorporating cholesterol in their structure, which allows them to better penetrate the cell membranes and thus to favour entry, not requiring so much transfection reagent which improves viability.

Specifically, the antagomiRs used in this application (antagomiR-218-5p: SEQ ID NO:10, and antagomiR23b-3p: SEQ ID NO:11), as reflected in the corresponding Creative Biogen website on synthesis of agomiRs and antagomiRs (http://www.creative-biogene.com/Services/MicroRNA-Agomir-Antagomir-Synthesis-Service.html) differ from the basic oligonucleotide sequences represented by SEQ ID NO:1 and SEQ ID NO:2 in presenting the following chemical modifications: 2 phosphorothioate groups at the 5'end, 4 phosphorothioate groups at the 3' end, 4 cholesterol groups at the 3' end and 2'-methoxy modifications in the ribose of all the nucleotide positions, i.e., throughout the oligonucleotide sequence. The basic oligonucleotide sequences of each one of them, SEQ ID NO:1 and SEQ ID NO:2, respectively, are complementary to those of the miRNAs to be blocked, namely, those of the miR-23b-3p, 5'-AUCA-CAUUGCCAGGGAUUACC-3' (SEQ ID NO:12), and miR-218-5p, 5'-UUGUGCUUGAUCUAACCAUGU-3' (SEQ ID NO:13). For clarity reasons, the sequences can be also transcribed as follows:

```
5'-mG*mG*mUmAmAmUmCmCmUmGmGmCmAmAmUmGmU*mG*mA*
mU*-3'-chol (antagomiR-23b-3p)

5'-mA*mC*mAmUmGmGmUmUmAmGmAmUmCmAmAmGmCmA*mC*mA*
mA*-3'-chol (antagomiR-218-5p)
```

The transfection experiments were carried out in fibroblasts from patients. In particular, these tests used skin fibroblasts which, have been transduced with lentiviral vectors, a construct that allows expression, inducible by doxycycline, of MyoD (which allows their transdifferentiation in myoblasts), and which are cells immortalized by expression of hTERT. They come from Dr. Denis Furling's laboratory, at the Institute of Myology (http://www.institut-myolog.ie.org/en/)

Both antagomiRs were transfected in said fibroblasts of patients, using increasing amounts thereof: 10 nM, 50 nM, 100 nM, 200 nM. As control, only the transfection reagent was used but not antagomiR. The transfection medium was left along with the cells for 4 hours and, after this time, the medium was again changed for DMEM medium. At 48 hours after transfection, images of the cells were taken in the microscope with visible light to observe the presence and morphology of the cells, and with fluorescence to observe the distribution and presence of the antagomiR as it is marked with the fluorescent marker Cy3 (red).

Cell Culture Toxicity Test

Healthy control fibroblasts were cultured making them grow in Dulbecco's Modified Eagle medium-high glucose (DMEM 4500 mg/l, Gibco) supplemented with 1% P/S and 10% inactivated bovine foetal serum in cell culture bottles. Given their adherent growth, to pass these cells, they were washed with PBS and trypsinized 2 min at 37° C., and then fresh medium was added to inhibit the action of trypsin.

The cells for this assay were seeded at a density of $10^5$ cells/ml in 96-well plates (10000 cells per well). The plate was seeded following the template represented in Table 2, in which the numbers of the columns can be found in the last row: in the case of column 1, no cells are seeded, as this column will be the blank of the colorimetric analysis. Rows A to D (underlined concentrations) correspond to the antagomiR of miRNA 23b-3p, while rows E to H correspond to the antagomiR of miRNA-218 (concentrations in bold):

TABLE 2

Seeding template for the toxicity test in cell culture

| | | | | | | | | | | | | |
|---|---|---|---|---|---|---|---|---|---|---|---|---|
| A. | blank | endogenous control | 1 nM | 10 nM | 50 nM | 100 nM | 200 nM | 500 nM | 1000 nM | | | |
| B | blank | endogenous control | 1 nM | 10 nM | 50 nM | 100 nM | 200 nM | 500 nM | 1000 nM | | | |
| C | blank | endogenous control | 1 nM | 10 nM | 50 nM | 100 nM | 200 nM | 500 nM | 1000 nM | | | |
| D | blank | endogenous control | 1 nM | 10 nM | 50 nM | 100 nM | 200 nM | 500 nM | 1000 nM | | | |
| E. | blank | endogenous control | 1 nM | 10 nM | 50 nM | 100 nM | 200 nM | 500 nM | 1000 nM | | | |
| F | blank | endogenous control | 1 nM | 10 nM | 50 nM | 100 nM | 200 nM | 500 nM | 1000 nM | | | |
| G | blank | endogenous control | 1 nM | 10 nM | 50 nM | 100 nM | 200 nM | 500 nM | 1000 nM | | | |
| H | blank | endogenous control | 1 nM | 10 nM | 50 nM | 100 nM | 200 nM | 500 nM | 1000 nM | | | |
| | 1 | 2 | 3 | 4 | 5 | 6 | 7 | 8 | 9 | 10 | 11 | 12 |

Both antagomiRs were transfected in fibroblasts of patients, using increasing amounts thereof: 1 nM, 10 nM, 50 nM, 100 nM, 200 nM, 500 nM and 1000 nM (1 μM), and as control only transfection reagent was used but not antagomiR. The transfection medium was left along with the cells for 4 hours and, after this time, it was changed for transdifferentiation medium. To transdifferentiate fibroblasts to myoblasts, the expression of MyoD was induced. To do this, the whole medium was replaced by muscle differentiation medium (MDM) consisting of DMEM supplemented with 1% P/S, 2% horse serum (Gibco), 0.1 mg/ml apotransferrin, 0.01 mg/ml insulin and 0.02 mg/ml doxycycline (Sigma) for 60 h.

After these 60 hours, the transdifferentiation medium was replaced by 100 μl of new medium in all the plate wells including column 1, and 20 μl of the MTS/PMS solution (Kit CellTiter 96® Aqueous non-radioactive cell proliferation assay) was added to each well and incubated for 2 hours at 37° C. After the incubation time, the colorimetric assay was read in the Infinite 200 PRO Microplate reader, Tecan, following the manufacturer's instructions. The data obtained with the reader were processed and analysed in order to obtain IC10 (inhibitory concentration of 10% of the cells) and IC50 (inhibitory concentration of 50% of the cells) that allow knowing how much antagomiR we should work with so that it is not toxic in the cell model.

Quantitative PCR and Splicing Assays

Fibroblasts from DM1 patients and from healthy controls were cultured in Dulbecco's Modified Eagle medium high glucose (DMEM 4500 mg/l, Gibco) supplemented with 1% P/S and 10% inactivated bovine foetal serum in cell culture bottles. The cells were seeded in 60 mm Petri dishes, at a density of 125000 cell/plate, putting 10 ml of cells in each well. After about 16 hours following the seeding of the cells and with these to 80% of confluence, the cells were transfected with the antagomiRs synthesized on the applicants' request by Creative Biogene (antagomiR-23b-3p and antagomiR-218-5p) using X-tremeGENE HP reagent (Roche) according to manufacturer's instructions for use in fibroblast cells, except that only 5 μl of transfection reagent were added.

Both antagomiRs were transfected in fibroblasts of patients, using increasing amounts: 50 nM, 100 nM y 200 nM. As control only transfection reagent was used, but not antagomiR in both healthy control cells and patient fibroblasts. The transfection medium was left together with the cells for 4 hours and after this time it was changed for transdifferentiation medium (DMEM supplemented with 1% P/S, 2% horse serum (GIBCO), 0.1 mg/ml apotransferrin, 0.01 mg/ml insulin and 0.02 mg/ml doxycycline (Sigma)). Fibroblasts were transdifferentiated to myoblasts for in two times: 48 hours and 96 hours.

The total RNA from HeLa cells and human myoblasts was extracted at 48 hours and 96 hours after transfection with the antagomiRs, using Trizol (Sigma). Total RNA from murine muscle tissues was isolated using the miRNeasy Mini Kit (Quiagen, Valencia, Calif.) according to the manufacturer instructions. In each case, a microgram of RNA was digested with DNase I (Invitrogen) and retrotranscribed with SuperScript II (Invitrogen) using random hexamers. The concentration of each RNA sample was determined with the Nanodrop 1000 spectrophotometer (Thermo Scientific, Waltham, Mass.).

The quantification of the expression of MBNL1 and 2 at the transcript level by qPCR was carried out from 10 ng of cDNA with commercial TaqMan probes (QuantiFast probe PCR kits, Qiagen), to quantify the expression of MBNL1 and 2 (genes of interest, marked with the fluorescent marker FAM: fluorescein, ThermoFisher); GAPDH and ACTB (as endogenous genes, marked with fluorophore known as MAX or Fluoro-Max and TAMRA respectively, also from ThermoFisher).

For the amplification of transcripts by RT-PCR GoTaq® DNA polymerase (Promega) was used. To do this, cDNA obtained as a mould from the previous step was used in accordance with the manufacturer's conditions. PCR products were separated in 2.5% agarose gel. The primers used for the analysis of each splicing event studied, the expected pattern in DM1 patient myoblasts, the exon studied and the conditions used are shown in the following table:

TABLE 3

Conditions for amplification of transcripts by RT-PCR in the splicing assay

| Gene | Sequence of primers (5' → 3') (F: Direct, R: Inverse) | cDNA (μl) | Cycles | Myoblast Pattern - DM1 |
|---|---|---|---|---|
| GAPDH | F: CATCTTCCAGGAGCGAGATC (SEQ ID NO: 14) R: GTTCACACCCATGACGAACAT (SEQ ID NO: 15) | 1 | 29 | Endogenous Control — |

| Gene | Sequence of primers (5' → 3') (F: Direct, R: Inverse) | cDNA (μl) | Cycles | Myoblast pattern DM1 | Exon |
|---|---|---|---|---|---|
| cTNT | F: ATAGAAGAGGTGGTGGAAGAGTAC (SEQ ID NO: 16) R: GTCTCAGCCTCTGCTTCAGCATCC (SEQ ID NO: 17) | 1 | 27 | Inclusion | 5 |
| IR | F: TGCTGCTCCTGTCCAAAGAC (SEQ ID NO: 18) R: GAAGTGTTGGGGAAAGCTG (SEQ ID NO: 19) | 4 | 30 | Exclusion | 11 |
| BIN1 | F: CTCAACCAGAACCTCAATGATGTG (SEQ ID NO: 20) R: CTGAGATGGGGACTTGGGGAG (SEQ ID NO: 21) | 1 | 30 | Exclusion | 11 |
| DMD | F: GTGAGGAAGATCTTCTCAGTCC (SEQ ID NO: 22) R: CTCCATCGCTCTGCCCAAATC (SEQ ID NO: 23) | 4 | 30 | Exclusion | 79 |
| SERCA1 | F: GATGATCTTCAAGCTCCGGGC (SEQ ID NO: 24) R: CAGCTCTGCCTGAAGATGTG (SEQ ID NO: 25) | 4 | 30 | Exclusion | 22 |
| DLG1 | F: AGCCCGATTAAAAAACAGTGA (SEQ ID NO: 67) R: CGTATTCTTCTTCGACCACGGT (SEQ ID NO: 68) | | | Inclusion | 19 |
| CAPZB | F: GGAGAAGGATGAAACTGTGAGTG (SEQ ID NO: 69) R: CAGAGGTTTAGCATTGCTGCT (SEQ ID NO: 70) | | | Exclusion | 8 |
| Atp2a1 | F: GCTCATGGTCCTCAAGATCTCAC (SEQ ID NO: 71) R: GGGTCAGTGCCTCAGCTTTG (SEQ ID NO: 72) | | | | 22 |
| Clcn1 | F: GTCCTCAGCAAGTTTATGTCC (SEQ ID NO: 73) R: GAATCCTCGCCAGTAATTCC (SEQ ID NO: 74) | | | | 7a |
| Nfix | F: TCGACGACAGTGAGATGGAG (SEQ ID NO: 75) R: CAAACTCCTTCAGCGAGTCC (SEQ ID NO: 76) | | | | 7 |
| Capzb | F: GCACGCTGAATGAGATCTACTTTG (SEQ ID NO: 77) R: CCGGTTAGCGTGAAGCAGAG (SEQ ID NO: 78) | | | | 8 |
| Gapdh | F: ATCAACGGGAAGCCCATCAC (SEQ ID NO: 79) R: CTTCCACAATGCCAAAGTTGT (SEQ ID NO: 80) | | | | |

Transgenic Mice and AntagomiR Administration

Mouse handling and experimental procedures conformed to the European law regarding laboratory animal care and experimentation (2003/65/CE) and were approved by our institutional review board (reference number A1458832800370). Homozygous transgenic HSALR (line 20 b) mice 25 were provided by Prof. C. Thornton (University of Rochester Medical Center, Rochester, N.Y., USA, and mice with the corresponding genetic background (FVB) were used as controls. A total of four gender and age-matched (<5 months old) mice received three subcutaneous injections (every 12 h) of 100 µl of 1×PBS (vehicle) or antagomir delivered to the interscapular area. The overall quantity of antagomir finally administered divided among all the injections was 12.5 mg/kg. Four days after the first injection, the mice were sacrificed and the tissues of interest were harvested and divided into two samples each. One part was frozen in liquid nitrogen for the molecular analyses, including the PCR assays of the section above, and the other was fixed in 4% paraformaldehyde (PFA) and cryoprotected in 30% sucrose before histological processing. Cy3-labelled antagomirs were administered as described above in a single subcutaneous injection of 10 mg/kg.

Cell Proliferation Assay

Cells were seeded at $10^5$ cells/mL in 96-well plates and transfected with antagomiRs, as previously explained; 96 h post-transfection, cell proliferation was measured using the CellTiter 96® AQueous Non-Radioactive Cell Proliferation Assay (Promega) following the manufacturer's instructions. The $IC_{10}$ and dose-response inhibition curves were calculated using non-linear least squares regression, and absorbance levels were determined using a Tecan Infinite M200 PRO plate reader (Life Sciences).

Immunofluorescence Methods

For MBNL1 and MBNL2, immunofluorescent myoblasts were fixed with 4% PFA for 15 min at room temperature (RT) followed by several washes in 1×PBS. Cells were then permeabilized with PBS-T (0.3% Triton-X in PBS) and blocked (PBS-T, 0.5% BSA, 1% donkey serum) for 30 min at RT, and incubated either with primary antibody mouse anti-MBNL1 (1:200, ab77017, Abcam) or rabbit anti-MBNL2 (1:200, ab105331, Abcam) at 4° C. overnight. After several PBS-T washes the cells were incubated for 1 h with a biotin-conjugated secondary antibody, and anti-mouse-IgG (1:200, Sigma-Aldrich) to detect anti-MBNL1 either anti-rabbit-IgG (1:200, Sigma-Aldrich) to detect anti-MBNL2. The fluorescence signal was amplified with an Elite ABC kit (VECTASTAIN) for 30 min at RT, followed by PBS-T washes and incubation with either streptavidin-FITC (1:200, Vector) to detect anti-MBNL1 or streptavidin-Texas Red (1:200, Vector) to detect anti-MBNL2, for 45 min at RT. After several washes with PBS the cells were mounted with VECTASHIELD® mounting medium containing DAPI (Vector) to detect the nuclei.

The Cy3 moiety was synthetically attached to the 5' end of the oligonucleotide to allow the distribution of the compound to be visualised. Frozen sections (10 µm) of mouse tissues including heart, brain, gastrocnemius, and quadriceps were immunostained using anti-Cy3 antibody (1:50, Santa Cruz) followed by a secondary goat biotin-conjugated anti-mouse-IgG (1:200, Sigma-Aldrich). Cy3-labeled antagomirs were directly detectable under a fluorescence microscope in myoblast cells, liver, and kidney tissues. Images of myoblast cells were taken on an Olympus FluoView FV100 confocal microscope and images of human myoblast and mouse tissues containing Cy3-antagomirs were obtained using a Leica DM4000 B LED fluorescence microscope. In all cases, the images were taken at a 40× magnification and processed with Adobe Photoshop software (Adobe System Inc.).

Electromyography Studies

Electromyography was performed before the treatment and at the time of sacrifice under general anaesthesia, as previously described[26]. Briefly, five needle insertions were performed in each quadriceps muscle of both hind limbs, and myotonic discharges were graded on a fivepoint scale: 0, no myotonia; 1, occasional myotonic discharge in ≤50% of the needle insertions; 2, myotonic discharge in >50% of the insertions; and 3, myotonic discharge in nearly all of the insertions, myotonic discharge in all insertions; 4.

Muscle Histology

Frozen 15 µm-sections of mouse gastrocnemius and quadriceps muscles were stained with haematoxylin eosin (H&E) and mounted with VECTASHIELD® mounting medium (Vector) according to standard procedures. Images were taken at a 100× magnification with a Leica DM2500 microscope. The percentage of fibres containing central nuclei was quantified in a total of 200 fibres in each mouse.

Example 1

Proof of Concept in DM1 Models of Drosophila Melanogaster 1.1. dme-miR-277 or dme-miR-304 Silencing Causes Overexpression of Muscleblind in the Muscle of Drosophila The sequestration of Muscleblind in foci of RNA and the subsequent loss of protein function is one of the main trigger factors of the molecular pathology of DM1. In order to identify miRNAs that repress muscleblind, the inventors selected candidate miRNAs and proceeded to block their activity using specific miRNA sponges.

Initially dme-miR-92a, dme-miR-100 and miR-dme-124 were selected, based on previous data generated by the group of inventors and their orthology relationship with human miRNAs; to obtain this data, the miRanda algorithm was used, among other tools, developed at the Memorial Sloan-Kettering Cancer Center Computational Biology Center (2010 version downloadable from, among other sites, the microRNA.org download webpage: http://www.microrna.org/microrna/getDownloads.do; manual available at: http://cbio.mskcc.org/microrna_data/manual.html). To broaden the search for candidate miRNAs, TargetScan was used, an online software provided by the Whitehead Institute for the prediction of miRNA targets (www.targetscan.org), to search for miRNA recognition sites in the 3' UTR region of muscleblind and sites for two miRNAs: dme-miR-277 and dme-miR-304, among others, were identified. Table 4 shows the recognition sites of several miRNAs predicted according to different algorithms in the 3' UTR region of Muscleblind, as well as the access number both of their precursor sequences with hairpin loops (codes headed by the abbreviation MI) and of the mature miRNAs (codes headed by the abbreviation MIMAT) in the database of MiRBase (www.mirbase.org).

TABLE 4

Number of recognition sites of several miRNAs predicted according to different algorithms in the 3' UTR region of Muscleblind

| miRNA | miRanda | TargetScan | Isoform of mbl |
|---|---|---|---|
| dme-miR-92a-3p | — | | mblA |
| (SEQ ID NO: 26) | — | | mblB |
| MI0000360 | — | — | mblC |

TABLE 4-continued

Number of recognition sites of several miRNAs predicted according to different algorithms in the 3' UTR region of Muscleblind

| miRNA | miRanda | TargetScan | Isoform of mbl |
|---|---|---|---|
| MIMAT0000334 | 1 site | — | mblD |
| dme-miR-100-5p | — | — | mblA |
| (SEQ ID NO: 27) | — | — | mblB |
| MI0000378 | — | — | mblC |
| MIMAT0000357 | — | — | mblD |
| dme-miR-124-3p | 1 site | — | mblA |
| (SEQ ID NO: 28) | — | — | mblB |
| MI0000373 | — | — | mblC |
| MIMAT0000351 | 1 site | — | mblD |
| dme-miR-277-3p | 1 site | — | mblA |
| (SEQ ID NO: 29) | 2 Sites | — | mblB |
| MI0000360 | — | — | mblC |
| MIMAT0000338 | 2 Sites | 1 site | mblD |
| dme-miR-304-5p | — | — | mblA |
| (SEQ ID NO: 30) | — | — | mblB |
| MI0000411 | 1 site | — | mblC |
| MIMAT0000390 | — | 1 site | mblD |

In order to validate miRNAs that regulate muscleblind, the expression of the sponge constructs (Fulga et al., 2015), UAS-miR-XSP, was directed to the muscles of Drosophila by the line Mhc-Gal4, abbreviation of the promoter elements of the gene myosin heavy chain and coding region of the gene Gal4 corresponding to the protein activating the transcription of yeasts Gal4, which is known to act as a transcription activator in different organisms, including Drosophila. In this system, the UAS (upstream activation sequence) elements act as transcription enhancers, as the protein GAL4 binds specifically to them to activate the transcription of genes, while the fact that the coding region of the gene Gal4 is operatively bound to the endogenous promoter of the gene Mhc directs the expression of the miRNA sponges to the muscle. Muscleblind transcription levels were analysed by qRT-PCR, using specific primers to amplify a region of exon 2 of muscleblind, which is shared by all known transcript isoforms to date. As a control, a line with a random sequence (UAS-scrambled-SP) was used.

No significant increase was detected in the level of expression of muscleblind in flies expressing miR-92aSP, miR-100SP or miR-124SP under the control of MHC-Gal4. In contrast, the levels of muscleblind transcripts increased significantly in the flies that expressed the miR-277SP or miR-304SP in the muscle, compared with the controls of Scrambled-SP (FIG. 1a). The levels of muscleblind RNA were 14 times higher when the blocked miRNA was dme-miR-227, while the silencing of dme-miR-304 resulted in a 6-fold increase. Therefore, these results show that the silencing of dme-miR-277 or dme-miR-304 causes overexpression of Muscleblind.

1.2. dme-miR-277 and dme-miR-304 Regulate Different Isoforms of Muscleblind

The muscleblind gene of Drosophila melanogaster is a large gene, which covers more than 110 kb, which gives rise to several different transcripts by alternative splicing (Begemann et al., 1997; Trion et al., 2012). Experimental evidence suggests that isoforms of muscleblind are not functionally redundant (Vicente et al., 2007). To determine which isoforms of muscleblind are regulated by dme-miR-277 or dme-miR-304, the miRanda algorithm (Enright et al., 2003) was used to identify recognition sites of dme-miR-277 and dme-miR-304 in the 3' UTRs region of isoforms of muscleblind (table 4). It is important to note that MiRanda performs the search in the transcripts of mblA, mblB, mblC and mblD, following the denomination used by Begemann et al. 1997 in the aforementioned reference, but does not include the recently identified isoforms, mblH, mblH', mblJ and mblK (Irion et al., 2012).

A potential recognition site of dme-miR-277 was found in the isoform mblA and two in mblB and mblD. qRT-PCR analyses determined that the mblB level increased significantly when dme-miR-277 was blocked/depleted. The levels of expression of mblD were reduced in the flies Mhc-Gal4 miR-277SP and no significant differences were detected with regard to mblA when compared with the control flies that expressed Scrambled-SP (FIG. 1b). Strangely, the levels of expression of mblC, an isoform for which no recognition sites had been predicted for dme-miR-277, were significantly reduced in the flies Mhc-Gal4 miR-277SP.

For dme-miR-304, a recognition site was found in the 3'UTR region of mblC and mblD, and a significant up-regulation was detected of the two isoforms in flies Mhc-Ga/4 miR-304SP (FIG. 1b). In particular, the blocking/depletion of dme-miR-304 in the muscle caused a strong increase in the levels of mblC, the most expressed isoform in adult flies (Vicente et al., 2007).

The fact that the silencing of dme-miR-277 and dme-miR-304 originate changes in the specific expression levels of each isoform of Muscleblind suggests a direct regulation of the muscleblind transcripts through these miRNAs.

Considering that a miRNA can typically act in terms of mRNA stability or the blocking of its translation, we decided to analyse the levels of the Muscleblind protein to validate the candidate regulator miRNAs. With this objective, an anti-Mbl antibody was used to detect the up-regulation of proteins MblA, MblB and MblC. Western blot transfer analyses revealed an increase in the levels of the muscleblind protein only in the flies Mhc-Gal4 miR-304SP (FIG. 1c). Consistent with the determinations by qRT-PCR, the band detected in the Western blot transfer corresponded to the protein MblC. It should be noted that the antibody used has only previously worked in overexpression experiments (Houseley et al., 2005) (Vicente-Crespo et al., 2008).

In order to analyse the effect of silencing dme-miR-277 o dme-miR-304, longitudinal sections of the indirect flight muscles (IFMs) were stained to verify the distribution of Muscleblind: The anti-Mbl signal was detected in green, while the nuclei appeared counterstained in blue with DAPI. The group of the present inventors had previously shown that the endogenous protein Muscleblind is mainly located in the sarcomeric bands Z and H of the muscle (Llamusi et al., 2013). Consistent with this, the confocal images obtained from these sections allowed to detect muscleblind proteins preferably in the bands of the muscle sarcomeres in the control flies that expressed the construct of Scrambled-SP, obtaining a low signal in some nuclei of these cells. Interestingly, the reduced function of dme-miR-277 and dme-miR-304 had different effects on the protein distribution: while the silencing of dme-miR-277 increased the signal of the cytoplasmic muscleblind protein, particularly in the sarcomeric bands, in the flies Mhc-Gal4 miR-304SP, a strong nuclear location was detected.

Taken in combination, these results show that endogenous isoforms of Muscleblind can be up-regulated by blocking the inhibitory activity of dme-miR-277 and dme-miR-304.

1.3. Decreasing Function of dme-miR-277 o dme-miR-304 Favours the Expression of Muscleblind in a Model of DM1 in Drosophila Previous models of DM1 in Drosophila had ribonuclear foci in muscle cells containing muscleblind proteins (Garcia-Lopez et al., 2008; Picchio et al., 2013). To test the specific effect of silencing the repressor miRNAs of muscleblind in a model of DM1 of Drosophila, the expression of muscleblind was studied in flies that express interrupted CTG 480 repeats ("i(CTG)480") with myosin heavy chain promoter as a specific determinant driver of expression in muscles with simultaneous expression of sponge constructs (Mhc-Gal4 UAS-i(CTG)480 UAS-miR-XSP).

Figure 2:
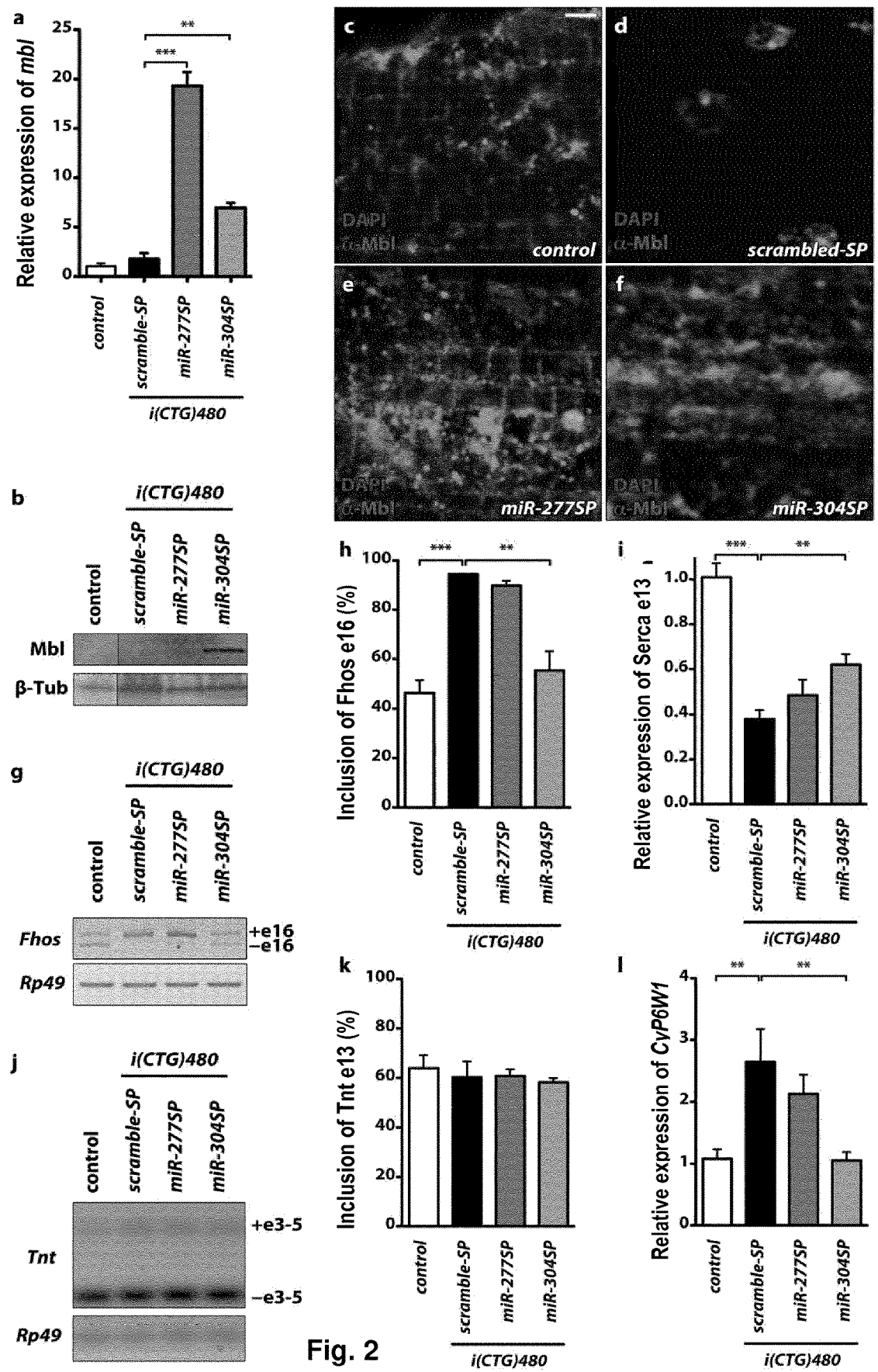
FIG. 2. Silencing dme-miR-277 and dme-miR-304 potentiates the expression of Muscleblind and rescues incorrect splicing events in a DM1 context. (A) Bar chart showing the levels of expression of muscleblind according to the data obtained by qRT-PCR in flies i(CTG)480 expressing the sponge constructs indicated under the graph: it is shown that muscleblind mRNA was significantly up-regulated in the model flies that expressed miR-277SP and miR-304SP compared to flies that do not express the expansions (control, Mhc-Gal4/+) or model flies expressing scrambled-SP (scramble-SP in the figure). (B) Western Blot transfer analysis in samples of the same flies, which showed overexpression of Muscleblind C only in model flies expressing miR-304SP. (C-F) Confocal images of longitudinal sections of IFM (indirect flight muscles) of flies expressing or not expressing miRNA sponges as shown in the lower right corner, showing the location of the anti-Muscleblind signal (green in the original, light grey in grayscale), with counterstaining of the nuclei with DAPI (blue signal in the original, faded grey in grayscale): Muscleblind signal is observed in the sarcomeric bands of the control flies (c); conversely, Muscleblind was found in the nuclear aggregates of the IFM in which CTG expansions were expressed (d); the expression of miR-277SP in the model flies released Muscleblind from the aggregates and restored its distribution in the sarcomere bands (e); the expression of miR-304SP gave rise to a dispersed overexpression of Muscleblind both in the nuclei and in the cytoplasm. (G) Results obtained after RT-PCR to evaluate the inclusion of Fhos exon 16' (+e16') or its exclusion (−e16') in flies with different genotypes and expression of microRNA sponges, as indicated in the photographs; the results corresponding to Rp49 transcripts, detected as endogenous control, are also shown. (H) Quantification of the inclusion percentage of Fhos exon 16' from the results shown in Panel G, which confirmed an improvement of the erroneous splicing of Fhos in the model flies expressing miR-304SP. (I, L) Bar charts showing the results, obtained by qRT-PCR, of expression of Serca exon 13 (Serca e13) and exon 2 of the gene CyP6W1 (CyP6W1 e2) in relation to Rp49, which confirmed a significant rescue of Serca splicing in model flies expressing miR-304SP and of the relative expression of CyP6W1 in these flies. (J) Results obtained after RT-PCR to evaluate the inclusion of exons 3-5 of the gene TnT (+e3-5), which did not differ in the genotypes studied. (K) Quantification of the percentage of inclusion of exons 3 to 5 of Tnt from the results shown in Panel J. The transgenes of all the genotypes indicated were directed to the muscle using Mhc-Gal4. Scale bar=2 micrometres. *$p<0.05$, $p<0.01$, *$p<0.001$ (Student's t test).
Figure 3:
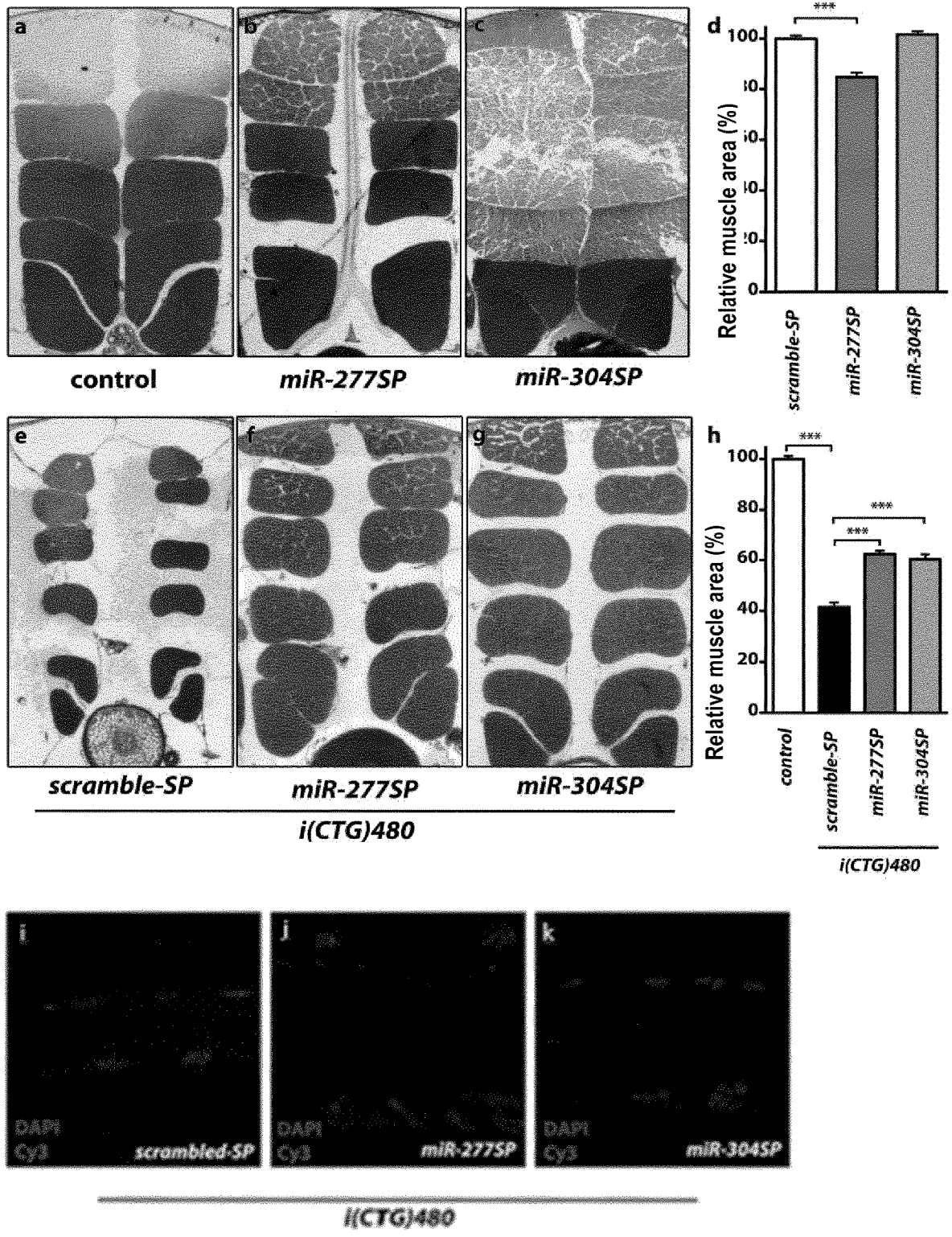
FIG. 3. Dme-miR-277 and dme-miR-304 silencing rescues muscular atrophy and the presence of ribonuclear foci in model flies. (a-c, e-g): Dorsoventral sections of the thorax embedded in resin, of flies with the genotypes indicated below the pictures: it is noted how, in comparison with the control flies (a), the expression of miR-277SP resulted in a significant reduction of the muscle area (b), while the expression of miR-304SP had no effect on this phenotype (c); in DM1 model flies, the muscle area was reduced up to 40% with regard to normal (e); however, in model flies expressing any one of either miR-277SP or miR-304SP, the muscular area increased up to 60% with regard to normal (f, g). (d, h): Quantification of the average percentage of the muscular area according to the genotype indicated below the bars; the graphs show the mean±S.E.M. Six individuals per genotype were analysed and six photographs of each were quantified. In all the images the dorsal part is positioned upwards. (i-k) In situ hybridization of transverse sections of musculature of flies with the genotypes indicated below the photographs: it is noted how, in comparison with the control flies in which there is a clear presence of foci (i) the expression of miR-277SP and miR-304SP resulted in a significant reduction of these, being practically inappreciable in the latter case (j and k). All the genotypes specified were directed to the muscle using Mhc-Gal4. *p<0.05, p<0.01, *p<0.001 (Student's t test).

The analysis of the mbl transcript levels by qRT-PCR showed that the silencing of dme-miR-277 or dme-miR-304 resulted in an increased expression of muscleblind in the DM1 model flies (FIG. 2a). It is important to note that the positive regulation of Muscleblind was stronger in DM1 model flies than in flies that only expressed sponge constructs (compare FIG. 1a and FIG. 2a). Muscleblind transcript levels were 19 times higher in flies expressing both i(CTG)480 and miR-277SP and 7 times higher in flies Mhc-Gal4 UAS-i(CTG)480 UAS-miR-304SP compared to controls. On the other hand, in line with the protein analysis carried out in the presence of different sponge constructs (FIG. 1c), the silencing of dme-miR-304 caused an increase of the levels of the protein MblC in the DM1 model flies (FIG. 2b).

To study the effect of silencing of dme-miR-277 or dme-miR-304 in the subcellular localization of Muscleblind in DM1 model flies, the distribution of muscleblind proteins was analysed by immunodetection in IFMs (FIGS. 2c-f). Both the expression of miR-277SP (FIG. 2e) and that of miR-304SP (FIG. 2f) in DM1 model flies released Muscleblind from the ribonuclear foci and increased the level of proteins, both in the nuclei and in the cytoplasm. In the case of model flies expressing the miR-277SP, the distribution of Muscleblind in the sarcomeric bands of the muscle, which is characteristic of the control flies that do not express the repeats, was completely rescued. Likewise, the expression of miR-304SP led to a detectable increase in Muscleblind dispersed in nuclei and cytoplasm. Therefore, the silencing of dme-miR-277 or dme-miR-304 up-regulates the Muscleblind levels and rescues its subcellular distribution in DM1 model fly muscles.

1.4. dme-miR-304 Silencing Rescues Alterations in the Splicing and in the Global Levels of Gene Expression in a DM1 Model in Drosophila Spliceopathy is the main biochemical milestone of DM1 and the only one that has been directly linked to the symptoms. To test whether the increase in Muscleblind, caused by the silencing of dme-miR-277 or dme-miR-304, was sufficient to rescue the alterations in the splicing in DM1 model flies, splicing events characteristically altered were studied These events were:

The exclusion of exon 16' of the Fhos gene in model flies of DM1, which the present inventors have identified, verifying that it is regulated by Muscleblind;

The inclusion of exon 13 of the Serca gene, which is a splicing event regulated by Muscleblind.

It was also found to occur with another molecular function described for Mbl: the regulation of global levels of gene expression. Specifically, exon 2 of the gene CyP6W1 was amplified, to check the levels of expression of that gene, for which increase in its expression in DM1 model flies has been described (Picchio et al., 2013).

In DM1 model flies, a 2-fold increase of the inclusion of exon 16' of Fhos and a 2.4-fold reduction of transcripts of Serca with exon 13, was confirmed as well as a 3-fold increase of transcripts of CyP6W1, compared with control flies that do not express repeats.

The expression of miR-304SP in these flies achieved a complete rescue of exon 16' of Fhos and of the normal expression of the gene CyP6W1 and a significant 20% increase of the transcripts of Serca that include exon 13 (FIGS. 2g-i, l). It is noteworthy that the silencing of dme-miR-304 in the muscle caused a strong increase in the levels of mblC (FIG. 2b), an isoform that has previously been shown to act as a splicing regulator (Vicente et al., 2007). On the contrary, the expression of miR-277SP, which rescued the Muscleblind expression in the cytoplasm, and reduced the levels of expression of mblC, did not modify these splicing events. As control, it was confirmed that the splicing pattern of the exons 3-5 of Tnt, that is not altered in model adult flies of DM1 (Garcia-Lopez et al., 2008), was not modified either by the expression of the sponge constructs nor by the alterations in the expression of muscleblind (FIG. 2j, FIG. 2k).

These results show that the level of derepression of Muscleblind obtained through miRNA sponges is enough to trigger, potentially, significant molecular rescues.

1.5. dme-miR-277 or dme-miR-304 Silencing Rescues Muscular Atrophy and Motor Function in a DM1 Model in Drosophila To evaluate the functional relevance of the increase in Muscleblind achieved by the expression of specific sponge constructs, the effect of silencing dme-miR-277 or dme-miR-304 on muscular atrophy was studied, an alteration which is one of the traits that characterize individuals with DM1. For the study of muscular atrophy, the muscle area was first measured in dorsoventral sections of the IFMs in the control flies that expressed either miR-277SP or miR-304SP in the muscle (FIGS. 3a-d). The decrease in the function of dme-miR-277 induced a 15% reduction in the IFM area, compared to flies expressing Scrambled-SP as control. Importantly, the expression of miR-304SP had no effect on this parameter.

The present inventors' research group had previously reported on the existence of muscular atrophy in flies that express i(CTG)480 in the muscles. In these DM1 model flies, it was found that the specific tissue silencing of dme-miR-277 or dme-miR-304 was sufficient to significantly rescue the percentage of muscle area (FIGS. 3e-h). Compared to control flies that did not express CUG repeats, the mean area of IFMs in model flies expressing the scrambled-SP was significantly reduced to 40%. The simultaneous expression of the CUG repeats and any one of either miR-277SP or miR-304SP resulted in a 20% increase of the muscle area in these flies. In addition, in situ hybridization tests on cross-sections of fly muscle (FIGS. 3i-k) showed how the expression of miR-277SP (FIG. 3j) and miR-304SP (FIG. 3k) resulted in a significant reduction of a typical histopathological parameter of the disease, the ribonuclear foci of the model of DM1 in Fly (FIG. 3i), which were negligible after the expression miR-304SP. These data confirm that the up-regulation of different isoforms of Muscleblind was sufficient to rescue muscular atrophy and the formation of ribonuclear foci in Drosophila.

Figure 4:
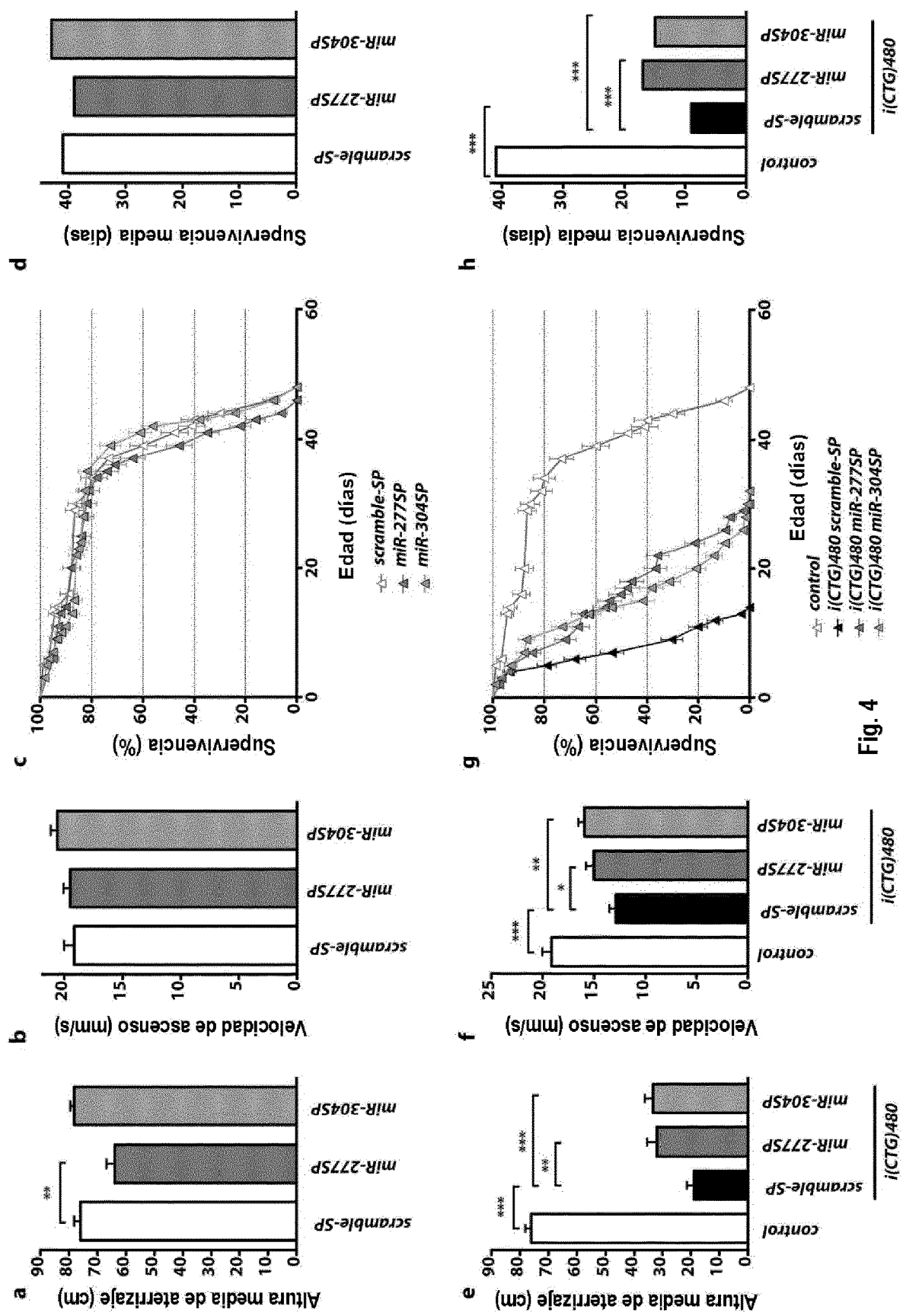
FIG. 4. Inhibition of dme-miR-277 or dme-miR-304 improves locomotion and survival of DM1 model flies. (a, e) Average landing height of flies with the relevant genotypes indicated below the chart. In control subjects (a), the silencing of dme-miR-277 decreased the landing height while the silencing of dme-miR-304 did not affect flight. In the DM1 model flies (e), the expression of miR-277SP or miR-304SP rescued the decreased flight capacity observed. (b, f) Histograms of the ascent rate by surfaces expressed as the average speed±S.E.M. in mm/s. In control flies (b), the silencing of either dme-miR-277 or dme-miR-304 had no effect on ascent rate. However, in the DM1 model flies (f), which have a very low ascent rate, the expression of miR-277SP or miR-304SP significantly rescued this phenotype. (c, g) Survival curves and (d, h) mean survival, which show that the expression of miR-277SP or miR-304SP had no effect on the control flies, but improved survival of the DM1 model flies. Between 140 and 160 individuals of each genotype were analysed. All the transgenes specified were directed to the muscle using Mhc-Ga14. *p<0.05, p<0.01, *p<0.001 (Student's t test).

In order to evaluate the correlation between the muscular area and the locomotive activity, the ascent and flight capacity of flies of different genotypes was analysed. The expression of miR-277SP in the muscle resulted in a reduction of the average landing height of about 10% in comparison with the control flies expressing the scrambled-SP, indicating that the muscle area reduction found in these flies has a functional correlation (FIG. 4a). However, muscular atrophy was apparently specific to IFMs, as surface ascent rate remained unchanged in these flies (FIG. 4b). On the contrary, the silencing of dme-miR-304 in the muscle did not affect the locomotion activity of the flies (FIGS. 4a, b). In the DM1 model flies, compared to control flies that did not express repeats, the simultaneous expression of CUG repeats and the scrambled-SP construct resulted in a drastic reduction in average landing height and surface ascent rate (FIGS. 4e, f). However, the expression of any one of either miR-277SP or miR-304SP in the model flies resulted in the rescue of all these parameters at similar levels (FIGS. 4e, f). Therefore, these results showed that the specific silencing of miRNAs regulating muscleblind can rescue muscular atrophy and the characteristic functional phenotype of DM1.

1.6. Functional Depletion of dme-miR-277 or dme-miR-304 Extends the Survival Rate of DM1 Model Flies The reduction of muscle function, particularly of the respiratory system, is the main cause of death in DM1. The present inventors' group had previously reported that flies that express i(CTG)480 in the muscles have a reduced survival rate and reduced average survival in comparison with control flies (Garcia-Lopez et al., 2008). To study whether the dme-miR-277 or dme-miR-304 silencing rescues the survival rate of DM1 model flies, analyses of the survival curves in flies of different genotypes were carried out. It is important to note that the survival curves of the flies that expressed miR-277SP or miR-304SP in muscles were not different from those of the ones expressing scrambled-SP, which indicates that dme-miR-277 or dme-miR-304 silencing did not alter the survival rate (FIGS. 4c, d). The survival rate of the DM1 model flies expressing scrambled-SP was significantly reduced compared to control flies that did not express CTG repeats (FIGS. 4g, h). The expression of miR-277SP or miR-304SP in model flies increased the survival rate and average survival. Dme-miR-277 silencing increased the average survival by eight days, while an increase of six days was detected for the DM1 model flies that express miR-304SP (FIGS. 4g, h). Therefore, the positive regulation of muscleblind caused by the decrease of the function of dme-miR-277 or dme-miR-304 improves the survival of the DM1 model flies.

Taken as a whole, these results show that the silencing of specific miRNAs in Drosophila causes an increase in the levels of muscleblind that is sufficient to rescue several molecular and physiological characteristics, including an increase in survival. This therefore supports an approach to blocking Muscleblind-like repression by miRNAs as a potential strategy for the treatment of DM1 in humans and other mammals.

Therefore, the present inventors went on to identify miRNAs repressors of MBNL1 and/or 2 and, among them, look for those expressing themselves in tissues with DM1 symptoms and whose blocking is effective in rescuing molecular characteristics of DM1 and thereby improving symptoms of the disease.

Example 2

Identification, Validation and Characterization of miRNAs Repressors of MBNL1 and/or MBNL2

2.1. Screening to Identify miRNAs that Negatively Regulate MBNL1 or MBNL2

First, an initial screening was conducted based on libraries of miRNA mimetics, using the commercial kit SureFIND Transcriptome PCR array from Qiagen, as described in the preceding methodological section. This study allowed the initial identification, in HeLa cells, of 18 miRNAs as potential repressors of MBNL1 and 9 microRNAs as potential repressors of MBNL2 in HeLa cells, in showing a repression of the expression of the aforementioned genes at least 4-fold with respect to the control, GAPDH. Four of these miRNAs initially seemed able to inhibit the expression of both.

2.2. Confirmation of Repressive Action

Since it was a large number of microRNAs to be validated, the number of microRNAs with which to continue the assays was limited to a total of 6, basing the choice on the number of bioinformatics predictions collected in the Databases mirDIP (https://omictools.com/mirdip-tool) and miRecords (https://omictools.com/mirecords-tool), which collect the information of a total of 9 prediction programs providing information on the existence of the targets of a specific microRNA in the transcripts of a given gene, suggesting that regulation exists.

To carry out the confirmation tests of the initial results checking the possible modulation by direct regulation, several miRs were initially selected, including both potential regulators of both genes, and specific repressors of MBNL1 or MBNL2. MiR-146b and miR-23b as potential regulators of both MBNL1 and MBNL2; and miR-218 and miR-372 as specific repressors of MBNL2.

Figure 5:
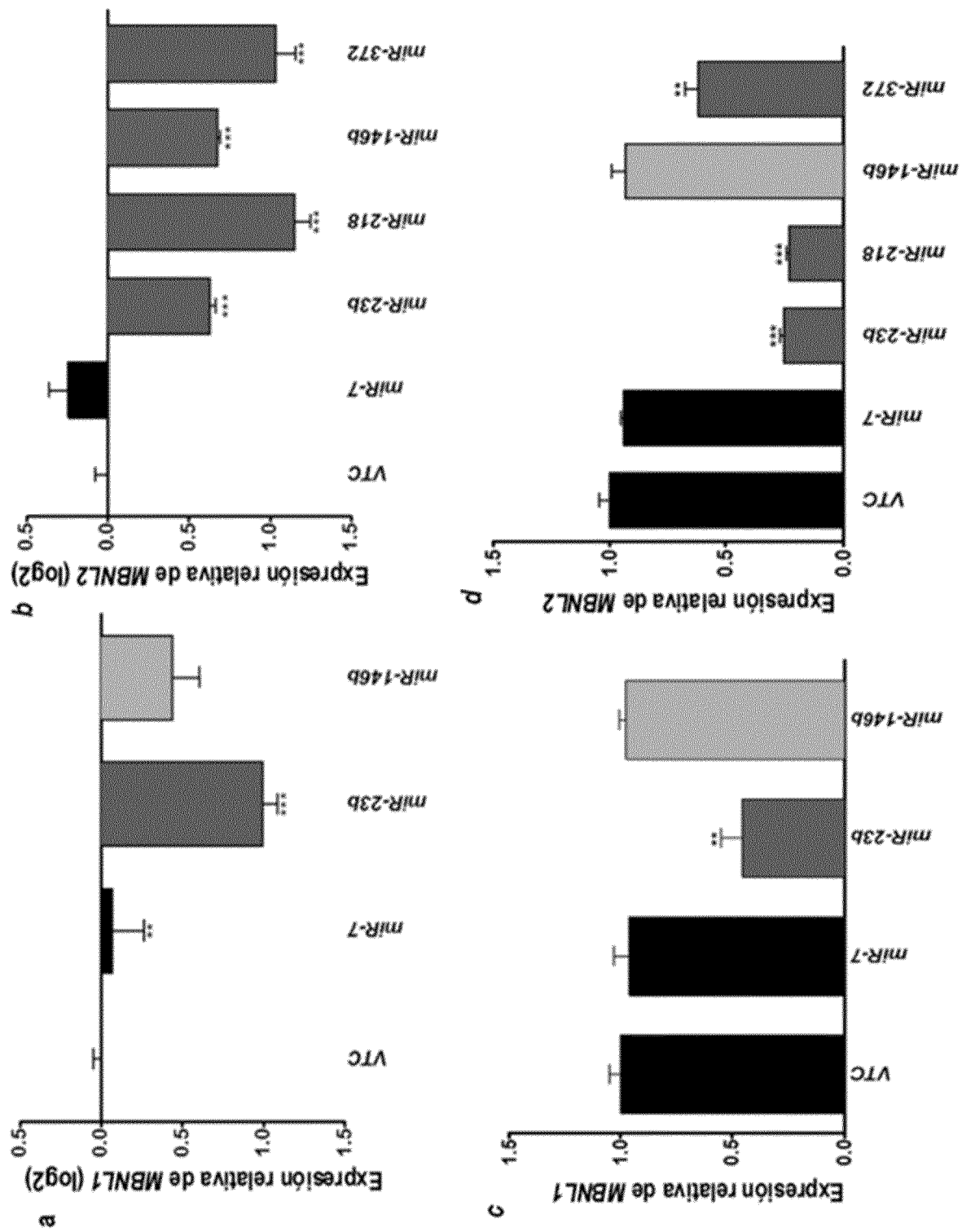
FIG. 5. Validation of primary screening results of miRNAs repressors of MBNL1 or MBNL2. (a-b) Logarithmic representation in base 2 (log 2) of the relative expression level of MBNL1 (a) and MBNL2 (b) in HeLa cells transfected with plasmids derived from pCMV-MIR that express different human miRNAs (miR-7, miR-23b, miR-146b, miR-218, miR-372), the reference value for both genes being that detected in HeLa cells transfected with the empty plasmid pCMV-MIR (VTC in the figure) and the endogenous gene used to normalize GAPDH. As a control of transfection the vector expressed the GFP protein. *p<0.05, p<0.01, *p<0.001. (c-d) Representation of the relative level of expression of the protein MBNL1 (panel c) and MBNL2 (panel d) in HeLa cells transfected with the plasmids of the trials shown in (a) and (b), equally using as reference value for both genes that detected in HeLa cells transfected with the empty plasmid pCMV-MIR (VTC in the figure) and using β-actin as an endogenous control. p<0.01, *p<0.001 (Student's t test).

The previous results were confirmed for some miRNAs by transfection in HeLa cells of expression plasmids derived from pCMV-MIR (Origene) expressing precursors of the selected miRNAs, along with the empty plasmid pCMV-MIR and miR-7 as negative controls, the latter in not being identified as an inhibitor of MBNL1 or MBNL2 in the initial screening. The expression of MBNL1 or MBNL2 was then quantified in terms of mRNA and protein, as described in the part on "Validation tests" in the methodological section. FIG. 5 shows the results obtained for miR-146b and miR-23b (initially identified as potential regulators of both MBNL1 and MBNL2), as well as for miR-218 and miR-372 (initially identified as specific repressors of MBNL2).

Indeed, it was observed both in the case of MBNL1 (FIG. 5a) and in the case of MBNL2 (FIG. 5b), that the selected microRNAs exerted a repressive effect on the messenger of the genes for which initially a repressive effect had been detected although the repressive effect caused by miR-146b was less significant.

With regard to the quantification of proteins, a decrease was observed at the level of protein MBNL1 in the case of miR-23b (FIG. 5c), at 72 hours after transfection, while in the case of MBNL2 (FIG. 5d), this decrease at protein level occurred both with the microRNA miR-23b and with miR-218. The decrease caused by miR-372 was much lower than with the two other microRNAs.

Therefore, the data obtained confirmed that miR-23b down-regulates, at protein level, both MBNL1 and MBNL2, while miR-218 represses MBNL2.

2.3. Identification of miRNA Target Sequences and Demonstration of the Functional Relevance of the Potential miRNA-mRNA Interaction The specific sequences to which the miRNAs need to bind to exert their repressive action were then identified. This is necessary to design blockmiR type inhibitors and to confirm the direct binding of the miRNA to its target, ruling out indirect regulation.

Figure 6:
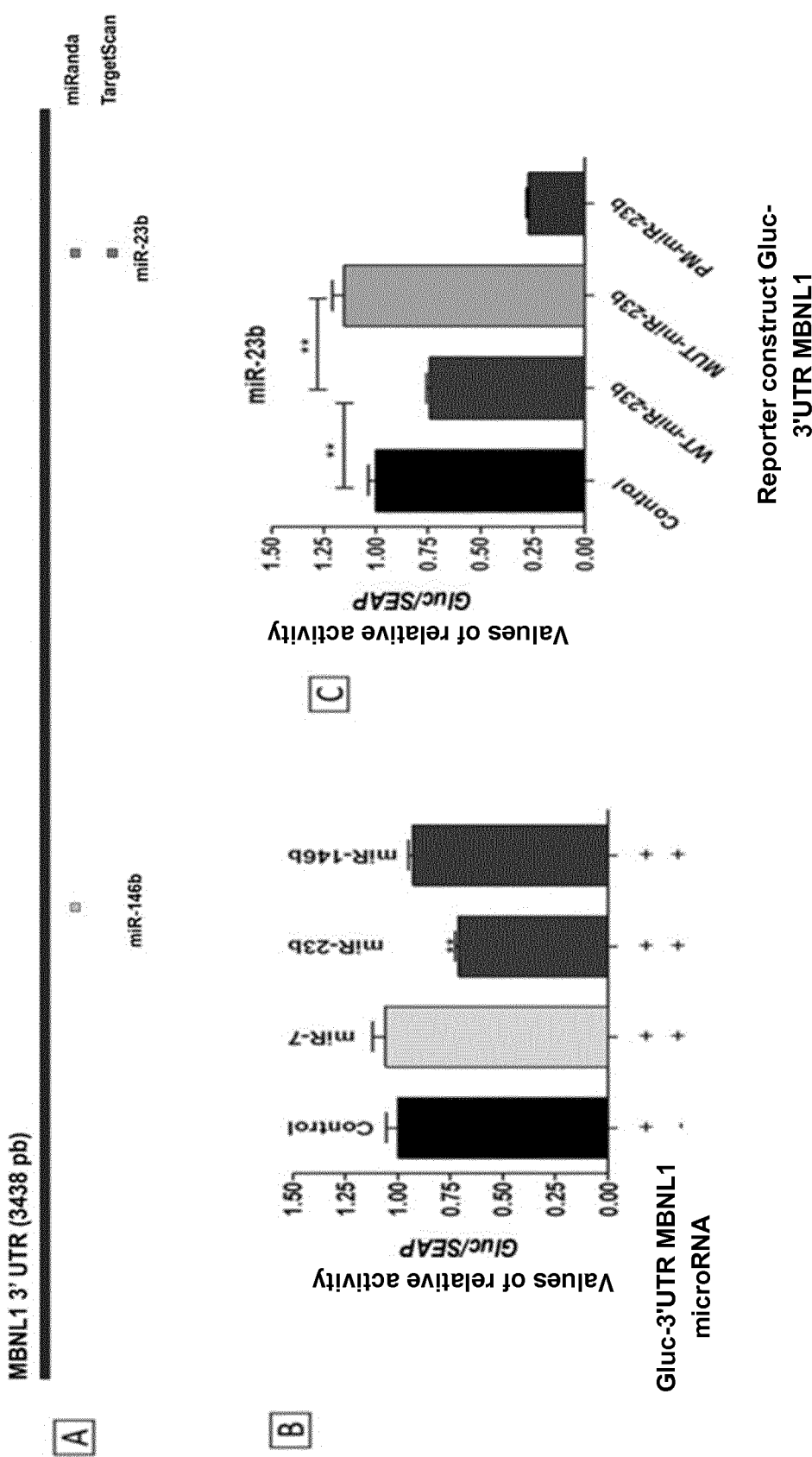
FIG. 6. Experimental confirmation of the target sequences recognized by the candidate miRNAs in 3' UTRs by means of luciferase reporters. (A) Schematic representation, on scale, of the binding sites predicted by the programs miRanda and Targetscan of the microRNAs indicated on the 3'UTRs of MBNL1. Although said gene suffers alternative splicing, none of the known isoforms affects the presence in the transcript of the targets shown. (B) Graphical representation of the activity of the different microRNAs on sensors luc:3'-UTR MBNL1 expressed in relative units of Gaussia luciferase, standardized with respect to the internal control SEAP (Gluc/SEAP). (C) To verify the direct binding of miR-23b, also shown are the data of the sensor 3'UTR of this candidate miRNA with the predicted target sequence mutated (MUT) and also its version with the perfect complementary target (PM), as well as the data obtained when the natural target (WT) is present in the sensor 3'UTR. The activity of miR-23b on the sensors 3'UTR, natural, mutated and PM, is expressed in relative units of Gaussia luciferase, standardized with respect to the internal control Seap (Gluc/SEAP). *p<0.05, p<0.01, *p<0.001. (D) Schematic representation, on scale, of the binding sites predicted by the programs miRanda and Targetscan of the microRNAs indicated on the 3'UTRs of MBNL2. As in the case of MBNL1, although this gene suffers alternative splicing, none of the known isoforms affects the presence in the transcript of the targets shown. (E) Graphical representation of the activity of the different microRNAs on sensors luc:3'UTR of MBNL2 expressed in relative units of Gaussia luciferase, standardized with respect to the internal control SEAP (Gluc/SEAP). (F, G): Graphical representation of the activity of the microRNAs miR-23b (F), miR-218 (G) that were positive in the previous trial. As in the case of MBNL1, also shown are the data obtained with the versions of the sensor 3'UTR designed for each candidate miRNA with the predicted target sequence mutated (MUT) and also its version with the perfect complementary target (PM), as well as the data obtained when the natural target (WT) is present in the sensor 3'UTR. The activity of different microRNAs on the 3'UTR, natural, mutated and PM, is expressed in relative units of Gaussia luciferase, standardized with respect to the internal control SEAP (Gluc/SEAP). *p<0.05, p<0.01, *p<0.001 (Student's t test).
Figure 6:
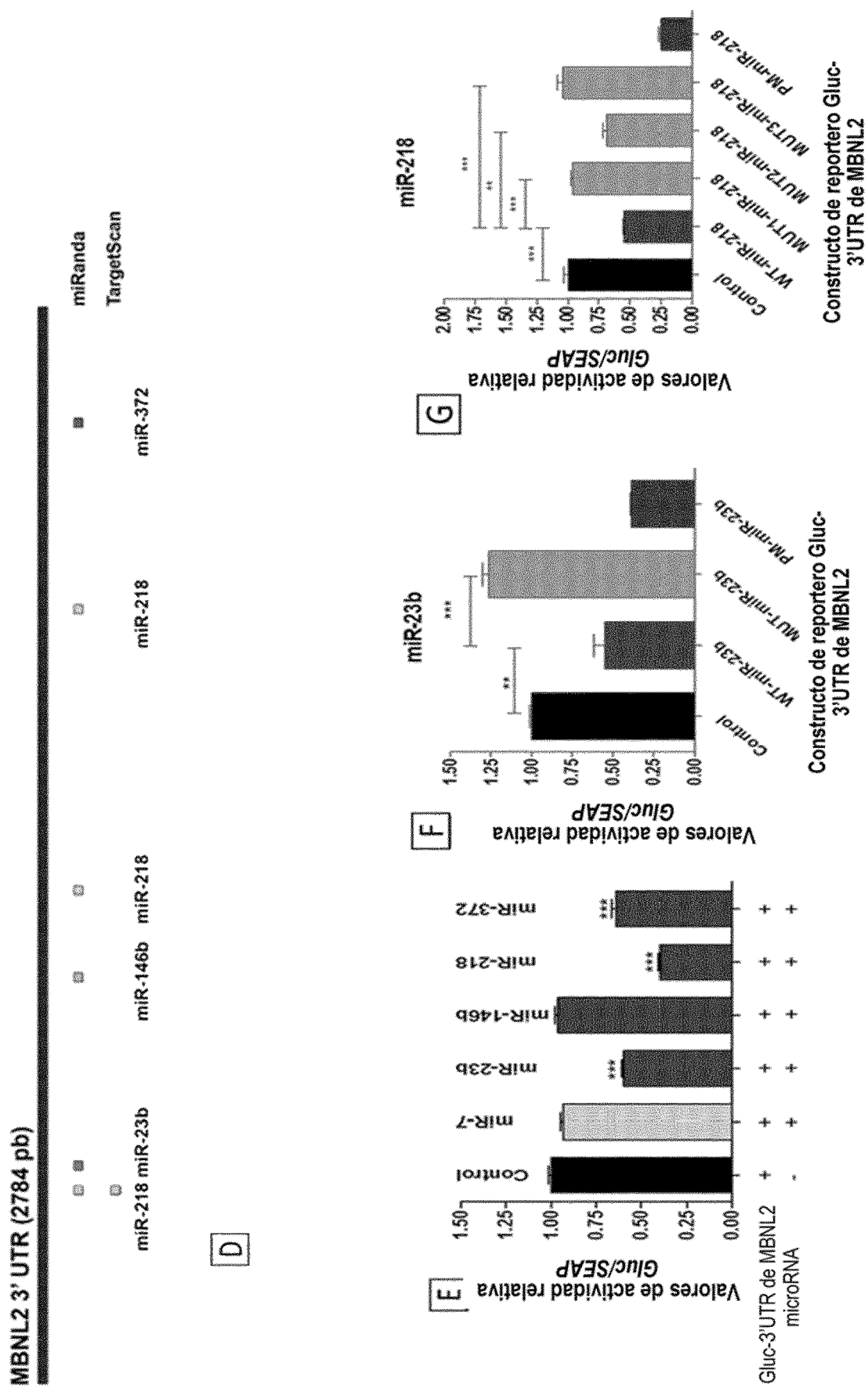

To this end, a bioinformatics prediction was made of the targets of the pre-selected miRNAs after screening, using the applications miRanda and TargetScan already used in the tests carried out in Drosophila. FIGS. 6A and 6F show a schematic representation, to scale, of the binding sites predicted by the aforementioned programs on the 3'UTR regions of MBNL1 and MBNL2, respectively. In both cases, none of the isoforms of said genes, resulting from alternative splicing, affects the presence in the corresponding transcript of the predicted targets.

To demonstrate the functional relevance of a potential miRNA-mRNA interaction, sensors were used to show that, in effect, the pre-selected microRNAs bind to their predicted targets in the 3'UTRs of both genes. This was experimentally demonstrated by generating a construct in which the 3'UTR ends of MBNL1 or MBNL2 merge into a luciferase coding sequence as a reporter gene, so that the eventual repressive regulation resulting from overexpressing the miRNA is observed as a reduction in the amount of luciferase detected. Specifically, the methodology described in the section "3' UTR Binding test (dual luciferase kit)" was used.

As explained in the same methodological section, in this test, a lower signal of the Gaussia luciferase (Gluc) indicates binding of the microRNA to 3' UTR, since the binding of the latter to 3' UTR prevents the translation of the reporter and therefore a decrease of the Gluc released to the medium (see the diagrams offered on the specific Genecopoeia website, http://www.genecopoeia.com/product/mirna-targets/).

From the readings observed 48 hours after the co-transfection of both the plasmid from which the microRNA is expressed and the vector pEZX-MT05 (which carries the 3' UTR region of both genes, MBNL1 and MBNL2, downstream of the coding sequence of Gaussia luciferase), it was observed that all the microRNAs tested, except for miR-146b and the negative control, miR-7, have a repressive effect on the reporter, inferring the specific binding of the sequence to 3'UTR of the target gene (see FIGS. 6B and 6E).

Once the previous experiment was completed, it was verified that the observed biding was direct, which indicates a direct regulation of the microRNA on the 3'UTR. To this end, additional versions of the construct were designed with the 3' UTR sensor for each candidate miRNA, wherein the predicted target sequence was mutated (mut) by deletion, and also another version wherein said predicted target in the 3' UTR had mutated giving rise to a perfect complementary target (PM) of the corresponding miRNA, a perfect target to which microRNAs bind completely and with the highest efficiency. As explained in the methodological section mentioned above, the binding of the different microRNAs to the mutated 3' UTR and with PM targets was expressed in relative units of Gaussia luciferase, standardized with respect to the internal control of alkaline phosphatase SEAP (Gluc/SEAP). These target mutagenesis tests were performed for miR-23b in MBNL1 (FIG. 6C) and for miR-218 and miR-23b in MBNL2 (FIGS. 6F y 6G).

In the case of MBNL1, the direct binding of the microRNA miR-23b is shown in FIG. 6b, as by transfecting HeLa cells with the mutated versions (mut) of the reporter constructs MBNL1 and miR-23b (FIG. 6C), said miRNA stopped repressing, with a similar increase in luciferase to that occurring in the control, where the sensor construct is transfected with the empty vector pCMV-MIR. Together with the microRNAs, the constructs with the perfect match version (PM) of the binding target were also transfected, which allows us to know the extent of effectiveness of the binding of a microRNA to the 3'UTR (WT: Wild type) of the gene in question with respect to perfect binding noted with the PM. These tests are very useful as they are an important basis in the design of the blockmiRs. In all cases, there was a greater decrease in the luciferase signal than that observed with the natural target.

In the case of MBNL2, it was shown that there is a direct binding of the microRNAs miR-23b and miR-218, because on transfecting the HeLa cells with constructs with the mutated versions (mut) of the targets along with the different microRNAs miR-23b (FIG. 6F), and miR-218 (FIG. 6G), the repression of the reporter was lost, again observing a similar increase in the luciferase to what happens with the control, where the sensor construct was transfected with the empty vector pCMV-MIR. Again, the constructs with the perfect match version (PM) of the binding target were also transfected together with the microRNAs. In both cases, there was a greater decrease in the luciferase signal than that observed with the natural target.

2.4.—Expression of Candidate miRNAs in Relevant Tissues

In addition to verifying the repressive capacity, it is important to check if the miRNAs to be act on are expressed in tissues relevant to the disease (heart, muscle and brain, among others), so that the action thereon can have a palliative effect for symptoms of the disease associated with these tissues. Therefore, this is important, because if a repressor is identified, but it is not expressed in the relevant tissues, blocking it will have no effect.

We proceeded to check the expression of the candidate miRNAs in human muscle biopsies from healthy individuals and DM1 patients, in cultures of human fibroblasts also derived from healthy individuals or from DM1 patients and in mouse tissues (forebrain, cerebellum, hippocampus, heart, gastrocnemius and quadriceps), as described in the methodological section "Expression of candidate miRNAs in the relevant tissues".

Figure 7:
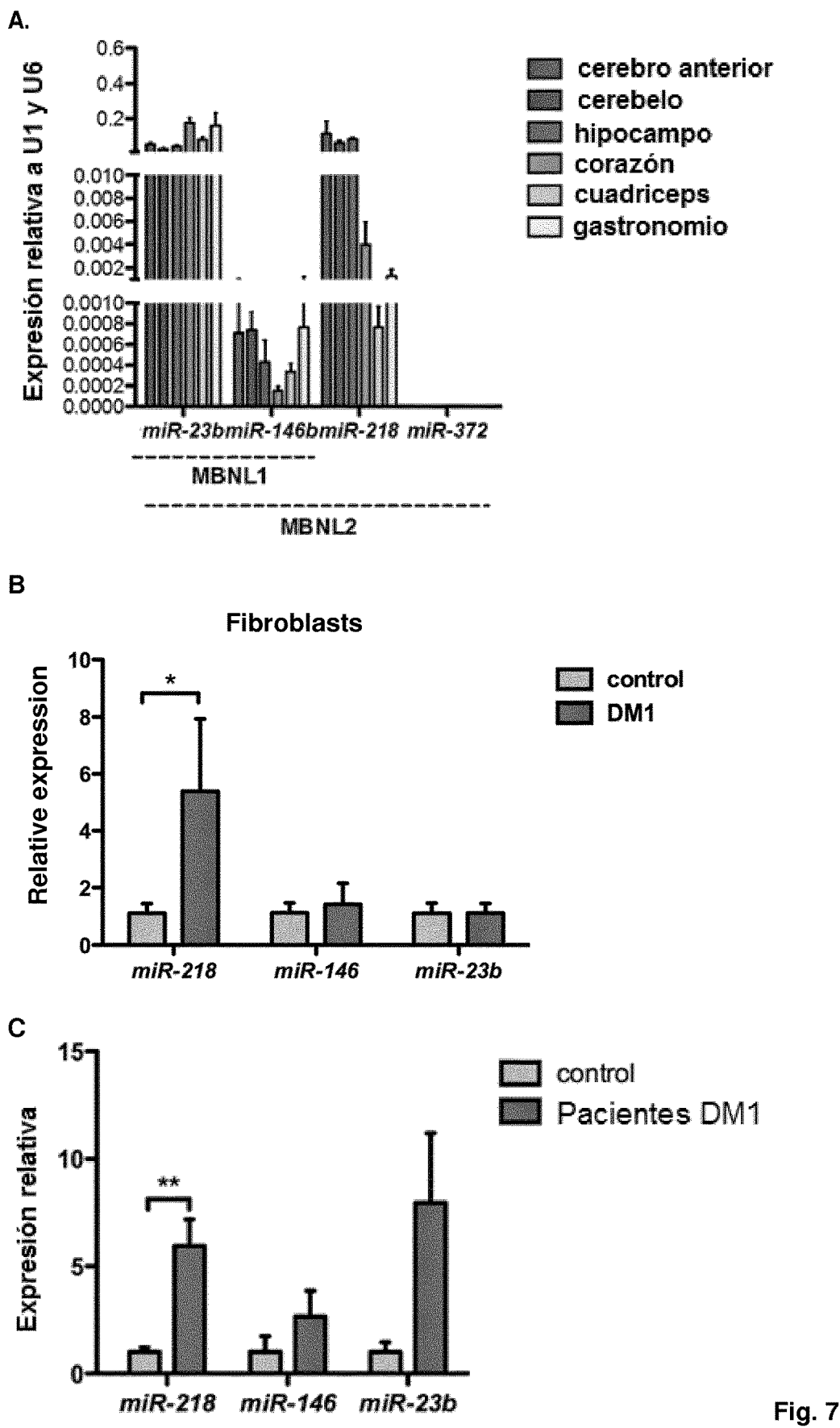
FIG. 7. Graphical representation of the relative level of expression of the different microRNAs (miR-23b, miR-146b, miR-218, miR-372) through qPCR. Genes U1 and U6 were used as endogenous controls for normalization of expression. (A) Expression of the microRNAs in the different mouse tissues (FVB strain); (B) Expression of microRNAs in fibroblasts of controls individuals and patients with DM1; (C) Expression of microRNAs in muscle biopsies of control individuals and patients with DM1. *p<0.05, **p<0.01 (Student's t test).

The results obtained in mice (FIG. 7A) were consistent with previous expression data available to the present inventors, either from public databases or proprietary data, indicating that certain miRNAs are expressed in tissues relevant to the disease (heart, muscle, brain). The results obtained with miR-23b and miR-218 are especially relevant, especially with the former, where the relative expression in all tissues was far higher than that of miR-146b and, in particular, to that of microRNA miR-372, for which no expression was detected.

Accordingly, the results obtained in muscle biopsies from human individuals (FIG. 7C) show a significant increase in the expression of miR-218 and a clear trend, although not significant with the data of the experiment performed, for miR-23b in the samples of patients with DM1, far higher than that observed for miR-146. Even in tests performed with human fibroblasts (FIG. 7B), the relative expression of miR-218 is far higher in the case of fibroblasts from DM1 patients compared to fibroblasts of control individuals not affected by the disease.

Example 3

Effects of the Transfection of AntagomiRs of miR-218 and miR-23b

When jointly considering the results of tests to confirm the repressor potential of the expression of mRNAs and proteins, those to confirm the direct action on the mRNAs of MBNL1 and/or MBNL2, and the data of expression in different tissues, it was decided to concentrate on designing blockers or inhibitors of miR-23b and miR-218, which were the two microRNAs with most expression in these tissues involved in the pathology.

AntagomiR type oligoribonucleotide inhibitors were selected since, as previously explained, they are analogous to RNAs with a particular chemistry that makes their binding to miRNA more stable, makes them less susceptible to degradation and increases their ability to penetrate cell membranes (it is common, as in the present case, for them to include cholesterol).

The supplier of the concrete antagomiRs with which the following tests were carried out has been: http://www.creative-biogene.com/Services/MicroRNA-Agomir-Antagomir-Synthesis-Service.html. As previously described, the antagomiRs referred to in this specification, are abbreviated as antagomiR-218 (antagomiR-218-5p: SEQ ID NO:10) and antagomiR-23b (antagomiR-23b-3p: SEQ ID NO:11), which differ from the basic sequences SEQ ID NO:1 and SEQ ID NO:2 (complementary, respectively, of human microRNAs miR-218-5p and miR-23b-5p) in the detailed modifications in the list of sequences and methodological section "Test on transfection with AntagomiRs".

3.1. AntagomiR Transfection Tests

As described in said section, first a test was carried out on the transfection of fibroblasts from DM1 patients with increasing concentrations (10 nM, 50 nM, 100 nM) of each of the antagomiRs, marked with the fluorophore Cy3 (which emits a red signal) and two different concentrations of the transfection reagent XtremGene (0.5 µl and 1 µl).

This fibroblast transfection test experiment was conducted in order to determine the threshold concentration at which the antagomiR is detectable within the cells, as well as the amount of transfection reagent to be used, attempting to use the minimum amount possible, since this reagent is highly toxic for human fibroblasts.

Due to the presence of Cy3 in its structure, when the antagomiR enters the cells these are seen as red under the fluorescence microscope, indicating the presence of the antagomiR.

At the concentration of 10 nM, the red signal was barely detected, which implied the scarce presence of antagomiRs in the cells, so concentrations of 50 nM or higher were needed to make the signals intense. That is why these were used in the subsequent tests carried out with the antagomiRs.

3.2. Toxicity Tests

A first approximation was to perform a dose-response cell toxicity test to establish the antagomiR concentration threshold at which these began to become toxic to work with them in cells, because when working with compounds in a cell model it is advisable to work at a concentration lower than the IC10.

Figure 8:
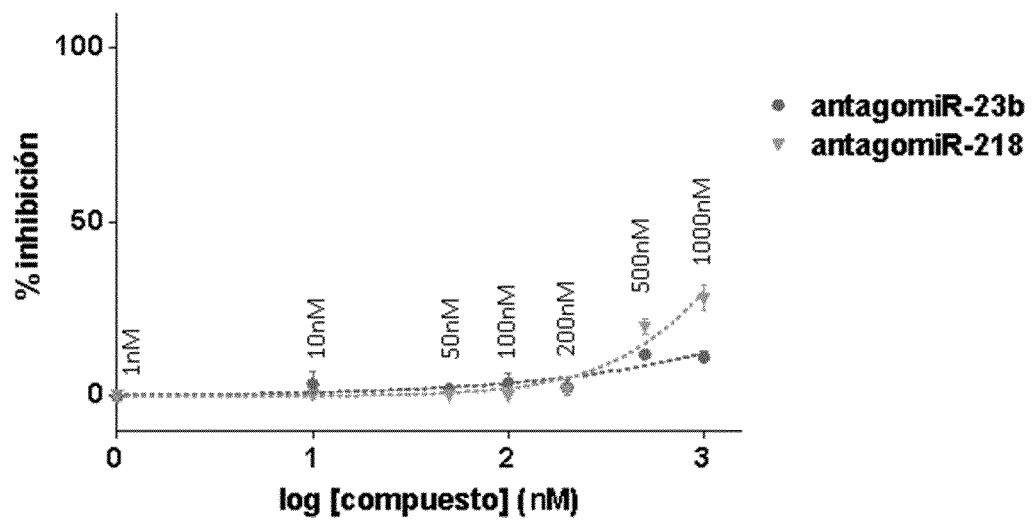
FIG. 8. Toxicity tests with antagomiRs of the microRNAs 218 and 23b in normal myoblasts. Graphical representation of the percentage of inhibition of cell survival at 60 h, obtained in control myoblasts caused by the toxicity associated with the dose response test with increasing amounts of the antagomiRs, relative to the logarithm in base 10 of the nanomolar concentration of the compound. The quantities tested in control myoblasts are indicated on the corresponding curves.

The toxicity profiles of both antagomiRs were obtained in healthy human myoblasts at 60 h of their addition to the medium (FIG. 8a), as described in the section "Cell culture toxicity test". The colorimetric assay performed allowed a rapid and sensitive quantification of cell proliferation and viability, with the addition of increasing concentrations of antagomiR. With the data obtained, the IC10 (which shows the concentration at which 10% of the cells have died due to the toxicity associated with the compound) and the IC50 (which is the concentration at which 50% of the cells have died due to toxicity) were calculated. The values obtained were:

|  | antagomiR-23b | antagomiR-218 |
| --- | --- | --- |
| IC10 | 654.7 nM | 347.0 nM |
| IC50 | 32281 nM | 1968 nM |

The value of the Z-factor was also calculated, as a positive Z-factor indicates that the toxicity test is being performed correctly. In this case it was: 0.46.

Once the study was carried out it was decided to continue with three concentrations (50 nM, 100 nM y 200 nM) with which to carry out the subsequent tests, since these are concentrations below the IC1010, that is, well below the toxicity threshold.

3.3. Dose Response Trials of AntagomiRs in Cells of Patients with DM1

Figure 9:
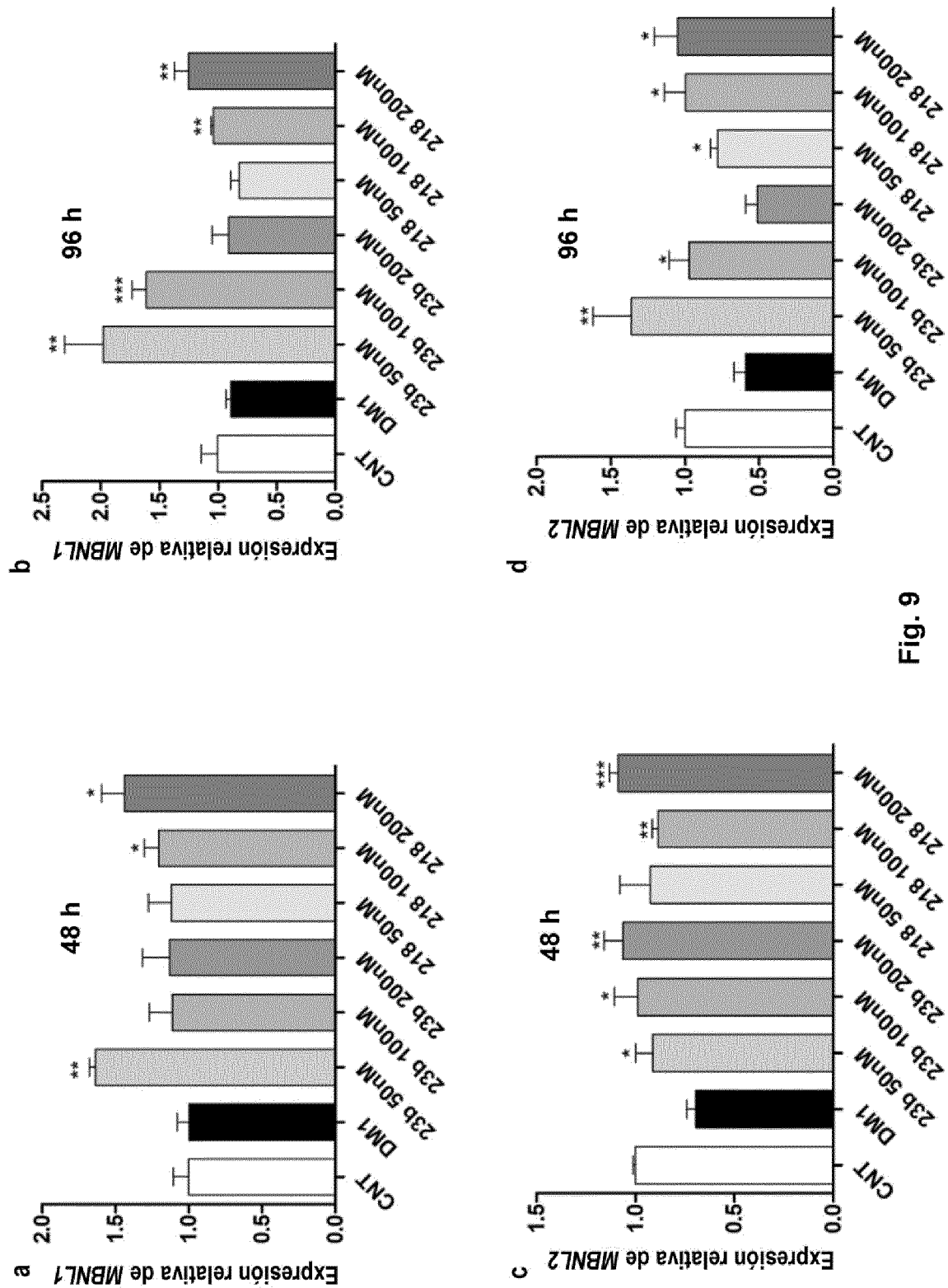
FIG. 9. Dose response trials of antagomiRs of microRNAs 218 and 23b: Graphical representation of the level of expression of MBNL1 (a, b) or MBNL2 (c, d) in healthy control, DM1 and myoblasts treated with antagomiR-23b and antagomiR-218 (50 µM, 100 µM, 200 µM). GAPDH and ACTB genes were used as endogenous controls for normalization of expression. The panels on the left show the expression of MBNL1 (a) or MBNL2 (c) at 48 hours post-transfection and transdifferentiation with the antagomiRs, while the panels on the right show the expression of MBNL1 (b) or MBNL2 (d) at 96 hours post-transfection and transdifferentiation with antagomiRs. *p<0.05, p<0.01, *p<0.001 (Student's t test).

With the aforementioned concentrations, tests were conducted on the transfection of transdifferentiated fibroblasts to myoblasts of DM1 patients, with the antagomiR-23 or the antagomiR-218, as described in the methodological section on "Splicing tests" and quantification assays of RNA of MBNL1 and MBNL2 commenced. As can be seen in FIG. 9, both the antagomiR mir-23b and the antagomiR mir-218 increased the expression of MBNL1 and MBNL2 at the level of mRNA by qPCR and this increase responds to the dose of antagomiR (by transfection). This was done at 48 and 96 h. Assuming a typical bell-shaped dose-response, the results obtained suggest that optimal concentration for antagomiR mir-23b is 50 nM, or lower, and 200 nM or higher for antagomiR mir-218.

Figure 10:
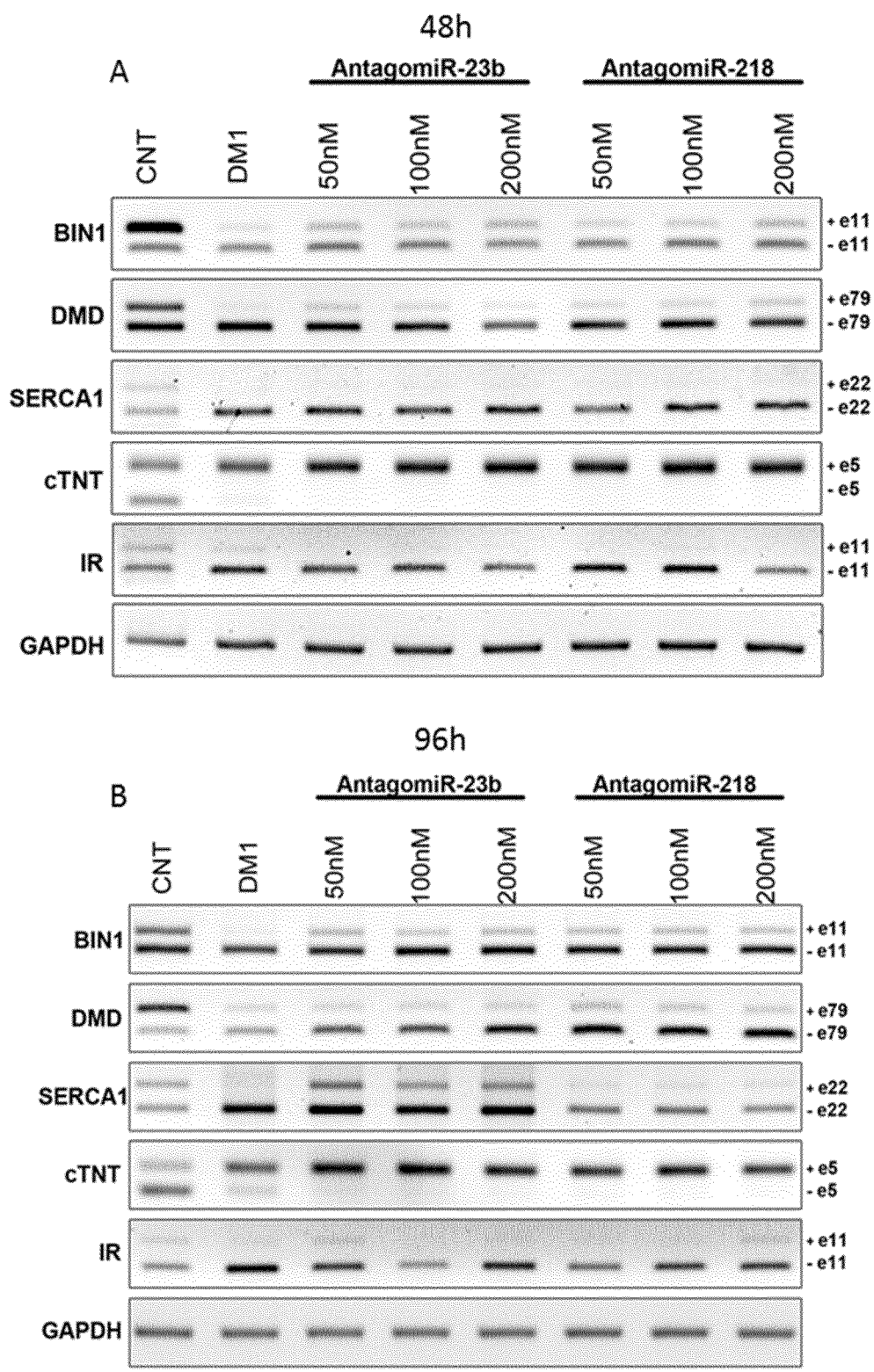
FIG. 10. Dose response trials of microRNAs 218 and 23b antagomiRs: evaluation of the alternative splicing of genes cTNT, DMD, SERCA1, BIN, IR and GAPDH using semi-quantitative RT-PCR in samples of myoblasts of healthy controls (CNT), and DM1 myoblasts untreated (DM1), or treated with antagomiR-23b and antagomiR-218 at the indicated concentrations (50 nM, 100 nM, 200 nM). The results obtained after 48 h (panels A, C, D, E, F, G) or 96 h (Panels B, H, I, J, K, L) of transdifferentiation are shown. Panels A and B show pictures of the corresponding fragments of the gels of electrophoresis performed after RT-PCR; the right part of the tests corresponding to each gene indicates the exon for which its inclusion (legend headed with the sign "+") or exclusion (legends with the sign "−") was verified. Panels C, D, E, F, G (test at 48 h) and H, I, J, K, L (at 96 h) show bar charts with the percentages of exclusion (part in light grey) or inclusion (upper part, in darker grey) of each of these exons for the controls CNT and DM1 and the concentrations of each antagomiR indicated below the bars.
Figure 10:
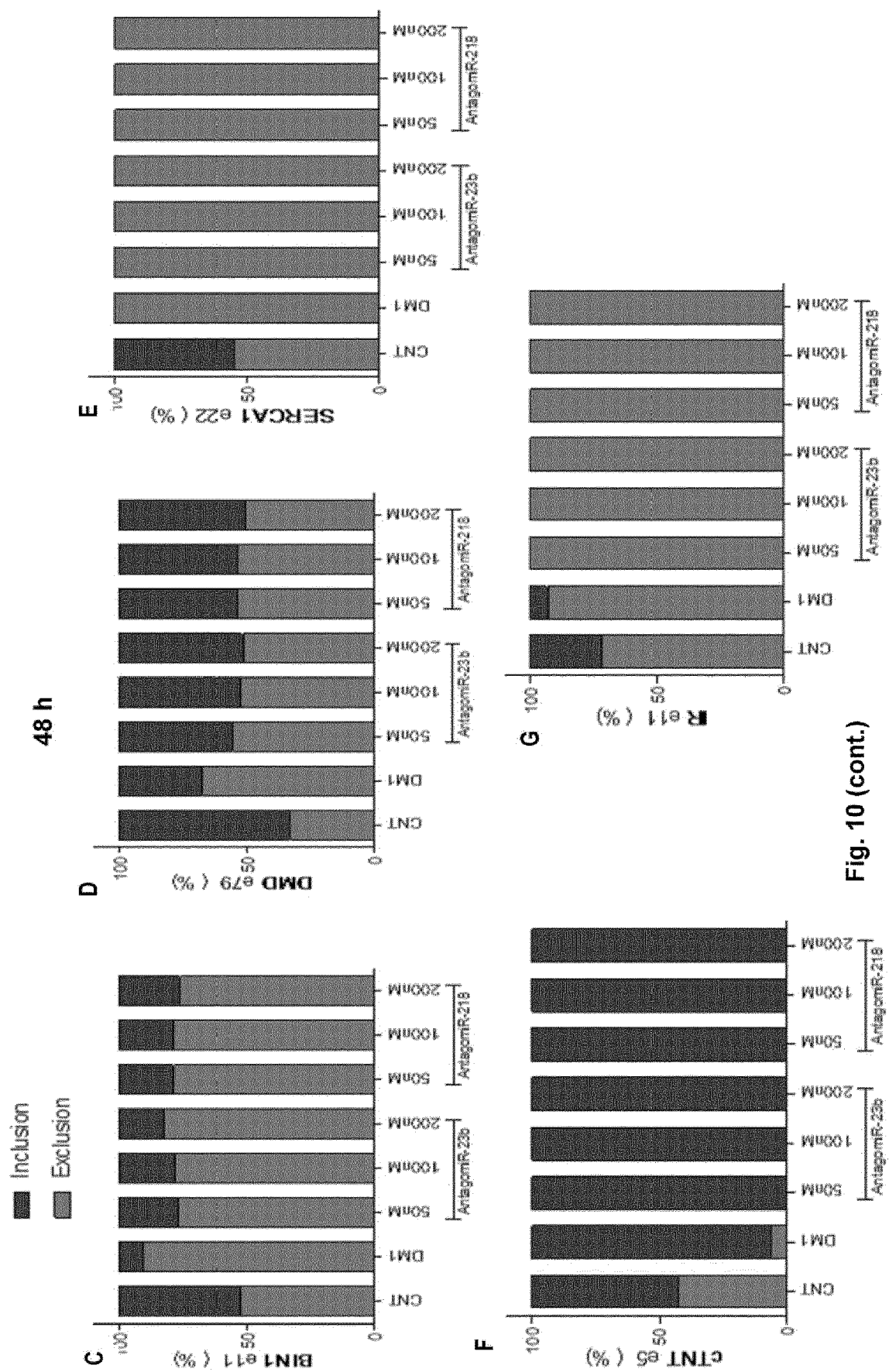
Figure 10:
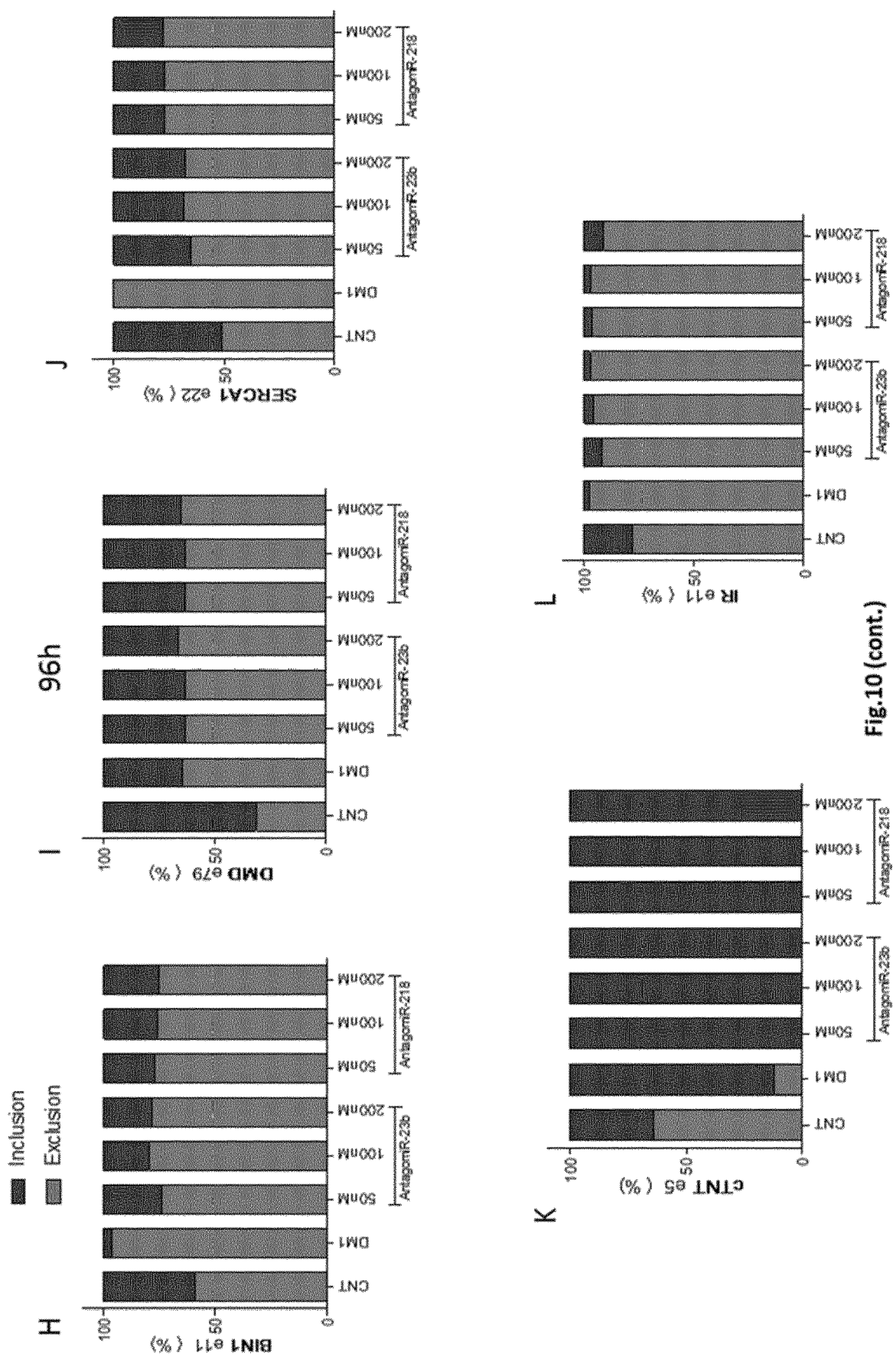

It was also verified whether it was possible to rescue some events of alternative splicing typically altered in DM1, in myoblasts of patients, in the presence of antagomiR23b or antagomiR218, following the methodology described in the section "Splicing assays". These experiments were conducted at 48 h (FIGS. 10A, C, D, E, F, G) and 96 h (FIGS. 10 B, H, I, J, K, L) after transfection of the AntagomiR.

As noted in these figures, the treatment of DM1 cells with antagomiRs improved the inclusion of exon 11 of BIN1 with both antagomiRs, at all concentrations and at both times after transfection.

Treatment with antagomiRs increases the percentage of inclusion of exon 79 of DMD as reflected in the gel (upper band), with both antagomiRs and at all concentrations in the assay performed at 48 h. In contrast, in the test performed at 96 h, no change was observed in the aberrant splicing of DMD.

In the assay performed at 48 h, no change was observed with antagomiRs at any concentration in the aberrant splicing of SERCA1, whereas in the assay at 96 h, treatment with both antagomiRs and at all concentrations results in an increase in the percentage of inclusion of exon 22 of SERCA1; this increase was notably more visible with the antagomiR-23b.

The assay at 48 h after transfection did not result in any change in the aberrant splicing of IR. The inclusion of exon 11 of IR only improved similarly to what is seen in the case of healthy myoblasts at the lower concentration of antagomiR-23b (50 nM) at 96 h and at the highest concentration of antagomiR-218 (200 nM).

Figure 11:
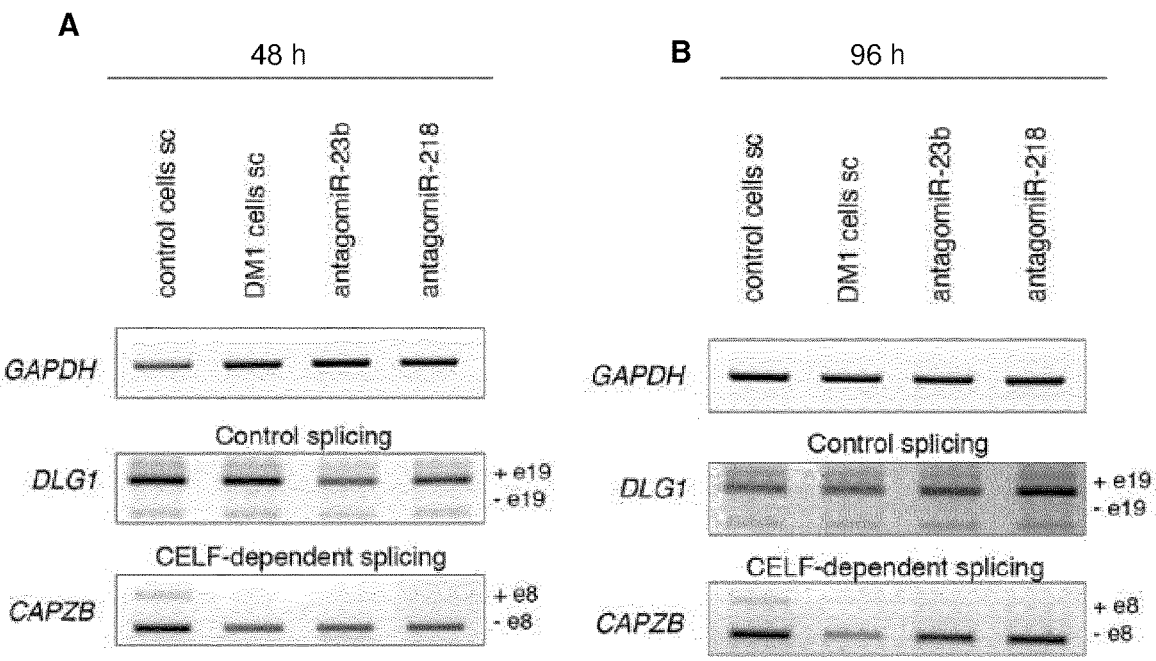
FIG. 11. Semiquantitative RT-PCR analyses, in myoblasts ("control cells sc") and muscle biopsies from DM1 patients transfected the scrambled miRNA ("DM1 cells sc") or the antagomiRs 23b or 218 (as indicated below the bars) of splicing events in DLG1 exon 9 (which is not altered in DM1), and CAPZB exon 8 (which is CELF-dependent), were used as additional controls BIN1 (exon 11), ATP2A1 (exon 22), cTNT (exon 5), INR (exon 11) and PKM isoforms in DM1 cells. GAPDH was used as internal control.

No change was observed with antagomiRs at any concentration in the aberrant splicing of cTNT. To test the specificity of antagomiRs-23b and antagomiR-218 the inclusion of exon 8 of CAPZB (which depends on CELF1) was quantified. It was observed that it was not rescued by the antagomiRs. Additionally, the regulated inclusion of exon 19 of DLG1, which is known to be MBNL1 and CELF1-independent, did not change under any of the experimental conditions thus discarding global effects on alternative splicing control upon antagomiR treatment (see FIGS. 11A and B). These results confirm Muscleblind-specific rescue of alternative splicing defects taking place in DM1 myoblasts as a result of antagomiR-mediated MBNL1 and MBNL2 derepression.

Figure 12:
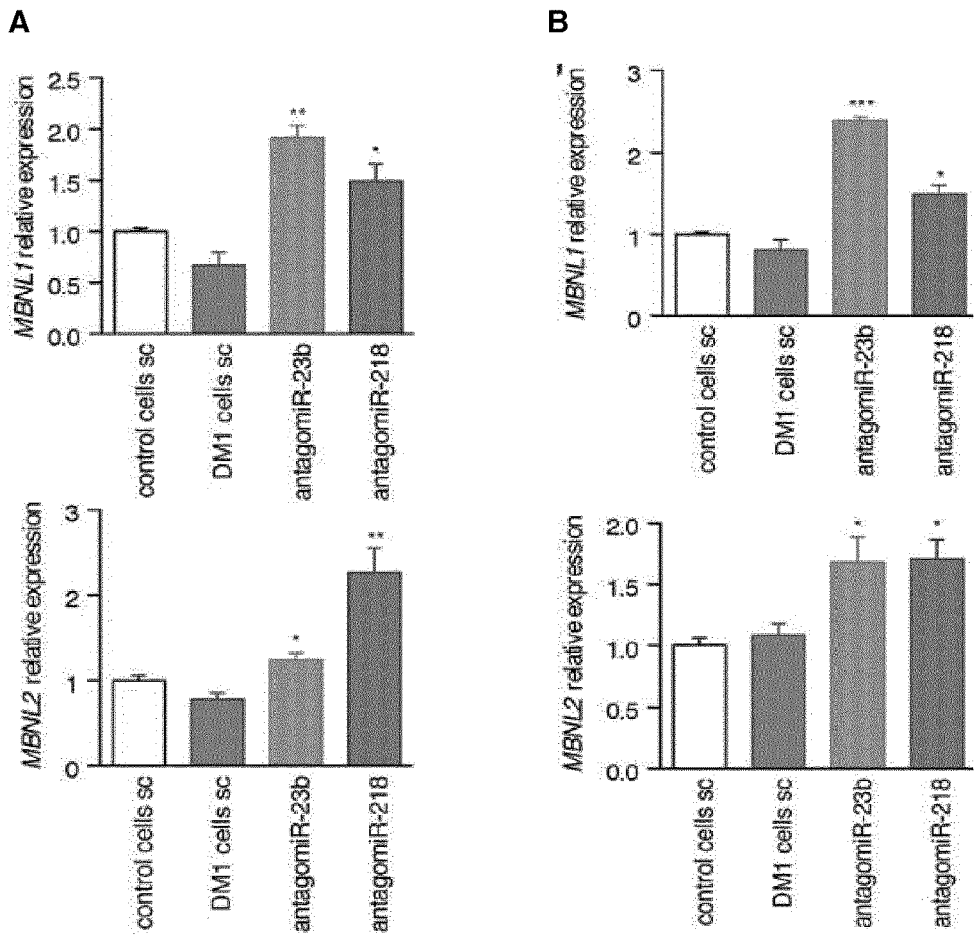
FIG. 12. qRT-PCR analyses of MBNL1 (upper charts) and MBNL2 (lower charts) expression relative to GAPDH and ACTB genes in human myoblasts 48 h (column A) or 96 h (column B) after transfection with 50 nM of antagomiR-23b or 200 nM of antagomiR-218.
Figure 13:
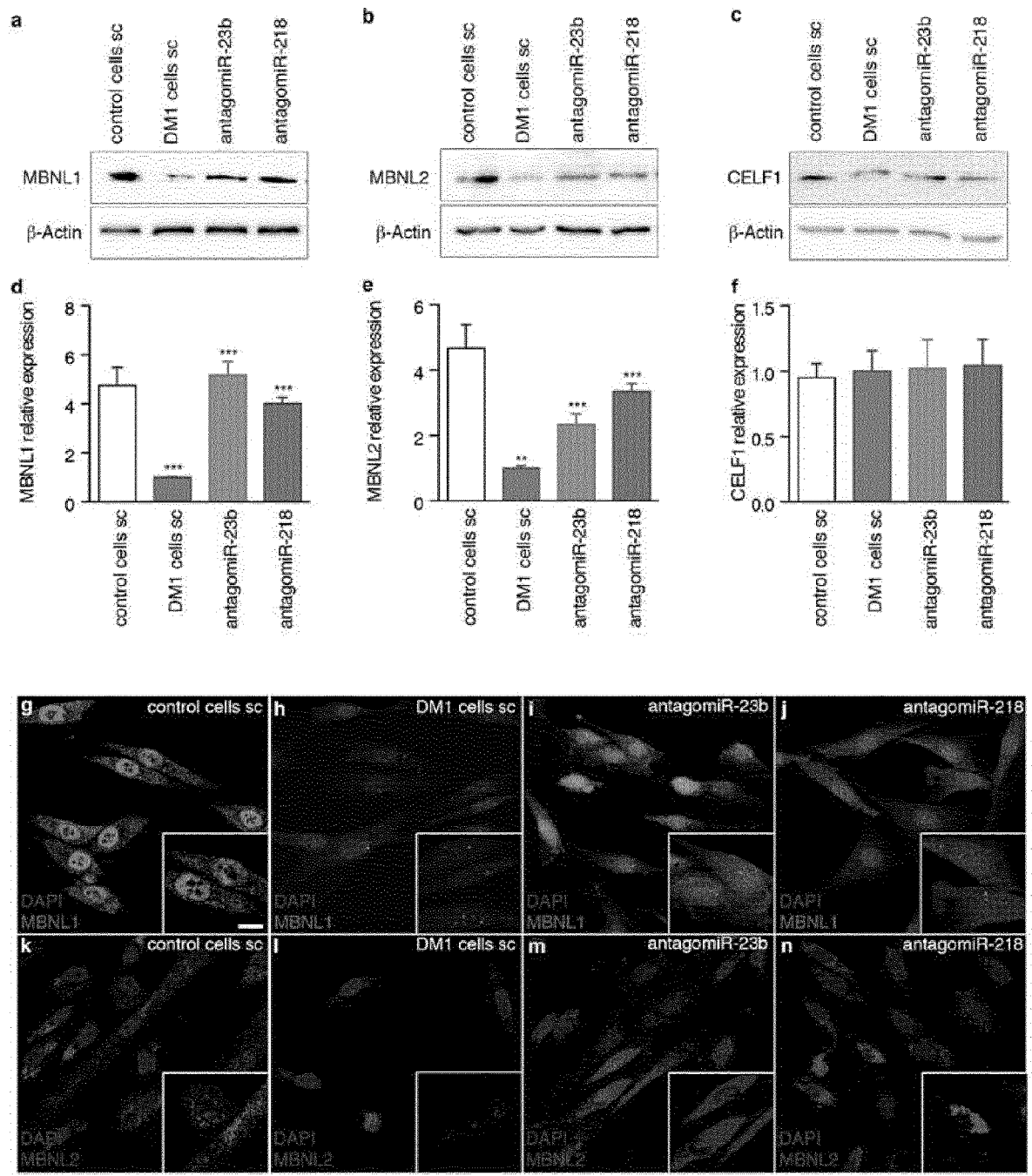
FIG. 13. Increase of MBNL1 and MBNL2 upon silencing of miR-23b or miR-218 in human myoblast. (a-f) Western blot quantification of MBNL1 (a, d), MBNL2 (b, e) and CELF1 (c, f) expression levels in healthy controls (Control cells) and DM1 human myoblast 96 h after transfection with 50 nM of antagomiR-23b, 200 nM of antagomiR-218 or a scrambled control antagomiR (sc). β-Actin expression was used as endogenous control (n=3). Error bars indicate SEM. p<0.01, *p<0.001 in Student's t test. (g-n) Representative confocal images of MBNL1 (green) and MBNL2 (red) staining in healthy controls (control cells) and DM1 human myoblast 96 h after transfection with antagomiRs against miR-23b (50 nM) or miR-218 (200 nM) and a scrambled control antagomiR (DM1 cells). Nuclei were counterstained with DAPI (blue). In DM1 cells, endogenous MBNL1 (h) and MBNL2 (l) were in nuclear aggregates (green and red puncta) and the total amount of both was reduced compared to control cells (g) and (k), respectively. In contrast, DM1 cells treated with antagomiRs against miR-23b or miR-218 showed a robust 20 increase in cytoplasmic and nuclear MBNL1 (i, j) and MBNL2 (m, n) levels compared to DM1 cells. Scale bar=20 μm.

3.4. AntagomiR-23b and AntagomiR-218 Upregulate MBNL Proteins and Restore their Normal Subcellular Distribution in DM1 Myoblasts Since miRNAs can regulate gene expression at the mRNA stability and translation levels, it was sought to determine the effect of antagomiRs on MBNL1 and MBNL2 protein expression. Upon antagomiR treatment, qPCR data confirmed a significant increase in the levels of MBNL1 and MBNL2 mRNA 48 h (FIG. 12A) or 96 h (FIG. 12B) post-transfection. At the protein level these differences were further enhanced and western blots detected 4-5 fold more MBNL1, and 3-5 fold higher MBNL2 proteins, in DM1 myoblasts after 96 h (FIGS. 13 a,b,d,e) and 48 h of antagomiR treatment. In contrast, CELF1 protein levels remained unchanged upon miR-23b or miR-218 silencing both after 96 h (FIGS. 13c,f) and 48 h and, consistently CAPZB alternative splicing remained the same. Importantly, this increase was clearly visible by immunofluorescence. Whereas both MBNL1 and MBNL2 were sequestered in ribonuclear foci of DM1 myoblasts (FIGS. 4 h,l), antagomiRs-23b and -218 robustly increased the protein expression and restored their distribution in the cytoplasm and in the cell nucleus (FIGS. 13 i,j;m,n). The increase of MBNL1 and MBNL2 proteins in the cell nucleus was consistent with the previously shown splicing rescue.

Example 4

Activity of AntagomiRs of miR-218 and miR-23b in a Mouse DM1 Model 4.1. AntagomiR-23b and -218 Reach Skeletal Muscle and Increase Mbnl Protein Expression in $HSA^{LR}$ Model Mice Next, the activity of antagomiR-23b and 218 in the $HSA^{LR}$ mouse DM1 model was investigated (Mankodi et al., 2000). First, the present inventors evaluated the ability of antagomiRs to reach skeletal muscle. Cy3-labelled versions of the antagomiRs were administered to a four month-old $HSA^{LR}$ mouse by a single subcutaneous injection. Four days post-injection, hind limb gastrocnemius and quadriceps 6 muscles were processed to detect the labelled oligonucleotide. The antagomiRs were observed by anti-Cy3 immunofluorescence in a strong punctate pattern in nuclei of both kinds of muscle fiber. The antagomiRs were also diffusely present throughout the cells (FIGS. 5b-e). These data demonstrate that antagomiR oligonucleotides that block miR-23b or miR-218 can reach the skeletal muscles of a DM1 mouse model.

Figure 14:
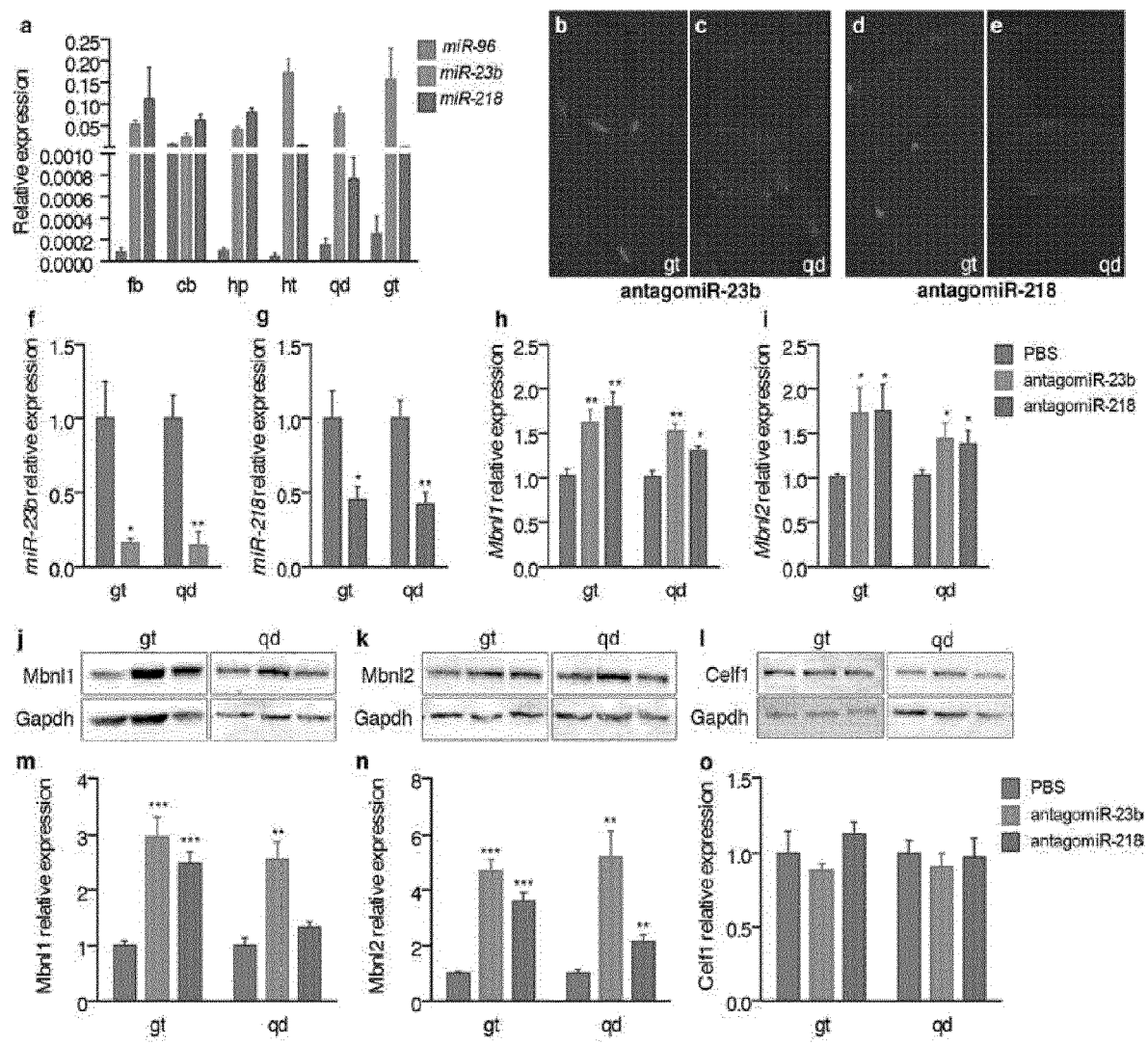
FIG. 14. Subcutaneous injection of antagomiR-23b or antagomiR-218 in HSA$^{LR}$ mice reduced target miRNA levels and increased Mbnl1 and Mbnl2 without affecting levels of Celf1. (a) qPCR quantification of miR-96, miR-23b and miR-218 expression levels in forebrain (fb), cerebellum (cb), hippocampus (hp), heart (ht), and quadriceps (qd) and gastrocnemius (gt) muscles (n=3). Average expression levels of U1 and U6 were used for normalization. (b-e) Immunodetection of Cy3-labelled antagomiRs in gastrocnemius (b, d) and quadriceps (c, e) cryosections of HSA$^{LR}$ treated mice (n=1). (f-g) Quantification of miR-23b and miR-218 in gt and qd muscles of untreated mice (PBS, first bar of each group, grey bars in the original) or treated with antagomiR-23b (second bar of each group, pink bars in the original) or antagomiR-218 (third bar of each group, blue bars in the original). Relative values (to average of U1 and U6 expression) were further normalized to the levels in untreated mice. (h-i) Real time PCR quantification of Mbnl1 and Mbnl2 transcript levels in gt and qd muscles. Expression levels relative to the endogenous Gapdh were normalized to the levels in untreated mice. (j-o) Western blotting analysis of Mbnl1 (j, m), Mbnl2 (k, n), and Celf1 (l, o) proteins in mouse gt and qd muscles. Representative blots used for quantification in (m-o) are shown in (j-l). The data were analyzed by unpaired Student's t-test compared to untreated HSA$^{LR}$ mice. *p<0.05, p<0.01, *p<0.001; HSALR PBS (n=5), HSALR PBS antagomiR-23b (n=4). HSA$^{LR}$ PBS antagomiR-23b (n=4).

The inventors decided to use the same administration method to inject unlabelled antagomiRs to four additional DM1 animals, in consecutive injections (12 h intervals) to a final dose of 12.5 mg/kg. The controls were injected with PBS1×. Four days after the first injection, animals were sacrificed and quadriceps and gastrocnemius were obtained for histological and molecular analysis. It was confirmed that miR-23b and miR-218 were strongly silenced by their complementary antagomiRs. miR-23b was reduced to 20% and miR-218 to 50% of the levels measured in the untreated $HSA^{LR}$ mice (FIGS. 14 f,g). As a result of miRNAs reduction Mbnl1 and Mbnl2 increased at the transcript and protein levels in both muscle types (FIGS. 14h,i; j,m; k,n). Nevertheless, in quadriceps antagomiR-23b achieved an important increase of both Mbnl1 and Mbnl2 protein levels, while antagomiR-218 only significantly upregulated Mbnl2. Importantly, levels of Celf1 protein were not altered by either treatment (FIGS. 14l,o).

Figure 15:
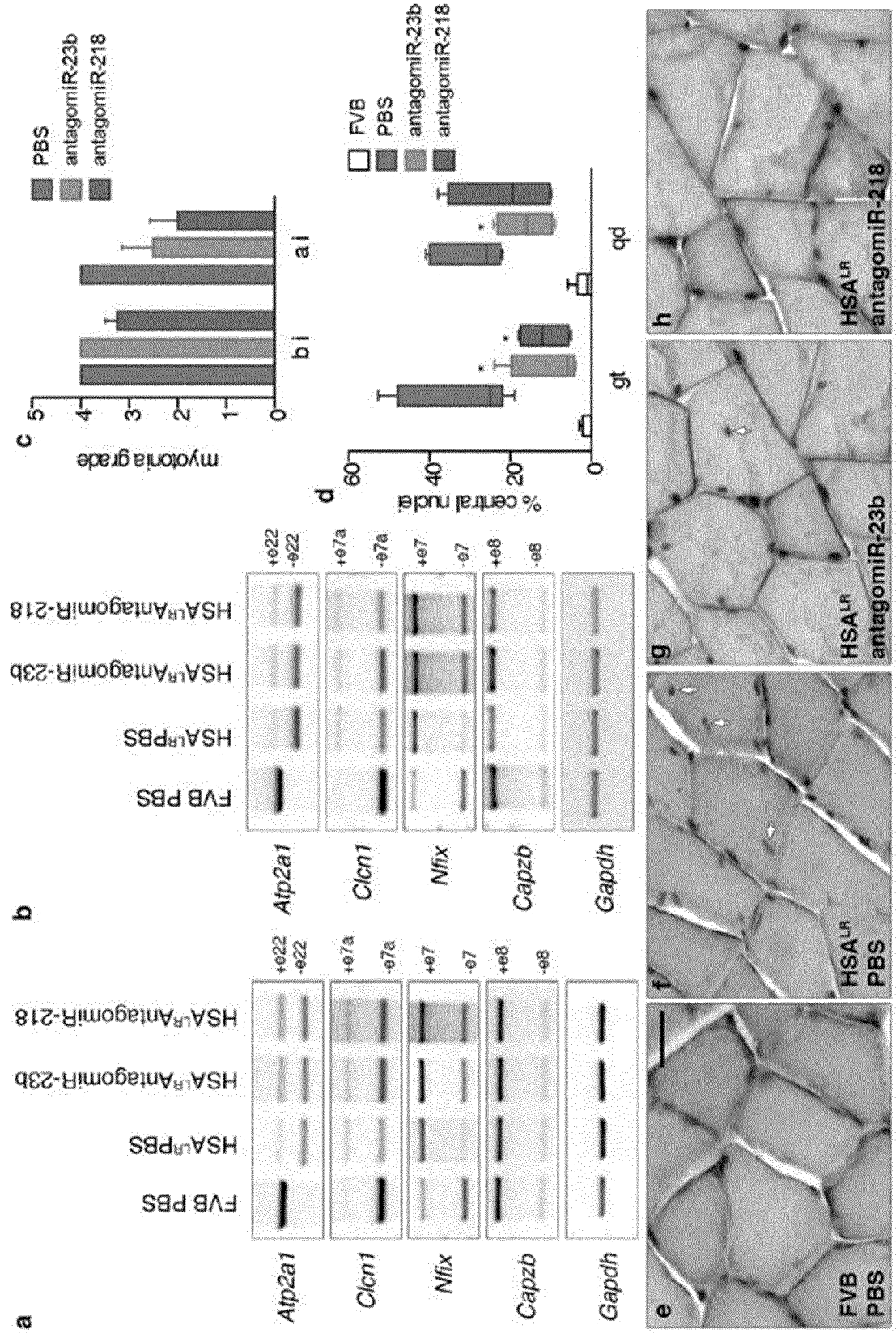
FIG. 15. Systemic delivery of antagomiRs improved missplicing of Mbnl-dependent transcripts, myotonia, and muscle histopathology in HSA$^{LR}$ mice. (a-b) RT-PCR analyses of the splicing of Atp2a1 exon 22, Clcn1 exon 7a, Nfix exon 7, and Capzb exon 8 in gastrocnemius (gt) (a) and quadriceps (qd) (b) muscles. Gadph values were used for normalization in the quantification of the exon inclusion in FIG. 16 and FIG. 17. (c) Electromyographic myotonia grade in antagomiR (second and third bar of each group, pink and blue bars in the original) or PBS-treated (first bar of each group, grey bars in the original) HSA$^{LR}$ mice before (bi) and four days after injection (ai). (d) Quantification of the percentage of muscle fibers with central nuclei in gt and qd muscles of control FVB (white bar), and PBS (grey bar) or antagomiR-treated (pink and blue bars) HSA$^{LR}$ mice. (e-h) Representative hematoxylin and eosin staining of gt muscles from all four groups of mice. Arrows point to examples of centrally located nuclei in muscle fibers. Scale bar=50 μm. The data were analyzed by unpaired Student's t-test compared to untreated HSALR mice. *p<0.05; FVB (n=3), HSA$^{LR}$ PBS (n=5), HSALR PBS antagomiR-23b (n=4) and HSA$^{LR}$ PBS antagomiR-23b (n=4).
Figure 16:
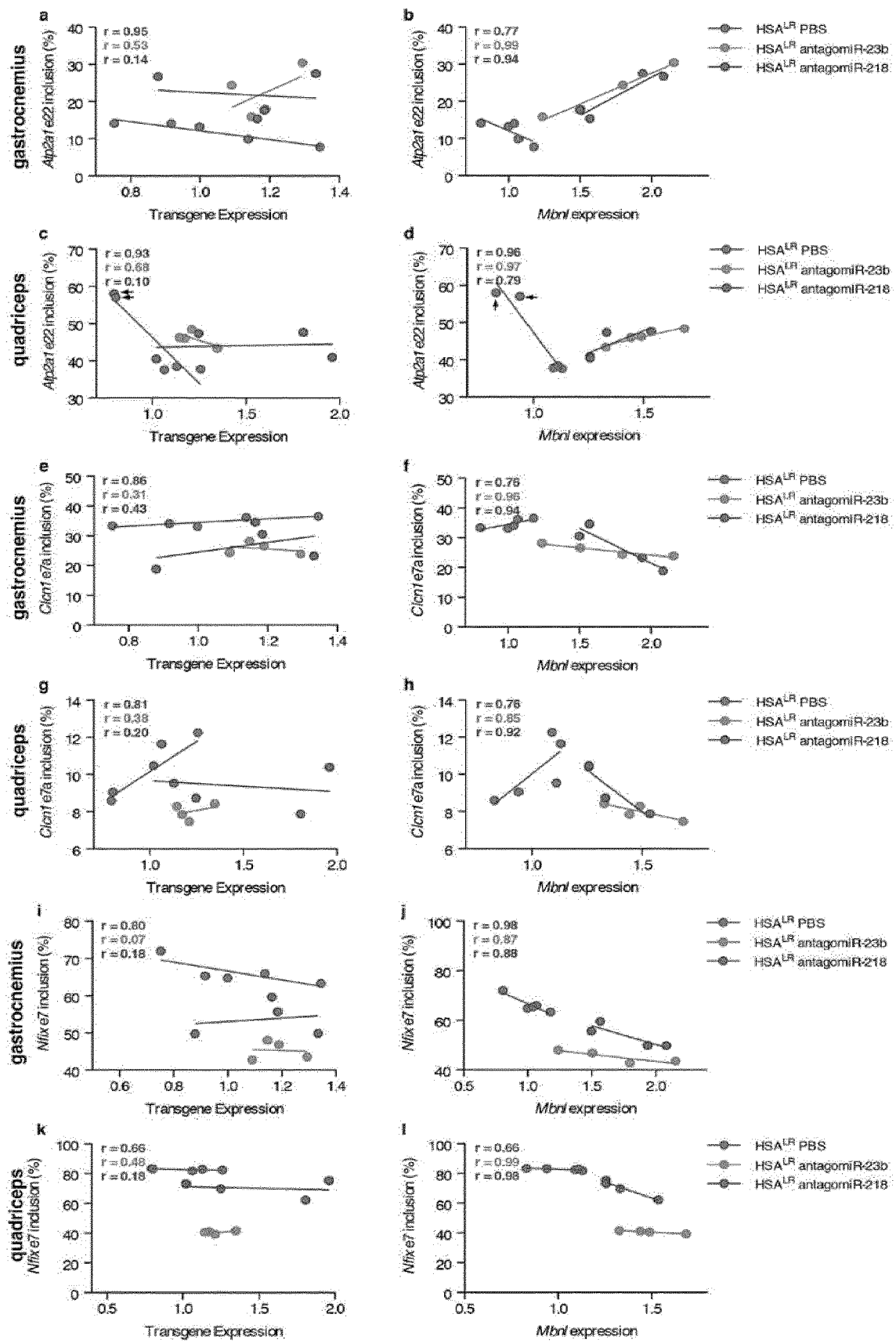
Figure 17:
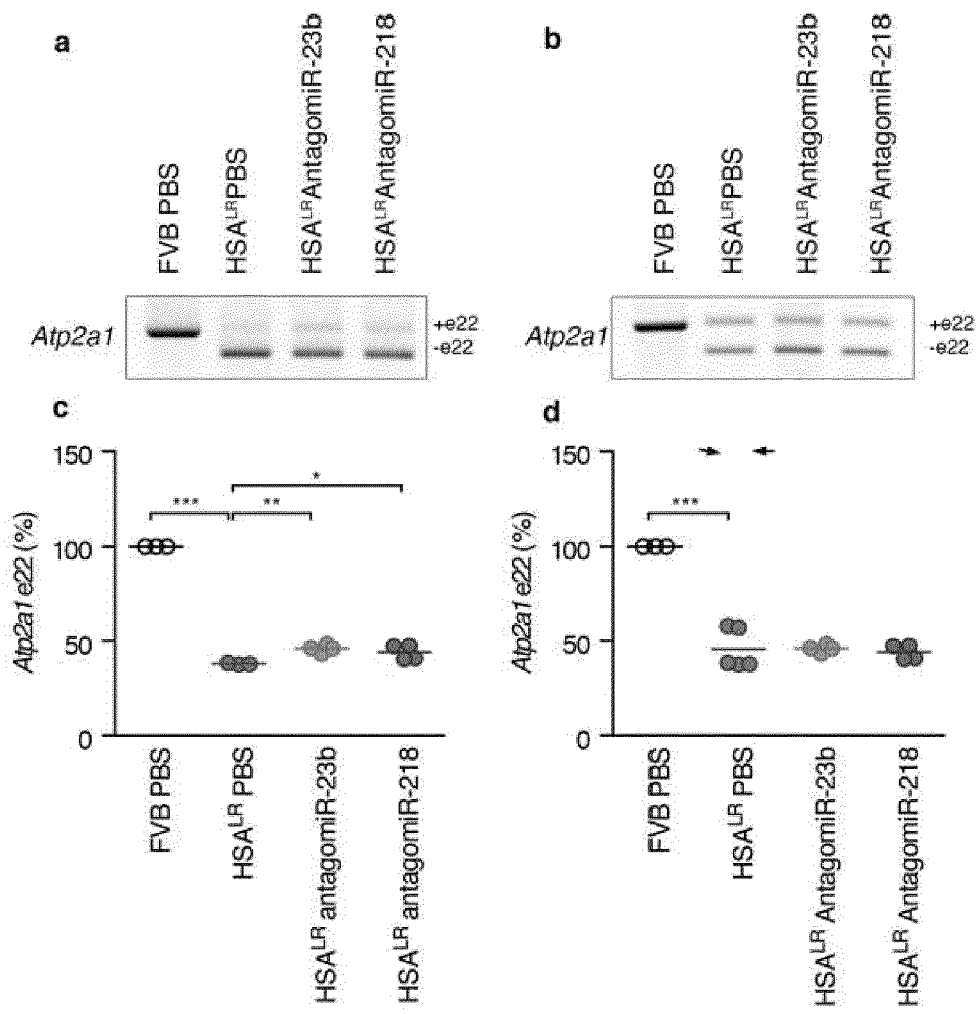

4.2. Blocking of miR-23b or miR-218 Activity Enhances Mbnl Expression and Rescues Missplicing of Muscle Transcripts in Mice Given the robust increase in Mbnl1 and 2 in treated gastrocnemius and quadriceps muscles, the present inventors sought to confirm a rescue of Mbnl-dependent splicing events Atp2a1, Clcn1, and Nfix in $HSA^{LR}$ mice (FIGS. 15a,b). AntagomiR administration ameliorated aberrant exon choices for Atp2a1 (exon 22) and Nfix (exon 7), and increased Clcn1 exon 7a PSI in gastrocnemius but not in quadriceps of $HSA^{LR}$ mice. In a routine test of transgene expression of $HSA^{LR}$ mice, it was discovered that CUG expression levels varied up to 0.5 fold among animals and that variation positively correlates with aberrant inclusion of alternative exons in gastrocnemius and quadriceps (FIG. 16). To note Atp2a1 exon 22 inclusion was bimodal. Two mice expressing low levels of transgene included exon 22 to levels significantly higher (closer to normal) than the rest of HSALR mice and were therefore excluded from the analysis (FIGS. 16 and 17). These data suggest that the lower the expression of CUG repeat RNA in muscles the less missplicing there is. In contrast, in the antagomiR-treated $HSA^{LR}$ muscle samples splicing defects correlated with Mbnl mRNA levels, instead of repeat expression, which supported a causal role of these proteins 7 in the rescue of the splicing events (FIG. 16). Despite the intrinsic variability of the model, we conclude that both antagomiRs achieved similar levels of rescue in all gastrocnemius missplicing events. However, antagomiR-23b rescued Nfix and Clcn1 splicing to a greater extent than antagomiR-218 in quadriceps, which correlated with the lower upregulation of Mbnl1 and 2 protein levels achieved by antagomiR-218 in this muscle. Consistent with the unchanged levels of Celf1 protein in the muscles of treated $HSA^{LR}$ mice, Capzb exon 8 inclusion in gastrocnemius and quadriceps of treated and control mice was very similar (FIGS. 15a,b). These results indicate that systemic delivery of antagomiRs was able to rescue muscle missplicing in vivo in a DM1 mouse model.

4.3. AntagomiRs Improve Muscle Histopathology and Reduce Myotonia Grade

Defective transitions of fetal to adult alternative splicing patterns have been proposed to originate DM1 muscle phenotypes44. In $HSA^{LR}$ DM1 model mice, alterations in ionic currents cause repetitive action potentials, or myotonia, that can be quantified by electromyography. Before treatment, all DM1 mice had grade 3 or 4 myotonia, i.e. abundant repetitive discharges with the vast majority of electrode insertions. Four days after, antagomiRs reduced myotonia to grade 2 (myotonic discharge in >50% of insertions) or grade 1 (occasional myotonic discharge) in 75% of the mice treated with antagomiR-218, and in 50% of the mice treated with antagomiR-23b, respectively (FIG. 15c). A typical histological hallmark of DM1 and $HSA^{LR}$ mouse muscle fibers is a central location of nuclei, which results from myopathic muscle attempting to regenerate. Both antagomiRs caused decentralization of nuclei in both gastrocnemius and quadriceps muscles (FIGS. 15d-h). Taken together, these results validate the potential of antagomiR-23b and -218 as drug that suppress CUG-repeat RNA-induced myopathy in mammals.

Example 5

Assays Carried Out with AntimiRs and BlockmiRs

In order to verify the applicability of the approach for other types of antagonists, the following antimiRs and blockmiRs were synthesized by MiRx Therapeutics (Lyngby, Denmark):

```
MbloCKnoMIR
                               (SEQ ID NO: 84)
TbsGbscsascscsusususgsTbsTbsAbsTbsTbsTb M1bloCK23-1
                              (SEQ ID NO: 845)
CbsCbsAbsTbsTbsAbsuscsascsasusususTbsGb M2bloCK23-1
                               (SEQ ID NO: 86)
AbsuscsascsasusgsasTbsTbsCbsAbsAbsCbsGb M1bloCK218-1
                               (SEQ ID NO: 87)
GbsAbsusgsusgscsusususAbsAbsAbsTbsAbsTb M1bloCK218-2
                               (SEQ ID NO: 88)
GbsususgsusgscsusgsTbsCbsTbsAbsTbsTbsGb M2bloCK218-1
                               (SEQ ID NO: 89)
AbsCbsTbsusgsusgscsususGbsAbsAbsusTbsTb M2bloCK218-2
                               (SEQ ID NO: 90)
GbsTbsTbsGbsusgsusgscsusasasTbsAbsAbsTb M2bloCK218-3
                               (SEQ ID NO: 91)
CbsGbsAbsTbsAbsgsusgscsususAbsAbsAbsAb AntimiR-23b
                               (SEQ ID NO: 92)
CbscscsusgsgsCbsasAbsusgsusGbsasTb AntimiR-218
                               (SEQ ID NO: 93)
TbsusasGbsasuscsAbsasgsGbsasCbsasAb AntimiR-SC
                               (SEQ ID NO: 94)
GbsCbsAbsTbsAbsAbsusgsascsusususasTbsGb
``` wherein:
LNA nucleotides are indicated by the combinations of a capital letter and a small letter: Ab, Gb, Tb, Cb.
Phosphorothioate bonds are indicated by small "s" letters
2'-O-methyl-nucleotides are represented by the small letters: a g c u.

For toxicity and transfection assays, blockmiRs or antimiRs were added to the culture medium following the same protocol followed for antagomiRs. RNA was collected as processed in the same ways also used for antagomiRs.

5.1. Assays with AntimiRs

Figure 18A:
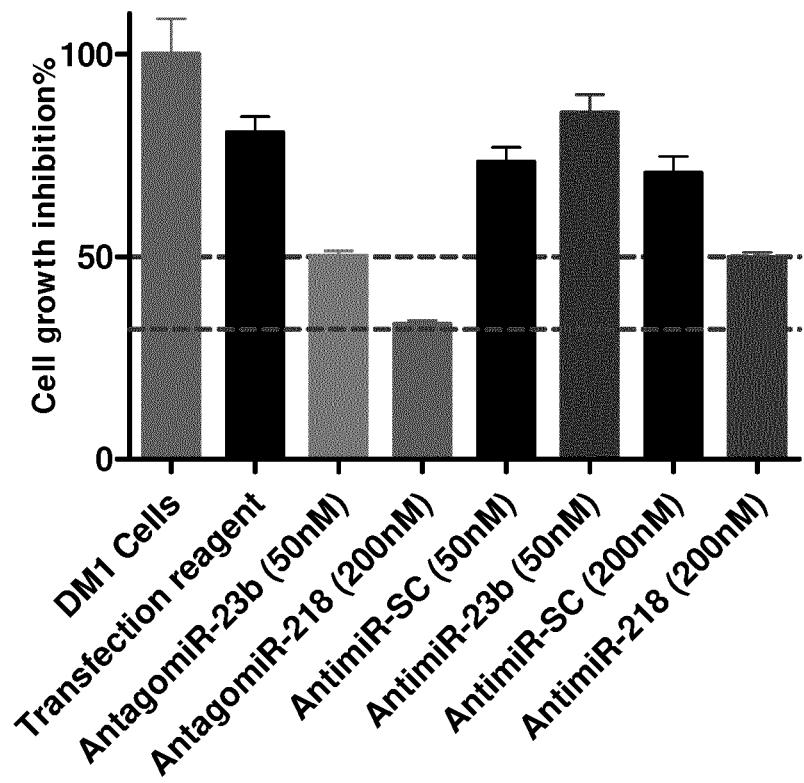
FIG. 18. Toxicity assays, expressed as cell growth inhibition (FIG. 18A), and MBNL1 (FIG. 18B) and MBNL2 (FIG. 18C) relative expression obtained by quantitative PCR, obtained in the assays performed with the antimiRs indicated in the X-axis, at the indicated concentrations. The results obtained with antagomiR-23b and antagomiR-218 are also shown FIG. 19. Toxicity assays, expressed as cell growth inhibition (FIG. 19A), and MBNL1 (FIG. 19B) and MBNL2 (FIG. 19C) relative expression obtained by quantitative PCR, obtained in the assays performed with the blockmiRs indicated in the X-axis. at the indicated concentrations. The results obtained with antagomiR-23b and antagomiR-218 are also shown.

As can be seen in FIG. 18A, antimiRs seemed to be less toxic than the antagomiRs in DM1 fibroblasts, what makes possible to increase the concentration in additional assays. It is important to point out that the transfection reactive killed by itself a 20% of the cells.

Figure 18B:
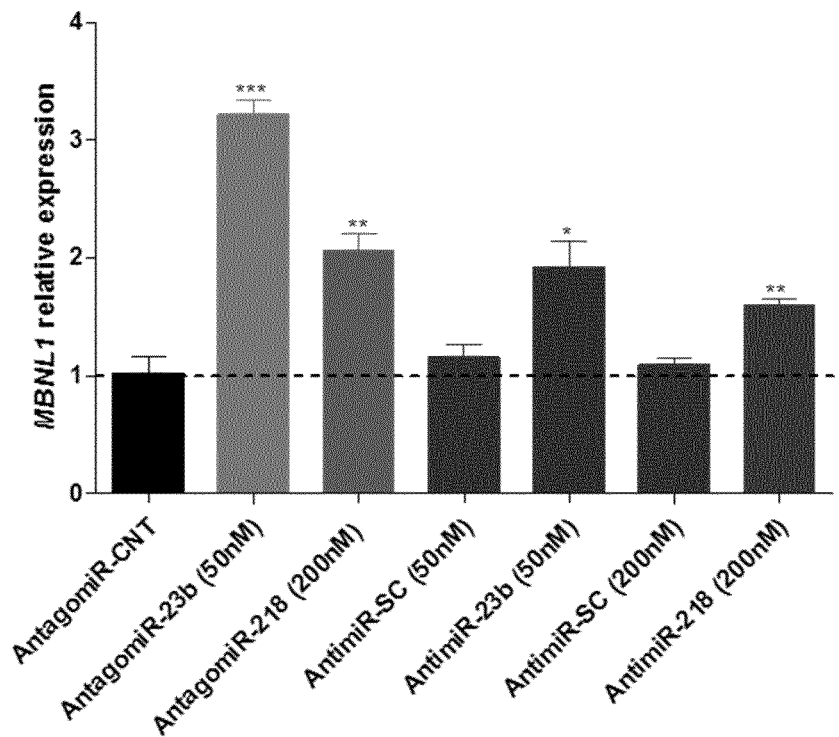
Figure 18C:
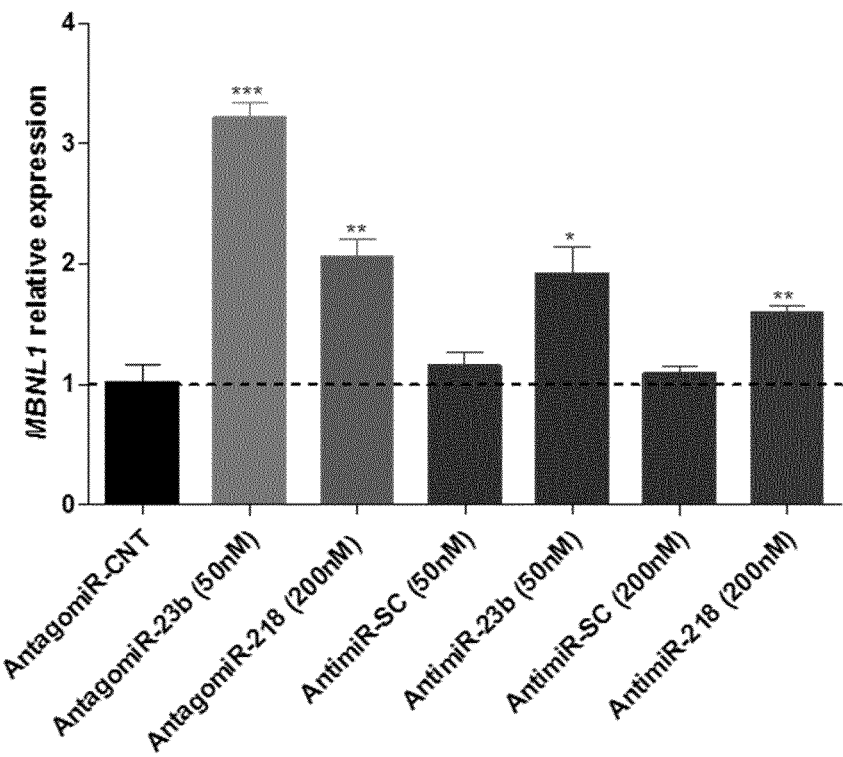

As can be seen in FIG. 18B and FIG. 18C, in a comparative assay also including the antagomiRs used in previous Examples, at the assayed concentrations (see the labels below the X-axis), the antagomiRs seemed to work better than antimiRs in order to increase MBNL1 or MBNL2 expression. Remarkable, the controls (CNT: scrambled RNAs), at the highest concentration (200 nM), improved MBNL2 expression.

5.2. Assays with BlockmiRs

Figure 19A:
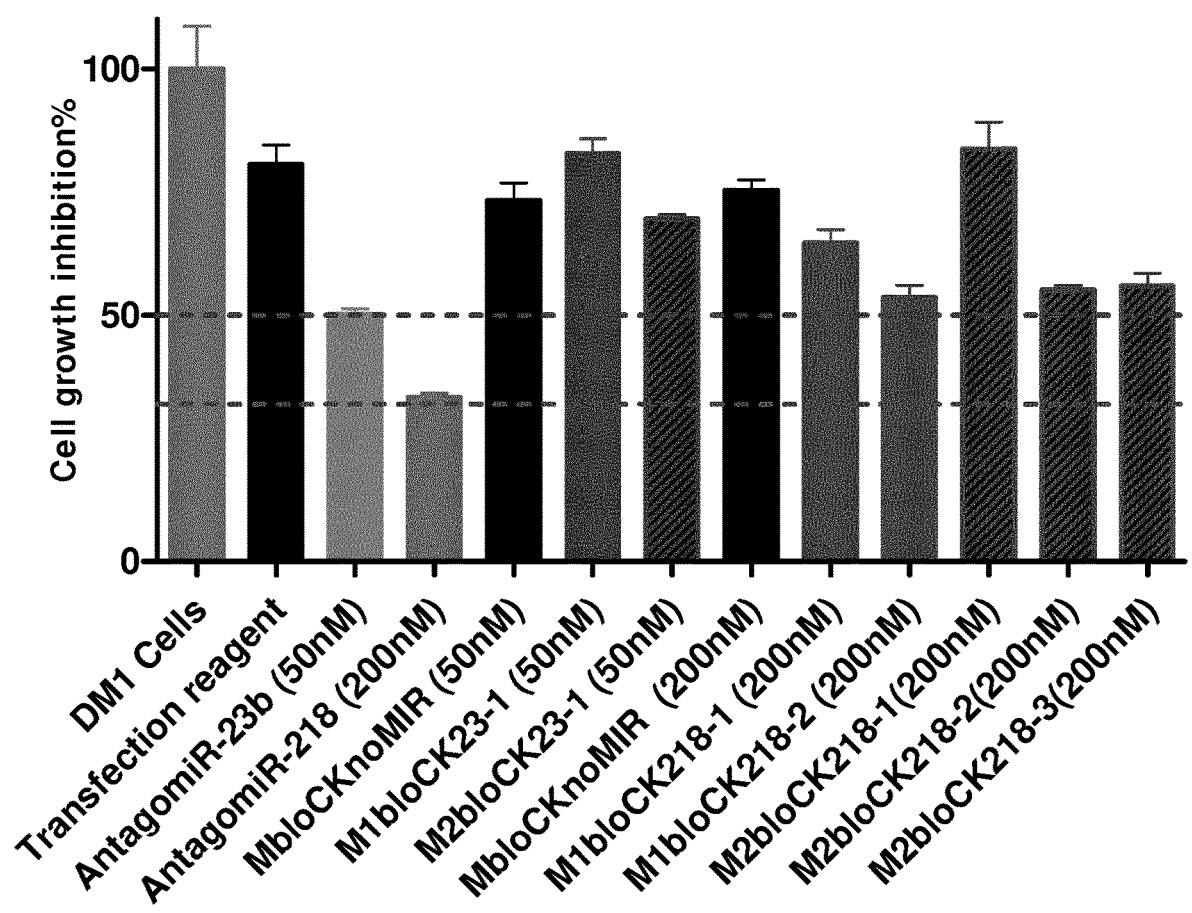

The toxicity assays performed with blockmiRs as transfection reactive showed a relatively low toxicity of blockmiRs, what again makes possible to increase the concentration in additional assays (see FIG. 19A).

Figure 19B:
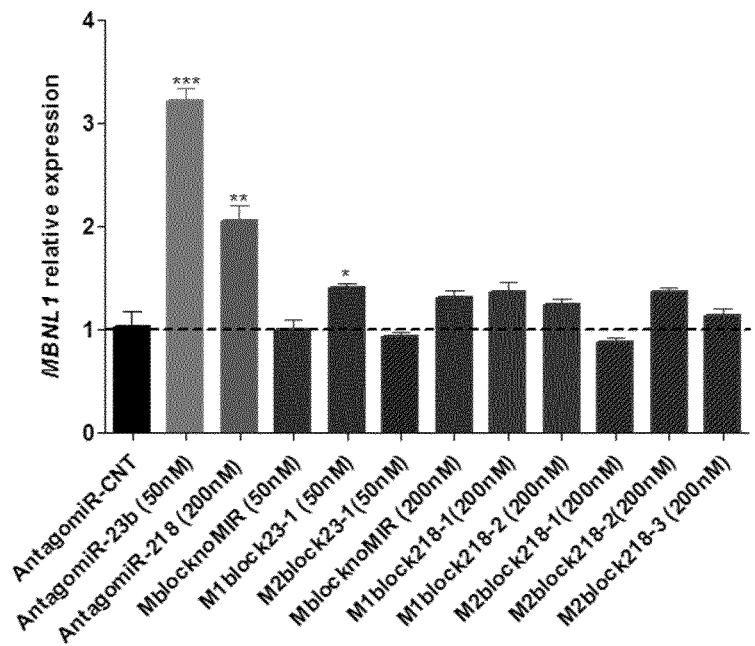
Figure 19C:
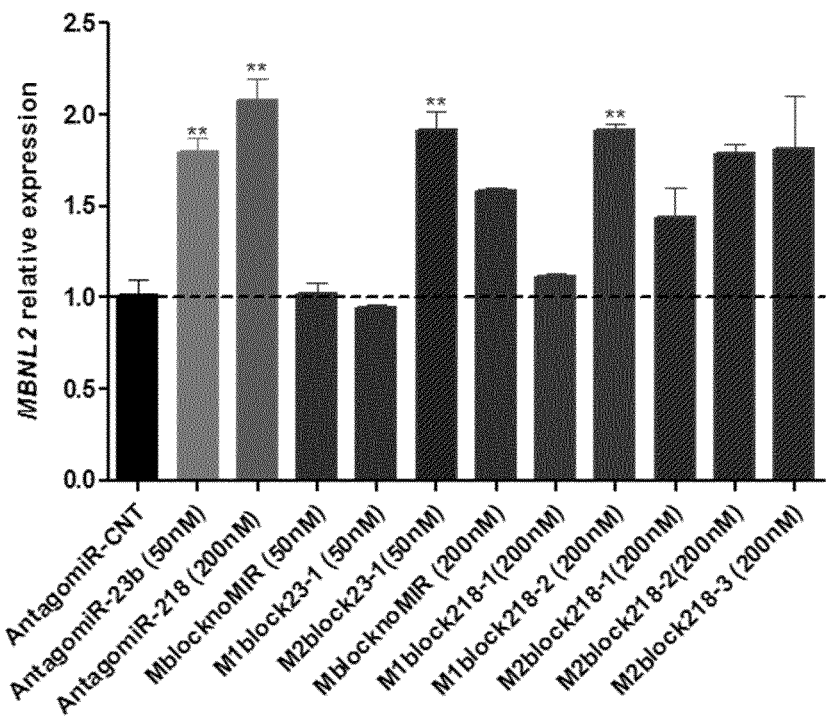

As can be seen in FIG. 19B and FIG. 19C, in a comparative assay also including the antagomiRs used in previous Examples, a significant increase of MBNL1 and MBNL2 expression was found for miR-23b when its target was blocked (M1bloCK23-1 and M2bloCK23-1, respectively). However, it was not possible to observe a significant increase of MBNL1 or MBNL2 when their respective targets were blocked (M1bloCK218-1 and M1bloCK218-2, or M2bloCK218-1, M2bloCK218-2 and M2bloCK218-3). It is surprising that blocking miR-218 target in 3'UTR of MBNL1 (M1bloCK218-2) leads to a significant increase of MBNL2 expression. Curiously, the controls (MblcknoMlR), at the highest concentration (200 nM), improved MBNL2. Expression.

Example 6

Assays Carried Out with FANA Oligonucleotides

The assays were carried out with the following FANA oligonucleotides, that were synthesized and provided by AUM Biotech LLC (Philadelphia, Pa., United States):

```
                                          (SEQ ID NO: 95)
AUM-miR-23b-1      GGUAAUCCCTGGCAAUGUGAU (SEQ ID NO: 96)
AUM-miR-23b-2:     GGUAATCCCTGGCAATGTGAU (SEQ ID NO: 97)
AUM-miR-23b-3      GGUAAUCCCUGGCAAUGUGAU (SEQ ID NO: 98)
AUM-miR-23b-4      GGUAATCCCTGGCAATGTGAU (SEQ ID NO: 99)
AUM-miR-218-1      ACAUGGUTAGATCAAGCACAA (SEQ ID NO: 100)
AUM-miR-218-2      ACATGGUUAGATCAAGCACAA (SEQ ID NO. 101)
AUM-miR-218-3      ACAUGGUUAGAUCAAGCACAA (SEQ ID NO: 102)
AUM-miR-218-4      ACATGGUTAGATCAAGCACAA (SEQ ID NO: 103)
AUM-SC-1           AUAUCCUTGTCGTAUCCCAGU (SEQ ID NO: 104)
AUM-SC-2           AUAUCCUTGTCGTAUCCCAGU
```

All oligonucleotides contain 2'F-arabinonucleotides at their ends and phosphorothioate bonds along their sequences.

Figure 20:
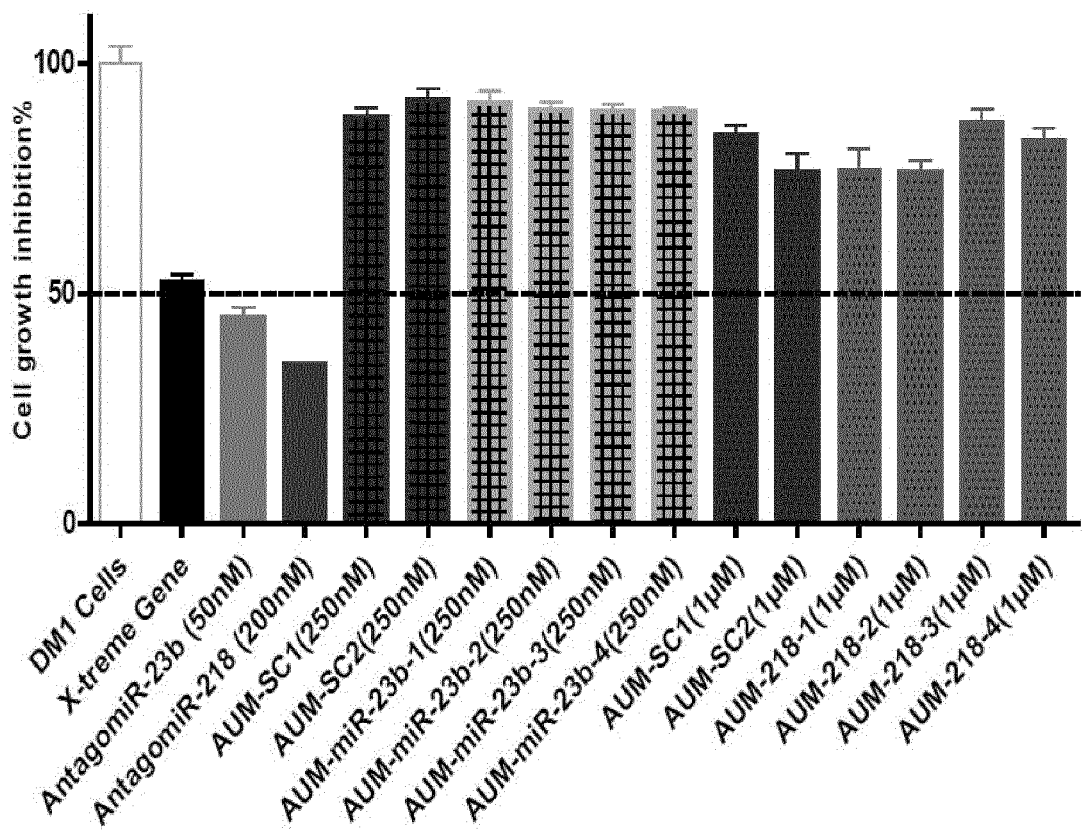
FIG. 20. Toxicity assays, expressed as cell growth inhibition, obtained after gymnotic delivery (FIG. 20A) or with transfection agents (FIG. 20B), obtained in the assays performed with the FANA oligonucleotides indicated in the X-axis, at the indicated concentrations. The results obtained with antagomiR-23b and antagomiR-218 are also shown.
Figure 20B:
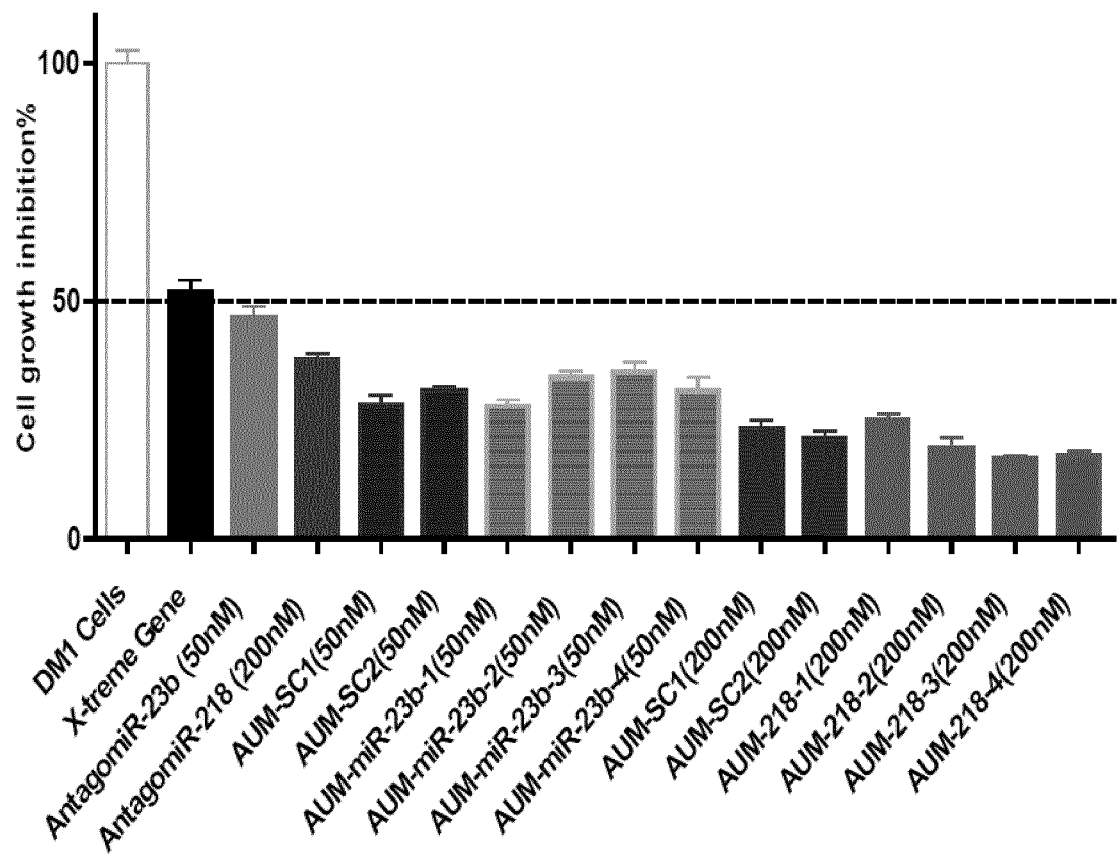
Figure 21A:
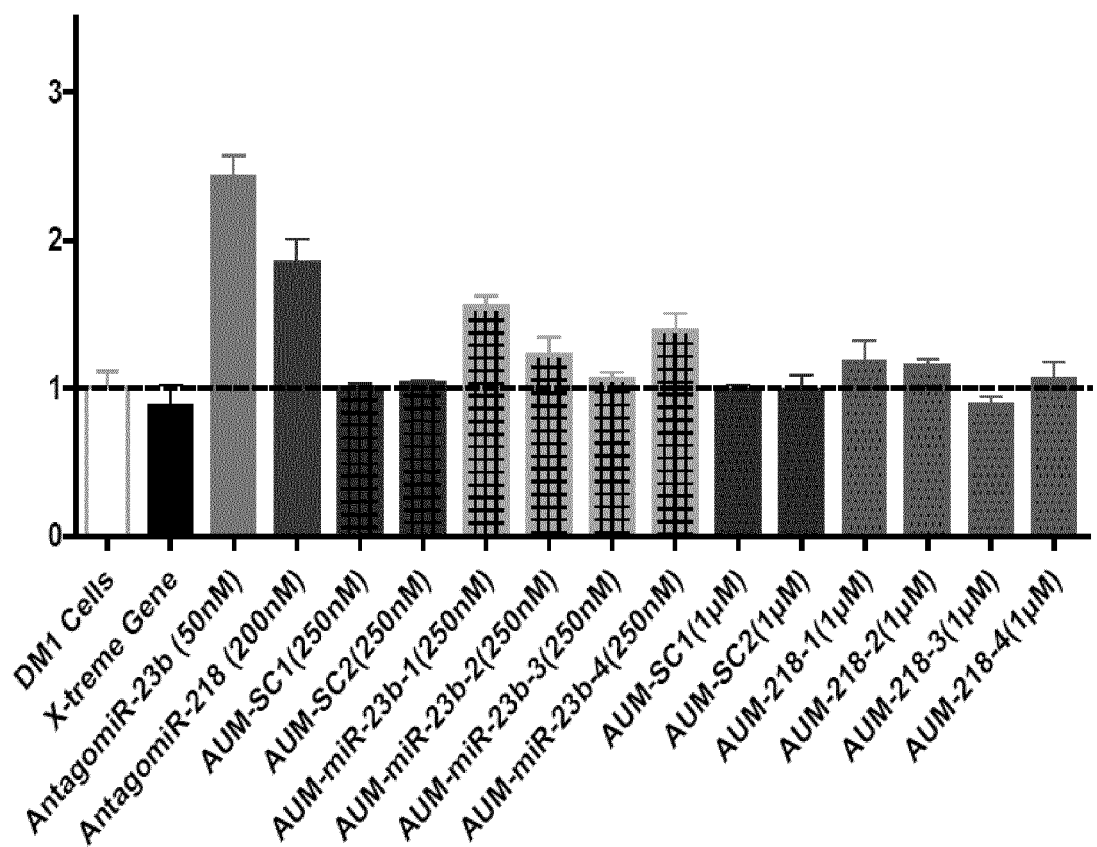
FIG. 21. MBNL1 relative expression results, obtained by quantitative PCR, obtained in the assays performed with the FANA oligonucleotides indicated in the X-axis, at the indicated concentrations. The results obtained with antagomiR-23b and antagomiR-218 are also shown. The results obtained after gymnotic delivery (FIG. 21A) or with transfection agents (FIG. 21B) are shown.
Figure 21B:
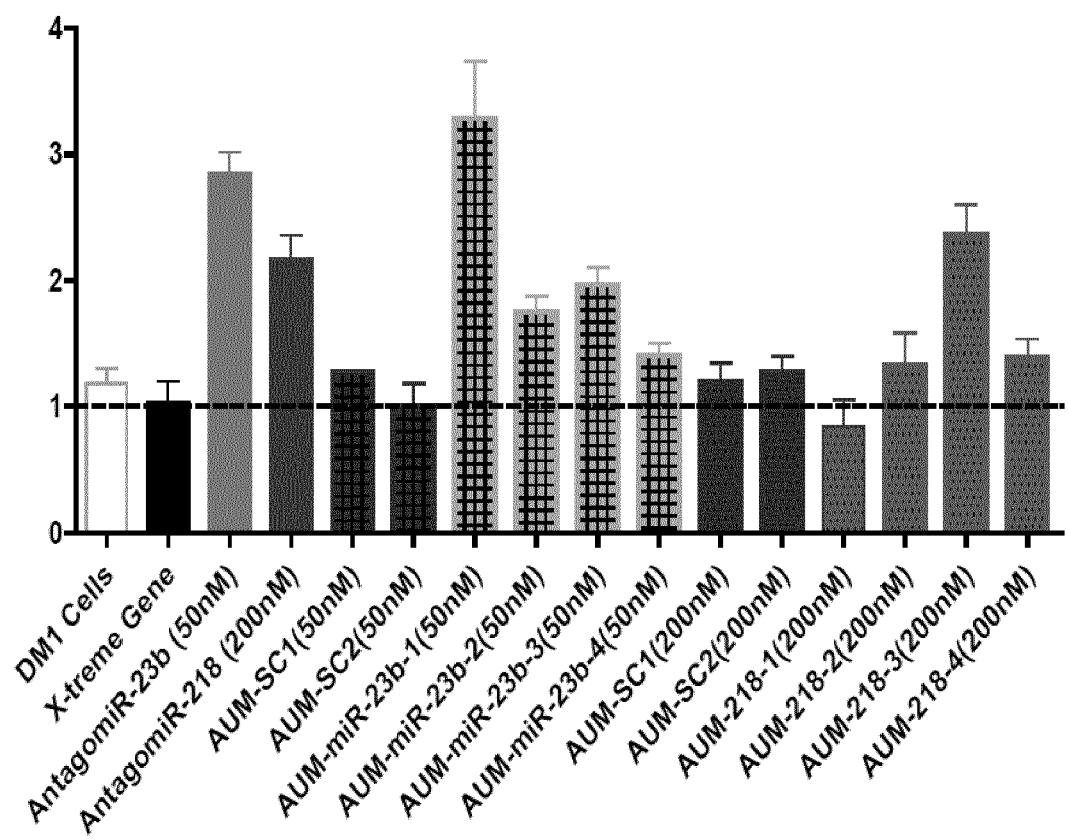
Figure 22A:
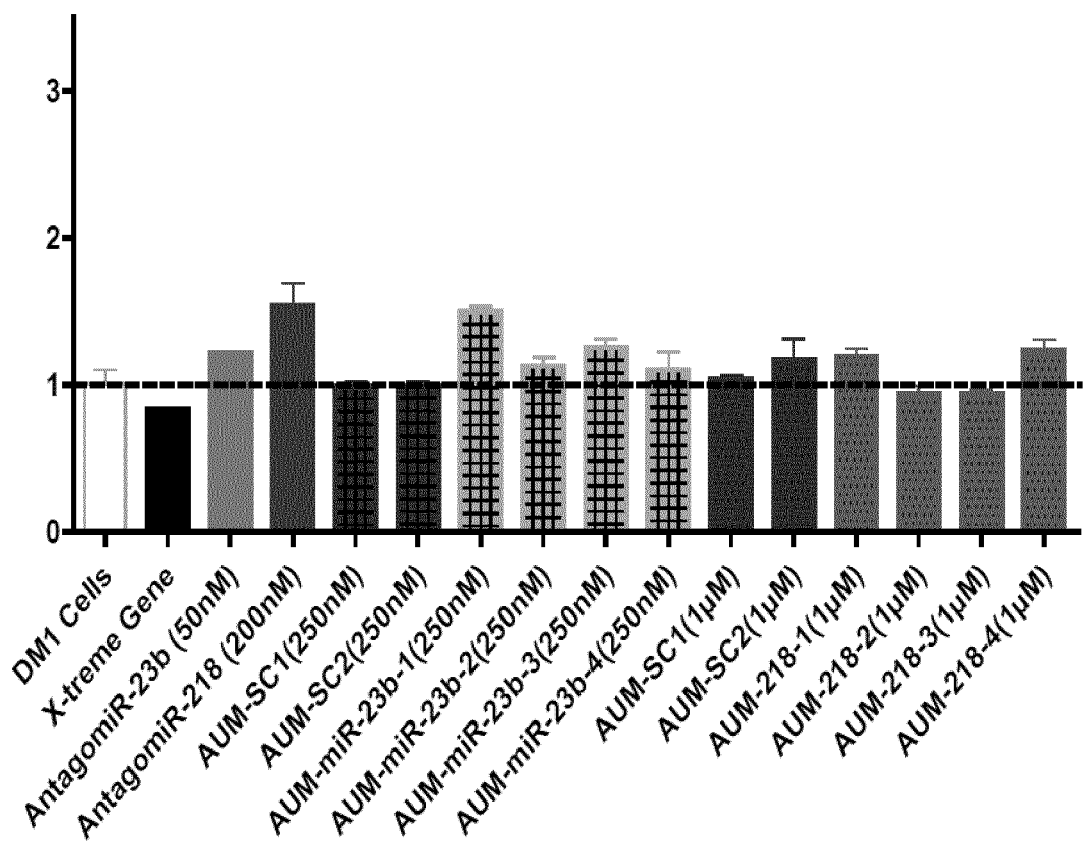
FIG. 22. MBNL2 relative expression results, obtained by quantitative PCR, obtained in the assays performed with the FANA oligonucleotides indicated in the X-axis, at the indicated concentrations. The results obtained with antagomiR-23b and antagomiR-218 are also shown. The results obtained after gymnotic delivery (FIG. 22A) or with transfection agents (FIG. 22B) are shown.
Figure 22B:
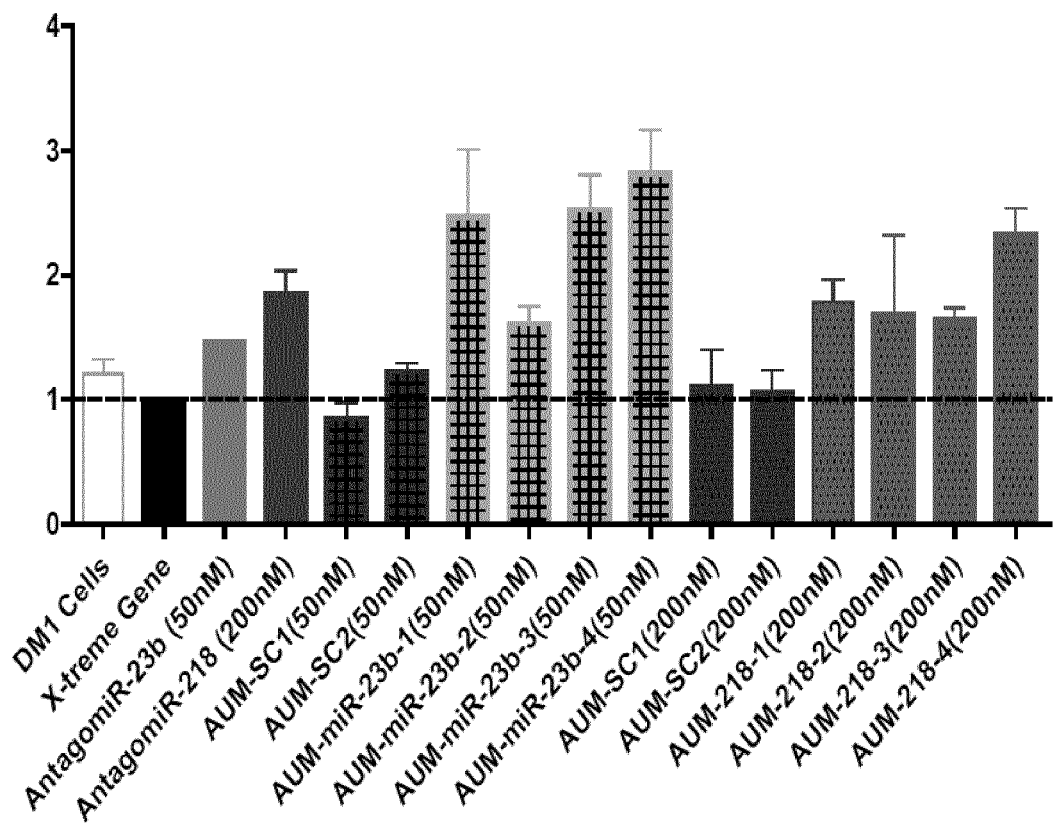

For toxicity and transfection assays, the FANA oligonucleotides were added to the culture medium following the same protocol followed for antagomiRs (RNA was also collected as processed in the same ways also used for antagomiRs), but in the case of the gymnotic delivery (FIG. 20A), where they were added at higher concentrations: 250 nM and 1 μM. For the gymnotic delivery, X-treme GENE was not added for the transfection and the FANA oligonucleotides were directly added to the cell culture media, because the oligonucleotides are able to enter the cells by themselves. For the qRT-PCR assays in the gymnotic delivery, fibroblasts were plated into Petri plates (1×10^6 cells/well), supplemented with FANA-antimiR in 3 ml MDM medium (DMEM with 4.5 g/L glucose, 1% P/S, 2% horse serum, 1% apo-transferrin (10 mg/ml), 0.1% insulin (10 mg/ml), and 0.02% doxycycline (10 mg/ml) for 6 hours. After that, 7 ml of MDM medium was added and samples were incubated for 96 h.

The results can be observed in FIGS. 20A-B, 21A-B and 22A-B, where comparative assays with the antagomiRs of previous Examples are shown.

The toxicity assays (FIG. 20A) carried out with gymnotic delivery showed that FANA oligonucleotides are of very toxic to DM1 myoblasts. For the comparison with antagomiRs, it must be taken into account that toxicity values are not comparable, because antagomiRs are transfected in the usual way. When toxicity was assayed with transfection reagents (FIG. 20B), FANA oligonucleotides were more toxic than antagomiRs at the same concentrations.

For assaying the effects on MBNL1 and MBNL2 expression, again, different assays were performed to see the effects of the gymnotic delivery and the transfection with transfection reagents.

In the cases of the "gymnotic delivery" (FIG. 21A and FIG. 22A, respectively, for MBNL1 and MBNL2), antagomiRs were transfected whereas FANAs were supplied directly, and comparison were made to untreated DM1 cells. It can be observed that two AUM-miR-23 FANA oligonucleotides (AUM-miR-23b-1 and AUM-miR-23b-4) increased MBNL1 levels, whereas the others did not seem to do much. AUM-218 FANA oligonucleotides did not work in this assay. Overall, it can be said that antagomiRs seemed to be more potent. Similar results were obtained for MBNL2: It can be observed that two AUM-miR-23 FANA oligonucleotides (AUM-miR-23b-1 and AUM-miR-23b-3) increased MBNL2 levels, whereas the others did not seem to do much, and AUM-218 FANA oligonucleotides did not work in this assay.

When transfection with transfection reagents was assayed (FIG. 21B and FIG. 22B), at the same concentration, AUM miR-23b, particularly AUM miR-23b-1 seemed to be slightly better at increasing MBNL1 level than the corresponding antagomiRs and additional designs of AUM miR23b show activity (compared to gymotic delivery). AUM miR-218 FNA oligonucleotides also showed activity (see FIG. 21B). Unspecific increase of MBNL1 expression levels in cells treated with the scrambled RNA was detected. The results obtained for MBNL2 were more or less the same as in the case of MBNL1 (see FIG. 22B). The quality of data was lower than in previous datasets (probably because of lower amount of RNA).

BIBLIOGRAPHICAL REFERENCES

Altschul, S. F. et al. Basic local alignment search tool. J. Mol. Biol., 215:403-410 (1990)

Babcock, D. T. & Ganetzky, B. An improved method for accurate and rapid measurement of flight performance in Drosophila. J Vis Exp, e51223, doi:10.3791/51223 (2014)

Batra, R. et al. Loss of MBNL leads to disruption of developmentally regulated alternative polyadenylation in RNA-mediated disease. Mol Cell 56, 311-322, doi: 10.1016/j.molcel.2014.08.027 (2014)

Begemann, G. et al. muscleblind, a gene required for photoreceptor differentiation in Drosophila, encodes novel nuclear Cys3His-type zinc-finger-containing proteins. Development 124, 4321-4331 (1997)

Chamberlain, C. M. & Ranum, L. P. Mouse model of muscleblind-like 1 overexpression: skeletal muscle effects and therapeutic promise. Hum Mol Genet 21, 4645-4654, doi:10.1093/hmg/dds306 (2012)

Davis, B. M., McCurrach, M. E., Taneja, K. L., Singer, R. H. & Housman, D. E. Expansion of a CUG trinucleotide repeat in the 3' untranslated region of myotonic dystrophy protein kinase transcripts results in nuclear retention of transcripts. Proc Natl Acad Sci USA 94, 7388-7393 (1997)

Dey, B. K., et al. miR-26a is required for skeletal muscle differentiation and regeneration in mice. Genes & Development 26, 2180-2191 (2012).

Dixon, D. M. et al. Loss of muscleblind-like 1 results in cardiac pathology and persistence of embryonic splice isoforms. Sci Rep 5, 9042, doi:10.1038/srep09042 (2015).

Du, H. et al. Aberrant alternative splicing and extracellular matrix gene expression in mouse models of myotonic dystrophy. Nat Struct Mol Biol 17, 187-193, doi:10.1038/nsmb.1720 (2010)

Enright, A. J. et al. MicroRNA targets in Drosophila. Genome Biol 5, R1, doi:10.1186/gb-2003-5-141 (2003)

Fernandez-Costa, J. M. et al. Alternative splicing regulation by Muscleblind proteins: from development to disease. Biol. Rev. Camb. Philos. Soc. 86(4), 947-58, (2011).

Fulga, T. A. et al. A transgenic resource for conditional competitive inhibition of conserved Drosophila microRNAs. Nat Commun 6, 7279, doi:10.1038/ncomms8279 (2015)

Gagno n, C. et al. Towards an integrative approach to the management of myotonic dystrophy type 1. Journal of Neurology, Neurosurgery & Psychiatry 78, 800-806 (2007)

Garcia-Casado, M. Z., Artero, R. D., Paricio, N., Terol, J. & Perez-Alonso, M. Generation of GAL4-responsive muscleblind constructs. Genesis 34, 111-114, doi: 10.1002/gene.10147 (2002)

Garcia-Lopez, A. et al. Genetic and chemical modifiers of a CUG toxicity model in Drosophila. PLoS One 3, e1595, doi:10.1371/journal.pone.0001595 (2008)

Harper, P. Myotonic dystrophy. (Saunders, 2001)

Houseley, J. M. et al. Myotonic dystrophy associated expanded CUG repeat muscleblind positive ribonuclear foci are not toxic to Drosophila. Hum Mol Genet 14, 873-883, doi:10.1093/hmg/ddi080 (2005)

Huin, V. et al. MBNL1 gene variants as modifiers of disease severity in myotonic dystrophy type 1. J Neurol 260, 998-1003, doi:10.1007/s00415-012-6740-y (2013)

Irion, U. Drosophila muscleblind codes for proteins with one and two tandem zinc finger motifs. PLoS One 7, e34248, doi:10.1371/journal.pone.0034248 (2012)

Kalsotra, A., et al. The Mef2 transcription network is disrupted in myotonic dystrophy heart tissue, dramatically altering miRNA and mRNA expression. Cell Rep. 6(2): 336-345. (2014). doi: 10.1016/j.celrep.2013.12.025. Epub 2014 Jan. 9

Kanadia, R. N. et al. A muscleblind knockout model for myotonic dystrophy. Science 302, 1978-1980, doi: 10.1126/science.1088583 (2003)

Kanadia, R. N. et al. Reversal of RNA missplicing and myotonia after muscleblind overexpression in a mouse poly(CUG) model for myotonic dystrophy. Proc Natl Acad Sci USA 103, 11748-11753, doi:10.1073/pnas.0604970103 (2006)

Kino, Y. et al. Nuclear localization of MBNL1: splicing-mediated autoregulation and repression of repeat-derived aberrant proteins. Hum Mol Genet 24, 740-756, doi: 10.1093/hmg/ddu492 (2015)

Klein, A. F., et al. Therapeutic Approaches for Dominant Muscle Diseases: Highlight on Myotonic Dystrophy. Curr. Gene Ther. 15(4), 329-337 (2015).

Kloosterman, W. P., et al. Targeted inhibition of miRNA maturation with morpholinos reveals a role for miR-375 in pancreatic islet development. PloS Biol 5, e203 (2007)

Kole, R., et al. RNA therapeutics: beyond RNA interference and antisense oligonucleotides. *Nature Reviews* 11, 125-140 (2012)

Krutzfeldt, J, et al. Silencing of microRNAs in vivo with 'antagomirs'. *Nature* 438, 685-689 (2005)

Landford, R. E., et al. Therapeutic silencing of microRNA-122 in primates with chronic hepatitis C virus infection. *Science* 327(5962): 198-201 (2010). Doi:10.1126/science.1178178

Lee, K. Y. et al. Compound loss of muscleblind-like function in myotonic dystrophy. *EMBO Mol Med* 5, 1887-1900, doi:10.1002/emmm.201303275 (2013)

Li Z. and Rana, T. M. Therapeutic targeting of miRNAs: current status and future challenges. Nature Reviews Drug Discovery, vol. 13, 622-638 (2014).

Lin, X. et al. Failure of MBNL1-dependent post-natal splicing transitions in myotonic dystrophy. *Hum Mol Genet* 15, 2087-2097, doi:10.1093/hmg/dd1132 (2006)

Llamusi, B. et al. Muscleblind, BSF and TBPH are mislocalized in the muscle sarcomere of a Drosophila myotonic dystrophy model. *Dis Model Mech* 6, 184-196, doi: 10.1242/dmm.009563 (2013)

Mankodi, A., et al. Myotonic dystrophy in transgenic mice expressing an expanded CUG repeat. *Science* 289, 1769-1773 (2000)

Needleman, S. B., Wunsch, C. D. A general method applicable to the search for similarities in the amino acid sequence of two proteins, J. Mol. Biol. 48:443-453 (1970)

Pascual, M., et al., The Muscleblind family of proteins: an emerging class of regulators of developmentally programmed alternative splicing. Differentiation 4(2-3):65-80 (2006).

Pearson, W. R., Lipman, D. J. Improved tools for biological sequence comparison. Proc. Natl. Acad. Sci. U.S.A. 85:2444-2448 (1988)

Picchio, L., Plantie, E., Renaud, Y., Poovthumkadavil, P. & Jagla, K. Novel Drosophila model of myotonic dystrophy type 1: phenotypic characterization and genome-wide view of altered gene expression. *Hum Mol Genet* 22, 2795-2810, doi:10.1093/hmg/ddt127 (2013)

Rottiers, V. et al. Pharmacological inhibition of a microRNA family in non-human primates by a seed-targeting 8-mer antimiR. *Sci Transl Med.* 5(212), 212ra162, doi: 10.1126/scitranslmed.3006840 (2013)

Souleimanian, N., et al. Antisense 2'-deoxy-2'-fluoroarabinonucleic acids (2'F-ANAs) antisense oligonucleotides: in vitro gymnotic silencers of gene expression whose potency is enhanced by fatty acids, Molecular Therapy-Nucleic Acids, September 18; 1:e43 (2012); doi: 10.1038/mtna.2012.35

Smith, T. F., Waterman, M. S. Comparison of biosequences. Adv. Appl. Math. 2:482 (1981);

Terenzi, F. & Ladd, A. N. Conserved developmental alternative splicing of muscleblind-like (MBNL) transcripts regulates MBNL localization and activity. *RNA Biol* 7, 43-55 (2010)

Thornton, C. A. Myotonic dystrophy. *Neurol Clin* 32, 705-719, viii, doi:10.1016/j.ncl.2014.04.011 (2014)

Vicente, M., et al. Muscleblind isoforms are functionally distinct and regulate alpha-actinin splicing. *Differentiation* 75, 427-440, doi:10,1111/j.1432-0436.2006.00156.x (2007)

Vicente-Crespo, M. et al. Drosophila muscleblind is involved in troponin T alternative splicing and apoptosis. PLoS One 3, e1613, doi:10.1371/journal.pone.0001613 (2008)

Wang, X. W., et al. MicroRNAs in liver disease. Gastroenterology 142(7), 1431-1443 (2012)

Yanava, R. S., et al. TWEAK Regulates Muscle Functions in a Mouse Model of RNA Toxicity. PLoS One. 22; 11(2): e0150192. doi: 10.1371/journal.pone.0150192 (2016). eCollection 2016.

---

The invention claimed is:

1. A method of treating a subject for myotonic dystrophy type 1, comprising administering to the subject a composition comprising: an oligoribonucleotide and/or oligoribonucleotide analog molecule which is an antagonist of the human microRNA-218-5p or of the human microRNA-23b 3p, or a mixture of two or more of said oligoribonucleotide and/or oligoribonucleotide analog molecules,
wherein the oligoribonucleotide and/or oligoribonucleotide analog molecule is at least 15 nucleotides in length and is at least 93% complementary to SEQ ID NO:3 or SEQ ID NO:4, and
wherein the oligoribonucleotide and/or oligoribonucleotide analog molecule comprises ribonucleotides or analogues thereof or a mixture of ribonucleotides or analogues thereof and deoxyribonucleotides or analogues thereof.

2. The method according to claim 1, wherein the oligoribonucleotide and/or oligoribonucleotide analog molecule is 100% complementary to, or 100% identical to, the sequence of the nitrogenous bases of human microRNA-218-5p.

3. The method according to claim 1, wherein the oligoribonucleotide and/or oligoribonucleotide analog molecule is 100% complementary to, or 100% identical to, the sequence of the nitrogenous bases of human microRNA-23b-3p.

4. The method according to claim 1, wherein the oligoribonucleotide and/or oligoribonucleotide analog molecule is identical at least in a percentage selected from the group consisting of 95%, 96%, 97%, 98%, 99%, 99.5%, and 100%, to the full length sequence of the nitrogenous bases of the oligoribonucleotide SEQ ID NO:1 or of the oligoribonucleotide SEQ ID NO:2.

5. The method according to claim 1, wherein the oligoribonucleotide and/or oligoribonucleotide analog molecule is an antagomiR, a antimiR or a microRNA sponge.

6. A method of treating a subject for myotonic dystrophy type 1, comprising administering to the subject a composition comprising: an oligoribonucleotide and/or oligoribonucleotide analog molecule that is an antagomiR-type oligoribonucleotide analogue represented by SEQ ID NO:10 (antagomiR-218-5p) or an antagomiR-type oligoribonucleotide analogue represented by SEQ ID NO:11 (antagomiR-23b-3p), a mixture of said oligoribonucleotide and/or oligoribonucleotide analog molecules, or an expression vector comprising the sequence of said oligoribonucleotide and/or oligoribonucleotide analog molecule.

7. A method of treating a subject for myotonic dystrophy type 1, comprising administering to the subject a composition comprising: an oligoribonucleotide and/or oligoribonucleotide analog molecule that is an antagomiR-type oligoribonucleotide selected from the group consisting of SEQ ID NO:84, SEQ ID NO: 85, SEQ ID NO: 86, SEQ ID NO: 87, SEQ ID NO: 88, SEQ ID NO: 89, SEQ ID NO: 90, and SEQ ID NO:91, a mixture of said oligoribonucleotide and/or oligoribonucleotide analog molecules, or an expression vector comprising the sequence of said oligoribonucleotide and/or oligoribonucleotide analog molecule.

8. A method of treating a subject for myotonic dystrophy type 1, comprising administering to the subject a composition comprising: an oligoribonucleotide and/or oligoribonucleotide analog molecule that is an antagomiR-type oligoribonucleotide selected from the group consisting of SEQ ID NO:92, SEQ ID NO: 93, and SEQ ID NO:94, a mixture of said oligoribonucleotide and/or oligoribonucleotide analog molecules, or an expression vector comprising the sequence of said oligoribonucleotide and/or oligoribonucleotide analog molecule.

9. The method of claim 1, wherein the composition additionally comprises a carrier and/or one or more pharmaceutically acceptable excipients.

10. The method according to claim 1, wherein the treatment is a palliative treatment of one or more symptoms of the myotonic dystrophy type 1.

11. The method according to claim 10, wherein the treatment is a palliative treatment of one or more muscular disorders that are part of the one or more symptoms of the myotonic dystrophy type 1.

12. The method according to claim 1, wherein the composition comprises the oligoribonucleotide and/or oligoribonucleotide analog molecule or a mixture of two or more of said oligoribonucleotide and/or oligoribonucleotide analog molecules.

13. The method according to claim 1, wherein the composition comprises the expression vector that comprises the sequence of said oligoribonucleotide and/or oligoribonucleotide analog molecule.

14. The method according to claim 1, wherein the oligoribonucleotide and/or oligoribonucleotide analogue molecule is a FANA oligonucleotide which contains at least a 2'-fluorine modification in at least one of its nucleotides or analogue of a nucleotide.

15. A method of treating a subject for myotonic dystrophy type 1, comprising administering to the subject a composition comprising: an oligoribonucleotide and/or oligoribonucleotide analogue molecule that is a FANA oligonucleotide which contains at least a 2'-fluorine modification in at least one of its nucleotides or analogue of a nucleotide, and wherein the FANA oligonucleotide is selected from the group consisting of SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, and SEQ ID NO:104, a mixture of said oligoribonucleotide and/or oligoribonucleotide analog molecules, or an expression vector comprising the sequence of said oligoribonucleotide and/or oligoribonucleotide analog molecule.

16. The method according to claim 1, wherein the oligoribonucleotide and/or oligoribonucleotide analog molecule is an antagomiR.

17. The method according to claim 1, wherein the oligoribonucleotide and/or oligoribonucleotide analog molecule is at least 15 nucleotides in length and has at least 93% identity with a fragment of SEQ ID NO: 1 or 2.

18. The method according to claim 1, wherein the oligoribonucleotide and/or oligoribonucleotide analog molecule is at least 15 nucleotides in length and has 100% identity with a fragment of SEQ ID NO: 1 or 2; or
  wherein the oligoribonucleotide and/or oligoribonucleotide analog molecule is at least 15 nucleotides in length and is 100% complementary to SEQ ID NO:3 or SEQ ID NO:4.

* * * * *